United States Patent
Croasdale-Wood et al.

(10) Patent No.: US 11,787,873 B2
(45) Date of Patent: Oct. 17, 2023

(54) BISPECIFIC HER2 ANTIBODIES AND METHODS OF USE

(71) Applicant: Hoffmann-La Roche Inc., Little Falls, NJ (US)

(72) Inventors: Rebecca Croasdale-Wood, Penzberg (DE); Lydia Jasmin Hanisch, Birmensdorf (CH); Guy Georges, Habach (DE); Thomas Hofer, Zurich (CH); Ralf Hosse, Mettmenstetten (CH); Christian Klein, Bonstetten (CH); Ekkehard Moessner, Kreuzlingen (CH); Samuel Moser, Rotkreuz (CH); Wolfgang Schaefer, Mannheim (DE); Juergen Michael Schanzer, Munich (DE); Werner Scheuer, Penzberg (DE); Claudio Sustmann, Munich (DE); Pablo Umana, Wollerau (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 443 days.

(21) Appl. No.: 16/744,697

(22) Filed: Jan. 16, 2020

(65) Prior Publication Data

US 2020/0291131 A1 Sep. 17, 2020

Related U.S. Application Data

(60) Division of application No. 15/186,098, filed on Jun. 17, 2016, now Pat. No. 10,584,178, which is a continuation of application No. PCT/EP2014/078375, filed on Dec. 18, 2014.

(51) Int. Cl.
| | | |
|---|---|---|
| C07K 16/32 | (2006.01) | |
| A61K 31/713 | (2006.01) | |
| C12N 5/10 | (2006.01) | |
| C12N 15/63 | (2006.01) | |
| A61K 39/00 | (2006.01) | |

(52) U.S. Cl.
CPC ............ *C07K 16/32* (2013.01); *A61K 31/713* (2013.01); *C12N 5/10* (2013.01); *C12N 15/63* (2013.01); *A61K 2039/505* (2013.01); *C07K 2317/24* (2013.01); *C07K 2317/31* (2013.01); *C07K 2317/35* (2013.01); *C07K 2317/41* (2013.01); *C07K 2317/51* (2013.01); *C07K 2317/515* (2013.01); *C07K 2317/52* (2013.01); *C07K 2317/522* (2013.01); *C07K 2317/55* (2013.01); *C07K 2317/56* (2013.01); *C07K 2317/565* (2013.01); *C07K 2317/567* (2013.01); *C07K 2317/622* (2013.01); *C07K 2317/64* (2013.01); *C07K 2317/66* (2013.01); *C07K 2317/73* (2013.01); *C07K 2317/732* (2013.01); *C07K 2317/734* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 5,821,337 A | 10/1998 | Carter et al. |
| 6,733,752 B1 | 5/2004 | Greene et al. |
| 7,862,817 B2 | 1/2011 | Adams et al. |
| 2003/0228663 A1 | 12/2003 | Lowman et al. |
| 2004/0043446 A1 | 3/2004 | DeFrees |
| 2006/0018899 A1 | 1/2006 | Kao et al. |
| 2012/0064069 A1* | 3/2012 | Williams ............... A61P 37/00 530/387.3 |
| 2012/0191435 A1* | 7/2012 | Guo ...................... C07K 16/32 703/11 |
| 2013/0266564 A1 | 10/2013 | Jaramillo et al. |
| 2013/0323787 A1* | 12/2013 | Yang ..................... C40B 50/06 435/235.1 |
| 2015/0196663 A1* | 7/2015 | Shusta ................. A61K 9/0085 435/254.11 |
| 2015/0266947 A1* | 9/2015 | Sierks .................. C07K 16/005 435/6.12 |
| 2017/0029529 A1 | 2/2017 | Coarsdale-Wood et al. |
| 2017/0355756 A1* | 12/2017 | Julien ..................... A61P 25/00 |

FOREIGN PATENT DOCUMENTS

| | | |
|---|---|---|
| EP | 2330131 A1 | 6/2011 |
| EP | 2482212 | 6/2012 |
| EP | 3243840 | 11/2017 |
| WO | 98/50431 | 11/1998 |
| WO | 03/074679 | 9/2003 |
| WO | 03/087131 | 10/2003 |
| WO | 2007/084181 A2 | 7/2007 |
| WO | WO 2008068048 * | 6/2008 |
| WO | 2009/080251 | 7/2009 |
| WO | 2009/080252 | 7/2009 |

(Continued)

OTHER PUBLICATIONS

Kussie "A Single Engineered Amino Acid Substitution Changes Antibody Fine Specificity" J immunol 152(1):146-52 (Year: 1994).*
Chen "Enhancement and destruction of antibody function by somatic mutation: unequal occurrence is controlled by V gene combinatorial associations" EMBO 14(12):2784-2794 (Year: 1995).*

(Continued)

*Primary Examiner* — Adam Weidner

(74) *Attorney, Agent, or Firm* — Lawrence S. Graham

(57) ABSTRACT

The present invention relates to bispecific HER2 antibodies, novel HER2 antibody variants, methods for their production, pharmaceutical compositions containing said antibodies, and uses thereof.

17 Claims, 43 Drawing Sheets

Specification includes a Sequence Listing.

(56) References Cited

FOREIGN PATENT DOCUMENTS

| WO | 2009/080253 | 7/2009 |
| --- | --- | --- |
| WO | 2009/080254 | 7/2009 |
| WO | 2010/136172 | 12/2010 |
| WO | 2010/145792 | 12/2010 |
| WO | 2011/069104 | 6/2011 |
| WO | 2011/084496 | 7/2011 |
| WO | 2011/117330 | 9/2011 |
| WO | 2011/147982 A2 | 12/2011 |
| WO | 2012/075581 | 6/2012 |
| WO | 2012/085111 | 6/2012 |
| WO | 2012/085113 | 6/2012 |
| WO | 2012/143523 | 10/2012 |
| WO | 2012/143524 | 10/2012 |
| WO | 2013/026831 | 2/2013 |
| WO | 2015/091738 | 6/2015 |
| WO | 2015/095392 | 6/2015 |
| WO | 2006/135793 | 12/2016 |

OTHER PUBLICATIONS

Almagro et al., "Humanization of antibodies" Front Biosci 13:1619-1633 (Jan. 1, 2008).

Atwell et al., "Stable Heterodimers from Remodeling the Domain Interface of a Homodimer using a Phage Dispaly Library" Journal of Mol. Biol. 270:26-35 ( 1997).

Barthelemy et al., "Comprehensive Analysis of the Factors Contributing to the Stability and Solubility of Autonomous Human VH Domains" Journal of Biological Chemistry 283(6):3639-3654 (Feb. 8, 2008).

Beiboer et al., "Guided selection of a pan carcinoma specific antibody reveals similar binding characteristics yet structural divergence between the original murine antibody and its human equivalent" J. Mol. Biol., 296:833-849 ( 2000).

Berglund et al., "The epitope space of the human proteome" Protein Science 17(4):606-613 (Apr. 1, 2008).

Bostrom et al., "High affinity antigen recognition of the dual specific variants of Herceptin is entropy-driven in spite of structural plasticity" PLoS One 6:e17887 ( 2011).

Carter, P., et al., "Humanization of an anti-p185 HER2 antibody for human cancer therapy" PNAS USA 89(10):4285-4289 (May 15, 1992).

Choi et al., "Predicting antibody complementarity determining region structures without classification" Mol. BioSyst 7:3327-3334 ( 2011).

Corada et al., "Monoclonal antibodies directed to different regions of vascular endothelial cadherin extracellular domain affect adhesion and clustering of the protein and modulate endothelial permeability" Blood Journal 97:1679-1687 ( 2001).

De Genst et al., "Antibody repertoire development in camelids" Dev Comp Immuno 30:187-198 ( 2006).

Drebin et al., "Down-Modulation of an Oncogene Protein Product and Reversion of the Transformed Phenotype by Monoclonal Antibodies" Cell 41(3):695-706 (Jul. 1985).

Gerstner et al., "Sequence Plasticity in the Antigen-binding Site of a Therapeutic Anti-HER2 Antibody" J Mol Biol 321:851-862 ( 2002).

Griffiths et al., "Human anti-self antibodies with high specificity from phage display libraries" EMBO Journal 12:725-734 (1993).

Harris et al., "Identification of multiple sources of charge heterogeneity in a recombinant antibody" J Chromatography B Biomedical Sciences Applications 752(2):233-245 (Mar. 10, 2001).

Huang et al., "In Vivo Deamidation Characterization of Monoclonal Antibody by LC/MS/MS" Anal.Chem. 77:1432-1439 ( 2005).

ISR for International Application No. PCT/EP2014/078375, dated Mar. 18, 2015, 8 pages.

Junttila et al., "Antitumor Efficacy of a Bispecific Antibody That Targets HER2 and Activates T Cells" Cancer Res 74(19) (2014).

Kelley et al., "Antigen binding thermodynamics and antiproliferative effects of chimeric and humanized anti-p185HER2 antibody Fab fragments" Biochem 31:5434-5441 ( 1992).

Kelley et al., "Thermodynamic analysis of an antibody functional epitope" Biochem 32:6828-6835 ( 1993).

Klein, C. et al., "Progress in overcoming the chain association issue in bispecific heterodimeric IgG antibodies" mAbs 4(6):653-663 ( 2012).

Klimka et al., British Journal of Cancer, 83:252-260 ( 2000).

Kulkarni-Kale et al., "CEP: a conformational epitope prediction server" Nucleic Acids Research (33:W168-W171), 33 ( 2005).

Li, B. et al., "Bispecific Antibody to ErbB2 Overcomes Trastuzumab Resistance trough Comprehensive Blockade of ErbB2 Heterodimerization" Cancer Research 73(21):6471-6483 ( 2013).

Natsume et al., "Engineered anti-CD20 antibodies with enhanced complement-activating capacity mediate potent anti-lymphoma activity" Cancer Science 100(12):2411-2418 (Jul. 12, 2009).

Padlan Advances in Protein Chemistry vol. 49:57-133 ( 1996).

Spiess et al., "Bispecific antibodies with natural architecture produced by co-culture of bacteria expressing two distinct half-antibodies" Nature Biotechnology 31(8):753-758 (Aug. 2013).

Ward et al., "Binding activities of a repertoire of single immunoglobulin variable domains secreted from *Escherichia coli*" Nature 341:544-546 (Oct. 12, 1989).

Written Opinion for International Application No. PCT/EP2014/078375, dated Mar. 18, 2015.

Yan et al., "Succinimide formation at Asn 55 in the complementarity determining region of a recombinant monoclonal antibody IgG1 heavy chain" J. Pharm. Sci. 98(10):3509-3521 ( 2009).

Yang et al., "Improving Trastuzumab's Stability Profile by Removing the Two Degradation Hotspots" J Pharm Sci 104(6):1960-1970 ( 2015).

\* cited by examiner

BISPECIFIC HER2 ANTIBODIES AND METHODS OF USE

CROSS REFERENCE TO RELATED APPLICATIONS

This application is a Division of U.S. patent application Ser. No. 15/186,098, filed Jun. 17, 2016, now U.S. Pat. No. 10,584,178, issued Mar. 10, 2020, which is a Continuation of International Patent Application No. PCT/EP2014/078375, filed Dec. 18, 2014, now publication WO 2015/091738, which claims the benefit of priority to European Patent Application No. 13198819.8, filed Dec. 20, 2013, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jan. 3, 2020, is named P31865-US-1_Sequence_Listing.txt and is 253,352 bytes in size.

FIELD OF THE INVENTION

The present invention relates to bispecific HER2 antibodies, novel HER2 variants, methods for their production, pharmaceutical compositions containing said antibodies, and uses thereof.

BACKGROUND

Antibodies specific for tumor-associated antigens are a valuable approach in cancer therapy because they mediate selective destruction of tumor cells, while leaving healthy cells and tissues undamaged.

Members of the ErbB family of receptor tyrosine kinases are important mediators of cell growth, differentiation and survival. The receptor family includes four distinct members, including epidermal growth factor receptor (EGFR or ErbB1), HER2 (ErbB2 or p185"e"), HER3 (ErbB3) and HER4 (ErbB4 or tyro2). HER2 is a transmembrane surface-bound receptor tyrosine kinase and is normally involved in the signal transduction pathways leading to cell growth and differentiation. HER2 is a promising target for treatment of breast cancer as it was found to be overexpressed in about one-quarter of breast cancer patients (Bange et al, 2001, Nature Medicine 7:548).

The murine monoclonal antibody 4D5 is targeting HER2 specifically in HER2 overexpressing cancer cells, while having no effect on cells expressing physiological levels of HER2. The humanized (4D5) monoclonal antibody (hu4D5) is commercially known as the drug HERCEPTIN© (trastuzumab, rhuMAb HER2, U.S. Pat. No. 5,821,337), which gained FDA marketing approval in late 1998.

ERCEPTIN© was the first monoclonal antibody developed for the treatment of HER2-positive breast cancer and has increased survival times for patients so that they are now the same as for patients with HER2-negative breast cancer. Before HERCEPTIN© treatment, shorter survival outcomes were expected for patients diagnosed with HER2-positive breast cancer, compared to patients with HER2-negative disease. In the CLEOPATRA study, PERJETA® in combination with HERCEPTIN© and chemotherapy has shown the extension of survival times for patients with this aggressive disease even further than HERCEPTIN©.

Pertuzumab (PERJETA©, rhuMab 2C4, U.S. Pat. No. 7,862,817) is a humanized monoclonal antibody, which is designed specifically to prevent the HER2 receptor from pairing (dimerising) with other HER receptors (EGFR/HER1, HER3 and HER4) on the surface of cells, a process that is believed to play a role in tumor growth and survival. The combination of PERJETA®, HERCEPTIN© and chemotherapy is thought to provide a more comprehensive blockade of HER signaling pathways. PERJETA© is approved in combination with HERCEPTIN© (trastuzumab) and docetaxel in adult patients with HER2-positive metastatic or locally recurrent unresectable breast cancer and gained FDA approval for neoadjuvant breast cancer treatment in September 2013. Pertuzumab binds to domain II of HER2, essential for dimerization, while Ttrastuzumab binds to extracellular domain IV of HER2.

Li et al (Cancer Research. 2013) describe bispecific, bivalent antibodies to ErbB2 that overcome trastuzumab resistance. The bispecific, bivalent antibodies described therein are based on the native Trastuzumab and Pertuzumab sequences.

Surprisingly the inventors of the present application found that optimizing the native Trastuzumab and Pertuzumab sequences and combining these optimized variants in two different improved bispecific, monovalent antibody formats leads to improved properties as compared to the combination of the monospecific antibodies rhuMab 2C4 and hu 4D5. Further the antibodies are superior to the bivalent antibody formats disclosed in Li et al, as they are monovalent and have the same molecular weight as the two monospecific antibodies Pertuzumab and Trastuzumab. Hence the new bispecific format combines the superior characteristics of the bispecific HER2 antibodies known in the art with the advantages of a classical monospecific antibody: The novel bispecific HER2 antibodies of the present invention are monovalent for the two different HER2 epitopes, resulting in the same avidity effect as the bivalent parental antibodies. In contrast, tetravalent antibodies may differ in their avidity for HER2 on cells. The avidity effect of the novel bispecific HER2 antibodies may result in a superior safety window on cell types with low HER2 expression such as in normal tissues or cardiac tissues where inhibition of HER2 and/or ADCC may not be desired.

Furthermore, the bispecific antibodies described herein have the same diffusion constants as the bivalent parental antibodies due to their natural IgG architecture that matches to the diffusion constant of the parental 150 KD IgG1 antibody. Due to the natural IgG architecture furthermore the risk for immunogenicity and the formation of anti-drug antibodies can be expected to be reduced. Last but not least as compared to tetravalent bispecific antibodies the risk for the formation of immune complexes with shed HER2 extracellular domain is reduced by being monovalent and comparable to the parental antibodies Immune complexes may result in the enhanced immunogenicity of the complex taken up by antigen presenting cells and ultimately can induce kidney toxicity if immune complexes are deposited in the kidney.

In one aspect of the invention a monovalent bispecific antibody is provided, wherein one of the Fab fragments of an IgG molecule is replaced by a crossover Fab fragment. Crossover Fab fragments are Fab fragments wherein either the variable regions or the constant regions of the heavy and light chain are exchanged. Bispecific antibody formats comprising crossover Fab fragments have been described, for example, in WO2009080252, WO2009080253, WO2009080251, WO2009080254, WO2010/136172, WO2010/145792 and WO2013/026831. The native Trastuzumab sequences has been optimized in their CDRs to improve the stability of the antibody CDRs against spontaneous chemical modification, the resulting sequences framework-grafted to avoid mispairing, and the bispecific antibody glycoengineered, resulting in highly potent bispecific antibodies that specifically bind to HER2 with enhanced FcgRIII binding resulting in enhanced recruitment of immune effector cells such as NK cells or monocytes/macrophages; finally they can be produced with high yield and only low percentage of side products comparable to the conventional parental Her2 antibodies. In the case of the HER2 bispecific CrossMAb antibody chain misparing of light chains resulting from the fact that both pertuzumab and trastuzumab are based on a comparable framework region has been overcome by grafting the CDRs on a completely novel antibody framework.

In another aspect of the invention monovalent bispecific antibodies specifically binding to the extracellular domains IV and II of HER2 are provided wherein the two binding moieties comprise identical light chains based on a consensus of the parental trastuzumab and pertuzumab light chains and the corresponding pertuzumab heavy chain has been remodeled. The use of this so-called 'common light chain' principle, i.e. combining two binders that share one light chain but still have separate specificities, prevents light chain mispairing and in this particular case retains the epitope specificity of the parental antibodies. As a consequence, there are less side products during production, facilitating the homogenous preparation of HER2 bispecific antigen binding molecules at high yields. Surprisingly the inventors of the present invention found that the bispecific HER2 antibodies in the monovalent common light chain format have an increased affinity to the pertuzumab epitope, and show superior inhibitory effects on cell proliferation and induction of cell dependent cytotoxicity (CDC) as compared to the combination of the parental antibodies. Complement dependent cytotoxicity (CDC) is very important for the optimal therapeutic monoclonal antibodies (mAb) function and is totally conserved even after a chemotherapy treatment. However, this activity is generated by some antibodies but not all of them.

SUMMARY

The present invention relates to bispecific antibodies specifically binding to HER2 comprising a first antigen binding site specific for the extracellular domain II of HER2 and a second antigen binding site specific for the extracellular domain IV of HER2, wherein the bispecific antibody is monovalent for both the extracellular domain II and IV of HER2. In one embodiment the bispecific antibody induces complement-dependent cytotoxicity (CDC) to a higher degree than the combination of Pertuzumab or Trastuzumab. In one such embodiment the complement dependent cytotoxicity of the bispecific antibody is determined by a LDH assay or a complement assay and compared to the complement dependent cytotoxicity of the combination of Pertuzumab and Trastuzumab as determined by the same assay. In one embodiment the complement dependent cytotoxicity is determined in vitro on cancer cells, preferably on breast cancer cells. In one aspect the bispecific antibody specifically binding to HER2, comprises a first Fab molecule capable of specific binding to extracellular domain II of HER2 and a second Fab molecule capable of specific binding to extracellular domain IV of HER2, wherein the sequence of the variable light chain of the first Fab molecule is identical to the sequence of the variable light chain of the second Fab molecule. In one aspect the bispecific antibody specifically binding to HER2 comprises (a) a first heavy chain comprising a heavy chain CDR1 selected from the group consisting of SEQ ID NO: 55, SEQ ID NO: 58 and SEQ ID NO: 14; a heavy chain CDR 2 selected from the group consisting of SEQ ID NO: 77; SEQ ID NO: 15 and SEQ ID NO: 60 and a heavy chain CDR 3 selected from the group consisting of SEQ ID NO: 56 or SEQ ID NO: 59 and SEQ ID NO: 16, and (b) a second heavy chain comprising a heavy chain CDR1 of SEQ ID NO: 20, a heavy chain CDR2 of SEQ ID NO: 29 and a heavy chain CDR3 selected from the group consisting of SEQ ID NO: 30 and SEQ ID NO: 79; and (c) a first and a second light chain, wherein the variable light chains of the first and second light chain comprise the CDRs of SEQ ID NO: 89, SEQ ID NO: 90 and SEQ ID NO: 19. In one aspect the bispecific antibody specifically binding to HER2 comprises two variable light chains comprising an amino acid sequence of SEQ ID NO: 54, a first heavy chain comprising a variable heavy chain comprising an amino acid sequence selected from the group consisting of SEQ ID NO: 64, SEQ ID NO: 70 and SEQ ID NO: 68, and a second heavy chain comprising a variable heavy chain comprising an amino acid sequence selected from the group consisting of SEQ ID NO: 92 and SEQ ID NO: 117. In one aspect the bispecific antibody specifically binding to HER2 comprises a first Fab molecule capable of specific binding to extracellular domain II of HER2 and a second Fab molecule capable of specific binding to extracellular domain IV of HER2, wherein either the variable regions or the constant regions of the heavy and light chain of at least one Fab fragment are exchanged. In one aspect the bispecific antibody specifically binding to HER2 comprises a first Fab molecule comprising a heavy chain CDR1 of SEQ ID NO: 14, a heavy chain CDR2 of SEQ ID NO: 15 and a heavy chain CDR3 of SEQ ID NO: 16; and a light chain CDR1 of SEQ ID NO: 11; a light chain CDR2 of SEQ ID NO: 12 and a light chain CDR3 of SEQ ID NO: 13, and a second Fab molecule comprising a heavy chain CDR1 of SEQ ID NO: 20; a heavy chain CDR2 of SEQ ID NO: 108; a heavy chain CDR3 of SEQ ID NO: 79; and a light chain CDR1 of SEQ ID NO: 107, a light chain CDR2 of SEQ ID NO: 18 and a light chain CDR3 of SEQ ID NO: 19. In one aspect the bispecific antibody specifically binding to HER2 comprises a first Fab molecule comprising a heavy chain CDR1 of SEQ ID NO: 14, a heavy chain CDR2 of SEQ ID NO: 15 and a heavy chain CDR3 of SEQ ID NO: 16; and a light chain CDR1 of SEQ ID NO: 11; a light chain CDR2 of SEQ ID NO: 12 and a light chain CDR3 of SEQ ID NO: 13, and a second Fab molecule comprising a heavy chain CDR1 of SEQ ID NO: 20, a heavy chain CDR2 of SEQ ID NO: 29, and a heavy chain CDR3 selected from the group consisting of SEQ ID NO: 79, SEQ ID NO: 78, SEQ ID NO: 80, SEQ ID NO: 87, SEQ ID NO: 88; and a light chain CDR1 selected from the group consisting of SEQ ID NO: 104, SEQ ID NO: 103 and SEQ ID NO: 158; a light chain CDR2 of SEQ ID NO: 18 and a light chain CDR3 of SEQ ID NO: 19. In one aspect the bispecific antibody specifically binding to HER2 comprises a first Fab molecule comprising a variable heavy chain comprising an amino acid sequence of SEQ ID NO: 22 and a variable light chain comprising an amino acid sequence of SEQ ID NO: 24 and wherein a second Fab molecule comprising an amino acid sequence of SEQ ID NO: 105 and a light chain variable region comprising an amino acid sequence of SEQ ID NO: 106.

In a second object the present invention relates to a pharmaceutical composition comprising a bispecific antibody of the present invention.

In a third object the present invention relates to a bispecific antibody of the present invention for the treatment of cancer. In another embodiment, use of the bispecific antibody as a medicament is provided. Preferably said use is for the treatment of cancer.

In further objects the present invention relates to a nucleic acid sequence comprising a sequence encoding a heavy chain of a bispecific antibody of the present invention, a nucleic acid sequence comprising a sequence encoding a light chain of a bispecific antibody of the present invention, an expression vector comprising a nucleic acid sequence of the present invention and to a prokaryotic or eukaryotic host cell comprising a vector of the present invention. In addition a method of producing an antibody comprising culturing the host cell so that the antibody is produced is provided.

DETAILED DESCRIPTION OF EMBODIMENTS OF THE INVENTION

I. Definitions

Figure 1A:
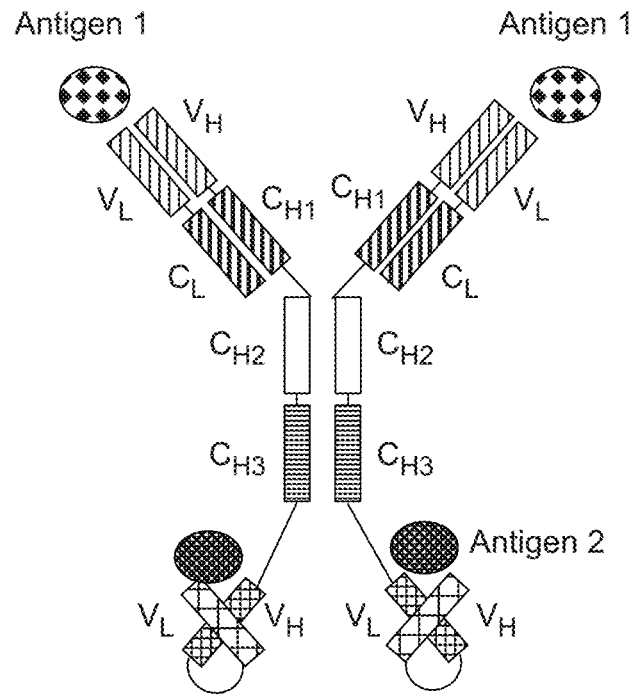
FIGS. 1A-1D: Schematic drawing of Trastuzumab and Pertuzumab bispecific antibodies in a 2+2 IgG-scFv format. The antibodies are bivalent for each antigen binding site and are able to bind two different paratopes in the ErbB2/HER2 receptor (antigen1=trastuzumab specificity, i.e. extracellular domain IV of HER2; antigen2=pertuzumab specificity extracellular domain II of HER2) (1A): The single chain Fv (scFv) is fused C-terminally to the heavy chain in the order VH-VL (TvAB12, SEQ ID NOs 123 and 124). (1B): The single chain Fv (scFv) is fused N-terminally to the light chain in the order VL-VH (TvAB13, SEQ ID NOs 125 and 126). (1C) The single chain Fv (scFv) is fused C-terminally to the light chain in the order VL-VH (TvAB16: SEQ ID NOs 127 and 128, TvAB20: SEQ ID NOs 131 and 132). (1D): The single chain Fv (scFv) is fused C-terminally to the heavy chain in the order VL-VH (TvAB17: SEQ ID NOs 129 and 130).
Figure 1B:
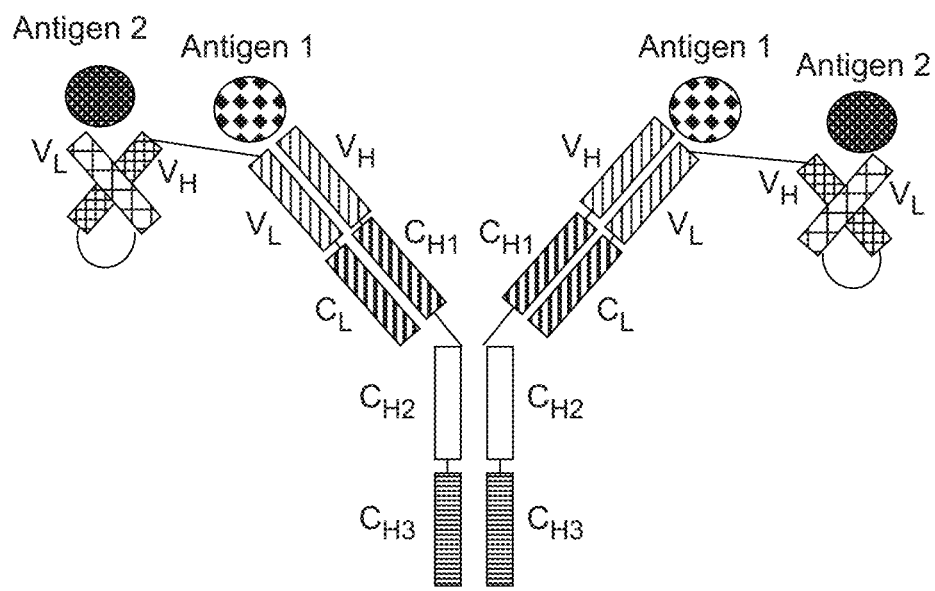
Figure 1C:
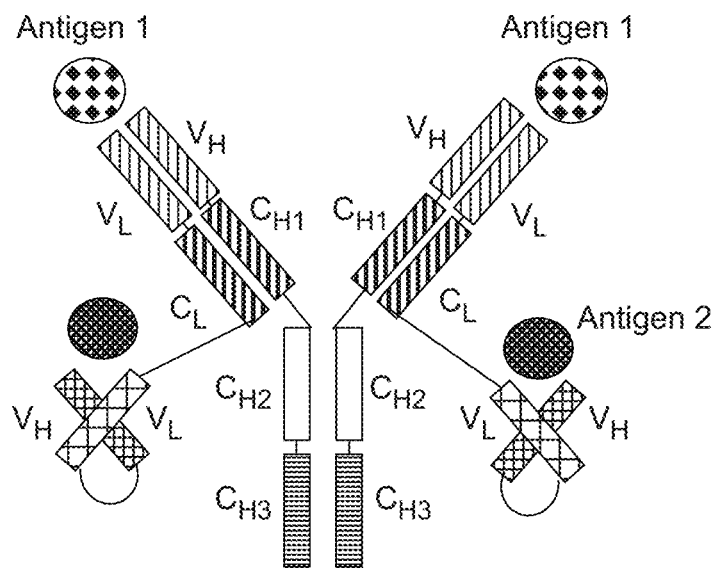
Figure 1D:
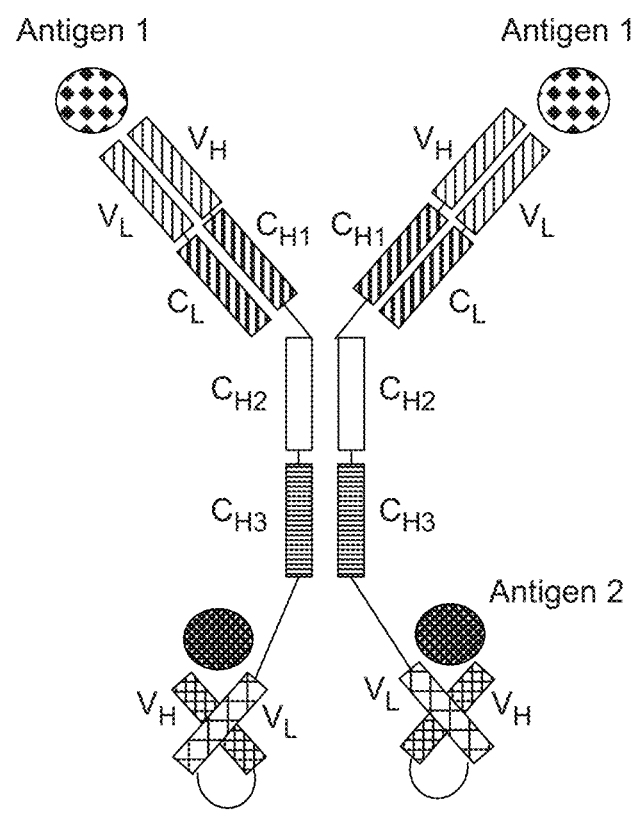
Figure 2A:
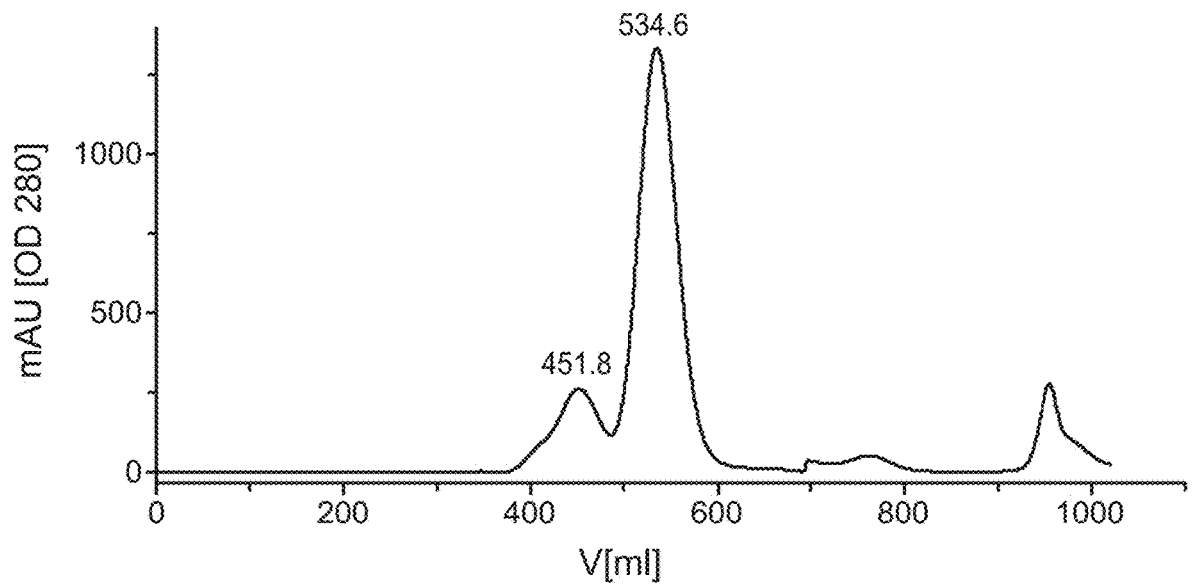
FIGS. 2A and 2B: Purification of Trastuzumab and Pertuzumab bispecific antibodies in a 2+2 IgG-scFv format. (2A): Size-exclusion purification of TvAb12 (SEQ ID NOs 123 and 124) on a 26/60 Superdex 200 column. (2B): SDS-Page analysis of main peak fraction originating from size-exclusion chromatography (NR=non-reducing, R=reducing conditions).
Figure 2B:
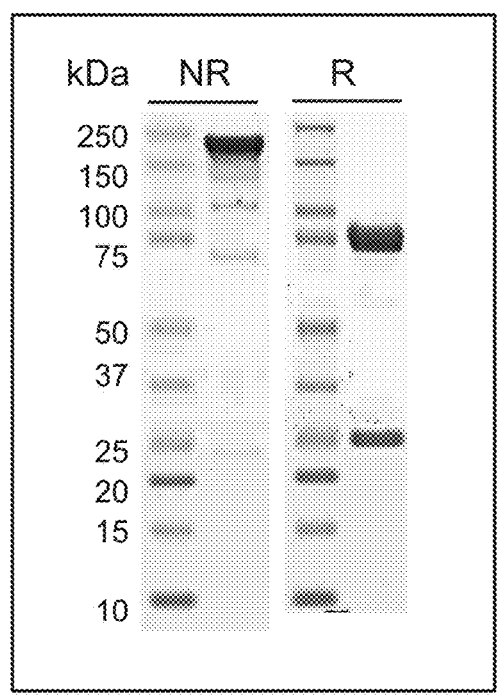
Figure 3A:
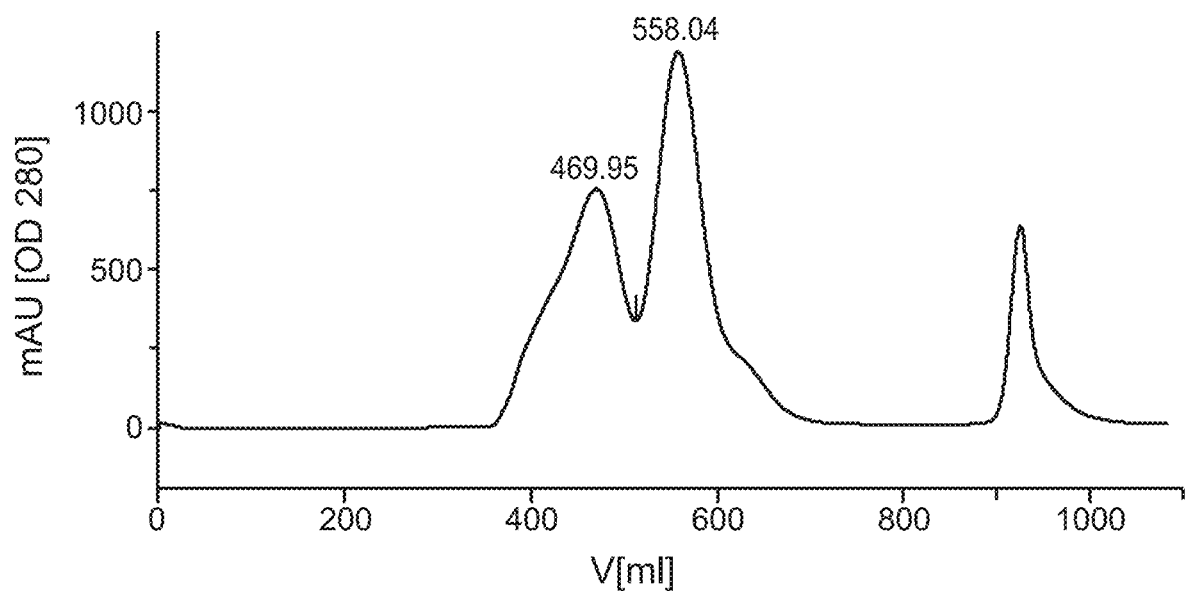
FIGS. 3A and 3B: Purification of Trastuzumab and Pertuzumab bispecific antibodies in a 2+2 IgG-scFv format. (3A): Size-exclusion purification of TvAb16 (SEQ ID NOs 127 and 128) on a 26/60 Superdex 200 column. (3B): SDS-Page analysis of main peak fraction originating from size-exclusion chromatography (NR=non-reducing, R=reducing conditions).
Figure 3B:
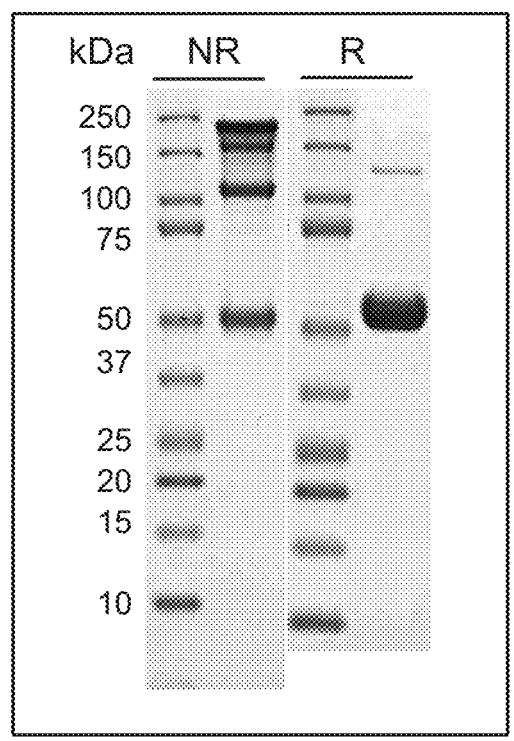
Figure 4A:
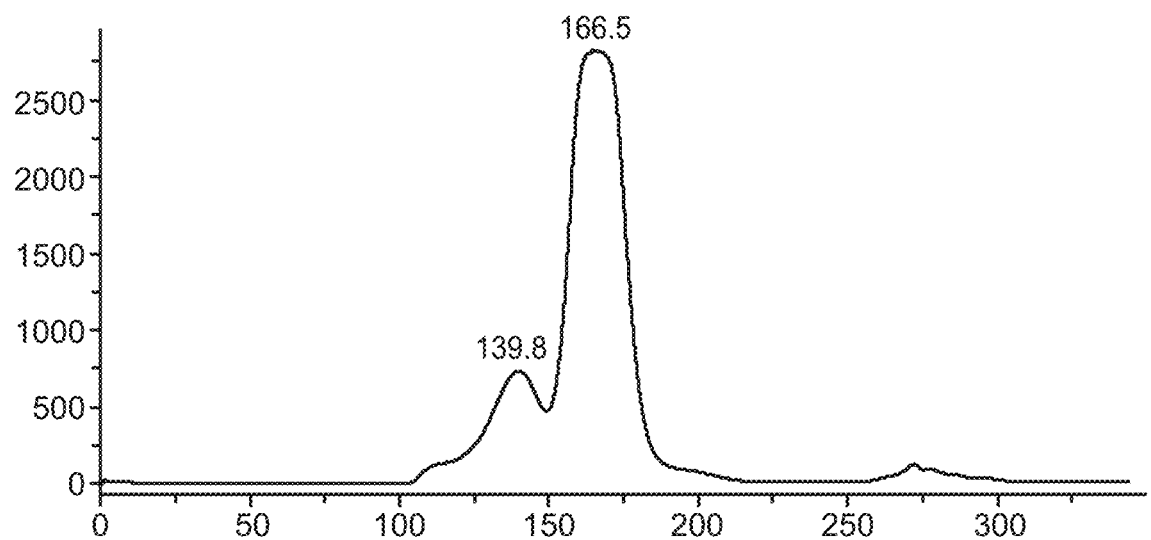
FIGS. 4A and 4B: Purification of Trastuzumab and Pertuzumab bispecific antibodies in a 2+2 IgG-scFv format. (4A): Size-exclusion purification of TvAb20 (SEQ ID NOs 131 and 132) on a 26/60 Superdex 200 column. Main product peak marked with "1". (4B) SDS-Page analysis of main peak fraction originating from size-exclusion chromatography (NR=non-reducing, R=reducing conditions).
Figure 4B:
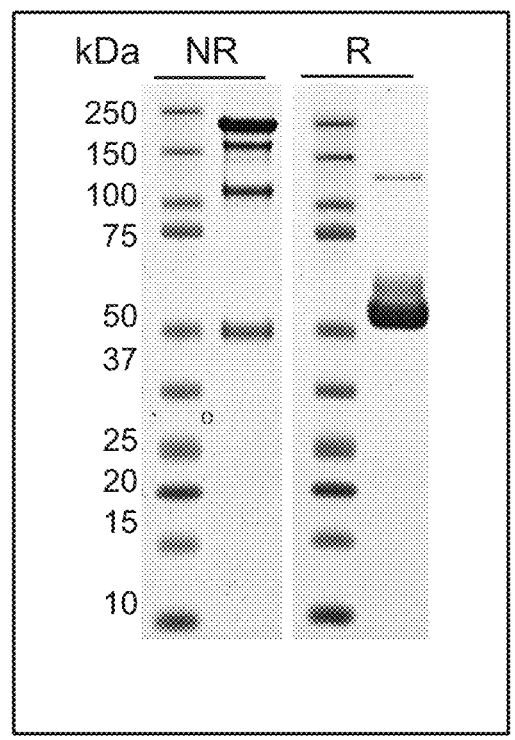
Figure 5A:
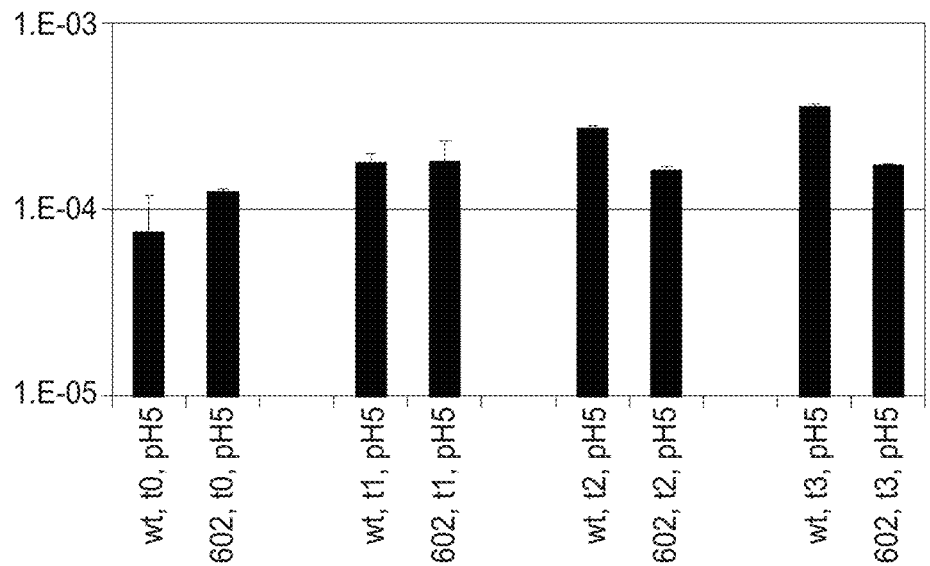
FIGS. 5A and 5B: Off-rates of Trastuzumab variants as determined by SPR method (ProteOn instrument) after incubating the samples for 1, 2, or 3 months at 40° C. in buffer 40 mM Histidin, 150 mM NaCl, pH5.0. The off rates of the variant does not change over the investigated time period. "602": D98E mutation in heavy chain and T31V mutation in light chain.
Figure 5B:
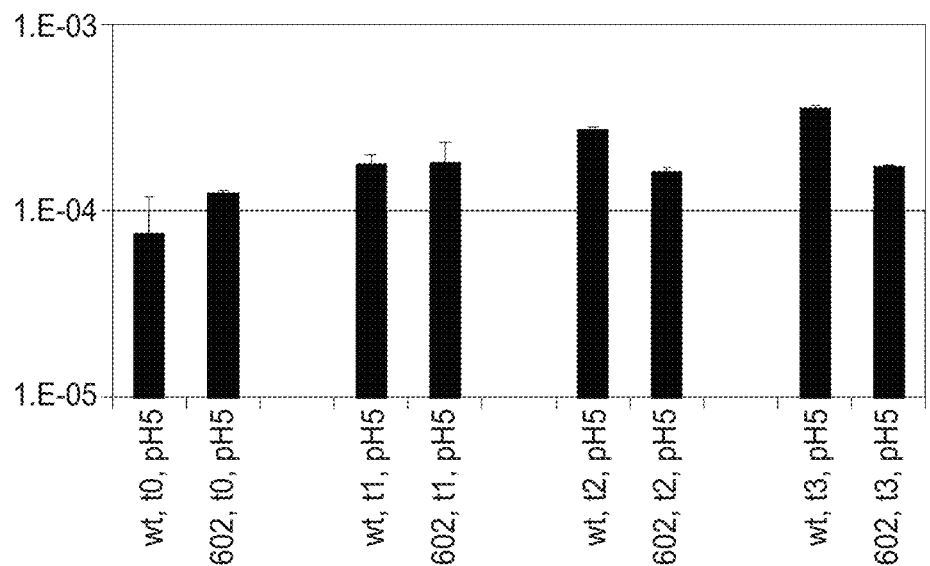
Figure 6A:
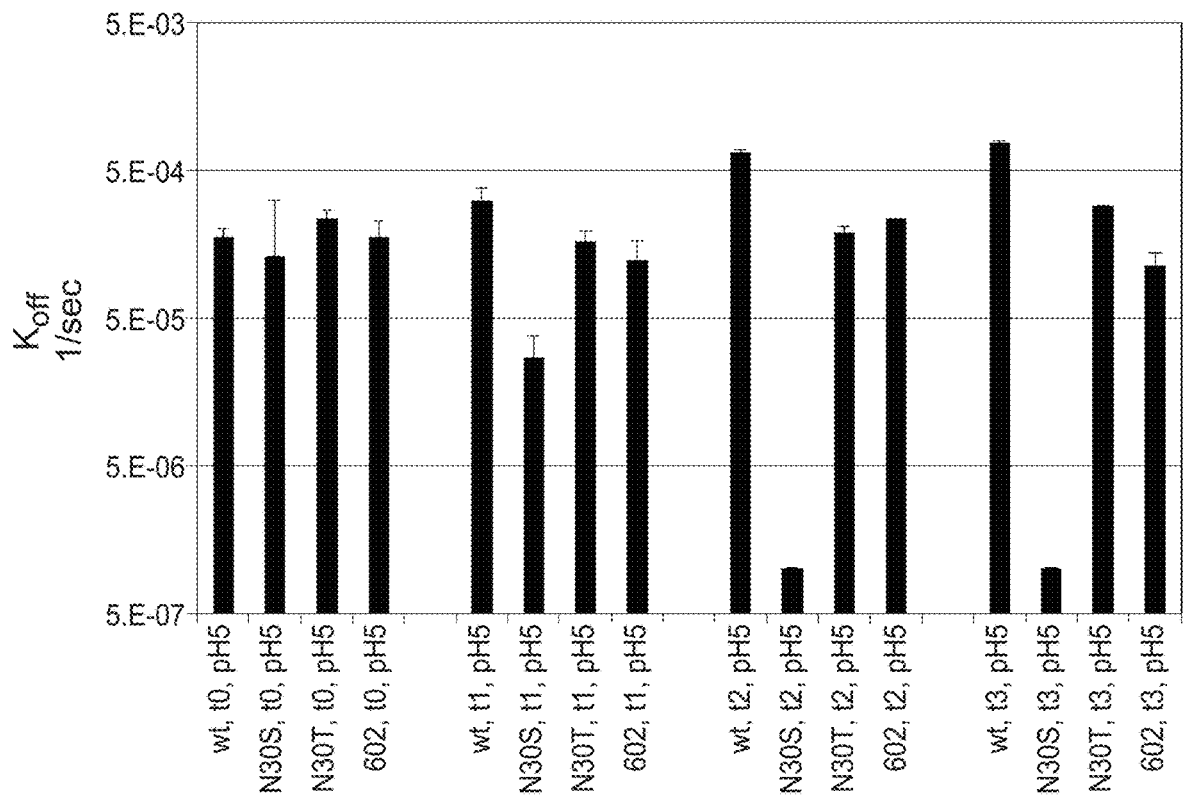
FIGS. 6A-6C: Off-rates of Trastuzumab variants as determined by SPR method (ProteOn instrument) after incubating the samples for 1, 2, or 3 months at 40° C. in 40 mM Histidin, 150 mM NaCl, at different pH. The off rates of the N30S variant were very slow, and therefore contain a high degree of uncertainty. "602": D98E mutation in heavy chain and T31V mutation in light chain, "N30T": D98E mutation in heavy chain and N30T mutation in light chain, "N30S": D98E mutation in heavy chain and N30S mutation in light chain. (6A): pH5.0. (6B): pH6.0, (6C): pH7.4.
Figure 6B:
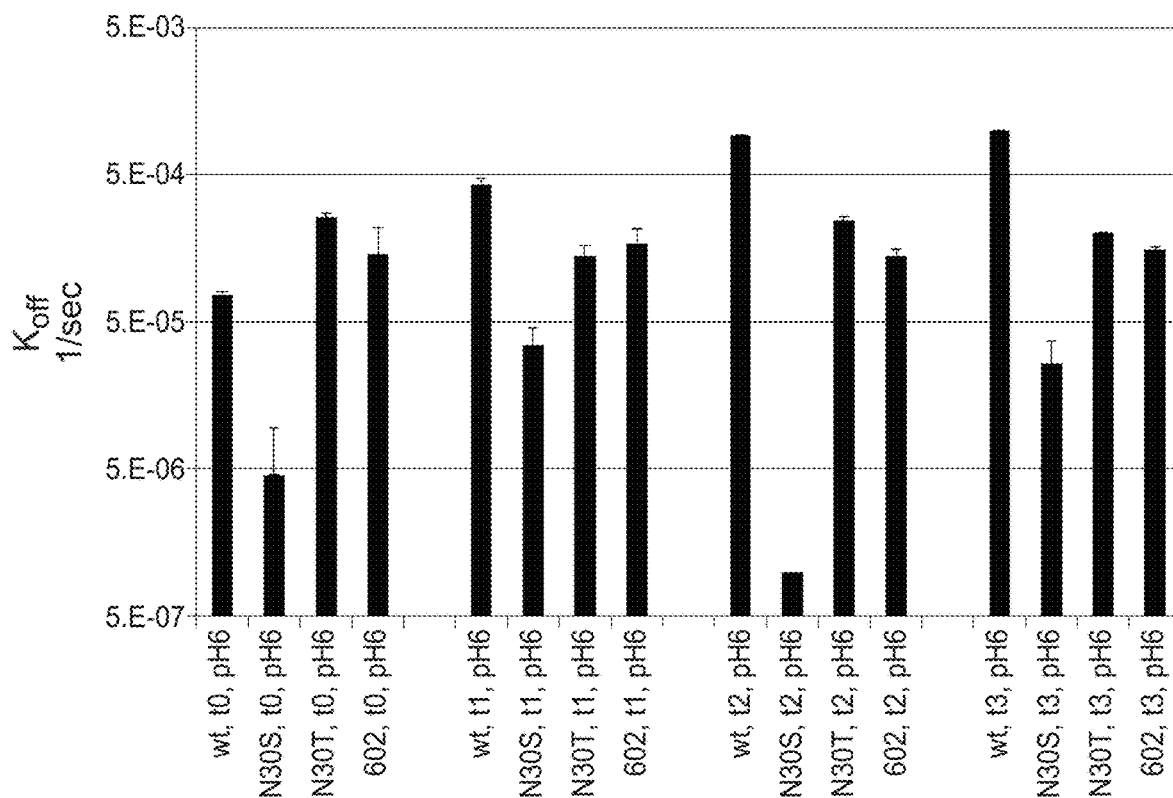
Figure 6C:
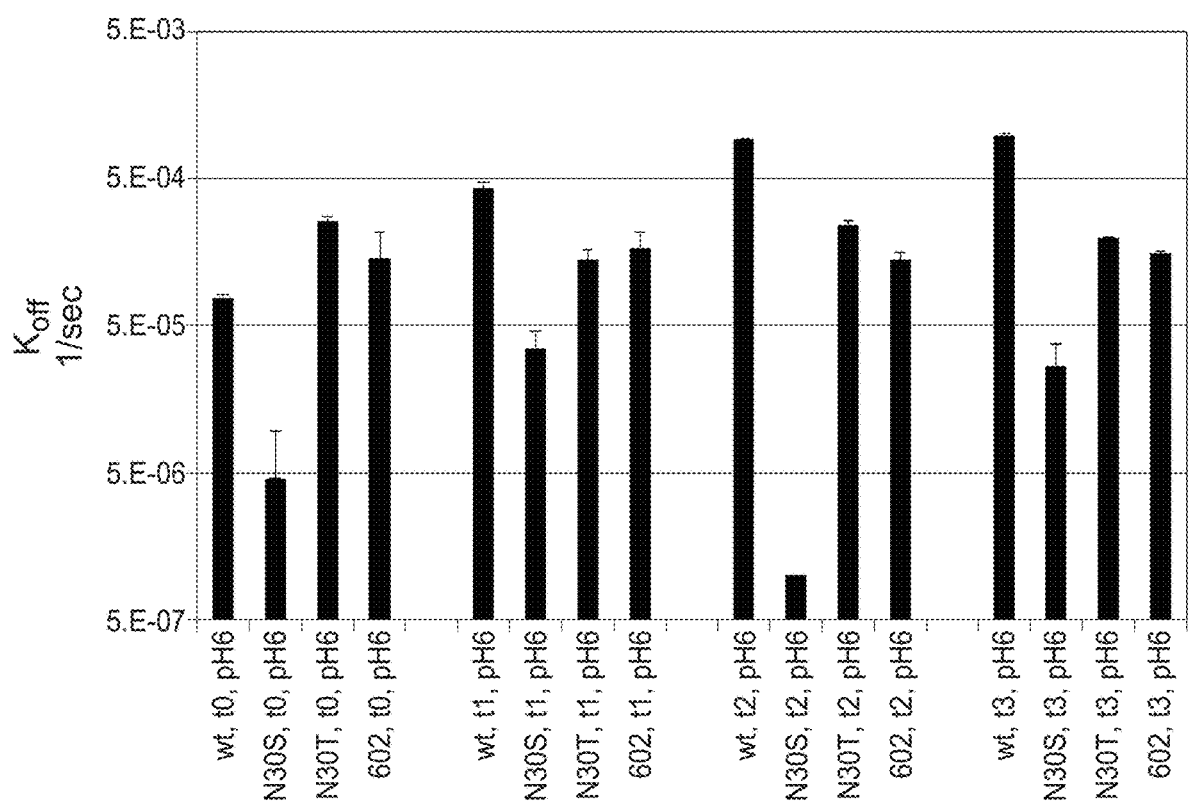
Figure 7A:
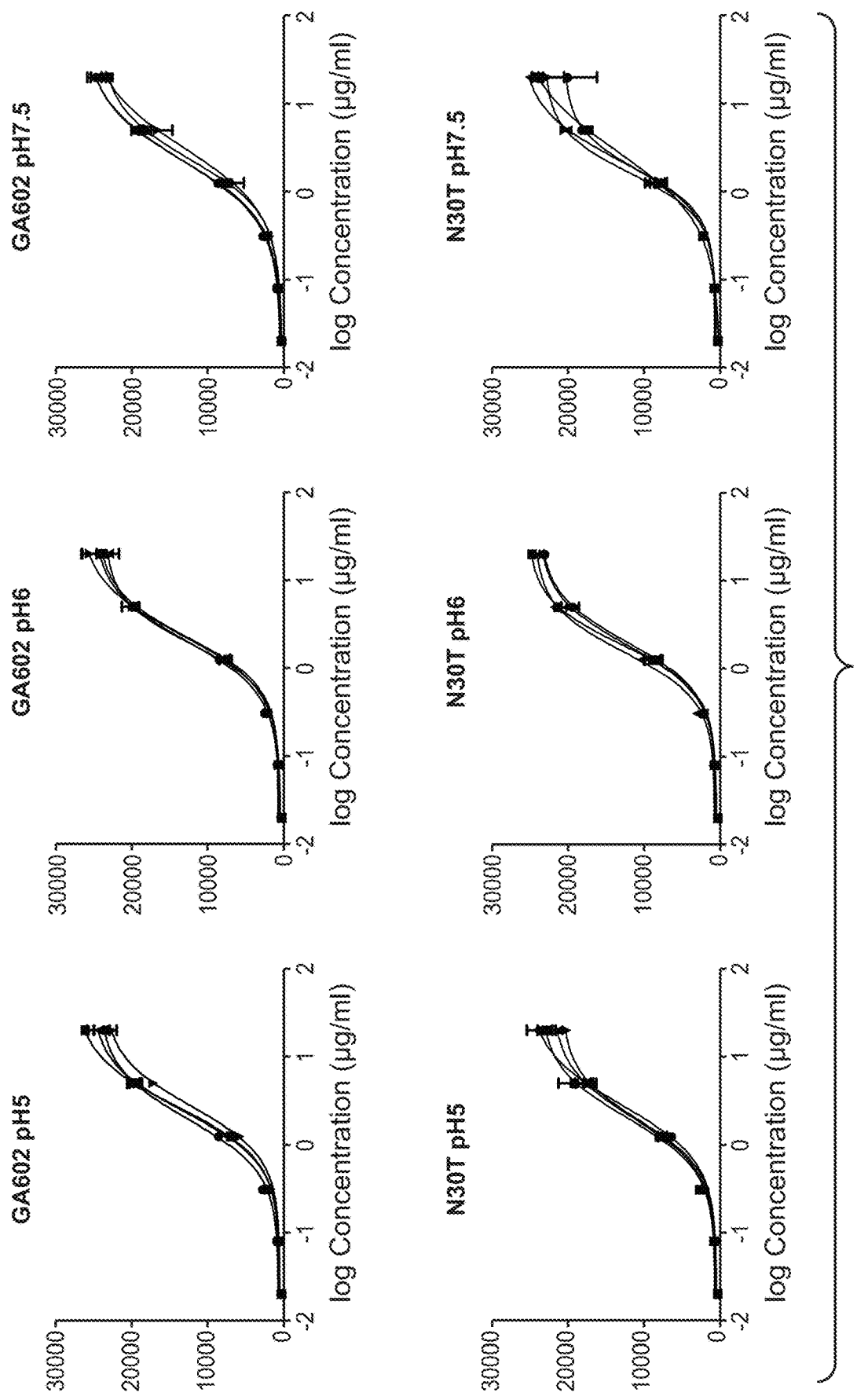
FIGS. 7A and 7B: Binding of Trastuzumab and Trastuzumab stabilization variants after stress to KPL-4 cells. Trastuzumab and 3 different stabilized Trastuzumab variants were incubated for one, two and three month in buffer with different pH values at 40° C. The stressed antibodies were tested compared to the antibody at time point zero for binding to KPL-4 cells by flow cytometry. "602": D98E mutation in heavy chain and T31V mutation in light chain, "N30T": D98E mutation in heavy chain and N30T mutation in light chain, "N30S": D98E mutation in heavy chain and N30S mutation in light chain.
Figure 7B:
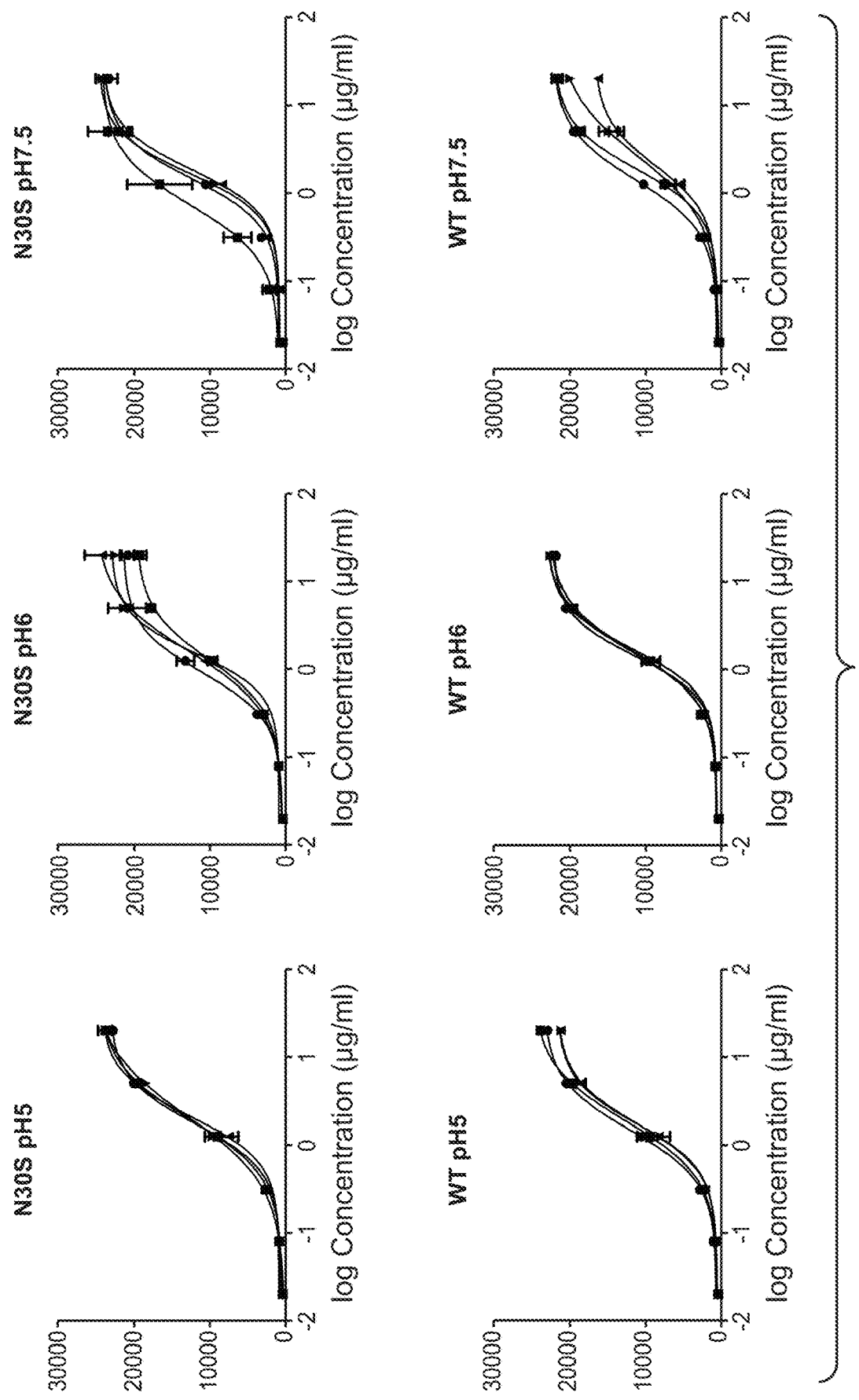
Figure 8:
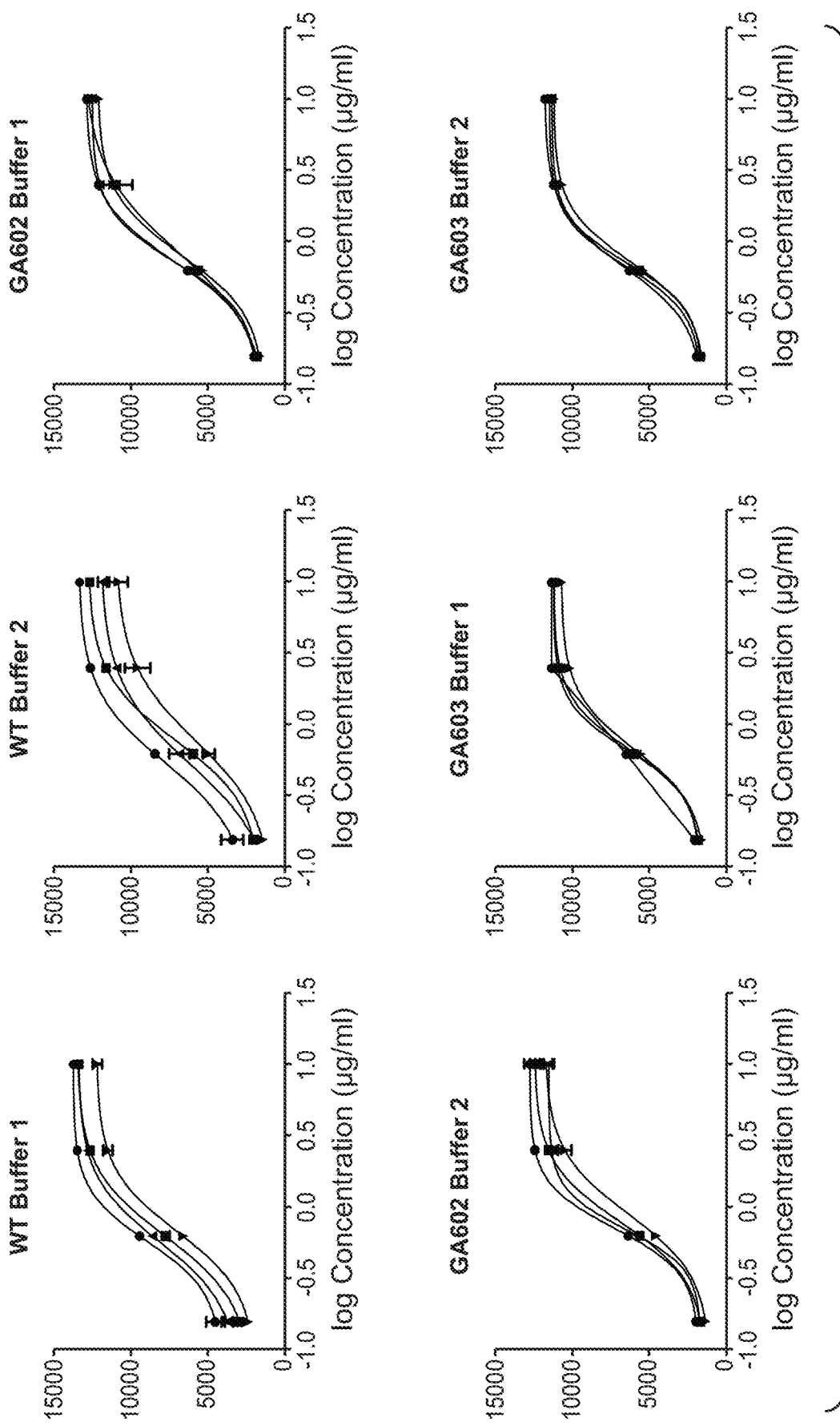
FIG. 8: Binding of Trastuzumab and Trastuzumab stabilization variants after stress to KPL-4 cells. Trastuzumab and the 2 stabilization variants GA602 (D98E mutation in heavy chain and T31V mutation in light chain) and GA603 (D98E mutation in heavy chain and T31V mutation in light chain and FcRN mutation T307Q and N434A) were incubated for one, two and three month in buffer 1 (40 mM Histidin 150 mM NaCl, pH5.0) or buffer 2 (2.40 mM Histidin 150 mM NaCl, pH6.0) at 40° C. The stressed antibodies were tested compared to the antibody at time point zero for binding to KPL-4 cells by flow cytometry.
Figure 9:
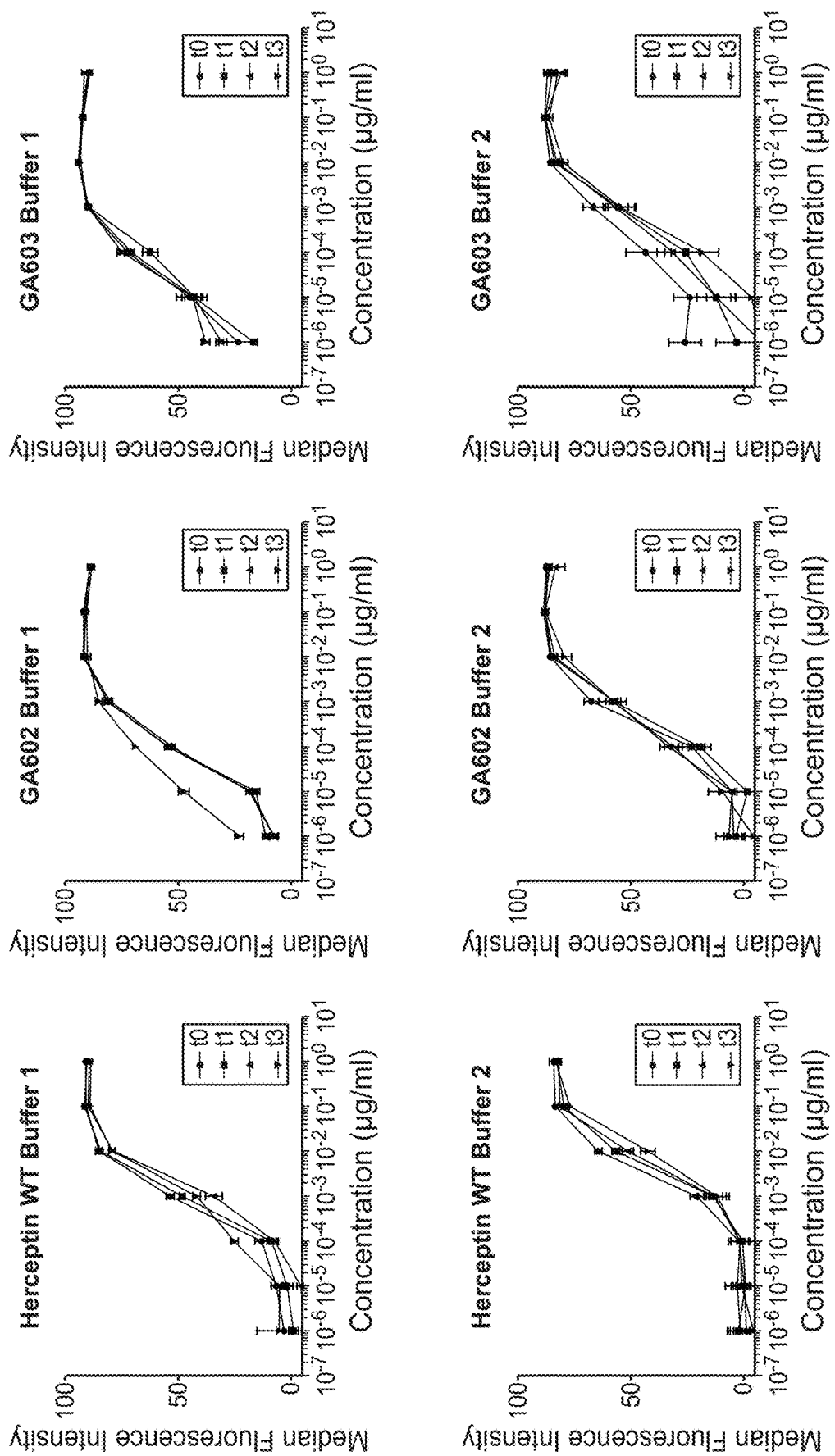
FIG. 9: ADCC induction with Trastuzumab, GA602 and GA603 after stress on KPL-4 cells. Trastuzumab and the 2 stabilization variants GA602 (D98E mutation in heavy chain and T31V mutation in light chain) and GA603 (D98E mutation in heavy chain and T31V mutation in light chain and FcRN mutation T307Q and N434A) were incubated for one, two and three month in buffer 1 (40 mM Histidin 150 mM NaCl, pH 5.0) or buffer 2 (2.40 mM Histidin 150 mM NaCl, pH6.0) at 40° C. The stressed antibodies were tested compared to the antibody at time point zero for ADCC induction after 4 h on KPL-4 cells.

Throughout the disclosure, the terms "ErbB2", "ErbB2 receptor", "c-Erb-B2", and "HER2" are used interchangeably, and, unless otherwise indicated, refer to a native sequence ErbB2 human polypeptide, or a functional derivative thereof. "ber2", "erbB2" and "c-erb-B2" refer to the corresponding human gene.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "a bispecific HER2 antibody" and "a bispecific antibody that specifically binds to HER2" are used interchangeably and refer to a bispecific antibody that is capable of binding HER2 on both extracellular domains II and IV, respectively, with sufficient affinity such that the antibody is useful as a diagnostic and/or therapeutic agent in targeting cells expressing HER2. In one embodiment, the extent of binding of a bispecific antibody that specifically binds to HER2 on both extracellular domains II and IV to an unrelated, non-HER2 protein is less than about 10% of the binding of the antibody to HER2 as measured, e.g., by a Enzyme-linked immunosorbent assay (ELISA), surface plasmon resonance (SPR) based assays (e.g. Biacore) or flow cytometry (FACS). In certain embodiments, a bispecific antibody that specifically binds to HER2 has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies, cross-Fab fragments; linear antibodies; single-chain antibody molecules (e.g. scFv); and multispecific antibodies formed from antibody fragments. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

As used herein, "Fab fragment" refers to an antibody fragment comprising a light chain fragment comprising a VL domain and a constant domain of a light chain (CL), and a VH domain and a first constant domain (CH1) of a heavy chain. In one embodiment the bispecific antibodies of the invention comprise at least one Fab fragment, wherein either the variable regions or the constant regions of the heavy and light chain are exchanged. Due to the exchange of either the variable regions or the constant regions, said Fab fragment is also referred to as "cross-Fab fragment" or "xFab fragment" or "crossover Fab fragment". Two different chain compositions of a crossover Fab molecule are possible and comprised in the bispecific antibodies of the invention: On the one hand, the variable regions of the Fab heavy and light chain are exchanged, i.e. the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as CrossFab $_{(VLVH)}$. On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as CrossFab $_{(CLCH1)}$.

A "single chain Fab fragment" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction:
a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments a) VH-CH1-linker-VL-CL, b) VL-CL-linker-VH-CH1, c) VH-CL-linker-VL-CH1 and d) VL-CH1-linker-VH-CL, are stabilized via the natural disulfide bond between the CL domain and the CH1 domain. In addition, these single chain Fab molecules might be further stabilized by generation of interchain disulfide bonds via insertion of cysteine residues (e.g. position 44 in the variable heavy chain and position 100 in the variable light chain according to Kabat numbering). The term "N-terminus denotes the last amino acid of the N-terminus. The term "C-terminus denotes the last amino acid of the C-terminus.

By "fused" or "connected" is meant that the components (e.g. a Fab molecule and an Fc domain subunit) are linked by peptide bonds, either directly or via one or more peptide linkers.

The term "linker" as used herein refers to a peptide linker and is preferably a peptide with an amino acid sequence with a length of at least 5 amino acids, preferably with a length of 5 to 100, more preferably of 10 to 50 amino acids. In one embodiment said peptide linker is (GxS)n or (GxS)nGm with G=glycine, S=serine, and (x=3, n=3, 4, 5 or 6, and m=0, 1, 2 or 3) or (x=4, n=2, 3, 4 or 5 and m=0, 1, 2 or 3), preferably x=4 and n=2 or 3, more preferably with x=4, n=2. In one embodiment said peptide linker is $(G_4S)_2$.

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The heavy chain of an immunoglobulin may be assigned to one of five types, called α (IgA), δ (IgD), ε (IgE), γ (IgG), or μ (IgM), some of which may be further divided into subtypes, e.g. $\gamma_1$ (IgG$_1$), $\gamma_2$ (IgG$_2$), $\gamma_3$ (IgG$_3$), $\gamma_4$ (IgG$_4$), $\alpha_1$ (IgA$_1$) and $\alpha_2$ (IgA$_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "antigen binding domain" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more antibody variable domains (also called antibody variable regions). Preferably, an antigen binding domain comprises an antibody light chain variable region (VL) and an antibody heavy chain variable region (VH).

The term "chimeric" antibody refers to an antibody in which a portion of the heavy and/or light chain is derived from a particular source or species, while the remainder of the heavy and/or light chain is derived from a different source or species, usually prepared by recombinant DNA techniques. Chimeric antibodies comprising a rabbit variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See e.g. Morrison, S. L., et al., Proc. Natl. Acad. Sci. USA 81 (1984) 6851-6855; U.S. Pat. Nos. 5,202,238 and 5,204,244.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y_{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); antibody-dependent cellular phagocytosis (ADCP), cytokine secretion, immune complex-mediated antigen uptake by antigen presenting cells; down regulation of cell surface receptors (e.g. B cell receptor); and B cell activation.

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or increased association with another peptide Amino acid sequence deletions and insertions include amino- and/or carboxy-terminal deletions and insertions of amino acids. Particular amino acid mutations are amino acid substitutions. For the purpose of altering e.g. the binding characteristics of an Fc region, non-conservative amino acid substitutions, i.e. replacing one amino acid with another amino acid having different structural and/or chemical properties, are particularly preferred Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, $G_{329}$, P329G, or Pro329Gly.

An "effective amount" of an agent, e.g., a pharmaceutical formulation, refers to an amount effective, at dosages and for periods of time necessary, to achieve the desired therapeutic or prophylactic result.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991. A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g. antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3 (L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. As also mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation.)

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "hypervariable region" or "HVR," as used herein refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, "Sequences of Proteins of Immunological Interest" (1983) and by Chothia et al., *J. Mol. Biol.* 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table A as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE A

| CDR Definitions[1] | | | |
|---|---|---|---|
| CDR | Kabat | Chothia | AbM[2] |
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table A is according to the numbering conventions set forth by Kabat et al. (see below).
[2]"AbM" with a lowercase "b" as used in Table A refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding a bispecific antibody that specifically binds HER2" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"No substantial cross-reactivity" means that a molecule (e.g., an antibody) does not recognize or specifically bind an antigen different from the actual target antigen of the molecule (e.g. an antigen closely related to the target antigen), particularly when compared to that target antigen. For example, an antibody may bind less than about 10% to less than about 5% to an antigen different from the actual target antigen, or may bind said antigen different from the actual target antigen at an amount consisting of less than about 10%, 9%, 8% 7%, 6%, 5%, 4%, 3%, 2%, 1%, 0.5%, 0.2%, or 0.1%, preferably less than about 2%, 1%, or 0.5%, and most preferably less than about 0.2% or 0.1% antigen different from the actual target antigen.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term cancer as used herein refers to proliferative diseases, such as lymphomas, lymphocytic leukemias, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "antigen-binding site of an antibody" when used herein refer to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, Md. (1991) and/or those residues from a "hypervariable loop".

Antibody specificity refers to selective recognition of the antibody for a particular epitope of an antigen. Natural antibodies, for example, are monospecific. The term "monospecific" antibody as used herein denotes an antibody that has one or more binding sites each of which bind to the same epitope of the same antigen.

"Bispecific antibodies" according to the invention are antibodies which have two different antigen-binding specificities. Antibodies of the present invention are specific for two different epitopes of HER2, i.e. the extracellular domains II and IV of HER2. The term "bispecific" antibody as used herein denotes an antibody that has at least two binding sites each of which bind to different epitopes of the same antigen.

Bispecific antibodies may also be used to localize cytotoxic agents to cells which express HER2. Bispecific antibodies can be prepared as full length antibodies or antibody fragments.

The term "valent" as used within the current application denotes the presence of a specified number of binding sites in an antibody molecule. As such, the terms "bivalent", "tetravalent", and "hexavalent" denote the presence of two binding sites, four binding sites, and six binding sites, respectively, in an antibody molecule. The bispecific antibodies according to the invention are at least "bivalent" and may be "trivalent" or "multivalent" (e.g. "tetravalent" or "hexavalent").

Antibodies of the present invention have two or more binding sites and are bispecific. That is, the antibodies may be bispecific even in cases where there are more than two binding sites (i.e. that the antibody is trivalent or multivalent). Bispecific antibodies of the invention include, for example, multivalent single chain antibodies, diabodies and triabodies, as well as antibodies having the constant domain structure of full length antibodies to which further antigen-binding sites (e.g., single chain Fv, a VH domain and/or a VL domain, Fab, or (Fab)2) are linked via one or more peptide-linkers. The antibodies can be full length from a single species, or be chimerized or humanized.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

As used herein, the expressions "cell", "cell line", and "cell culture" are used interchangeably and all such designations include progeny. Thus, the words "transfectants" and "transfected cells" include the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

As used herein, the term "binding" or "specifically binding" refers to the binding of the antibody to an epitope of the antigen in an in-vitro assay, preferably in a surface plasmon resonance assay (SPR, BIAcore, GE-Healthcare Uppsala, Sweden). The affinity of the binding is defined by the terms ka (rate constant for the association of the antibody from the antibody/antigen complex), kD (dissociation constant), and KD (kD/ka). Binding or specifically binding means a binding affinity (KD) of 10-8 mol/1 or less, preferably 10-9 M to 10-13 mol/1.

Binding of the antibody to the death receptor can be investigated by a BIAcore assay (GE-Healthcare Uppsala, Sweden). The affinity of the binding is defined by the terms ka (rate constant for the association of the antibody from the antibody/antigen complex), kD (dissociation constant), and KD (kD/ka)

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

As used herein, the terms "engineer, engineered, engineering," particularly with the prefix "glyco-," as well as the term "glycosylation engineering" are considered to include any manipulation of the glycosylation pattern of a naturally occurring or recombinant polypeptide or fragment thereof. Glycosylation engineering includes metabolic engineering of the glycosylation machinery of a cell, including genetic manipulations of the oligosaccharide synthesis pathways to achieve altered glycosylation of glycoproteins expressed in cells. Furthermore, glycosylation engineering includes the effects of mutations and cell environment on glycosylation. In one embodiment, the glycosylation engineering is an alteration in glycosyltransferase activity. In a particular embodiment, the engineering results in altered glucosaminyltransferase activity and/or fucosyltransferase activity.

II. Compositions and Methods

In one aspect, the invention is based on bispecific antibodies specifically binding to HER2. Antibodies of the invention are useful, e.g., for the treatment or diagnosis of cancer.

A. Exemplary Bispecific Antibodies Specifically Binding to HER2 with a Common Light Chain In one aspect of the invention, a bispecific antibody specifically binding to HER2 is provided, wherein the antibody comprises a first binding moiety that specifically binds the extracellular domain II of HER2 and a second binding moiety that specifically binds the extracellular domain IV of HER2. The inventors of the present invention surprisingly generated a monovalent bispecific antibody wherein both binding moieties share a common light chain that retains the efficacy of the parent monospecific antibodies in terms of inhibition of tumor cell proliferation and has an increased affinity to the extracellular domain II of HER2. The generation of a bispecific molecule with a common light chain that retains the binding properties of both of the parent antibodies is not straight-forward as the common CDRs of the hybrid light chain have to retain the binding specifity for both the extracellular domains II and IV of HER2. The use of this so-called 'common light chain' principle, i.e. combining two binders that share one light chain but still have separate specificities, prevents light chain mispairing and in this particular case retains the epitope specificity of the parental antibodies. As a consequence, there are less side products during production, facilitating the homogenous preparation of HER2 bispecific antigen binding molecules at high yields. The heavy chain of Pertuzumab was further optimized, resulting in a more potent molecule in terms of affinity to the extracellular domain II of HER2. In addition, the Trastuzumab heavy chain has been stabilized by introducing certain mutations into the CDRs. The resulting molecule is superior to the parent Pertuzumab and Trastuzumab monospecific antibodies. The bispecific HER2 antibodies in the monovalent common light chain format have an increased affinity to the pertuzumab epitope, and show superior inhibitory effects on cell proliferation as compared to the combination of the parental antibodies.

In one embodiment a bispecific antibody is provided, comprising a first Fab molecule capable of specific binding to extracellular domain II of HER2 and a second Fab molecule capable of specific binding to extracellular domain IV of HER2, wherein the sequence of the variable light chain of the first Fab molecule is identical to the sequence of the variable light chain of the second Fab molecule (i.e. the first and the second Fab molecule comprise a common light chain).

In one embodiment, the invention provides a bispecific antibody that specifically binds to extracellular domains II and IV of HER2 comprising
a first heavy chain comprising
(a) a heavy chain CDR1 of SEQ ID NO: 55;
(b) a heavy chain CDR2 of SEQ ID NO: 77;
(c) a heavy chain CDR3 of SEQ ID NO: 56;

and a second heavy chain comprising
(a) a heavy chain CDR1 of SEQ ID NO: 20;
(b) a heavy chain CDR2 of SEQ ID NO: 29;
(c) a heavy chain CDR3 of SEQ ID NO: 30;
and a first and a second light chain comprising
(a) a light chain CDR1 of SEQ ID NO: 89;
(b) a light chain CDR2 of SEQ ID NO: 90;
(c) a light chain CDR3 of SEQ ID NO: 19.

In one embodiment, the invention provides a bispecific antibody that specifically binds to extracellular domains II and IV of HER2 comprising
a first heavy chain comprising
(a) a heavy chain CDR1 of SEQ ID NO: 14;
(b) a heavy chain CDR2 of SEQ ID NO: 60;
(c) a heavy chain CDR3 of SEQ ID NO: 16;
and a second heavy chain comprising
(a) a heavy chain CDR1 of SEQ ID NO: 20;
(b) a heavy chain CDR2 of SEQ ID NO: 29;
(c) a heavy chain CDR3 of SEQ ID NO: 30;
and a first and a second light chain comprising
(a) a light chain CDR1 of SEQ ID NO: 89;
(b) a light chain CDR2 of SEQ ID NO: 90;
(c) a light chain CDR3 of SEQ ID NO: 19.

In one embodiment, the invention provides a bispecific antibody that specifically binds to extracellular domains II and IV of HER2 comprising
a first heavy chain comprising
(a) a heavy chain CDR1 of SEQ ID NO: 58;
(b) a heavy chain CDR2 of SEQ ID NO: 15;
(c) a heavy chain CDR3 of SEQ ID NO: 59;
and a second heavy chain comprising
(a) a heavy chain CDR1 of SEQ ID NO: 20;
(b) a heavy chain CDR2 of SEQ ID NO: 29;
(c) a heavy chain CDR3 of SEQ ID NO: 30;
and a first and a second light chain comprising
(a) a light chain CDR1 of SEQ ID NO: 89;
(b) a light chain CDR2 of SEQ ID NO: 90;
(c) a light chain CDR3 of SEQ ID NO: 19.

In one embodiment the second heavy chain of any of the embodiments above bears at least one modification in the amino acid sequence that confers higher chemical stability to the CDR, resulting in retained binding to HER2 under stress conditions. Modifications useful herein are e.g. D98E, D98N, D98T, G99A or G99S. Surprisingly the inventors found that some modifications of the CDRs did not only improve the stability of the molecule but also improved the binding affinity to HER2.

Hence in one embodiment, the invention provides a bispecific antibody that specifically binds to extracellular domains II and IV of HER2 comprising
a first heavy chain comprising
(a) a heavy chain CDR1 of SEQ ID NO: 55;
(b) a heavy chain CDR2 of SEQ ID NO: 77;
(c) a heavy chain CDR3 of SEQ ID NO: 56;
and a second heavy chain comprising
(a) a heavy chain CDR1 of SEQ ID NO: 20;
(b) a heavy chain CDR2 of SEQ ID NO: 29;
(c) a heavy chain CDR3 of SEQ ID NO: 79;
and a first and a second light chain comprising
(a) a light chain CDR1 of SEQ ID NO: 89;
(b) a light chain CDR2 of SEQ ID NO: 90;
(c) a light chain CDR3 of SEQ ID NO: 19.

In one embodiment, the invention provides a bispecific antibody that specifically binds to extracellular domains II and IV of HER2 comprising
a first heavy chain comprising
(a) a heavy chain CDR1 of SEQ ID NO: 14;
(b) a heavy chain CDR2 of SEQ ID NO: 60;
(c) a heavy chain CDR3 of SEQ ID NO: 16;
and a second heavy chain comprising
(a) a heavy chain CDR1 of SEQ ID NO: 20;
(b) a heavy chain CDR2 of SEQ ID NO: 29;
(c) a heavy chain CDR3 of SEQ ID NO: 79;
and a first and a second light chain comprising
(a) a light chain CDR1 of SEQ ID NO: 89;
(b) a light chain CDR2 of SEQ ID NO: 90;
(c) a light chain CDR3 of SEQ ID NO: 19.

In one embodiment, the invention provides a bispecific antibody that specifically binds to extracellular domains II and IV of HER2 comprising
a first heavy chain comprising
(a) a heavy chain CDR1 of SEQ ID NO: 58;
(b) a heavy chain CDR2 of SEQ ID NO: 15;
(c) a heavy chain CDR3 of SEQ ID NO: 59;
and a second heavy chain comprising
(a) a heavy chain CDR1 of SEQ ID NO: 20;
(b) a heavy chain CDR2 of SEQ ID NO: 29;
(c) a heavy chain CDR3 of SEQ ID NO: 79;
and a first and a second light chain comprising
(a) a light chain CDR1 of SEQ ID NO: 89;
(b) a light chain CDR2 of SEQ ID NO: 90;
(c) a light chain CDR3 of SEQ ID NO: 19.

In one embodiment, the bispecific antibody comprises two variable light chains comprising an amino acid sequence of SEQ ID NO 54 (i.e. a common light chain), a first heavy chain comprising a variable heavy chain comprising an amino acid sequence of SEQ ID NO: 64, and a second heavy chain comprising a variable heavy chain comprising an amino acid sequence of SEQ ID NO 92.

In one embodiment, the bispecific antibody comprises two variable light chains comprising an amino acid sequence of SEQ ID NO 54 (i.e. a common light chain), a first heavy chain comprising a variable heavy chain comprising an amino acid sequence of SEQ ID NO: 70, and a second heavy chain comprising a variable heavy chain comprising an amino acid sequence of SEQ ID NO 92.

In one embodiment, the bispecific antibody comprises two variable light chains comprising an amino acid sequence of SEQ ID NO 54 (i.e. a common light chain), a first heavy chain comprising a variable heavy chain comprising an amino acid sequence of SEQ ID NO: 68, and a second heavy chain comprising a variable heavy chain comprising an amino acid sequence of SEQ ID NO: 92.

In one embodiment the second heavy chain of any of the embodiments above bears at least one modification in the amino acid sequence that confers stability to the CDRs and the binding to the target, e.g. D98E, D98N, D98T, G99A or G99S.

Hence in one embodiment, the bispecific antibody comprises two variable light chains comprising an amino acid sequence of SEQ ID NO: 54 (i.e. a common light chain), a first heavy chain comprising a variable heavy chain comprising an amino acid sequence of SEQ ID NO: 64, and a second heavy chain comprising a variable heavy chain comprising an amino acid sequence of SEQ ID NO: 117.

In one embodiment, the bispecific antibody comprises two variable light chains comprising an amino acid sequence of SEQ ID NO:54 (i.e. a common light chain), a first heavy chain comprising a variable heavy chain comprising an amino acid sequence of SEQ ID NO: 70, and a second heavy chain comprising a variable heavy chain comprising an amino acid sequence of SEQ ID NO: 117.

In one embodiment, the bispecific antibody comprises two variable light chains comprising an amino acid sequence of SEQ ID NO:54 (i.e. a common light chain), a first heavy chain comprising a variable heavy chain comprising an amino acid sequence of SEQ ID NO: 68, and a second heavy chain comprising a variable heavy chain comprising an amino acid sequence of SEQ ID NO: 117.

In one embodiment, the bispecific antibody of the invention comprises a first heavy chain constant region comprising the amino acid sequence of SEQ ID NO: 114.

In one embodiment, the bispecific antibody of the invention comprises a second heavy chain constant region comprising the amino acid sequence of SEQ ID NO: 115.

In another embodiment the bispecific antibody of the invention comprises a first light chain constant region comprising the amino acid sequence of SEQ ID NO: 113.

In another embodiment the bispecific antibody of the invention comprises a second light chain constant region comprising the amino acid sequence of SEQ ID NO: 116.

In one embodiment a bispecific antibody is provided comprising SEQ ID NOs: 54, 113, 64, 114, 82, 116, 92 and 115.

In one embodiment a bispecific antibody is provided comprising SEQ ID NOs: 54, 113, 64, 114, 82, 116, 96 and 115.

In one embodiment the bispecific antibody of any of the above embodiments is glycoengineered, as outlined in section F below. In one embodiment the bispecific antibody of any of the above embodiments comprises a Fc domain modification that promotes heterodimerization as outlined in section D below.

B. Exemplary HER2 Bispecific Antibodies Comprising a Crossover Fab Fragment

In one embodiment of the invention, a bispecific antibody specifically binding to HER2 is provided, wherein the antibody comprises a first binding moiety that specifically binds to the extracellular domain II of HER2 and a second binding moiety that specifically binds to the extracellular domain IV of HER2. The inventors of the present invention generated a second monovalent bispecific antibody format wherein one of the binding moieties is a crossover Fab fragment. In one aspect of the invention a monovalent bispecific antibody is provided, wherein one of the Fab fragments of an IgG molecule is replaced by a crossover Fab fragment. Crossover Fab fragments are Fab fragments wherein either the variable regions or the constant regions of the heavy and light chain are exchanged. Bispecific antibody formats comprising crossover Fab fragments have been described, for example, in WO2009080252, WO2009080253, WO2009080251, WO2009080254, WO2010/136172, WO2010/145792 and WO2013/026831. The native Trastuzumab sequence has been optimized by introducing modifications into the CDRs of both the variable heavy chain and the variable light chain to improve stability and affinity, the resulting sequences framework-grafted to avoid mispairing of the light chains in the bispecific molecule, and the bispecific antibody glycoengineered, resulting in highly potent bispecific antibodies that target HER2 that can be produced with high yield and only low percentage of side products. In addition it shows superior inhibition of tumor cell proliferation as compared to the combination of the respective parentnal antibodies.

In one embodiment, the invention provides a bispecific antibody specifically binding to HER2 comprising
a first antigen binding site specific for extracellular domain II of HER2, comprising
(a) a heavy chain CDR1 of SEQ ID NO: 14;
(b) a heavy chain CDR2 of SEQ ID NO: 15;
(c) a heavy chain CDR3 of SEQ ID NO: 16;
(d) a light chain CDR1 of SEQ ID NO: 11;
(e) a light chain CDR2 of SEQ ID NO: 12;
(f) a light chain CDR3 of SEQ ID NO: 13;
And a second antigen binding site specific for extracellular domain IV of HER2 comprising
(a) a heavy chain CDR1 of SEQ ID NO: 20;
(b) a heavy chain CDR2 of SEQ ID NO: 108;
(c) a heavy chain CDR3 of SEQ ID NO: 79;
(d) a light chain CDR1 of SEQ ID NO: 107;
(e) a light chain CDR2 of SEQ ID NO: 18;
(f) a light chain CDR3 of SEQ ID NO: 19;

In one embodiment, the bispecific antibody comprises a first antigen binding site specific for the extracellular domain II of HER2 comprising a variable heavy chain comprising an amino acid sequence of SEQ ID NO: 22 and a variable light chain comprising an amino acid sequence of SEQ ID NO: 24; and a second antigen binding site specific for the extracellular domain IV of HER2, comprising a heavy chain variable region comprising an amino acid sequence of SEQ ID NO: 105 and a light chain variable region comprising an amino acid sequence of SEQ ID NO: 106.

In one embodiment, the invention provides a bispecific antibody that specifically binds to HER2 comprising
a first antigen binding site specific for extracellular domain II of HER2 comprising
(a) a heavy chain CDR1 of SEQ ID NO: 14;
(b) a heavy chain CDR2 of SEQ ID NO: 15;
(c) a heavy chain CDR3 of SEQ ID NO: 16;
(d) a light chain CDR1 of SEQ ID NO: 11;
(e) a light chain CDR2 of SEQ ID NO: 12;
(f) a light chain CDR3 of SEQ ID NO: 13.
and a second antigen binding site specific for extracellular domain IV of HER2, comprising
(a) a heavy chain CDR1 of SEQ ID NO: 20;
(b) a heavy chain CDR2 of SEQ ID NO: 29;
(c) a heavy chain CDR3 of SEQ ID NO: 79;
(d) a light chain CDR1 of SEQ ID NO: 104;
(e) a light chain CDR2 of SEQ ID NO: 18;
(f) a light chain CDR3 of SEQ ID NO: 19.

In one embodiment, the bispecific antibody comprises a first antigen binding site specific for the extracellular domain II of HER2 comprising a variable heavy chain comprising an amino acid sequence of SEQ ID NO: 22 and a variable light chain comprising an amino acid sequence of SEQ ID NO: 24; and a second antigen binding site specific for the extracellular domain IV of HER2, comprising a heavy chain variable region comprising an amino acid sequence of SEQ ID NO: 117 and a light chain variable region comprising an amino acid sequence of SEQ ID NO: 118.

In one embodiment, the invention provides a bispecific antibody that specifically binds to HER2 comprising
a first antigen binding site specific for extracellular domain II of HER2 comprising
(a) a heavy chain CDR1 of SEQ ID NO: 14;
(b) a heavy chain CDR2 of SEQ ID NO: 15;
(c) a heavy chain CDR3 of SEQ ID NO: 16;
(d) a light chain CDR1 of SEQ ID NO: 11;

(e) a light chain CDR2 of SEQ ID NO: 12;
(f) a light chain CDR3 of SEQ ID NO: 13.
and a second antigen binding site specific for extracellular domain IV of HER2, comprising
(a) a heavy chain CDR1 of SEQ ID NO: 20;
(b) a heavy chain CDR2 of SEQ ID NO: 29;
(c) a heavy chain CDR3 selected from the group consisting of SEQ ID NO: 79, SEQ ID NO: 78, SEQ ID NO: 80, SEQ ID NO: 87, SEQ ID NO: 88;
(d) a light chain CDR1 selected from the group consisting of SEQ ID NO: 104, SEQ ID NO: 103 and SEQ ID NO: 158;
(e) a light chain CDR2 of SEQ ID NO: 18;
(f) a light chain CDR3 of SEQ ID NO: 19;

In one embodiment, the bispecific antibody of the invention comprises a first heavy chain constant region comprising the amino acid sequence of SEQ ID NO: 114.

In one embodiment, the bispecific antibody of the invention comprises a first heavy chain constant region comprising the amino acid sequence of SEQ ID NO: 114, wherein the C-terminal Lysine has been removed.

In one embodiment, the bispecific antibody of the invention comprises a second heavy chain constant region comprising the amino acid sequence of SEQ ID NO: 115.

In one embodiment, the bispecific antibody of the invention comprises a second heavy chain constant region comprising the amino acid sequence of SEQ ID NO: 115, wherein the C-terminal Lysine has been removed.

In another embodiment the bispecific antibody of the invention comprises a first light chain constant region comprising the amino acid sequence of SEQ ID NO: 113.

In another embodiment the bispecific antibody of the invention comprises a second light chain constant region comprising the amino acid sequence of SEQ ID NO: 116.

In one embodiment a bispecific antibody is provided comprising SEQ ID NOs: 109, 110, 111 and 112.

In one embodiment a bispecific antibody that specifically binds to HER2 according to any of the above embodiments comprises
an Fc domain,
one Fab fragment comprising a first antigen binding site specific for the extracellular domain II of HER2,
and one Fab fragment comprising a second antigen binding site specific for the extracellular domain IV of HER2, wherein either the variable regions or the constant regions of the heavy and light chain of at least one Fab fragment are exchanged.

Figure 10A:
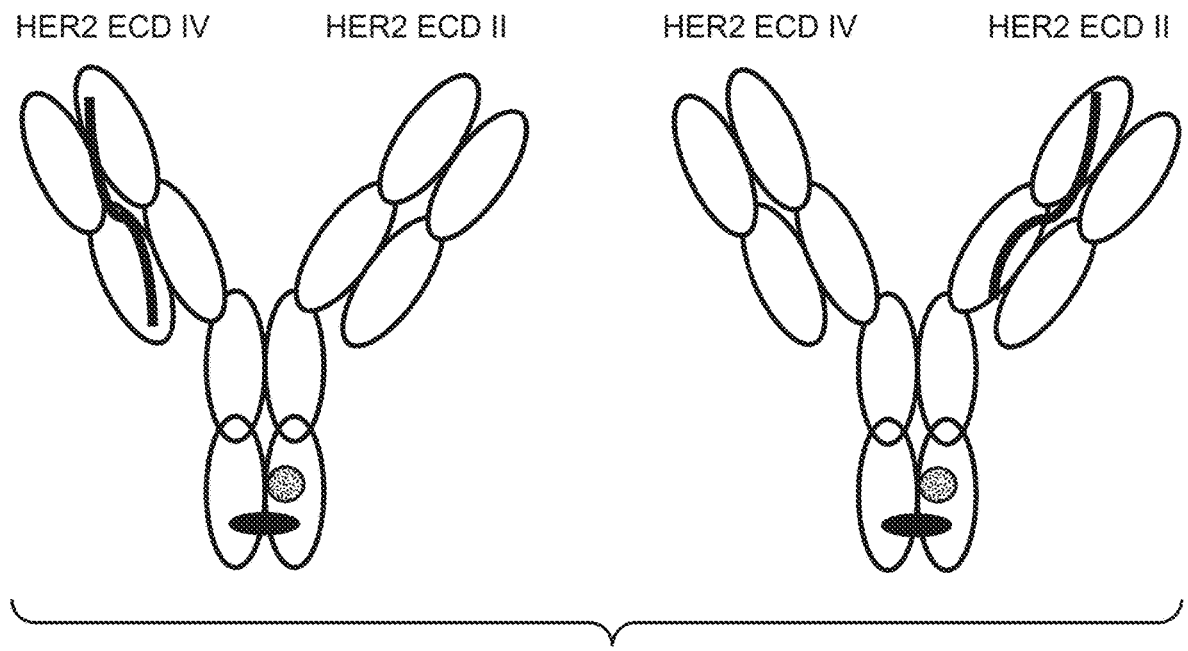
FIGS. 10A and 10B: Schematic drawing of Trastuzumab and Pertuzumab bispecific antibodies in a 1+1 format. (10A): single chain Fab (scFab) based molecules (10B): cross-over Fab (xFab) based molecules.
Figure 10B:
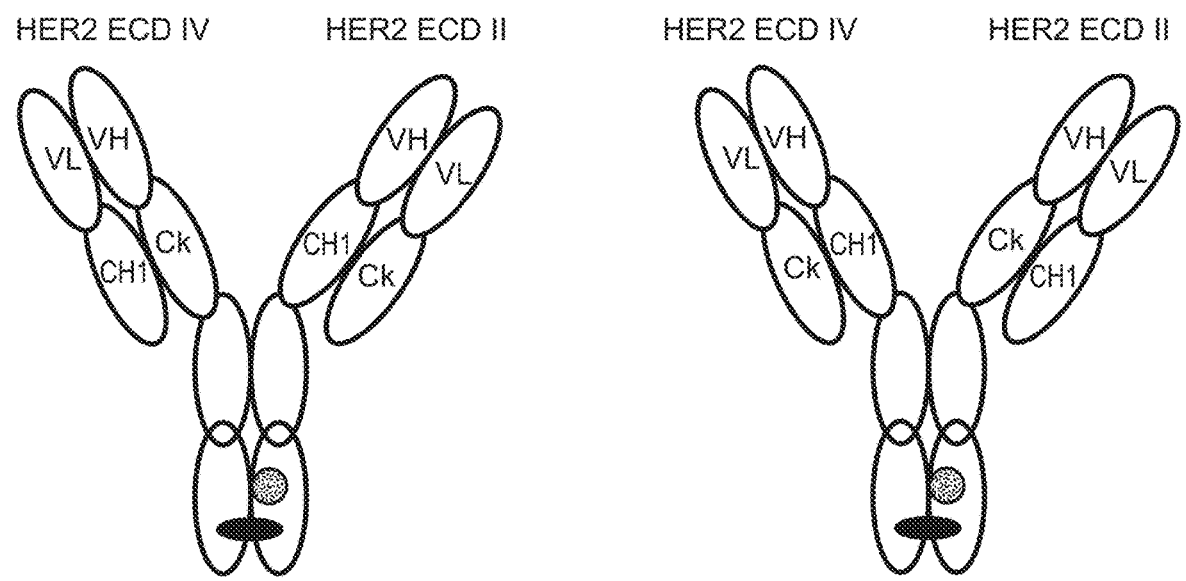

Since the above bispecific antibody is bivalent with one binding site for the extracellular domain II of HER2 and one binding site for the extracellular domain IV of HER2, this format is also referred to as "1+1" format. Hence the bispecific antibodies described in this section are monovalent for the extracellular domain II of HER2 and monovalent for the extracellular domain IV of HER2. An exemplary structure of a bispecific antibody with a 1+1 format is depicted in FIGS. 10A and 10B. Due to the exchange of either the variable regions or the constant regions, the Fab fragment above is also referred to as "cross-Fab fragment" or "xFab fragment" or "crossover Fab fragment". The IgG molecule in a 1+1 format is also referred to as Crossmab format (see Schaefer et al. Proc Natl Acad Sci USA 2011; 108:11187-92).

In one embodiment a bispecific antibody that specifically binds to HER2 according to any of the above embodiments comprises
an Fc domain,
one Fab fragment comprising an antigen binding site specific for the extracellular domain II of HER2, wherein either the variable regions or the constant regions of the heavy and light chain are exchanged.
and one Fab fragment comprising an antigen binding site specific for the extracellular domain IV of HER2.

In one embodiment a bispecific antibody that specifically binds to HER2 according to any of the above embodiments comprises
an Fc domain,
one Fab fragment comprising an antigen binding site specific for the extracellular domain II of HER2,
and one Fab fragment comprising an antigen binding site specific for the extracellular domain IV of HER2, wherein either the variable regions or the constant regions of the heavy and light chain are exchanged.

In one embodiment a bispecific antibody that specifically binds to HER2 according to any of the above embodiments comprises
an Fc domain,
one Fab fragment comprising an antigen binding site specific for the extracellular domain II of HER2,
and one Fab fragment comprising an antigen binding site specific for the extracellular domain IV of HER2, wherein the variable regions of the heavy and light chain of the Fab fragment are exchanged.

In one embodiment a bispecific antibody that specifically binds to HER2 according to any of the above embodiments comprises
an Fc domain,
one Fab fragments comprising an antigen binding site specific for the extracellular domain II of HER2,
and one Fab fragment comprising an antigen binding site specific for the extracellular domain IV of HER2, wherein the constant regions of the heavy and light chain are exchanged.

In one embodiment said bispecific antibody that specifically binds to HER2 according to any of the above embodiments comprises an Fc domain to which two Fab fragments are fused to the N-terminus, wherein either the variable regions or the constant regions of the heavy and light chain of at least one Fab fragment are exchanged. In one embodiment the two Fab fragments are fused to the N-terminus of the Fc domain through an immunoglobulin hinge region. In one embodiment, the immunoglobulin hinge region is a human IgG1 hinge region. In one embodiment the Fab fragment comprising an antigen binding site specific for the extracellular domain II of HER2, the Fab fragment comprising an antigen binding site specific for the extracellular domain IV of HER2 and the Fc domain are part of an immunoglobulin molecule. In a particular embodiment the immunoglobulin molecule is an IgG class immunoglobulin. In an even more particular embodiment the immunoglobulin is an IgG1 subclass immunoglobulin. In another embodiment the immunoglobulin is an IgG4 subclass immunoglobulin. In a further particular embodiment the immunoglobulin is a human immunoglobulin. In other embodiments the immunoglobulin is a chimeric immunoglobulin or a humanized immunoglobulin.

In one embodiment a bispecific antibody that specifically binds to HER2 according to any of the above embodiments comprises an Immunoglobulin G (IgG) molecule with one binding site specific for the extracellular domain II of HER2 and one binding site specific for the extracellular domain IV of HER2, wherein either the variable regions or the constant regions of the heavy and light chain of one arm (Fab fragment) of the IgG molecule are exchanged.

In one embodiment a bispecific antibody that specifically binds to HER2 according to any of the above embodiments comprises an Immunoglobulin G (IgG) molecule with one binding site specific for the extracellular domain II of HER2 and one binding site specific for the extracellular domain IV of HER2, wherein the variable regions of the heavy and light chain of one arm (Fab fragment) of the IgG molecule are exchanged. This antibody format is also referred to as CrossMab$_{(VHVL)}$.

In one embodiment the variable regions of the heavy and light chain of the one arm (Fab fragment) of the IgG molecule which comprises the binding site specific for the extracellular domain IV of HER2 are exchanged.

In one embodiment a bispecific antibody that specifically binds to HER2 according to any of the above embodiments comprises an Immunoglobulin G (IgG) molecule with one binding site specific for the extracellular domain II of HER2 and one binding site specific for the extracellular domain IV of HER2, wherein the constant regions of the heavy and light chain of one arm (Fab fragment) of the IgG molecule are exchanged. This antibody format is also referred to as CrossMab$_{(CH1CL)}$.

In one embodiment the constant regions of the heavy and light chain of the one arm (Fab fragment) of the IgG molecule which comprises the binding site specific for the extracellular domain IV of HER2 are exchanged.

In one embodiment a bispecific antibody that specifically binds to HER2 according to any of the above embodiments comprises an Immunoglobulin G (IgG) molecule with one binding site specific for the extracellular domain II of HER2 and one binding site specific for the extracellular domain IV of HER2, wherein the complete VH-CH1 and VL-CL domains of one arm (Fab fragment) of the IgG molecule are exchanged. This means that at least one of the Fab fragments is fused to the N-terminus of the Fc domain via the light chain (VLCL). In one embodiment the other Fab fragment is fused to the the N-terminus of the Fc domain via the heavy chain (VHCH1).

This antibody format is also referred to as CrossMab$_{Fab}$. In one embodiment both Fab fragments are are fused to the N-terminus of the Fc domain through an immunoglobulin hinge region.

In one embodiment the bispecific antibody of any of the above embodiments is glycoengineered, as outlined in section F below. In one embodiment the bispecific antibody of any of the above embodiments comprises a Fc domain modification that promotes heterodimerization as outlined in section D below.

C. Fc Domain Modifications Promoting Heterodimerization

The bispecific HER2 antibodies of the invention comprise different antigen binding moieties, fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of the bispecific antibodies of the invention in recombinant production, it will thus be advantageous to introduce in the Fc domain of the bispecific antibodies of the invention a modification promoting the association of the desired polypeptides.

Accordingly, in particular embodiments the Fc domain of the bispecific antibodies of the invention comprises a modification promoting the association of the first and the second subunit of the Fc domain. The site of most extensive protein-protein interaction between the two subunits of a human IgG Fc domain is in the CH3 domain of the Fc domain. Thus, in one embodiment said modification is in the CH3 domain of the Fc domain.

In a specific embodiment said modification is a so-called "knob-into-hole" modification, comprising a "knob" modification in one of the two subunits of the Fc domain and a "hole" modification in the other one of the two subunits of the Fc domain.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a particular embodiment, in the CH3 domain of the first subunit of the Fc domain of the bispecific antibodies of the invention an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

The protuberance and cavity can be made by altering the nucleic acid encoding the polypeptides, e.g. by site-specific mutagenesis, or by peptide synthesis.

In a specific embodiment, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). In one embodiment, in the second subunit of the Fc domain additionally the threonine residue at position 366 is replaced with a serine residue (T366S) and the leucine residue at position 368 is replaced with an alanine residue (L368A).

In yet a further embodiment, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). Introduction of these two cysteine residues results in formation of a disulfide bridge between the two subunits of the Fc domain, further stabilizing the dimer (Carter, J Immunol Methods 248, 7-15 (2001)).

In an alternative embodiment a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

In one embodiment a bispecific antibody that specifically binds to HER2 according to any of the above embodiments comprises an Immunoglobulin G (IgG) molecule comprising a first antigen binding site specific for extracellular domain II of HER2 and a second antigen binding site specific for extracellular domain IV of HER2, wherein the Fc part of the first heavy chain comprises a first dimerization module and the Fc part of the second heavy chain comprises a second dimerization module allowing a heterodimerization of the two heavy chains of the IgG molecule.

In a further preferred embodiment, the first dimerization module comprises knobs and the second dimerization module comprises holes according to the knobs into holes strategy (see Carter P.; Ridgway J. B. B.; Presta L G Immunotechnology, Volume 2, Number 1, February 1996, pp. 73-73(1)).

D. Nucleic Acid Sequences, Vectors and Methods of

The invention further provides isolated polynucleotides encoding a bispecific antibody specifically binding to HER2 as described herein or a fragment thereof. The polynucleotides encoding bispecific antibodies of the invention may be expressed as a single polynucleotide that encodes the entire bispecific antigen binding molecule or as multiple (e.g., two or more) polynucleotides that are co-expressed. Polypeptides encoded by polynucleotides that are co-expressed may associate through, e.g., disulfide bonds or other means to form a functional bispecific antibody. For example, the light chain portion of a Fab fragment may be encoded by a separate polynucleotide from the portion of the bispecific antibody comprising the heavy chain portion of the Fab fragment, an Fc domain subunit and optionally (part of) another Fab fragment. When co-expressed, the heavy chain polypeptides will associate with the light chain polypeptides to form the Fab fragment. In another example, the portion of the bispecific antibody provided therein comprising one of the two Fc domain subunits and optionally (part of) one or more Fab fragments could be encoded by a separate polynucleotide from the portion of the bispecific antibody provided therein comprising the other of the two Fc domain subunits and optionally (part of) a Fab fragment. When co-expressed, the Fc domain subunits will associate to form the Fc domain.

In one embodiment, the present invention is directed to an isolated polynucleotide encoding a bispecific antibody of the invention or a fragment thereof, wherein the polynucleotide comprises a sequence that encodes a first variable heavy chain sequence as shown in SEQ ID NOs 63, 67 and 69. In one embodiment, the present invention is directed to an isolated polynucleotide encoding a bispecific antibody of the invention or a fragment thereof, wherein the polynucleotide comprises a sequence that encodes a second variable heavy chain sequence as shown in SEQ ID NOs 91 and 133.

In one embodiment, the present invention is directed to an isolated polynucleotide encoding a bispecific antibody of the invention or a fragment thereof, wherein the polynucleotide comprises a sequence that encodes a variable light chain sequence as shown in SEQ ID NO: 53.

In another embodiment, the present invention is directed to an isolated polynucleotide encoding a bispecific antibody or fragment thereof, wherein the polynucleotide comprises a sequence that encodes a polypeptide sequence as shown in SEQ ID NOs 83, 85, 91, 93, 95, 97, 99, 101, 63, 67, 69, 53, 21 and 23.

In another embodiment, the invention is directed to an isolated polynucleotide encoding a bispecific antibody of the invention or a fragment thereof, wherein the polynucleotide comprises a sequence that encodes a first variable heavy chain sequence that is at least about 80%, 85%, 90%, 95%, 96%, 97%, 98%, or 99% identical to an amino acid sequence in SEQ ID NOs 63, 67 and 69.

In another embodiment, the invention is directed to an isolated polynucleotide encoding a bispecific antibody of the invention or a fragment thereof, wherein the polynucleotide comprises a sequence that encodes a second variable heavy chain sequence that is at least about 80%, 85%, 90%, 95%, 96%, 97%, 98%, or 99% identical to an amino acid sequence in SEQ ID NOs 91 and 133.

In another embodiment, the invention is directed to an isolated polynucleotide encoding a bispecific antibody of the invention or a fragment thereof, wherein the polynucleotide comprises a sequence that encodes a variable light chain sequence that is at least about 80%, 85%, 90%, 95%, 96%, 97%, 98%, or 99% identical to an amino acid sequence in SEQ ID NO: 53.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

In further objects the present invention relates to an expression vector comprising a nucleic acid sequence of the present invention and to a prokaryotic or eukaryotic host cell comprising a vector of the present invention. In addition a method of producing an antibody comprising culturing the host cell so that the antibody is produced is provided.

E. Fc Domain Modifications Reducing Fc Receptor Binding and/or Effector Function In one aspect a bispecific antibody that specifically binds to HER2 according to any of the above embodiments comprises an Immunoglobulin G (IgG) molecule wherein the Fc part is modified. The modified Fc part has a reduced binding affinity for the Fcγ receptors compared to a wildtype Fc part.

The Fc domain of the bispecific antibodies of the invention consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other.

In one embodiment according the invention the Fc domain of the bispecific antibodies of the invention is an IgG Fc domain. In a particular embodiment the Fc domain is an IgG$_1$ Fc domain. In another embodiment the Fc domain is an IgG$_4$ Fc domain. In a more specific embodiment, the Fc domain is an IgG$_4$ Fc domain comprising an amino acid substitution at position S228 (Kabat numbering), particularly the amino acid substitution S228P. In a more specific embodiment, the Fc domain is an IgG4 Fc domain comprising amino acid substitutions L235E and S228P and P329G. This amino acid substitution reduces in vivo Fab arm exchange of IgG$_4$ antibodies (see Stubenrauch et al., Drug Metabolism and Disposition 38, 84-91 (2010)). In a further particular embodiment the Fc domain is human.

The Fc domain confers favorable pharmacokinetic properties to the bispecific antibodies of the invention, including a long serum half-life which contributes to good accumulation in the target tissue and a favorable tissue-blood distribution ratio. At the same time it may, however, lead to undesirable targeting of the bispecific antibodies of the invention to cells expressing Fc receptors rather than to the preferred antigen-bearing cells. Accordingly, in particular embodiments the Fc domain of the the bispecific antibodies of the invention exhibits reduced binding affinity to an Fc receptor and/or reduced effector function, as compared to a native IgG$_1$ Fc domain. In one such embodiment the Fc domain (or the bispecific antibodies of the invention comprising said Fc domain) exhibits less than 50%, preferably less than 20%, more preferably less than 10% and most preferably less than 5% of the binding affinity to an Fc receptor, as compared to a native $IgG_1$ Fc domain (or a bispecific antibodies of the invention comprising a native $IgG_1$ Fc domain), and/or less than 50%, preferably less than 20%, more preferably less than 10% and most preferably less than 5% of the effector function, as compared to a native $IgG_1$ Fc domain domain (or a bispecific antibodies of the invention comprising a native $IgG_1$ Fc domain). In one embodiment, the Fc domain (or the bispecific antibodies of the invention comprising said Fc domain) does not substantially bind to an Fc receptor and/or induce effector function. In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the Fc receptor is an inhibitory Fc receptor. In a specific embodiment the Fc receptor is an inhibitory human Fcγ receptor, more specifically human FcgRIIB. In one embodiment the effector function is one or more of CDC, ADCC, ADCP, and cytokine secretion. In a particular embodiment the effector function is ADCC. In one embodiment the Fc domain domain exhibits substantially similar binding affinity to neonatal Fc receptor (FcRn), as compared to a native $IgG_1$ Fc domain domain. Substantially similar binding to FcRn is achieved when the Fc domain (or the bispecific antibodies of the invention comprising said Fc domain) exhibits greater than about 70%, particularly greater than about 80%, more particularly greater than about 90% of the binding affinity of a native $IgG_1$ Fc domain (or the bispecific antibodies of the invention comprising a native $IgG_1$ Fc domain) to FcRn.

In certain embodiments the Fc domain is engineered to have reduced binding affinity to an Fc receptor and/or reduced effector function, as compared to a non-engineered Fc domain. In particular embodiments, the Fc domain of the bispecific antibodies of the invention comprises one or more amino acid mutation that reduces the binding affinity of the Fc domain to an Fc receptor and/or effector function. Typically, the same one or more amino acid mutation is present in each of the two subunits of the Fc domain. In one embodiment the amino acid mutation reduces the binding affinity of the Fc domain to an Fc receptor. In one embodiment the amino acid mutation reduces the binding affinity of the Fc domain to an Fc receptor by at least 2-fold, at least 5-fold, or at least 10-fold. In embodiments where there is more than one amino acid mutation that reduces the binding affinity of the Fc domain to the Fc receptor, the combination of these amino acid mutations may reduce the binding affinity of the Fc domain to an Fc receptor by at least 10-fold, at least 20-fold, or even at least 50-fold. In one embodiment the bispecific antibodies of the invention comprising an engineered Fc domain exhibits less than 20%, particularly less than 10%, more particularly less than 5% of the binding affinity to an Fc receptor as compared to a bispecific antibodies of the invention comprising a non-engineered Fc domain. In a particular embodiment the Fc receptor is an Fcγ receptor. In some embodiments the Fc receptor is a human Fc receptor. In one embodiment the Fc receptor is an inhibitory Fc receptor. In a specific embodiment the Fc receptor is an inhibitory human Fcγ receptor, more specifically human FcgRIIB. In some embodiments the Fc receptor is an activating Fc receptor. In a specific embodiment the Fc receptor is an activating human Fcγ receptor, more specifically human FcγRIIIa, FcγRI or FcγRIIa, most specifically human FcγRIIIa. Preferably, binding to each of these receptors is reduced. In some embodiments binding affinity to a complement component, specifically binding affinity to C1q, is also reduced. In one embodiment binding affinity to neonatal Fc receptor (FcRn) is not reduced. Substantially similar binding to FcRn, i.e. preservation of the binding affinity of the Fc domain to said receptor, is achieved when the Fc domain (or the bispecific antibodies of the invention comprising said Fc domain) exhibits greater than about 70% of the binding affinity of a non-engineered form of the Fc domain (or the bispecific antibodies of the invention comprising said non-engineered form of the Fc domain) to FcRn. The Fc domain, or the bispecific antibodies of the invention of the invention comprising said Fc domain, may exhibit greater than about 80% and even greater than about 90% of such affinity. In certain embodiments the Fc domain of the bispecific antibodies of the invention is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced dendritic cell maturation, or reduced T cell priming. In one embodiment the reduced effector function is one or more of reduced CDC, reduced ADCC, reduced ADCP, and reduced cytokine secretion. In a particular embodiment the reduced effector function is reduced ADCC. In one embodiment the reduced ADCC is less than 20% of the ADCC induced by a non-engineered Fc domain (or a bispecific antibody of the invention comprising a non-engineered Fc domain).

In one embodiment the amino acid mutation that reduces the binding affinity of the Fc domain to an Fc receptor and/or effector function is an amino acid substitution. In one embodiment the Fc domain comprises an amino acid substitution at a position of E233, L234, L235, N297, P331 and P329. In a more specific embodiment the Fc domain comprises an amino acid substitution at a position of L234, L235 and P329. In some embodiments the Fc domain comprises the amino acid substitutions L234A and L235A. In one such embodiment, the Fc domain is an $IgG_1$ Fc domain, particularly a human $IgG_1$ Fc domain. In one embodiment the Fc domain comprises an amino acid substitution at position P329. In a more specific embodiment the amino acid substitution is P329A or P329G, particularly P329G. In one embodiment the Fc domain comprises an amino acid substitution at position P329 and a further amino acid substitution at a position selected from E233, L234, L235, N297 and P331. In a more specific embodiment the further amino acid substitution is E233P, L234A, L235A, L235E, N297A, N297D or P331S. In particular embodiments the Fc domain comprises amino acid substitutions at positions P329, L234 and L235. In more particular embodiments the Fc domain comprises the amino acid mutations L234A, L235A and P329G ("P329G LALA"). In one such embodiment, the Fc domain is an $IgG_1$ Fc domain, particularly a human $IgG_1$ Fc domain. The "P329G LALA" combination of amino acid substitutions almost completely abolishes Fcγ receptor binding of a human $IgG_1$ Fc domain, as described in PCT patent application no. PCT/EP2012/055393, incorporated herein by reference in its entirety. PCT/EP2012/055393 also describes methods of preparing such mutant Fc domains and methods for determining its properties such as Fc receptor binding or effector functions.

IgG4 antibodies exhibit reduced binding affinity to Fc receptors and reduced effector functions as compared to $IgG_1$ antibodies. Hence, in some embodiments the Fc domain of the bispecific antibodies of the invention is an IgG4 Fc domain, particularly a human IgG4 Fc domain. In one embodiment the IgG4 Fc domain comprises amino acid substitutions at position S228, specifically the amino acid substitution S228P. To further reduce its binding affinity to an Fc receptor and/or its effector function, in one embodiment the $IgG_4$ Fc domain comprises an amino acid substitution at position L235, specifically the amino acid substitution L235E. In another embodiment, the $IgG_4$ Fc domain comprises an amino acid substitution at position P329, specifically the amino acid substitution P329G. In a particular embodiment, the $IgG_4$ Fc domain comprises amino acid substitutions at positions S228, L235 and P329, specifically amino acid substitutions S228P, L235E and P329G. Such $IgG_4$ Fc domain mutants and their Fcγ receptor binding properties are described in PCT patent application no. PCT/EP2012/055393, incorporated herein by reference in its entirety.

In a particular embodiment the Fc domain exhibiting reduced binding affinity to an Fc receptor and/or reduced effector function, as compared to a native $IgG_1$ Fc domain, is a human $IgG_1$ Fc domain comprising the amino acid substitutions L234A, L235A and optionally P329G, or a human $IgG_4$ Fc domain comprising the amino acid substitutions S228P, L235E and optionally P329G.

In certain embodiments N-glycosylation of the Fc domain has been eliminated. In one such embodiment the Fc domain comprises an amino acid mutation at position N297, particularly an amino acid substitution replacing asparagine by alanine (N297A) or aspartic acid (N297D). In addition to the Fc domains described hereinabove and in PCT patent application no. PCT/EP2012/055393, Fc domains with reduced Fc receptor binding and/or effector function also include those with substitution of one or more of Fc domain residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. A suitable such binding assay is described herein. Alternatively, binding affinity of Fc domains or cell activating bispecific antigen binding molecules comprising an Fc domain for Fc receptors may be evaluated using cell lines known to express particular Fc receptors, such as human NK cells expressing FcγIIIa receptor.

Effector function of an Fc domain, or bispecific antibodies of the invention comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the bispecific antibodies of the invention is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

The following section describes preferred embodiments of the bispecific antibodies of the invention comprising Fc domain modifications reducing Fc receptor binding and/or effector function.

F. Antibody Variants

In certain embodiments, amino acid sequence variants of the bispecific antibodies provided herein are contemplated, in addition to those described above. For example, it may be desirable to improve the binding affinity and/or other biological properties of the bispecific antibody Amino acid sequence variants of a bispecific antibody may be prepared by introducing appropriate modifications into the nucleotide sequence encoding the bispecific antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

1. Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table B under the heading of "conservative substitutions." More substantial changes are provided in Table B under the heading of "exemplary substitutions," and as further described below in reference to amino acid side chain classes Amino acid substitutions may be introduced into an antibody of interest and the products screened for a desired activity, e.g., retained/improved antigen binding, decreased immunogenicity, or improved ADCC or CDC.

TABLE B

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

2. Glycosylation Variants

In certain embodiments, a bispecific antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the bispecific antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in a bispecific antibody of the invention may be made in order to create antibody variants with certain improved properties.

In one embodiment, bispecific antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Bispecific antibodies variants are further provided with bisected oligosaccharides, e.g., in which a biantennary oligosaccharide attached to the Fc region of the bispecific antibody is bisected by GlcNAc. Such bispecific antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

3. Cysteine Engineered Antibody Variants

In certain embodiments, it may be desirable to create cysteine engineered bispecific antibodies, e.g., "thioMAbs," in which one or more residues of a bispecific antibody are substituted with cysteine residues. In particular embodiments, the substituted residues occur at accessible sites of the bispecific antibody. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

G. Recombinant Methods and Compositions

Bispecific antibodies of the invention may be obtained, for example, by solid-state peptide synthesis (e.g. Merrifield solid phase synthesis) or recombinant production. For recombinant production one or more polynucleotide encoding the bispecific antibodies (or fragments), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides of the invention is provided. Methods which are well known to those skilled in the art can be used to construct expression vectors containing the coding sequence of a bispecific antibody (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y (1989). The expression vector can be part of a plasmid, virus, or may be a nucleic acid fragment. The expression vector includes an expression cassette into which the polynucleotide encoding the bispecific antibody (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the bispecific antibody (fragment) of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit â-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the bispecific antibody is desired, DNA encoding a signal sequence may be placed upstream of the nucleic acid encoding a bispecific antibody of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the bispecific antibody may be included within or at the ends of the bispecific antibody (fragment) encoding polynucleotide.

In a further embodiment, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one such embodiment a host cell comprises (e.g. has been transformed or transfected with) a vector comprising a polynucleotide that encodes (part of) a bispecific antibody of the invention. As used herein, the term "host cell" refers to any kind of cellular system which can be engineered to generate the bispecific antibodies of the invention or fragments thereof. Host cells suitable for replicating and for supporting expression of bispecific antibodies are well known in the art. Such cells may be transfected or transduced as appropriate with the particular expression vector and large quantities of vector containing cells can be grown for seeding large scale fermenters to obtain sufficient quantities of the bispecific antibody for clinical applications. Suitable host cells include prokaryotic microorganisms, such as E. coli, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr⁻ CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell). Standard technologies are known in the art to express foreign genes in these systems. Cells expressing a polypeptide comprising either the heavy or the light chain of an antigen binding domain such as an antibody, may be engineered so as to also express the other of the antibody chains such that the expressed product is an antibody that has both a heavy and a light chain.

In one embodiment, a method of producing a bispecific antibody according to the invention is provided, wherein the method comprises culturing a host cell comprising a polynucleotide encoding the bispecific antibody, as provided herein, under conditions suitable for expression of the bispecific antibody, and recovering the bispecific antibody from the host cell (or host cell culture medium).

The components of the bispecific antibody are genetically fused to each other. Bispecific antibodies can be designed such that its components are fused directly to each other or indirectly through a linker sequence. The composition and length of the linker may be determined in accordance with methods well known in the art and may be tested for efficacy. Examples of linker sequences between different components of bispecific antibodies are found in the sequences provided herein. Additional sequences may also be included to incorporate a cleavage site to separate the individual components of the fusion if desired, for example an endopeptidase recognition sequence.

In certain embodiments the Fab fragments forming part of the bispecific antibody comprise at least an antibody variable region capable of binding an antigenic determinant Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of antibody, antibody fragment, antigen binding domain or variable region can be used in the bispecific antibodies of the invention. Non-limiting antibodies, antibody fragments, antigen binding domains or variable regions useful in the present invention can be of murine, primate, or human origin. If the bispecific antibody is intended for human use, a chimeric form of antibody may be used wherein the constant regions of the antibody are from a human. A humanized or fully human form of the antibody can also be prepared in accordance with methods well known in the art (see e.g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, N.J., 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain embodiments, the Fab fragments useful in the present invention are engineered to have enhanced binding affinity according to, for example, the methods disclosed in U.S. Pat. Appl. Publ. No. 2004/0132066, the entire contents of which are hereby incorporated by reference. The ability of the bispecific antibody of the invention to bind to a specific antigenic determinant can be measured either through an enzyme-linked immunosorbent assay (ELISA) or other techniques familiar to one of skill in the art, e.g. surface plasmon resonance technique (analyzed on a BIACORE® T100 system) (Liljeblad, et al., Glyco J 17, 323-329 (2000)), and traditional binding assays (Heeley, Endocr Res 28, 217-229 (2002)). Competition assays may be used to identify an antibody, antibody fragment, antigen binding domain or variable domain that competes with a reference antibody for binding to a particular antigen. In certain embodiments, such a competing antibody binds to the same epitope (e.g. a linear or a conformational epitope) that is bound by the reference antibody. Detailed exemplary methods for mapping an epitope to which an antibody binds are provided in Morris (1996) "Epitope Mapping Protocols," in Methods in Molecular Biology vol. 66 (Humana Press, Totowa, N.J.). In an exemplary competition assay, immobilized antigen is incubated in a solution comprising a first labeled antibody that binds to the antigen and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to the antigen. See Harlow and Lane (1988) Antibodies: A Laboratory Manual ch. 14 (Cold Spring Harbor Laboratory, Cold Spring Harbor, N.Y.).

Bispecific antibodies prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the bispecific antibody binds. For example, for affinity chromatography purification of bispecific antibodies of the invention, a matrix with protein A or protein G may be used. Sequential Protein A or G affinity chromatography and size exclusion chromatography can be used to isolate a bispecific antibody essentially as described in the Examples. The purity of the bispecific antibody can be determined by any of a variety of well known analytical methods including gel electrophoresis, high pressure liquid chromatography, and the like.

H. Assays

Bispecific antibodies that specifically bind to HER2 provided herein may be identified, screened for, or characterized for their physical/chemical properties and/or biological activities by various assays known in the art.

1. Affinity Assays

The affinity of the bispecific antibody specifically binding to HER2 can be determined in accordance with the methods set forth in the Examples by surface plasmon resonance (SPR), using standard instrumentation such as a BIACORE® instrument (GE Healthcare), and receptors or target proteins such as may be obtained by recombinant expression. Alternatively, binding of bispecific antibody provided therein to HER2 may be evaluated using cell lines expressing the particular receptor or target antigen, for example by flow cytometry (FACS). A specific illustrative and exemplary embodiment for measuring binding affinity is described in the following and in the Examples below.

According to one embodiment, $K_D$ is measured by surface plasmon resonance using a BIACORE® T100 machine (GE Healthcare) at 25° C.

To analyze the interaction between the Fc-portion and Fc receptors, His-tagged recombinant Fc-receptor is captured by an anti-Penta His antibody (Qiagen) immobilized on CM5 chips and the bispecific constructs are used as analytes. Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NHS) according to the supplier's instructions. Anti Penta-His antibody is diluted with 10 mM sodium acetate, pH 5.0, to 40 µg/ml before injection at a flow rate of 5 µl/min to achieve approximately 6500 response units (RU) of coupled protein. Following the injection of the ligand, 1 M ethanolamine is injected to block unreacted groups. Subsequently the Fc-receptor is captured for 60 s at 4 or 10 nM. For kinetic measurements, four-fold serial dilutions of the bispecific construct (range between 500 nM and 4000 nM) are injected in HBS-EP (GE Healthcare, 10 mM HEPES, 150 mM NaCl, 3 mM EDTA, 0.05% Surfactant P20, pH 7.4) at 25° C. at a flow rate of 30 µl/min for 120 s.

To determine the affinity to the target antigen, bispecific constructs are captured by an anti human Fab specific antibody (GE Healthcare) that is immobilized on an activated CM5-sensor chip surface as described for the anti Penta-His antibody. The final amount of coupled protein is is approximately 12000 RU. The bispecific constructs are captured for 90 s at 300 nM. The target antigens are passed through the flow cells for 180 s at a concentration range from 250 to 1000 nM with a flowrate of 30 µl/min. The dissociation is monitored for 180 s.

Bulk refractive index differences are corrected for by subtracting the response obtained on reference flow cell. The steady state response was used to derive the dissociation constant $K_D$ by non-linear curve fitting of the Langmuir binding isotherm. Association rates ($k_{on}$) and dissociation rates ($k_{off}$) are calculated using a simple one-to-one Langmuir binding model (BIACORE® T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., J Mol Biol 293, 865-881 (1999).

2. Binding Assays and Other Assays

In one aspect, a bispecific antibody of the invention is tested for its antigen binding activity, e.g., by known methods such as ELISA, Western blot, etc.

In another aspect, competition assays may be used to identify an antibody that competes with a specific anti-HER2 for binding to HER2. In certain embodiments, such a competing antibody binds to the same epitope (e.g., a linear or a conformational epitope) that is bound by a specific anti-HER2 antibody. Detailed exemplary methods for mapping an epitope to which an antibody binds are provided in Morris (1996) "Epitope Mapping Protocols," in *Methods in Molecular Biology* vol. 66 (Humana Press, Totowa, N.J.). Further methods are described in the example section.

3. Activity Assays

In one aspect, assays are provided for identifying bispecific antibodies that bind to HER2 thereof having biological activity. Biological activity may include, e.g., DNA fragmentation, induction of apoptosis and lysis of targeted cells. Antibodies having such biological activity in vivo and/or in vitro are also provided. In one embodiment said activity is induction of complement-dependent cytotoxicity (CDC). In one embodiment said bispecific antibodies induce CDC to a higher degree than pertuzumab or trastuzumab alone. In one embodiment said bispecific antibodies induce CDC to at least an about 10 times higher degree, an about 20 times higher degree or an about 30 times higher degree than pertuzumab or trastuzumab alone. In another embodiment said bispecific antibodies induce CDC to a higher degree than the combination of pertuzumab or trastuzumab. In another embodiment said bispecific antibodies induce CDC to about a 30%, 40%, 50% or 60%, or at least a 30% to 70%, or at least a 40% to 60% higher degree than the combination of pertuzumab or trastuzumab. The complement-dependent cytotoxicity (CDC) assay can be performed with non heat-treated serum or commercially available complement fractions (see e.g. Lazar, G. A. et al. Engineered antibody Fc variants with enhanced effector function. Proc. Natl Acad. Sci. USA 103, 4005-4010 (2006)). Target cell killing can be assessed by several cell viability reagents such as Alamar Blue (Lazar, G. A. et al. Engineered antibody Fc variants with enhanced effector function. Proc. Natl Acad. Sci. USA 103, 4005-4010 (2006), Idusogie, E. E. et al. Engineered antibodies with increased activity to recruit complement. J. Immunol. 166, 2571-2575 (2001)), CellTiter-Glo (see e.g. Zhao, X. et al. Targeting C-type lectin-like molecule-1 for antibody-mediated immunotherapy in acute myeloid leukemia. Haematologica 95, 71-78 (2009)), LDH release (see e.g. Konishi, E., Kitai, Y. & Kondo, T. Utilization of complement-dependent cytotoxicity to measure low levels of antibodies: application to nonstructural protein 1 in a model of Japanese encephalitis virus. Clin. Vaccine Immunol. 15, 88-94 (2008) and the examples disclosed herein) or calcein-AM release. In some embodiments said degree of induction of CDC is determined by a LDH release assay or a complement assay measuring binding of complement protein C1q to the antibodies of the invention bound to a cellular antigen. The CDC induction of the bispecific antibody is then compared to the CDC induction of either Pertuzumab or Trastuzumab alone, or the combination of Pertuzumab and Trastuzumab, with all values for CDC induction being assayed in the same assay, with the same cell line and the same respective antibody concentration. If performed in a microtiterplate, the capability of the bispecific antibodies and the controls (either Pertuzumab or Trastuzumab alone, or the combination of Pertuzumab and Trastuzumab) to induce CDC are preferably measured in the same microtiterplate using the same assay. Exemplary assays are disclosed, e.g. in example 18 or 19. In one embodiment said induction of CDC is determined on cancer cells, e.g. breast cancer cells.

In certain embodiments, a bispecific antibody of the invention is tested for such biological activity. Assays for detecting cell lysis (e.g. by measurement of LDH release) or apoptosis (e.g. using the TUNEL assay) are well known in the art. Assays for measuring ADCC or CDC are also described in WO 2004/065540 (see Example 1 therein), the entire content of which is incorporated herein by reference.

I. Pharmaceutical Formulations

Pharmaceutical formulations of a bispecific antibody that specifically binds to HER2 as described herein are prepared by mixing such bispecific antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

J. Therapeutic Methods and Compositions

Any of the bispecific antibodies that bind to HER2 provided herein may be used in therapeutic methods.

In one aspect, a bispecific antibody that specifically binds to HER2 for use as a medicament is provided. In further aspects, a bispecific antibody that specifically binds to HER2 for use in treating cancer is provided. In certain embodiments, a bispecific antibody that specifically binds to HER2 for use in a method of treatment is provided. In certain embodiments, the invention provides a bispecific antibody that specifically binds to HER2 for use in a method of treating an individual having cancer comprising administering to the individual an effective amount of the bispecific antibody that specifically binds to HER2. In one such embodiment, the method further comprises administering to the individual an effective amount of at least one additional therapeutic agent, e.g., as described below. An "individual" according to any of the above embodiments is preferably a human.

In a further aspect, the invention provides for the use of a bispecific antibody that specifically binds to HER2 in the manufacture or preparation of a medicament. In one embodiment, the medicament is for treatment of cancer. In a further embodiment, the medicament is for use in a method of treating cancer comprising administering to an individual having cancer an effective amount of the medicament. In one such embodiment, the method further comprises administering to the individual an effective amount of at least one additional therapeutic agent, e.g., as described below. An "individual" according to any of the above embodiments may be a human.

In a further aspect, the invention provides a method for treating cancer. In one embodiment, the method comprises administering to an individual having cancer an effective amount of a bispecific antibody that binds to HER2. In one such embodiment, the method further comprises administering to the individual an effective amount of at least one additional therapeutic agent, as described below. An "individual" according to any of the above embodiments may be a human.

In a further aspect, the invention provides pharmaceutical formulations comprising any of the bispecific antibodies that bind to HER2 provided herein, e.g., for use in any of the above therapeutic methods. In one embodiment, a pharmaceutical formulation comprises any of the bispecific antibodies that bind to HER2 provided herein and a pharmaceutically acceptable carrier. In another embodiment, a pharmaceutical formulation comprises any of the bispecific antibodies that bind to HER2 provided herein and at least one additional therapeutic agent, e.g., as described below.

A bispecific antibody of the invention can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Bispecific antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The bispecific antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a bispecific antibody of the invention will depend on the type of disease to be treated, the type of antibody, the severity and course of the disease, whether the bispecific antibody is administered for preventive or therapeutic purposes, previous therapy, the patient's clinical history and response to the bispecific antibody, and the discretion of the attending physician. The bispecific antibody is suitably administered to the patient at one time or over a series of treatments. Depending on the type and severity of the disease, about 1 µg/kg to 15 mg/kg (e.g. 0.1 mg/kg-10 mg/kg) of the bispecific antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the bispecific antibody would be in the range from about 0.05 mg/kg to about 10 mg/kg. Thus, one or more doses of about 0.5 mg/kg, 2.0 mg/kg, 4.0 mg/kg or 10 mg/kg may be administered to the patient. Such doses may be administered intermittently, e.g. every week or every three weeks (e.g. such that the patient receives from about two to about twenty, or e.g. about six doses of the bispecific antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to a bispecific antibody that specifically binds to HER2 of the invention.

K. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a bispecific antibody of the invention. The label or package insert indicates that the composition is used for treating the condition of choice. Moreover, the article of manufacture may comprise (a) a first container with a composition contained therein, wherein the composition comprises a bispecific antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to a bispecific antibody that specifically binds to HER2 of the invention.

L. Immunoconjugates

The invention also provides immunoconjugates comprising an bispecific antibody that specifically binds to HER2 herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

III. Examples

The following are examples of methods and compositions of the invention. It is understood that various other embodiments may be practiced, given the general description provided above.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Example 1: Materials and Methods

Unless stated otherwise the following general methods have been applied:

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

DNA and Protein Sequence Analysis and Sequence Data Management

General information regarding the nucleotide sequences of human immunoglobulins light and heavy chains is given in: Kabat, E., A., et al., (1991) Sequences of Proteins of Immunological Interest, Fifth Ed., NIH Publication No 91-3242 Amino acids of antibody chains are numbered according to EU numbering (Edelman, G. M., et al., PNAS 63 (1969) 78-85; Kabat, E. A., et al., (1991) Sequences of Proteins of Immunological Interest, Fifth Ed., NIH Publication No 91-3242). The GCG's (Genetics Computer Group, Madison, Wis.) software package version 10.2 and Infomax's Vector NTI Advance suite version 8.0 was used for sequence creation, mapping, analysis, annotation and illustration.

DNA Sequencing

DNA sequences were determined by double strand sequencing performed at SequiServe (Vaterstetten, Germany) and Geneart AG (Regensburg, Germany).

Example 2: Generation of Trastuzumab and Pertuzumab Bispecific Antibodies in a 2+2 IgG-scFv Format Gene Synthesis Desired gene segments were prepared by Geneart AG (Regensburg, Germany) from synthetic oligonucleotides and PCR products by automated gene synthesis. The gene segments which are flanked by singular restriction endonuclease cleavage sites were cloned into pGA18 (ampR) plasmids. The plasmid DNA was purified from transformed bacteria and concentration determined by UV spectroscopy. The DNA sequence of the subcloned gene fragments was confirmed by DNA sequencing.

Construction of the Expression Plasmids

The following expression vector was used for the construction of all heavy and light chain encoding expression plasmids. The vector is composed of the following elements:
- a hygromycin resistance gene as a selection marker,
- an origin of replication, oriP, of Epstein-Barr virus (EBV),
- an origin of replication from the vector pUC18 which allows replication of this plasmid in E. coli
- a beta-lactamase gene which confers ampicillin resistance in E. coli,
- the immediate early enhancer and promoter from the human cytomegalovirus (HCMV),
- the human 1-immunoglobulin polyadenylation ("poly A") signal sequence, and The immunoglobulin genes comprising the heavy or light chain were prepared by gene synthesis and cloned into pGA18 (ampR) plasmids as described above. Variable heavy chain constructs were constructed by directional cloning using unique restriction sites. Variable light chain constructs were ordered as gene synthesis comprising VL and CL and constructed by directional cloning using unique restriction sites. The final expression vectors were transformed into E. coli cells, expression plasmid DNA was isolated (Miniprep) and subjected to restriction enzyme analysis and DNA sequencing. Correct clones were grown in 150 ml LB-Amp medium, again plasmid DNA was isolated (Maxiprep) and sequence integrity confirmed by DNA sequencing.

Transient Expression of Immunoglobulin Variants in HEK293 Cells

Recombinant immunoglobulin variants were expressed by transient transfection of human embryonic kidney 293-F cells using the FreeStyle™ 293 Expression System according to the manufacturer's instruction (Invitrogen, USA). For small scale test expressions 30 ml of $0.5 \times 10^6$ HEK293F cells/ml were seeded one day prior to transfection. The next day, plasmid DNA (1 µg DNA per ml culture volume) was mixed with 1.2 ml OPTI-MEM® I Reduced Serum Medium (Invitrogen, Carlsbad, Calif., USA) followed by addition of 40 µl of 293Fectin™ Transfection Reagent (Invitrogen, Carlsbad, Calif., USA). The mixture was incubated for 15 min at room temperature and added drop wise to the cells. One day post-transfection each flask was fed with 300 µl L-Glutamine (200 mM, Sigma-Aldrich, Steinheim, Germany) and 600 µl feed7 containing L-asparagine, amino acids, trace elements, ammonium-Fe(III) citrate, ethanolamine, trace elements, D-glucose, FreeStyle medium without RPMI. Three days post-transfection cell concentration, viability and glucose concentration in the medium were determined using an automated cell viability analyzer (VI-CELL™ XR, Beckman Coulter, Fullerton, Calif., USA) and a glucose meter (ACCU-CHEK® Sensor comfort, Roche Diagnostics GmbH, Mannheim, Germany). In addition each flask was fed with 300 µl of L-glutamine, 300 µl non-essential amino acids solution (PAN™ Biotech, Aidenbach, Germany), 300 µl sodium pyruvate (100 mM, Gibco, Invitrogen), 1.2 ml feed7 and ad 5 g/L glucose (D-(+)-Glucose solution 45%, Sigma). Finally, six days post-transfection antibodies were harvested by centrifugation at 3500 rpm in a X3R Multifuge (Heraeus, Buckinghamshire, England) for 15 min at ambient temperature, the supernatant was sterile filtered through a Steriflip filter unit (0.22 mm Millipore Express PLUS PES membrane, Millipore, Bedford, Mass.) and stored at −20° C. until further use. Large scale transfections up to 5 L were scaled linearly.

Purification of Bispecific and Control Antibodies

Bispecific antibodies were purified from cell culture supernatants by affinity chromatography using Protein A-SepharoseA-SEPHAROSE™ (GE Healthcare, Sweden) and Superdex® 200 size exclusion chromatography. Briefly, sterile filtered cell culture supernatants were applied on a HiTrap ProteinA HP (5 ml) column equilibrated with PBS buffer (10 mM $Na_2HPO_4$, 1 mM $KH_2PO_4$, 137 mM NaCl and 2.7 mM KCl, pH 7.4). Unbound proteins were washed out with equilibration buffer. Antibody and antibody variants were eluted with 0.1 M citrate buffer, pH 2.8, and the protein containing fractions were neutralized with 0.1 ml 1 M Tris, pH 8.5. Eluted protein fractions were pooled, concentrated with an Amicon Ultra centrifugal filter device (MWCO: 30 K, Millipore) to a volume of 3 ml and loaded on a SUPERDEX® 200 HiLoad 120 ml 16/60 gel filtration column (GE Healthcare, Sweden) equilibrated with 20 mM Histidin, 140 mM NaCl, pH 6.0. Fractions containing purified bispecific and control antibodies with less than 5% high molecular weight aggregates were pooled and stored as 1.0 mg/ml aliquots at −80° C.

Protein Quantification

Proteins were quantified by affinity chromatography using the automated ULTIMATE™ 3000 system (Dionex, Idstein, Germany) with a pre-packed Poros® A protein A column (Applied Biosystems, Foster City, Calif., USA). All samples were loaded in buffer A (0.2 M $Na_2HPO_4 \cdot [2H_2O]$, pH 7.4) and eluted in buffer B (0.1 M citric acid, 0.2 M NaCl, pH 2.5). In order to determine the protein concentration an extinction coefficient of 1.62 was used for all samples.

Analysis of Purified Proteins

The protein concentration of purified protein samples was determined by measuring the optical density (OD) at 280 nm, using the molar extinction coefficient calculated on the basis of the amino acid sequence. Purity and molecular weight of bispecific and control antibodies were analyzed by SDS-PAGE in the presence and absence of a reducing agent (5 mM 1,4-dithiothreitol) and staining with Coomassie brilliant blue. The NuPAGE® Pre-Cast gel system (Invitrogen, USA) was used according to the manufacturer's instruction (4-20% Tris-Glycine gels). The aggregate content of bispecific and control antibody samples was analyzed by high-performance SEC using a SUPERDEX® 200 analytical size-exclusion column (GE Healthcare, Sweden) in 200 mM $KH_2PO_4$, 250 mM KCl, pH 7.0 running buffer at 25° C. 25 µg protein were injected on the column at a flow rate of 0.5 ml/min and eluted isocratic over 50 minutes. Integrity of the amino acid backbone of reduced bispecific antibody light and heavy chains was verified by NanoElectrospray Q-TOF mass spectrometry after removal of N-glycans by enzymatic treatment with Peptide-N-Glycosidase F (Roche Molecular Biochemicals).

Analytical HPLC

Antibodies were analyzed using a Agilent HPLC 1100 (Agilent Technologies, Palo Alto, Calif., USA) with a TSK-GEL G3000SW gel filtration column (7.5 mm ID×30 cm, TosoHaas Corp., Montgomeryville, Pa., USA). 18 µl of the eluted proteins were loaded onto the column in Buffer A (0.05 M $K_2HPO_4/KH_2PO_4$ in 300 mM NaCl, pH 7.5) and separated based on size.

Reducing and Non-Reducing SDS-PAGE

7 µl of the eluted proteins were mixed with 2× sample buffer (NuPAGE® LDS Sample buffer, Invitrogen, Carlsbad, Calif., USA) and another 7 µl were mixed with 2× sample buffer containing 10% reducing agent (NuPAGE® Sample Reducing Agent, Invitrogen, Carlsbad, Calif., USA). Samples were heated to 70° for 10 min and loaded onto a pre-cast NuPAGE® 4-12% BisTris Gel (Invitrogen, Carlsbad, Calif., USA). The gel was run for 45 min at 200V and 125 mA. Afterwards the gel was washed three times with Millipore water and stained with SimplyBlue™ SafeStain (Invitrogen, Carlsbad, Calif., USA). The gel was destained overnight in Millipore water. FIGS. 1A-1D depict schematically the different variants of Trastuzumab and Pertuzumab bispecific antibodies in a 2+2 IgG-scFv format. All bispecific antibodies are bivalent for each antigen binding site and bind two different paratopes in the ErbB2/HER2 receptor (antigen1=trastuzumab specificity; antigen2=pertuzumab specificity). All bispecific antibodies in a 2+2 IgG-scFv format described herein are non frame-work grafted, non-CDR optimized, not glycoengineered and do not bear any mutation in the Fc part.

FIGS. 2A, 2B to 4 show exemplary size-exclusion purification graphs, SDS-PAGE analysis and analytical HPLC of variants of Trastuzumab and Pertuzumab bispecific antibodies in a 2+2 IgG-scFv format. No data shown for TvAB17, TvAB13 and variants Herceptin-scFv_A to E; all variants of Trastuzumab and Pertuzumab bispecific antibodies in a 2+2 IgG-scFv format were produced with the same quality.

TABLE 1a

Sequences of Trastuzumab and Pertuzumab bispecific antibodies in a 2 + 2 IgG-scFv format

| SEQ ID NO | Name | Sequence |
|---|---|---|
| | TvAB12_2431_TrastuzumabHCseFvOmnitarg(HC_LC) | |
| 123 | Light chain (kappa) [Trastuzumab, 1016] | diqmtqspsslsasvgdrvtitcrasqdvntavawyqqkpgkapklliysasflysgvpsrfsgs rsgtdftltisslqpedfatyycqqhyttpptfgqgtkveikrtvaapsvfifppsdeqlksgtasvv cllnnfypreakvqwkvdnalqsgnsqesvteqdskdstyslsstltlskadyekhkvyacevt hqglsspvtksfnrgec |
| 124 | Heavy chain [Trastuzumab + scFv Omnitarg, RB40] | evqlvesgggglvqpggslrlscaasgfnikdtyihwvrqapgkglewvariyptngytryadsv kgrftisadtskntaylqmnslraedtavyycsrwggdgfyamdywgqgtlvtvssastkgps vfplapssksstsggtaalgclvkdyfpepvtvswnsgaltsgvhtfpavlqssglyslssvvtvps sslgtqtyicnvnhkpsntkvdkkvepkscdkthtcppcpapellggpsvflfppkpkdtlmis rtpevtcvvvdvshedpevkfnwyvdgvevhnaktkpreeqynstyrvvsyltvlhqdwlng keykckvsnkalpapiektiskakgqprepqvytlppsreemtknqvsltclvkgfypsdiave wesngqpennykttppvldsdgsfflyskltvdksrwqqgnvfscsvmhealhnhytqkslsl spgkggggsggggsggggsggggsevqlvesgggglvqpggslrlscaasgftftdytmdwvrqapgk clewvadvnpnsggsiynqrfkgrftlsvdrskntlylqmnslraedtavyycarnlgpsfyfdy wgqgtlvtvssggggsggggsggggsggggsdiqmtqspsslsasvgdrvtitckasqdvsig vawyqqkpgkapklliysasyrytgvpsrfsgsgsgtdftltisslqpedfatyycqqyyipytf gcgtkveik |
| | TvAB13 [TvAb13_1330scFvTrastuzumab(LC_HC)OmnitargLC_IntronA_cDNA] | |
| 125 | Light chain [scFv Trastuzumab + Omnitarg, RB34] | diqmtqspsslsasvgdrvtitcrasqdvntavawyqqkpgkapklliysasflysgvpsrfsgs rsgtdftltisslqpedfatyycqqhyttpptfgqgtkveikggggsggggsggggsevqlvesg gglvqpggslrlscaasgfnikdtyihwvrqapgkglewvariyptngytryadsvkgrftisad tskntaylqmnslraedtavyycsrwggdgfyamdywgqgtlvtvssggggsggggsggggs sdiqmtqspsslsasvgdrvtitckasqdvsigvawyqqkpgkapklliysasyrytgvpsrfsg sgsgtdftltisslqpedfatyycqqyyipytfgqgtkveikrtvaapsvfifppsdeqlksgtas vvcllnnfypreakvqwkvdnalqsgnsqesvteqdskdstyslsstltlskadyekhkvyace vthqglsspvtksfnrgec |
| 126 | Heavy chain (Omnitarg, RB33) | evqlvesgggglvqpggslrlscaasgftftdytmdwvrqapgkglewvadvnpnsggsiynqr fkgrftlsvdrskntlylqmnslraedtavyycarnlgpsfyfdywgqgtlvtvssastkgpsvfp lapssksstsggtaalgclvkdyfpepvtvswnsgaltsgvhtfpavlqssglyslssvvtvpsslg tqtyicnvnhkpsntkvdkkvepkscdkthtcppcpapellggpsvflfppkpkdtlmisrtpe vtcvvvdvshedpevkfnwyvdgvevhnaktkpreeqynstyrvvsvltvlhqdwlngkey kckvsnkalpapiektiskakgqprepqvytlppsrdeltknqvsltclvkgfypsdiavewesn gqpennykttppvldsdgsfflyskltvdksrwqqgnvfscsvmhealhnhytqkslslspgk |
| | TvAB16 [TVAb16_2330TrastuzumabLCseFvOmnitarg(LC_HC)] | |
| 127 | Light chain [Trastuzumab + scFvOmnitarg, RB35] | diqmtqspsslsasvgdrvtitcrasqdvntavawyqqkpgkapklliysasflysgvpsrfsgs rsgtdftltisslqpedfatyycqqhyttpptfgqgtkveikrtvaapsvfifppsdeqlksgtasvv cllnnfypreakvqwkvdnalqsgnsqesvteqdskdstyslsstltlskadyekhkvyacevt hqglsspvtksfnrgecggggsggggsggggsdiqmtqspsslsasvgdrvtitckasqdvsig vawyqqkpgkapklliysasyrytgvpsrfsgsgsgtdftltisslqpedfatyycqqyyipytf gqgtkveikggggsggggsggggsevqlvesgggglvqpggslrlscaasgftftdytmdwvrq apgkglewvadvnpnsggsiynqrfkgrftlsvdrskntlylqmnslraedtavyycarnlgps fyfdywgqgtlvtvss |
| 128 | Heavy chain [Trastuzumab, 1036] | evqlvesgggglvqpggslrlscaasgfnikdtyihwvrqapgkglewvariyptngytryadsv kgrftisadtskntaylqmnslraedtavyycsrwggdgfyamdywgqgtlvtvssastkgps vfplapssksstsggtaalgclvkdyfpepvtvswnsgaltsgvhtfpavlqssglyslssvvtvps sslgtqtyicnvnhkpsntkvdkkvepkscdkthtcppcpapellggpsvflfppkpkdtlmis rtpevtcvvvdvshedpevkfnwyvdgvevhnaktkpreeqynstyrvvsvltvlhqdwlng keykckvsnkalpapiektiskakgqprepqvytlppsrdeltknqvsltclvkgfypsdiave wesngqpennykttppvldsdgsfflyskltvdksrwqqgnvfscsvmhealhnhytqkslsl spgk |

TABLE 1a-continued

Sequences of Trastuzumab and Pertuzumab bispecific antibodies in a 2 + 2 IgG-scFv format

| SEQ ID NO | Name | Sequence |
|---|---|---|

TvAB17 [TvAb17_2431_TrastuzumabHCscFvOmnitarg(LC_HC)]

| | | |
|---|---|---|
| 129 | Light chain (kappa) [Trastuzumab, 1016] | diqmtqspsslsasvgdrvtitcrasqdvntavawyqqkpgkapklliysasflysgvpsrfsgs rsgtdftltisslqpedfatyycqqhyttpptfgqgtkveikrtvaapsvfifppsdeqlksgtasvv cllnnfypreakvqwkvdnalqsgnsqesvteqdskdstyslsstltlskadyekhkvyacevt hqglsspvtksfnrgec |
| 130 | Heavy chain [Trastuzumab + scFvOmnitarg, RB43] | evqlvesgggvqpggslrlscaasgfnikdtyihwvrqapgkglewvariyptngytryadsv kgrftisadtskntaylqmnslraedtavyycsrwggdgfyamdywgqgtlvtvssastkgps vfplapsskstsggtaalgclvkdyfpepvtvswnsgaltsgvhtfpavlqssglyslssvvtvps sslgtqtyicnvnhkpsntkvdkkvepkscdkthtcppcpapellggpsvflfppkpkdtlmis rtpevtcvvvdvshedpevkfnwyvdgvevhnaktkpreeqynstyrvvsvltvlhqdwlng keykckvsnkalpapiektiskakgqprepqvytlppsreemtknqvsltclvkgfypsdiave wesngqpennykttppvldsdgsffflyskltvdksrwqqgnvfscsvmhealhnhytqkslsl spgkggggsggggsggggsdiqmtqspsslsasvgdrvtitckasqdvsigvawyqqkpgka pklliysasyrytgvpsrfsgsgsgtdftltisslqpedfatyycqqyyiypytfgcgtkveikggg gsggggsggggsggggsevqlvesgggvqpggslrlscaasgftftdytmdwvrqapgkcle wvadvnpnsggsiynqrfkgrftlsvdrskntlylqmnslraedtavyycarnlgpsfyfdywg qgtlvtvss |

TvAB20 [TVAb20_4441TrastuzumabLCscFvOmnitarg(LC_HC)]

| 131 | Light chain [Trastuzumab + scFv Onrmitarg, RB61] | diqmtqspsslsasvgdrvtitcrasqdvntavawyqqkpgkapklliysasflysgvpsrfsgs rsgtdftltisslqpedfatyycqqhyttpptfgqgtkveikrtvaapsvfifppsdeqlksgtasvv cllnnfypreakvqwkvdnalqsgnsqesvteqdskdstyslsstltlskadyekhkvyacevt hqglsspvtksfnrgecggggsggggsggggsggggsdiqmtqspsslsasvgdrvtitckasq dvsigvawyqqkpgkapklliysasyrytgvpsrfsgsgsgtdftltisslqpedfatyycqqyyi ypytfgcgtkveikggggsggggsggggsggggsevqlvesgggvqpggslrlscaasgftft dytmdwvrqapgkclewvadvnpnsggsiynqrfkgrftlsvdrskntlylqmnslraedtav yycarnlgpsfyfdywgqgtlvtvss |
| 132 | Heavy chain [Trastuzumab, 1036] | evqlvesgggvqpggslrlscaasgfnikdtyihwvrqapgkglewvariyptngytryadsv kgrftisadtskntaylqmnslraedtavyycsrwggdgfyamdywgqgtlvtvssastkgps vfplapsskstsggtaalgclvkdyfpepvtvswnsgaltsgvhtfpavlqssglyslssvvtvps sslgtqtyicnvnhkpsntkvdkkvepkscdkthtcppcpapellggpsvflfppkpkdtlmis rtpevtcvvvdvshedpevkfnwyvdgvevhnaktkpreeqynstyrvvsvltvlhqdwlng keykckvsnkalpapiektiskakgqprepqvytlppsrdeltknqvsltclvkgfypsdiave wesngqpennykttppvldsdgsffflyskltvdksrwqqgnvfscsvmhealhnhytqkslsl spgk |

Herceptarg 2 + 2 OmniE

| 145 | Heavy chain with scFv Trastuzumab stabilized with disulphide bonding | evqlvesgggvqpggslrlscaasgftftdytmdwvrqapgkglewvadvnpnsggsiynqrfkgrftlsvdrskn tlylqmnslraedtavyycarnlgpsfyfdywgqgtlvtvssastkgpsvfplapsskstsggtaalgclvkdyfpepv tvswnsgaltsgvhtfpavlqssglyslssvvtvpssslgtqtyicnvnhkpsntkvdkkvepkscdkthtcppcpap ellggpsvflfppkpkdtlmisrtpevtcvvvdvshedpevkfnwyvdgvevhnaktkpreeqynstyrvvsvltv lhqdwlngkeykckvsnkalpapiektiskakgqprepqvytlppsrdeltknqvsltclvkgfypsdiavewesn gqpennykttppvldsdgsffflyskltvdksnvqqgnvfscsvmhealhnhytqkslslspgkggggsggggsev qlvesgggvqpggslrlscaasgfnikdtyihwvrqapgkglewvariyptngytryadsvkgrftisadtskntayl qmnslraedtavyycstwggegfyamdywgcgtlvtvssggggsggggsggggsdiqmtqspsslsasvgdrvt itcrasqdvnvavawyqqkpgkcpklliysasflysgvpsrfsgsrsgtdftltisslqpeclfatyycqqhyttpptfgq gtkveik |
| 146 | Pertuzumab light chain | diqmtqspsslsasvgdrvtitckasqdvsigvawyqqkpgkapklliysasyrytgvpsrfsgsgsgtdftltisslqp edfatyycqqyyiypytfgqgtkveikrtvaapsvfifppsdeqlksgtasvvcllnnfypreakvqwkvdnalqsg nsqesvteqdskdstyslsstltlskadyekhkvyacevthqglsspvtksfnrgec |

TABLE 1 b)

Variants of TvAB12_2431_TrastuzumabHCscFvOmnitarg(HC_LC) with a stabilizing disulphide bond in the scFv part to reduce aggregation levels

| Name of molecule | Disulphide position (VH-VL) |
| --- | --- |
| Trastuzumab_scFv_WT | WT |
| Trastuzumab_scFv_A | 44-100 |
| Trastuzumab_scFv_B | 45-98 |
| Trastuzumab_scFv_C | 101-46 |
| Trastuzumab_scFv_D | 103-44 |
| Trastuzumab_scFv_E | 105-43 |

Example 3: Proliferation Inhibition Assay with Trastuzumab and Pertuzumab Bispecific Antibodies in a 2+2 IgG-scFv Format Cell Lines MDA-MB 175 VII cells were maintained in DMEM/F12 medium (Gibco) supplemented with 10% fetal calf serum and 2 mL L-glutamine Propagation of cell lines followed standard cell culture protocols.

The ability of the bispecific antibodies to inhibit proliferation was assessed in the cell line MDA-MB-175 VII. MDA-MB-175 VII were cultured in DMEM/F12 medium (Gibco) supplemented with 10% fetal calf serum, 2 mM L-glutamine Cells in the logarithmic growth phase were detached, counted and 2×10e4 cells were seeded in 100 µL medium per well of a 96-well cell culture plate. Cells were maintained overnight in the incubator and the following day 100 µL of the respective antibodies diluted in medium were added in form of a dilution series to the cells. After a total incubation time of 6 days cell growth was assessed in an Alamar Blue (Invitrogen) assay. The assay was performed as recommended by the manufacturer.

Table 2 shows the potency of selected bispecific antibodies in the proliferation assay.

| Antibody | SEQ ID NO: | EC50 [nM] |
| --- | --- | --- |
| Herceptarg WT | | 1.84 |
| Herceptarg A | | 1.89 |
| Herceptarg B | | 2.66 |
| Herceptarg C | | 2.56 |
| Herceptarg D | | 1.63 |
| Herceptarg E | | 1.75 |
| TvAb12 | 123/124 | 4.90 |
| CrossMab | 119/120/ 121/122 | 4.75 |
| Pertuzumab | | 2.11 |
| Pertuzumab + HERCEPTIN © | | 1.70 |
| HERCEPTIN © | | 2.92 |

Example 4: Herceptarg Stabilisation

The aspartate isomerization site at position 98 of the heavy chain and the asparagine deamidation site at position 30 of the light chain are stability hotspots of trastuzumab. Those two positions affect the stability and integrity of the antigen binding capacity of the antibody. This problem was overcome by introducing the lyophilized formulations using either sodium succinate or histidine buffer. In order to increase stability and storage half-life we intended to replace those known sources of instability by amino acids, or amino acid streches that should have a higher intrinsic stability. We tested herefore the replacement of Asp98 by Glu in the heavy chain and the replacement of Asn30 by Ser, as well Thr31 by Val in the light chain. Those mutations were abbreviated D98E, N30S, and T31V. T31V does not directly influence the deamidation of N30, but it was assumed that the residue adjacent on the C-terminal side of an Asparagine would influence the stability properties of a polypeptide chain.

The antibody samples were incubated over a period of either 1, 2, or 3 months at 40° C. in one of the three buffers: 40 mM Histidin, 150 mM NaCl, pH5.0, 40 mM Histidin, 150 mM NaCl, pH6.0, or 40 mM Histidin, 150 mM NaCL, pH7.4. The protein concentration during this period was always 1 mg/ml. After the indicated time points, samples were taken and shock frozen in liquid nitrogen, and then kept at −80° C. until further analysis. This analysis was carried out on a ProteOn XPR36 instrument (BioRad). Approximately 700 RU of Her2, respectively, were immobilized on 2 channels of a GLM chip using amine coupling (vertical orientation). Trastuzumab variants were measured in duplicates at 6 different analyte concentrations (100, 50, 25, 12.5, 6.25, 0 nM) by injections in horizontal orientation at 100 µl/min Association rate were recorded for 180 s, the dissociation rate for 600 s. Regeneration was performed by two pulses of 10 mM glycine pH 1.5 and 50 mM NaOH for 60 s at 150 µl/min (horizontal orientation). In total four different Trastuzumab variants were measured. In the first experiment (Tables 3 and 4), only the unmodified Trastuzumab and variant 602 (D98E of heavy chain and T31V of light chain) were tested. In the second experiment the unmodified Trastuzumab, variant 602 (D98E of heavy chain and T31V of light chain) and variants VH:D98E/VL: N30S VH:D98E/VL: N30T were tested (Table 5, 6, 7).

Results:

All variants show the same affinity towards recombinant Her2 antigen as the parental Trastuzumab molecule. After exposure to pH5 or pH6 at 40° C., Trastuzumab lost affinity by a factor ~5, mainly driven by increasing the off-rate and keeping the on-rate unchanged. Variant 602 showed almost undistinguishable affinities before and after pH stress. Variant N30S had a higher affinity from the beginning compared to the parental Trastuzumab, which stayed approximately constant during the stress conditions. The variants D98E (VH) together with either N30S, N30T, or T31V (VL) were used in the further experiments. Results are shown in FIGS. 5A and 5B and 6A-6C and the tables below.

TABLE 3

Kinetic affinity parameters of Trastuzumab variants as determined by SPR method (ProteOn instrument) after incubating the samples for 1, 2, or 3 months at 40° in 40 mM Histidin, 150 mM NaCl, pH 5.0 buffer. Each measurement was done in duplicate and both experimental values are shown. Tested were the resynthesized Trastuzumab (wt) and compared to the D98E T31V variant in the heavy and light chain, respectively (named clone 602).

| pH 5 | | t0 | | | t1 | | |
|---|---|---|---|---|---|---|---|
| | | ka | kd | KD | ka | kd | KD |
| wt | 1 | 2.4E+05 | 1.1E−04 | 4.3E−10 | 3.3E+05 | 1.6E−04 | 5.0E−10 |
| | 2 | 2.4E+05 | 4.4E−05 | 1.8E−10 | 2.8E+05 | 1.9E−04 | 7.0E−10 |
| 602 | 1 | 2.6E+05 | 1.2E−04 | 4.6E−10 | 2.7E+05 | 2.2E−04 | 8.0E−10 |
| | 2 | 2.3E+05 | 1.3E−04 | 5.4E−10 | 2.8E+05 | 1.4E−04 | 5.2E−10 |

| pH 5 | | t2 | | | t3 | | |
|---|---|---|---|---|---|---|---|
| | | ka | kd | KD | ka | kd | KD |
| wt | 1 | 2.9E+05 | 2.6E−04 | 9.2E−10 | 2.8E+05 | 3.4E−04 | 1.2E−09 |
| | 2 | 2.8E+05 | 2.8E−04 | 9.9E−10 | 2.9E+05 | 3.6E−04 | 1.3E−09 |
| 602 | 1 | 2.9E+05 | 1.7E−04 | 5.8E−10 | 3.0E+05 | 1.7E−04 | 5.8E−10 |
| | 2 | 2.9E+05 | 1.6E−04 | 5.3E−10 | 3.1E+05 | 1.7E−04 | 5.5E−10 |

TABLE 4

Kinetic affinity parameters of Trastuzumab variants similar to table 3. Here the samples are incubated at 40° in 40 mM Histidin, 150 mM NaCl, pH 6.0 for the same time intervals as before.

| pH 6 | | t0 | | | t1 | | |
|---|---|---|---|---|---|---|---|
| | | ka | kd | KD | ka | kd | KD |
| wt | 1 | 2.8E+05 | 9.5E−05 | 3.4E−10 | 3.0E+05 | 1.5E−04 | 5.1E−10 |
| | 2 | 2.8E+05 | 8.6E−05 | 3.1E−10 | 2.8E+05 | 2.1E−04 | 7.7E−10 |
| 602 | 1 | 2.9E+05 | 1.4E−04 | 4.8E−10 | 3.0E+05 | 1.6E−04 | 5.2E−10 |
| | 2 | 2.8E+05 | 1.4E−04 | 5.0E−10 | 2.9E+05 | 1.5E−04 | 5.1E−10 |

| pH 6 | | t2 | | | t3 | | |
|---|---|---|---|---|---|---|---|
| | | ka | kd | KD | ka | kd | KD |
| wt | 1 | 2.5E+05 | 3.1E−04 | 1.2E−09 | 2.3E+05 | 4.0E−04 | 1.7E−09 |
| | 2 | 2.6E+05 | 3.3E−04 | 1.3E−09 | 2.4E+05 | 4.1E−04 | 1.8E−09 |
| 602 | 1 | 3.0E+05 | 1.6E−04 | 5.3E−10 | 3.0E+05 | 1.8E−04 | 5.9E−10 |
| | 2 | 2.9E+05 | 1.6E−04 | 5.5E−10 | 2.9E+05 | 1.7E−04 | 5.7E−10 |

TABLE 5

Kinetic affinity parameters of Trastuzumab variants similar to table 3. Here the samples are incubated at 40° in 40 mM Histidin, 150 mM NaCl, pH 5.0 for the same time intervals as before. Samples included are the resynthesized Trastuzumab (wt), the D98E T31V variant in the heavy and light chain, respectively (named clone 602. This was produced in CHO instead of HEK). Also the light chain variants N30S, and N30T (both have the D98E heavy chain variant)

| pH 5 | | | t0 | | | t1 | | |
|---|---|---|---|---|---|---|---|---|
| | | | ka | kd | KD | ka | kd | KD |
| 602 | | 1 | 2.20E+05 | 1.40E−04 | 6.34E−10 | 2.32E+05 | 9.14E−05 | 3.95E−10 |
| CHO | | 2 | 2.32E+05 | 2.13E−04 | 9.21E−10 | 2.10E+05 | 1.54E−04 | 7.35E−10 |
| N30T | | 1 | 2.19E+05 | 2.11E−04 | 9.64E−10 | 2.21E+05 | 1.46E−04 | 6.61E−10 |
| | | 2 | 2.18E+05 | 2.61E−04 | 1.20E−09 | 2.05E+05 | 1.85E−04 | 9.02E−10 |
| N30S * | | 1 | 2.59E+05 | 2.59E−19 | 1.00E−24 | 2.54E+05 | 1.93E−05 | 7.58E−11 |
| | | 2 | 2.44E+05 | 2.36E−17 | 9.68E−23 | 2.42E+05 | 3.47E−05 | 1.43E−10 |
| wt | | 1 | 2.51E+05 | 1.60E−04 | 6.39E−10 | 2.30E+05 | 3.62E−04 | 1.58E−09 |
| | | 2 | 2.29E+05 | 1.93E−04 | 8.43E−10 | 2.13E+05 | 2.66E−04 | 1.25E−09 |

TABLE 5-continued

Kinetic affinity parameters of Trastuzumab variants similar to table 3. Here the samples are incubated at 40° in 40 mM Histidin, 150 mM NaCl, pH 5.0 for the same time intervals as before. Samples included are the resynthesized Trastuzumab (wt), the D98E T31V variant in the heavy and light chain, respectively (named clone 602. This was produced in CHO instead of HEK). Also the light chain variants N30S, and N30T (both have the D98E heavy chain variant)

| pH 5 | | t2 ka | t2 kd | t2 KD | t3 ka | t3 kd | t3 KD |
|---|---|---|---|---|---|---|---|
| 602 | 1 | 2.32E+05 | 2.36E−04 | 1.02E−09 | 2.01E+05 | 9.67E−05 | 4.81E−10 |
| CHO | 2 | 2.37E+05 | 2.35E−04 | 9.89E−10 | 2.08E+05 | 1.30E−04 | 6.25E−10 |
| N30T | 1 | 2.20E+05 | 1.77E−04 | 8.05E−10 | 2.31E+05 | 2.87E−04 | 1.24E−09 |
|  | 2 | 2.01E+05 | 2.02E−04 | 1.00E−09 | 2.27E+05 | 2.82E−04 | 1.24E−09 |
| N30S * | 1 | 2.49E+05 | 1.16E−16 | 4.64E−22 | 2.54E+05 | 4.11E−18 | 1.62E−23 |
|  | 2 | 2.37E+05 | 3.71E−16 | 1.57E−21 | 2.37E+05 | 6.06E−17 | 2.55E−22 |
| wt | 1 | 2.38E+05 | 6.47E−04 | 2.72E−09 | 2.33E+05 | 7.72E−04 | 3.32E−09 |
|  | 2 | 2.26E+05 | 6.88E−04 | 3.05E−09 | 2.18E+05 | 7.91E−04 | 3.62E−09 |

* Due to slow dissociation rates, the off-rates and the dissociation constant contain a high degree of uncertainty.

TABLE 6

Kinetic affinity parameters of Trastuzumab variants similar to table 3. Here the samples are incubated at 40° in 40 mM Histidin, 150 mM NaCl, pH 6.0 for the same time intervals as before. Samples included are the resynthesized Trastuzumab (wt), the D98E T31V variant in the heavy and light chain, respectively (named clone 602. This was produced in CHO instead of HEK). Also the light chain variants N30S, and N30T (both have the D98E heavy chain variant)

| pH 6 | | t0 ka | t0 kd | t0 KD | t1 ka | t1 kd | t1 KD |
|---|---|---|---|---|---|---|---|
| 602 | 1 | 2.07E+05 | 9.33E−05 | 4.51E−10 | 2.30E+05 | 1.37E−04 | 5.94E−10 |
| CHO | 2 | 2.16E+05 | 1.97E−04 | 9.12E−10 | 2.16E+05 | 2.02E−04 | 9.32E−10 |
| N30T | 1 | 2.24E+05 | 2.45E−04 | 1.09E−09 | 2.03E+05 | 1.24E−04 | 6.10E−10 |
|  | 2 | 2.31E+05 | 2.71E−04 | 1.17E−09 | 1.93E+05 | 1.57E−04 | 8.13E−10 |
| N30S * | 1 | 2.56E+05 | 1.18E−17 | 4.62E−23 | 2.65E+05 | 2.77E−05 | 1.04E−10 |
|  | 2 | 2.48E+05 | 8.14E−06 | 3.28E−11 | 2.51E+05 | 4.23E−05 | 1.68E−10 |
| wt | 1 | 2.23E+05 | 7.43E−05 | 3.33E−10 | 2.22E+05 | 4.60E−04 | 2.07E−09 |
|  | 2 | 2.23E+05 | 7.98E−05 | 3.59E−10 | 2.21E+05 | 4.03E−04 | 1.82E−09 |

| pH 6 | | t2 ka | t2 kd | t2 KD | t3 ka | t3 kd | t3 KD |
|---|---|---|---|---|---|---|---|
| 602 | 1 | 2.19E+05 | 1.29E−04 | 5.87E−10 | 2.14E+05 | 1.50E−04 | 7.01E−10 |
| CHO | 2 | 2.07E+05 | 1.52E−04 | 7.31E−10 | 2.13E+05 | 1.60E−04 | 7.50E−10 |
| N30T | 1 | 2.11E+05 | 2.27E−04 | 1.08E−09 | 2.08E+05 | 2.01E−04 | 9.67E−10 |
|  | 2 | 2.05E+05 | 2.55E−04 | 1.24E−09 | 2.03E+05 | 1.98E−04 | 9.75E−10 |
| N30S * | 1 | 2.38E+05 | 8.97E−19 | 3.77E−24 | 2.36E+05 | 1.84E−05 | 7.80E−11 |
|  | 2 | 2.25E+05 | 4.30E−17 | 1.91E−22 | 2.33E+05 | 3.41E−05 | 1.46E−10 |
| wt | 1 | 2.31E+05 | 9.24E−04 | 4.00E−09 | 1.89E+05 | 9.91E−04 | 5.24E−09 |
|  | 2 | 2.20E+05 | 9.31E−04 | 4.24E−09 | 1.78E+05 | 9.95E−04 | 5.58E−09 |

* Due to slow dissociation rates, the off-rates and the dissociation constant contain a high degree of uncertainty.

TABLE 7

Kinetic affinity parameters of Trastuzumab variants similar to table 3. Here the samples are incubated at 40° in 40 mM Histidin, 150 mM NaCl, pH 7.4 for the same time intervals as before. Samples included are the resynthesized Trastuzumab (wt), the D98E T31V variant in the heavy and light chain, respectively (named clone 602. This was produced in CHO instead of HEK). Also the light chain variants N30S, and N30T (both have the D98E heavy chain variant)

|  |  | t0 | | | t1 | | |
|---|---|---|---|---|---|---|---|
| pH 7.4 | | ka | kd | KD | ka | kd | KD |
| 602 | 1 | 2.15E+05 | 1.23E−04 | 5.71E−10 | 2.32E+05 | 1.80E−04 | 7.78E−10 |
| CHO | 2 | 2.17E+05 | 2.08E−04 | 9.55E−10 | 2.19E+05 | 2.31E−04 | 1.06E−09 |
| N30T | 1 | 2.46E+05 | 2.19E−04 | 8.87E−10 | 2.15E+05 | 1.86E−04 | 8.65E−10 |
|  | 2 | 2.20E+05 | 2.30E−04 | 1.04E−09 | 2.00E+05 | 2.03E−04 | 1.02E−09 |
| N30S | 1 | 2.58E+05 | 1.35E−06 | 5.25E−12 | 2.60E+05 | 2.55E−05 | 9.82E−11 |
|  | 2 | 2.36E+05 | 2.24E−05 | 9.46E−11 | 2.49E+05 | 6.31E−18 | 2.53E−23 |
| wt | 1 | 2.25E+05 | 7.49E−05 | 3.33E−10 | 1.99E+05 | 8.80E−04 | 4.43E−09 |
|  | 2 | 2.12E+05 | 9.85E−05 | 4.65E−10 | 2.00E+05 | 8.78E−04 | 4.40E−09 |

|  |  | t2 | | | t3 | | |
|---|---|---|---|---|---|---|---|
| pH 7.4 | | ka | kd | KD | ka | kd | KD |
| 602 | 1 | 1.97E+05 | 1.05E−04 | 5.34E−10 | 2.02E+05 | 2.24E−04 | 1.11E−09 |
| CHO | 2 | 1.82E+05 | 1.33E−04 | 7.30E−10 | 2.00E+05 | 2.14E−04 | 1.07E−09 |
| N30T | 1 | 2.12E+05 | 2.64E−04 | 1.25E−09 | 1.94E+05 | 1.41E−04 | 7.26E−10 |
|  | 2 | 1.98E+05 | 2.84E−04 | 1.44E−09 | 1.73E+05 | 1.54E−04 | 8.87E−10 |
| N30S | 1 | 2.43E+05 | 7.28E−21 | 2.99E−26 | 2.37E+05 | 6.30E−05 | 2.66E−10 |
|  | 2 | 2.27E+05 | 1.24E−05 | 5.46E−11 | 2.21E+05 | 6.55E−05 | 2.97E−10 |
| wt | 1 | 1.64E+05 | 1.35E−03 | 8.27E−09 | 1.55E+05 | 1.79E−03 | 1.15E−08 |
|  | 2 | 1.67E+05 | 1.29E−03 | 7.72E−09 | 1.45E+05 | 1.63E−03 | 1.12E−08 |

* Due to slow dissociation rates, the off-rates and the dissociation constant contain a high degree of uncertainty.

Example 5: Binding of Trastuzumab and Trastuzumab Stabilization Variants after Stress to KPL-4 Cells Binding KPL-4 cells were harvested and resuspended in FACS buffer. 0.2 Mio cells were seeded into a 96 well round bottom plate. The plate was centrifuged at 400 g for 3 min to pellet the cells. The supernatant was removed and the cells were resuspended in 40 µl of the diluted antibodies. The plate was incubated for 30 min at 4° C. to allow binding of the antibodies. To remove unbound antibodies the cells were centrifuged again and washed twice with FACS buffer. To detect the antibodies the cells were resuspended in 12 µl diluted secondary goat anti-human Fc specific FITC-labeled secondary antibody (Jackson ImmunoResearch #109-096-098) and incubated again for 30 min at 4° C. Afterwards the cells were washed twice with FACS buffer, resuspended in 200 µl FACS buffer and the fluorescence was measured with BD CantoII.

ADCC

Target cells were harvested, washed, stained with calcein (Invitrogen), resuspended in AIM V® medium (Life Technologies), and plated at a concentration of $3 \times 10^4$ cells/well. The respective antibody dilutions were added in triplicates to the cells and incubated for 10 min before addition of the effector cells (peripheral blood mononuclear effector cells [PBMCs]). Effector (E) and target (T) cells were then incubated for the indicated time at 37° C. at the indicated E:T ratio (triplicates for all samples). After incubation the cells were washed once with PBS and then lysed with borate buffer. Calcein retention was measured in a Wallac Victor3 1420 Multilabel Counter. ADCC was calculated using the following formula:

$$\text{Percentage } ADCC = \left(\left[\frac{\text{sample release} - \text{spontaneous release}}{\text{maximal release} - \text{spontaneous release}}\right]\right) \times 100.$$

Spontaneous release, corresponding to target cells incubated with effector cells without antibody, was defined as 0% cytotoxicity, and maximal release (target cells lysed with 1% Triton X-100) was defined as 100% cytotoxicity. The average percentage of ADCC and standard deviations of the triplicates of each experiment were calculated.

Results are shown in FIGS. 7A and 7B to 9.

Example 6: Generation of Herceptarg CrossMab and Framework Grafting on Novel LCO6 Based Framework to Achieve Less Mispairing Gene Synthesis Desired gene segments were prepared by Geneart AG (Regensburg, Germany) from synthetic oligonucleotides and PCR products by automated gene synthesis. The gene segments encoding heavy or light chains with C-terminal attachment of scFv antibody fragments, "knobs-into-hole" antibody heavy chains carrying S354C and T366W mutations and "knobs-into-hole" heavy chains carrying Y349C, T366S, L368A and Y407V mutations in the CH3 domain in combination with unmodified VH domains, crossed C kappa domains or scFab antibody fragments as well as unmodified antibody light chains or CH1 domain exchanged light chains are flanked by singular restriction endonuclease cleavage sites (BamHI-XbaI, BamHI-XmnI or BamHI-KpnI) and were cloned into pGA18 (ampR) plasmids. The plasmid DNA was purified from transformed bacteria and concentration determined by UV spectroscopy. The DNA sequence of the subcloned gene fragments was confirmed by DNA sequencing. All constructs were designed with a 5'-end DNA sequence coding for a leader peptide (MGWSCIILFL-VATATGVHS), which targets proteins for secretion in eukaryotic cells.

Construction of the Expression Plasmids

The expression vector that was used for the construction of all "knobs-into-hole" heavy chain as well as antibody light chain encoding expression plasmids comprises the following elements:
- a hygromycin resistance gene as a selection marker,
- an origin of replication, oriP, of Epstein-Barr virus (EBV),
- an origin of replication from the vector pUC18 which allows replication of this plasmid in *E. coli*
- a beta-lactamase gene which confers ampicillin resistance in *E. coli*,
- the immediate early enhancer and promoter from the human cytomegalovirus (HCMV),
- the human 1-immunoglobulin polyadenylation ("poly A") signal sequence, and
- unique BamHI and XbaI restriction sites.

The immunoglobulin genes comprising heavy or light chains with C-terminal attachment of scFv antibody fragments, "knobs-into-hole" heavy chains with unmodified VH domains, crossed C kappa domains or scFab fragments as well as unmodified light chains or CH1 domain exchanged light chains were prepared by gene synthesis and cloned into pGA18 (ampR) plasmids as described. The pG18 (ampR) plasmids carrying the synthesized DNA segments and the expression vector were digested with BamHI and XbaI, BamHI and XmnI or BamHI and KpnI restriction enzymes (Roche Molecular Biochemicals) and subjected to agarose gel electrophoresis. Purified heavy or light chains with C-terminal attachment of scFv antibody fragments, "knobs-into-hole" heavy and unmodified or domain exchanged light chain encoding DNA segments were then ligated to the isolated expression vector BamHI/XbaI, BamHI/XmnI or BamHI/KpnI fragment resulting in the final expression vectors. The final expression vectors were transformed into *E. coli* cells, expression plasmid DNA was isolated (Miniprep) and subjected to restriction enzyme analysis and DNA sequencing. Correct clones were grown in 150 ml LB-Amp medium, again plasmid DNA was isolated (Maxiprep) and sequence integrity confirmed by DNA sequencing.

Transient Expression of Bispecific Antibodies in HEK293 Cells

Recombinant bispecific antibodies were expressed by transient transfection of human embryonic kidney 293-F cells using the FreeStyle™ 293 Expression System according to the manufacturer's instruction (Invitrogen, USA). Briefly, suspension FreeStyle™ 293-F cells were cultivated in FreeStyle™ 293 Expression medium at 37° C./8% $CO_2$ and the cells were seeded in fresh medium at a density of $1\times10^6$ viable cells/ml one day before transfection. For transfection, DNA was prepared in 10 ml Dulbecco's PBS (PAA, Austria) using 162.5 µl of 293-Free™ Transfection Reagent (Merck, USA) and 125 µg of heavy with N-terminal attachment of scFab encoding DNA in a plasmid ratio of 1:1 with "Knobs-into-hole" heavy chain 1 and 2 and light chain plasmid DNA in a 1:1:1 molar ratio in 250 ml final transfection volume. For transfection of Cross Mabs, a plasmid ratio of 1:1:1:1, 1:1:1:2, 1:1:1:4, 1:1:1:8 of "Knobs-into-hole" heavy chain 1:unmodified light chain:C kappa domain exchanged "Knobs-into-hole" heavy chain 2:CH1 domain exchanged light chain was prepared. The CH1-VL light chain plasmid ration was used at 1×, 2×, 4× and 8× molar ratios to assess the optimization of chain pairing using a combination of CE-SDS and Q-TOF spectrometry. Antibody containing cell culture supernatants were harvested 7 days after transfection by centrifugation at 14000 g for 30 minutes and filtered through a sterile filter (0.22 µm). Supernatants were stored at −20° C. until purification. The sequences of the resulting antibodies are shown below in table 8.

Preparation of the Glycoengineered Derivatives of Bispecific <Her2GlyMab> Antibodies Glycoengineered derivatives of bispecific <Her2GlyMab> antibodies were produced by co-transfecting HEK293-EBNA cells with the mammalian antibody heavy and light chain expression vectors using a calcium phosphate-transfection approach. Exponentially growing HEK293-EBNA cells were transfected by the calcium phosphate method. For the production of the glycoengineered antibody, the cells were co-transfected with a plasmid for a fusion GnTIII polypeptide expression and a second plasmid for mannosidase II expression, respectively. Plasmid ratios of bispecific antibodies were added as described in the material and methods section above. Cells were grown as adherent monolayer cultures in T flasks using DMEM culture medium supplemented with 10% FCS, and were transfected when they were between 50 and 80% confluent. For the transfection of a T75 flask, 7.5 (to 8) million cells were seeded 24 hours before transfection in ca 14 ml DMEM culture medium supplemented with FCS (at 10% V/V final), (eventually 250 µg/ml neomycin) and cells were placed at 37° C. in an incubator with a 5% CO2 atmosphere overnight. For each T75 flask to be transfected, a solution of DNA, CaCl2 and water was prepared by mixing 47 µg total plasmid vector DNA, 235 µl of a 1M CaCl2 solution, and adding water to a final volume of 469 To this solution, 469 µl of a 50 mM HEPES, 280 mM NaCl, 1.5 mM Na2HPO4 solution at pH 7.05 were added, mixed immediately for 10 sec and left to stand at room temperature for 20 sec. The suspension was diluted with ca. 12 ml of DMEM supplemented with 2% FCS, and added to the T75 in place of the existing medium. The cells were incubated at 37° C., 5% CO2 for about 17 to 20 hours, then medium was replaced with ca. 12 ml DMEM, 10% FCS. The conditioned culture medium was harvested 5 to 7 days post-transfection centrifuged for 5 min at 210-300 *g, sterile filtered through a 0.22 µm filter (or alternatively centrifuged for 5 min at 1200 rpm, followed by a second centrifugation for 10 min at 4000 rpm) and kept at 4° C.

Glycoengineered antibodies were purified and formulated as described above for the non-glycoengineered antibodies. The oligosaccharides attached to the Fc region of the antibodies were analysed as described below to determine the amount of fucose.

Framework Grafting

Rationale: Similar framework of trastuzumab and pertuzumab allows mis-pairing of light chains: Both Trastuzumab and Pertuzumab have a $V_H III V_L kI$ framework and therefore the light chain interface affinity to both heavy chains is identical.

In order to avoid mispairing of light chains in the crossMab Herceptarg bispecific antibody, the Trastuzumab framework of "CrossMabXPer Her2GlyMab" was exchanged with the framework of the non-related antibody LC06. Trastuzumab is related to germlines hVH3_66 and hVK1D_39 whereas the antibody LCO6 corresponds to germlines hVbase_VH1_1 germline and hVL_3, respectively. Pertuzumab is related to hVH3_23 and hVK1D_13 showing a very similar framework system compared to Trastuzumab.

Both germline acceptor frameworks of LC06 are different from the Trastuzumab framework, especially, the LC06 lambda light chain, compared to the Trastzumab kappa light chain. The antibody Fab crystal structure of Trastuzumab has been superimposed and the compatibility of the frameworks have been structrally evaluated. CDRI, II and III of the Trastuzumab light chain were grafted onto the new Lambda framework of LC06. Mutations included were D98E and N30S, the N30S was used in favour of T31V because of the increase in affinity to the Her2 extracellular domain with the N30S modification. It was thought that any reduction of the Kd caused by the CDR grafting could be compensated by the use of the N30S mutation. Some accomodations in the acceptor frameworks were required in order to get the CDRs in their biological active conformation; for example A (LCO6 lambda) at the Kabat position 71 of the light chain has been backmutated to F(Trastuzumab kappa). The original VHIII-VLkI (Kappa I family) framework of Pertuzumab was maintained. The resulting bispecific antibody is depicted as "CrossMab-CDRG Her2GlyMab", with sequences as shown in Table 8 below.

TABLE 8

Sequences of Herceptarq CrossMab bispecific antibodies.

| Construct | SEQ ID NO | Sequence |
|---|---|---|
| *OAscFab1 Her2GlyMab* | | |
| scFab Trastuzumab heavy chain 1 | 133 | diqmtqspsslsasvgdrvtitcrasqdvnvavawyqqkpgkapklliysasflysgvpsrfsg srsgtdftltisslqpedfatyycqqhyttpptfgqgtkveikrtvaapsvfifppsdeqlksgtas vvcllnnfypreakvqwkvdnalqsgnsqesvteqdskdstyslsstltlskadyekhkvyac evthqglsspvtksfnrgecggggsggggsggggsggggsggggsggggsggevqlvesgg glvqpggslrlscaasgfnikdtyihwvrqapgkglewvariyptngytryadsvkgrftisadt skntaylqmnslraedtavyycsrwggegfyamdywgqgtlvtvssastkgpsvfplapssk stsggtaalgclvkdyfpepvtvswnsgaltsgvhtfpavlqssglyslssvvtvpssslgtqtyi cnvnhkpsntkvdkkvepkscdkthtcppcpapellggpsvflfppkpkdtlmisrtpevtcv vvdvshedpevkfnwyvdgvevhnaktkpreeqynstyrvvsvltvlhqdwlngkeykck vsnkalpapiektiskakgqprepqvytlppcrdeltknqvslwclvkgfypsdiavewesng qpennykttppvldsdgsfflyskltvdksrwqqgnvfscsvmhealhnhytqkslslspgk |
| Pertuzumab heavy chain 2 | 134 | evqlvesgggglvqpggslrlscaasgftftdytmdwvrqapgkglewvadvnpnsggsiyn qrfkgrftlsvdrskntlylqmnslraedtavyycarnlgpsfyfdywgqgtlvtvssastkgps vfplapssktsggtaalgclvkdyfpepvtvswnsgaltsgvhtfpavlqssglyslssvvtvp ssslgtqtyicnvnhkpsntkvdkkvepkscdkthtcppcpapellggpsvflfppkpkdtlm isrtpevtcvvvdvshedpevkfnwyvdgvevhnaktkpreeqynstyrvvsyltvlhqdwl ngkeykckvsnkalpapiektiskakgqprepqvctlppsrdeltknqvslscavkgfypsdi avewesngqpennykttppvldsdgsfflvskltvdksrwqqgnvfscsvmhealhnhytq kslslspgk |
| Pertuzumab light chain 1 | 135 | diqmtqspsslsasvgdrytitckasqdvsigvawyqqkpgkapklliysasyrytgvpsrfsg sgsgtdftltisslqpedfatyycqqyyiypytfgqgtkveikrtvaapsvfifppsdeqlksgtas vvcllnnfypreakvqwkvdnalqsgnsqesvteqdskdstyslsstltlskadyekhkvyac evthqglsspytksfnrgec |
| *OAscFab2 Her2GlyMab* | | |
| Pertuzumab heavy chain 1 | 136 | evqlvesgggglvqpggslrlscaasgftftdytmdwvrqapgkglewvadvnpnsggsiyn qrfkgrftlsydrskntlylqmnslraedtavyycarnlgpsfyfdywgqgtlvtvssastkgps vfplapssktsggtaalgclvkdyfpepvtvswnsgaltsgvhtfpavlqssglyslssvvtvp ssslgtqtyicnvnhkpsntkvdkkvepkscdkthtcppcpapellggpsvflfppkpkdtlm isrtpevtcvvvdvshedpevkfnwyvdgvevhnaktkpreeqynstyrvvsvltvlhqdwl ngkeykckvsnkalpapiektiskakgqprepqvctlppsrdeltknqvslscavkgfypsdi avewesngqpennykttppvldsdgsfflvskltvdksrwqqgnvfscsvmhealhnhytq kslslspgk |
| Pertuzumab light chain 1 | 137 | diqmtqspsslsasvgdrvtitckasqdvsigvawyqqkpgkapklliysasyrytgvpsrfsg sgsgtdftltisslqpedfatyycqqyyiypytfgqgtkveikrtvaapsvfifppsdeqlksgtas vvcllnnfypreakvqwkvdnalqsgnsqesvteqdskdstyslsstltlskadyekhkvyac evthqglsspvtksfnrgec |
| scFab Trastuzumab heavy chain 2 | 138 | evqlvesgggglvqpggslrlscaasgfnikdtyihwvrqapgkglewvariyptngytryads vkgrftisadtskntaylqmnslraedtavyycsrwggegfyamdywgqgtlvtvssastkg psvfplapssktsggtaalgclvkdyfpepvtvswnsgaltsgvhtfpavlqssglyslssvvt vpssslgtqtyicnvnhkpsntkvdkkvepkscdkthtcppcpapellggpsvflfppkpkdt lmisrtpevtcvvvdvshedpevkfnwyvdgvevhnaktkpreeqynstyrvvsvltvlhq dwlngkeykckvsnkalpapiektiskakgqprepqvytlppcrdeltknqvslwclvkgfy psdiavewesngqpennykttppvldsdgsfflyskltvdksrwqqgnyfscsvmhealhn hytqkslslspgkggggsggggsggggsggggsggggsggggsggdiqmtqspsslsasvg drvtitcrasqdvnvavawyqqkpgkapklliysasflysgvpsrfsgsrsgtdftltisslqped fatyycqqhyttpptfgqgtkveikrtvaapsvfifppsdeqlksgtasvvcllnnfypreakvq wkvdnalqsgnsqesvteqdskdstyslsstltlskadyekhkvyacevthqglsspvtksfnr gec |
| *OAscFabPer1 Her2GlyMab* | | |
| scFab Pertuzumab heavy chain 1 | 139 | evqlvesgggglvqpggslrlscaasgftftdytmdwvrqapgkglewvadvnpnsggsiyn qrfkgrftlsvdrskntlylqmnslraedtavyycarnlgpsfyfdywgqgtlvtvssastkgps vfplapssktsggtaalgclvkdyfpepvtvswnsgaltsgvhtfpavlqssglyslssvvtyp ssslgtqtyicnvnhkpsntkvdkkvepkscdkthtcppcpapellggpsvflfppkpkdtlm isrtpevtcvvvdvshedpevkfnwyydgvevhnaktkpreeqynstyrvvsvltvlhqdwl |

TABLE 8-continued

Sequences of Herceptarg CrossMab bispecific antibodies.

| Construct | SEQ ID NO | Sequence |
|---|---|---|
| | | ngkeykckvsnkalpapiektiskakgqprepqvctlppsrdeltknqvslscavkgfypsdi aveweesngqpennykttppvldsdgsfflyskltvdksrwqqgnvfscsvmhealhnhytq kslslspgkggggsggggsggggsggggsggggsggggsggdiqmtqspsslsasvgdrvt itckasqdvsigvawyqqkpgkapklliysasyrytgvpsrfsgsgsgtdftltisslqpedfaty ycqqyyiypytfgqgtkveikrtvaapsvfifppsdeqlksgtasvvcllnnfypreakvqwk vdnalqsgnsqesvteqdskdstyslsstltlskadyekhkvyaceythqglsspvtksfnrgec |
| Trastuzumab heavy chain 2 | 140 | evqlvesgggglyqpggslrlscaasgfnikdtyihwvrqapgkglewvariyptngytryads vkgrftisadtskntaylqmnslraedtavyycsrwggegfyamdywgqgtlvtvssastkg psvfplapssksstsggtaalgclvkdyfpepvtvswnsgaltsgvhtfpavlqssglyslssvvt vpssslgtqtyicnvnhkpsntkvdkkvepkscdkthtcppcpapellggpsvflfppkpkdt lmisrtpevtcvvvdvshedpevkfnwyvdgvevhnaktkpreeqynstyrvvsvltvlhq dwlngkeykckvsnkalpapiektiskakgqprepqvytlpperdeltknqvslwclvkgfy psdiaveweesngqpennykttppvldsdgsfflyskltvdksrwqqgnvfscsvmhealhn hytqkslslspgk |
| Trastuzumab light chain 2 | 141 | diqmtqspsslsasvgdrvtitcrasqdvnavawyqqkpgkapklliysasflysgvpsrfsg srsgtdftltisslqpedfatyycqqhyttpptfgqgtkveikrtvaapsyfifppsdeqlksgtas vvcllnnfypreakvqwkydnalqsgnsqesvteqdskdstyslsstltlskadyekhkvyac evthqglsspvtksfnrge |

OAscFabPer2 Her2GlyMab

| Trastuzumab heavy chain 1 | 142 | evqlvesgggglvqpggslrlscaasgfnikdtyihwvrqapgkglewvariyptngytryads vkgrftisadtskntaylqmnslraedtavyycsrwggegfyamdywgqgtlvtvssastkg psvfplapssksstsggtaalgclvkdyfpepvtvswnsgaltsgvhtfpavlqssglyslssvvt vpssslgtqtyicnvnhkpsntkvdkkvepkscdkthtcppcpapellggpsvflfppkpkdt lmisrtpevtcvvvdvshedpevkfnwyvdgvevhnaktkpreeqynstyrvvsvltvlhq dwlngkeykckvsnkalpapiektiskakgqprepqvytlpperdeltknqvslwclvkgfy psdiaveweesngqpennykttppvldsdgsfflyskltvdksrwqqgnvfscsvmhealhn hytqkslslspgk |
| Trastuzumab light chain 1 | 143 | diqmtqspsslsasvgdrvtitcrasqdvnyavawyqqkpgkapklliysasflysgvpsrfsg srsgtdftltisslqpedfatyycqqhyttpptfgqgtkveikrtvaapsvfifppsdeqlksgtas vvcllnnfypreakvqwkvdnalqsgnsqesvteqdskdstyslsstltlskadyekhkvyac evthqglsspvtksfnrgec |
| scFab Pertuzumab heavy chain 2 | 144 | evqlvesgggglvqpggslrlscaasgftftdytmdwvrqapgkglewvadvnpnsggsiyn qrfkgrftlsvdrskntlylqmnslraedtavyycarnlgpsfyfdywgqgtlvtvssastkgps vfplapssksstsggtaalgclvkdyfpepvtvswnsgaltsgvhtfpavlqssglyslssvvtvp ssslgtqtyicnvnhkpsntkvdkkvepkscdkthtcppcpapellggpsvflfppkpkdtlm isrtpevtcvvvdvshedpevkfnwyvdgvevhnaktkpreeqynstyrvvsvltvlhqdwl ngkeykckvsnkalpapiektiskakgqprepqvctlppsrdeltknqvslscavkgfypsdi aveweesngqpennykttppvldsdgsfflyskltvdksrwqqgnvfscsvmhealhnhytq kslslspgkggggsggggsggggsggggsggggsggggsggdiqmtqspsslsasvgdrvt itckasqdvsigvawyqqkpgkapklliysasyrytgvpsrfsgsgsgtdftltisslqpedfaty ycqqyyiypytfgqgtkveikrtvaapsvfifppsdeqlksgtasvvcllnnfypreakvqwk vdnalqsgnsqesvteqdskdstyslsstltlskadyekhkvyacevthqglsspvtksfnrgec |

CrossMab-XPer Her2GlyMab

| XPertuzumab heavy chain | 109 | evqlvesgggglvqpggslrlscaasgftftdytmdwvrqapgkglewvadvnpnsggsiyn qrfkgrftlsvdrskntlylqmnslraedtavyycarnlgpsfyfdywgqgtlvtvssasvaaps vfifppsdeqlksgtasvvcllnnfypreakvqwkvdnalqsgnsqesvteqdskdstyslsst ltlskadyekhkvyacevthqglsspvtksfnrgecdkthtcppcpapellggpsvflfppkpk dtlmisrtpevtcvvvdvshedpevkfnwyydgvevhnaktkpreeqynstyrvvsvltvlh qdwlngkeykckvsnkalpapiektiskakgqprepqvytlppcrdeltknqvslwclvkgf ypsdiaveweesngqpennykttppvldsdgsfflyskltvdksrwqqgnvfscsvmhealh nhytqkslslspgk |
| XPertuzumab light chain | 110 | diqmtqspsslsasvgdrvtitckasqdvsigvawyqqkpgkapklliysasyrytgvpsrfsg sgsgtdftltisslqpedfatyycqqyyiypytfgqgtkveikssastkgpsvfplapssksstsggt aalgclvkdyfpepvtvswnsgaltsgvhtfpavlqssglyslssvvtypssslgtqtyicnvnh kpsntkvdkkvepksc |
| Trastuzumab heavy chain (VH$_{D98E}$ CH1) | 96 | evqlvesgggglvqpggslrlscaasgfnikdtyihwvrqapgkglewyariyptngytryads vkgrftisadtskntaylqmnslraedtavyycsrwggegfyamdywgqgtlvtvssastkg psvfplapssksstsggtaalgclvkdyfpepvtvswnsgaltsgvhtfpavlqssglyslssvvt vpssslgtqtyicnvnhkpsntkvdkkvepkscdkthtcppcpapellggpsvflfppkpkdt lmisrtpevtcvvvdvshedpevkfnwyvdgvevhnaktkpreeqynstyrvvsvltvlhq dwlngkeykckvsnkalpapiektiskakgqprepqvctlppsrdeltknqvslscavkgfyp sdiaveweesngqpennykttppvldsdgsfflyskltvdksrwqqgnvfscsvmhealhnh ytqkslslspgk |

TABLE 8-continued

Sequences of Herceptarg CrossMab bispecific antibodies.

| Construct | SEQ ID NO | Sequence |
|---|---|---|
| Trastuzumab light chain (VL$_{T31V}$ CL) | 86 | diqmtqspsslsasvgdrvtitcrasqdvnvavawyqqkpgkapklliysasflysgvpsrfsg srsgtdftltisslqpedfatyycqqhyttpptfgqgtkveikrtvaapsvfifppsdeqlksgtas vvcllnnfypreakvqwkydnalqsgnsqesvteqdskdstyslsstltlskadyekhkvyac evthqglsspvtksfnrgec |

CrossMab-XTra Her2GlyMab

| Construct | SEQ ID NO | Sequence |
|---|---|---|
| Pertuzumab heavy chain | 119 | evqlvesggglvqpggslrlscaasgftftdytmdwvrqapgkglewvadvnpnsggsiyn qrfkgrftlsvdrskntlylqmnslraedtavyycarnlgpsfyfdywgqgtlvtyssasvaaps vfifppsdeqlksgtasvvcllnnfypreakvqwkvdnalqsgnsqesvteqdskdstylsst ltlskadyekhkvyacevthqglsspvtksfurgecdkthtcppcpapellggpsvflfppkpk dtlmisrtpevtcvvvdvshedpevkfnwyvdgvevhnaktkpreeqynstyrvvsvltvlh qdwlngkeykckvsnkalpapiektiskakgqprepqvctlppsrdeltknqvslscavkgfy psdiavewesngqpennykttppvldsdgsfflvskltvdksrwqqgnvfscsvmhealhn hytqkslslspgk |
| Pertuzumab light chain | 120 | diqmtqspsslsasvgdrvtitckasqdvsigvawyqqkpgkapklliysasyrytgvpsrfsg sgsgtdftltisslqpedfatyycqqyyiypytfgqgtkveikrtvaapsvfifppsdeqlksgtas vvcllnnfypreakvqwkvdnalqsgnsqesvteqdskdstyslsstltlskadyekhkvyac evthqglsspvtksfnrgec |
| XTrastuzumab heavy chain | 121 | evqlvesgggvlqpggslrlscaasgfnikdtyihwvrqapgkglewvariyptngytryads vkgrftisadtskntaylqmnslraedtavyycsrwggegfyamdywgqgtlvtvssastkg psvfplapssksstsggtaalgclvkdyfpepvtvswnsgaltsgvhtfpavlqssglyslssvvt vpsssslgtqtyicnvnhkpsntkvdkkvepkscdkthtcppcpapellggpsvflfppkpkdt lmisrtpevtcvvvdvshedpevkfnwyvdgvevhnaktkpreeqynstyrvvsvltvlhq dwlngkeykckvsnkalpapiektiskakgqprepqvytlppcrdeltknqvslwclvkgfy psdiavewesngqpennykttppvldsdgsfflyskltvdksrwqqgnvfscsvmhealhn hytqkslslspgk |
| XTrastuzumab light chain | 122 | diqmtqspsslsasvgdrvtitcrasqdvnvavawyqqkpgkapklliysasflysgvpsrfsg srsgtdftltisslqpedfatyycqqhyttpptfgqgtkveikssastkgpsvfplapssksstsggta algclvkdyfpepvtvswnsgaltsgvhtfpavlqssglyslssvvtvpsssslgtqtyicnvnhk psntkvdkkvepksc |

Optimized Trastuzumab sequences: CrossMab-XTra Her2GlyMab and CrossMab-XPer Her2GlyMab

| Construct | SEQ ID NO | Sequence |
|---|---|---|
| Trastuzumab VH (D98E) | 117 | evqlvesgggvlqpggslrlscaasgfnikdtyihwvrqapgkglewvariyptngytryads vkgrftisadtskntaylqmnslraedtavyycsrwggegfyamdywgqgtlvtyss |
| Trastuzumab CH1 | 115 | astkgpsvfplapssksstsggtaalgclvkdyfpepvtvswnsgaltsgvhtfpavlqssglysl ssvvtypssslgtqtyicnvnhkpsntkvdkkvepkscdkth |
| Trastuzumab VL (T31V) | 118 | diqmtqspsslsasvgdrvtitcrasqdvnvavawyqqkpgkapklliysasflysgvpsrfsg srsgtdftltisslqpedfatyycqqhyttpptfgqgtkveikr |
| Trastuzumab CL | 116 | tvaapsvfifppsdeqlksgtasvvcllnnfypreakvqwkvdnalqsgnsqesvteqdskds tyslsstltlskadyekhkvyacevthqglsspvtksfnrgec |
| Trastuzumab VH CDR1 | 20 | gfnikdtyih |
| Trastuzumab VH CDR2 | 29 | riyptngytryadsvkg |
| Trastuzumab VH CDR3 | 79 | wggegfyamdy |
| Trastuzumab VL CDR1 | 104 | rasqdvnvava |
| Trastuzumab VL CDR2 | 18 | sasflys |
| Trastuzumab VL CDR3 | 19 | qqhyttppt |

CrossMab-CDRG Her2GlyMab

| Construct | SEQ ID NO | Sequence |
|---|---|---|
| XPertuzumab heavy chain (VHCL) | 109 | evqlvesgggvlqpggslrlscaasgftftdytmdwvrqapgkglewvadvnpnsggsiyn qrfkgrftlsvdrskntlylqmnslraedtavyycarnlgpsfyfdywgqgtlvtyssasvaaps vfifppsdeqlksgtasvvcllnnfypreakvqwkvdnalqsgnsqesvteqdskdstylsst ltlskadyekhkvyacevthqglsspvtksfnrgecdkthtcppcpapellggpsvflfppkpk dtlmisrtpevtcvvvdvshedpevkfnwyvdgvevhnaktkpreeqynstyrvvsvltvlh qdwlngkeykckvsnkalpapiektiskakgqprepqvytlpperdeltknqvslwclvkgf |

TABLE 8-continued

Sequences of Herceptarg CrossMab bispecific antibodies.

| Construct | SEQ ID NO | Sequence |
|---|---|---|
| | | ypsdiavewesngqpennykttppvldsdgsfflyskltvdksrwqqgnvfscsvmhealh nhytqkslslspgk |
| Pertuzumab light chain (VLCH1) | 110 | diqmtqspsslsasvgdrvtitckasqdvsigvawyqqkpgkapklliysasyrytgvpsrfsg sgsgtdftltisslqpedfatyycqqyyiypytfgqgtkveikssastkgpsvfplapssktsggt aalgclvkdyfpepvtvswnsgaltsgvhtfpavlqssglyslssvvtvpssslgtqtyicnvnh kpsntkvdkkvepksc |
| Trastuzumab CDRG heavy chain (VHCH1) | 111 | qvqlvqsgaevkkpgasvkvsckasgfnikdtyihwvrqapgqglewmgriyptngytrya qkfqgrvtmtrdtsistaymelsrlrsddtavyycsrwggegfyamdywgqgtmvtvssast kgpsvfplapssktsggtaalgclvkdyfpepvtvswnsgaltsgvhtfpavlqssglyslssv vtvpssslgtqtyicnvnhkpsntkvdkkvepkscdkthtcppcpapellggpsvflfppkpk dtlmisrtpevtcvvvdvshedpevkfnwyvdgvevhnaktkpreeqynstyrvvsvltvlh qdwlngkeykckvsnkalpapiektiskakgqprepqvctlppsrdeltknqvslscavkgfy psdiavewesngqpennykttppvldsdgsfflvskltvdksrwqqgnvfscsvmhealhn hytqkslslspgk |
| Trastuzumab CDRG light chain (VLCL) | 112 | diqltqppsvsvapgqtaritcgasqdvstavawyqqkpgqapvlvvysasflysgipsrfsgs rsgtdftltisrveagdeadyycqqhyttpptfgtgtkvtvlrtvaapsvfifppsdeqlksgtasv vcllnnfypreakvqwkvdnalqsgnsqesvteqdskdstyslsstltlskadyekhkvyace vthqglsspvtksfnrgec |
| Trastuzumab CDRG VH (D98E, CDRG) | 105 | evqlvqsgaevkkpgasvkvsckasgfnikdtyihwvrqapgqglewmgriyptngytrya qkfqgrvtmtrdtsistaymelsrlrsddtavyycsrwggegfyamdywgqgtmvtvss |
| Trastuzumab CH1 | 115 | astkgpsvfplapssktsggtaalgclvkdyfpepvtvswnsgaltsgvhtfpavlqssglysl ssvvtvpssslgtqtyicnvnhkpsntkvdkkvepkscdkth |
| Trastuzumab CDRG VL (N30T, CDRG) | 106 | diqltqppsvsvapgqtaritcgasqdvstavawyqqkpgqapvlvvysasflysgipsrfsgs rsgtdftltisrveagdeadyycqqhyttpptfgtgtkvtvlr |
| Trastuzumab CL | 116 | tvaapsvfifppsdeqlksgtasvvcllnnfypreakvqwkvdnalqsgnsqesvteqdskds tyslsstltlskadyekhkvyacevthqglsspvtksfnrgec |
| Trastuzumab CDRG VH CDR1 | 20 | gfnikdtyih |
| Trastuzumab CDRG VH CDR2 | 108 | riyptngytryaqkfqg |
| Trastuzumab CDRG VH CDR3 | 79 | wggegfyamdy |
| Trastuzumab CDRG VL CDR1 | 107 | gasqdvstava |
| Trastuzumab CDRG VL CDR2 | 18 | sasflys |
| Trastuzumab CDRG VL CDR3 | 19 | qqhyttppt |

Pertuzumab sequences in CrossMab-CDRG Her2GlyMab, CrossMab-XTra Her2GlyMab and CrossMab-XPer Her2GlyMab: see Pertuzumab wt (parent) sequences Table 32

Purification of Bispecific Antibodies

Bispecific antibodies were purified from cell culture supernatants by affinity chromatography using MabSelect-Sure-Sepharose™ (GE Healthcare, Sweden) and Superdex 200 size exclusion (GE Healthcare, Sweden) chromatography. Briefly, sterile filtered cell culture supernatants were captured on a MabSelect SuRe resin equilibrated with PBS buffer (10 mM $Na_2HPO_4$, 1 mM $KH_2PO_4$, 137 mM NaCl and 2.7 mM KCl, pH 7.4), washed with equilibration buffer and eluted with 25 mM sodium citrate at pH 3.0. The eluted protein fractions were pooled, neutralized with 2M Tris, pH 9.0 and further purified by size exclusion chromatography using a Superdex 200 26/60 GL (GE Healthcare, Sweden) column equilibrated with 20 mM histidine, 140 mM NaCl, pH 6.0. Size exclusion chromatography fractions were analysed by CE-SDS (Caliper Life Science, USA) and bispecific antibody containing fractions were pooled and stored at −80° C.

Analysis of Purified Proteins

The protein concentration of purified protein samples was determined by measuring the optical density (OD) at 280 nm, using the molar extinction coefficient calculated on the basis of the amino acid sequence. Purity, antibody integrity and molecular weight of bispecific and control antibodies were analyzed by CE-SDS using microfluidic LABCHIP® technology (Caliper Life Science, USA). 5 µl of protein solution was prepared for CE-SDS analysis using the HT Protein Express Reagent Kit according manufacturer's instructions and analysed on LabChip® GXII system using a HT Protein Express Chip. Data were analyzed using LABCHIP® GX Software version 3.0.618.0. The aggregate content of bispecific and control antibody samples was analyzed by high-performance SEC using a SUPERDEX® 200 analytical size-exclusion column (GE Healthcare, Sweden) in 200 mM $KH_2PO_4$, 250 mM KCl, pH 7.0 running buffer at 25° C. 25 µg protein were injected on the column at a flow rate of 0.5 ml/min and eluted isocratic over 50 minutes.

Mass Spectrometry

The integrity of the amino acid backbone of reduced bispecific antibody light and heavy chains was verified by NanoElectrospray Q-TOF mass spectrometry after removal of N-glycans by enzymatic treatment with Peptide-N-Glycosidase F (Roche Molecular Biochemicals). The amount of heavy and light chain mis-pairing was also quantified.

Surface Plasmon Resonance

Instrument:
  BIAacore T100 (GE Healthcare)
  Software:
    BIACORE® T100 Control, Version 2.02/2.03
    BIACORE® T100 Evaluation, Version 2.02/2.03
    BIACORE® B3000 (BIACORE®)
  Software:
    BIACORE® B3000 Control, Version 4.1.2
    BIAEvaluation, Version 4.1.1
Assayformat Chip: CM5-Chip Kinetic constants and resulting affinities of <Her2GlyMab>-molecules were measured for both "Trastuzumab"- and "Pertuzumab"-functionalities respecitively. These two functionalities were distinguished via pre-complexation of Her2 with either amine coupled parental MAb "Trastuzumab" (FC1/2) or "Pertuzumab" FC3/4). Complex formation of parental MAb and Her2 commensed after injection of Her2 ECD.

As a consequence of pre-complexed parental MAb "Trastuzumab"/Her2 all "Trastuzumab"-binding sites are saturated, but all "Pertuzumab"-binding sites are available and vice versa. Finally the binding of the "<Her2GlyMab>"-molecules to be analyzed was measured via injections using increasing concentrations with each cycle. Association and dissociation observed were calculated with a Langmuir 1:1 binding model. To minimize dissociation of Her2 during the measurements, the kinetic constants were measured at T=25° C.

Amine Coupling of Capture Molecules

Standard amine coupling on flow cells 1 to 4 according to the manufacturer's instructions: CM5 Chip, T=25° C., running buffer: HBS—N buffer, activation by mixture of EDC/NHS, aimed at 800 RU; the parental Abs "Trastuzumab" or "Pertuzumab" were diluted in coupling buffer sodium acetate, pH 4.5, c=2-3 µg/mL; finally remaining activated carboxyl groups were blocked by injection of 1 M Ethanolamine Chip surface on flow cell 1 and 3 (with either amine coupled parental mAb "Trastuzumab" or "Pertuzumab") were used as reference control surface for correction of possible buffer-effects or non-specific binding.

Kinetic Characterization of <Her2GlyMab> Molecules at 25° C.

Running buffer: PBS

All samples were diluted with running buffer+1 mg/mL BSA.

Capturing of HER2 ECD on flow cells 2 and 4: c=100 nM, flow 5 µl/min, time 120 sec. Analyte samples: A classical concentration series of the <Her2GlyMab>-molecules were analyzed at five concentrations (c=300, 100, 33.33, 11.11 and 3.7 nM.) at a flow rate of 50 µl/min was injected. Singles for each concentration, one as a duplicate; association time: 180 sec., dissociation time: 900 sec.

Final regeneration was performed after each cycle using 10 mM Glycin pH 2.5 for amine coupled Mab "Trastuzumab" and 25 mM NaOH for amine coupled Mab "Pertuzumab", contact time each 60 sec, flow rate 30 µl/min.

Kinetic parameters were calculated by using double referencing (control reference: binding of analyte to Mabs Trastuzumab and Pertuzumab respectively; Flow Cell: 1 respectively 3), concentration "0" used as the blank. Calculations were performed with model 'Langmuir binding 1:1, RI (refractive index)=0.

Results: Expression & Purification Bispecific, Bivalent <Her2GlyMab> Antibody Molecules According the procedures described in the materials and methods above, the bispecific, bivalent <Her2GlyMab> antibody molecules OAscFab1, OAscFab2, OAscFabPer1, OAscFabPer2, CrossMab-XPer, CrossMab-XTra and CrossMab-CDRG were expressed and purified. In each molecule the VH and VL of part are based on optimized Trastuzumab sequences with mutations T31V or N30T in the variable light chain and mutation D98E in the heavy chain and the Pertuzumab parent sequence respectively. The schematic structure of the antibodies is shown in FIGS. 10A and 10B. The sequences are shown in Table 8 above.

Figure 11A:
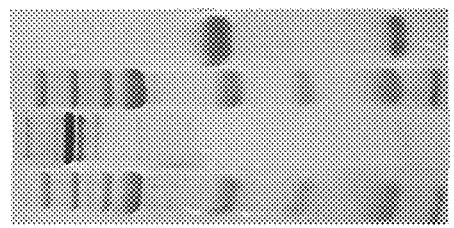
FIGS. 11A and 11B: Purification of CrossMab-XPer (SEQ ID NOs 109, 110, 96, 86). (11A): SDS-PAGE showing the purified antibody molecule under reduced and non-reduced conditions. (11B): HP-SEC analysis of purified CrossMab-XPer.
Figure 11B:
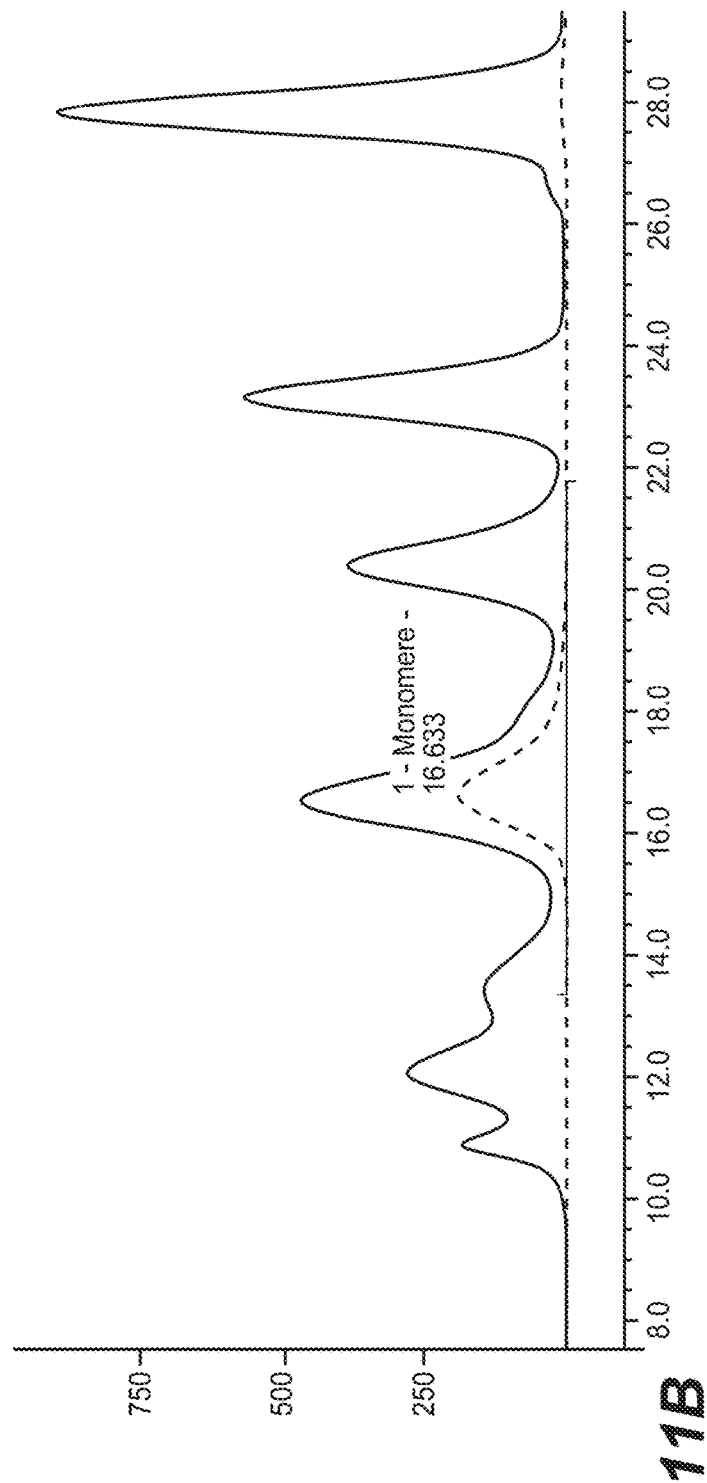

Expression of <Her2GlyMab> antibody molecules OAscFab1 Her2 GlyMab, OAscFab2 Her2 GlyMab, OAscFabPer1 Her2 GlyMab, OAscFabPer2 Her2 GlyMab (all glycoengineered, Knobs-into-holes, with the Trastuzumab scFab bearing D98E and T31V mutations), CrossMab-XPer Her2 GlyMab, CrossMab-XTra Her2 GlyMab (both glycoengineered, Knobs-into-holes, with the Trastuzumab cross-Fab bearing D98E and T31V mutations), and CrossMab-CDRG Her2 GlyMab (glycoengineered, Knobs-into-holes, CDR grafted, with the Trastuzumab cross-Fab bearing D98E and N30S mutations) was confirmed by western blotting and HP-SEC (FIGS. 11A and 11B). Purification of OAscFab1, OAscFab2, OAscFabPer1, OAscFabPer2, CrossMab-XPer, CrossMab XTra and CrossMab-CDRG led to the yields shown in Table 9. All OAscFab constructs showed less than 90% monomer post purification, the reduced purity of these molecules could not be increased by optimization of the plasmid ratios in expression (data not shown). However, optimization of the plasmid chain ratios in expression proved to increase the monomeric fraction present post purification of the CrossMab antibodies as described below.

TABLE 9

Her2GlyMab Purification - Analysis of the percentage aggregation post protein A and SEC purification using HP-SEC and the respective protein yields calculated by UV spectroscopy A280 of the glycoengineered constructs.

| Name | Purity post protein A (%) | Expression yield post protein A (mg/L) | Purity post SEC (%) | Expression yield post SEC (mg/L) |
|---|---|---|---|---|
| OAscFab1 (SEQ ID NOs 133, 134, 135) | 48.4 | 144 | 90 | 31.6 |
| OAscFab2 (SEQ ID NOs 136, 137, 138) | 41 | 42.9 | 93.6 | 12.6 |
| OAscFabPer1 (SEQ ID NOs 139, 140, 141) | 41.6 | 43.4 | 88.8 | 4.6 |
| OAscFabPer2 (SEQ ID NOs 142, 143, 144) | 38.2 | 34.2 | 86.7 | 6.6 |
| CrossMab-XTra (SEQ ID NOs 119, 120, 121, 122) | 65.1 | 28.4 | 73 | 10.6 |
| CrossMab-XPer (SEQ ID NOs 109, 110, 96, 86) | 76.4 | 30.9 | 85 | 17.9 |
| CrossMab-CDRG (SEQ ID NOs 109, 110, 111, 112) | 73 | 31.5 | 95 | 11.9 |

Example 7: Expression & Purification Bispecific, Bivalent <Her2GlyMab> Antibody Molecules Optimization of the Plasmid Ratios Used in Expression CrossMab-XTra According the procedures described in the materials and methods above, the bispecific, bivalent <Her2GlyMab> antibody molecule CrossMab-XTra, was expressed with molar plasmid ratios of 1:1:1:1, 1:1:1:2, 1:1:1:4 and 1:1:1:8 and purified. Expression of CrossMab-XTra was confirmed by Western blot. After Protein A purification of cell culture supernatants the construct showed at a 1:1:1:1 equimolar plasmid ratio approximately 73% of bispecific antibody with the expected molecular weight of approximately 148 kDa as detected by Q-TOF MS; 11% containing 2× Pertuzumab light chains paired with Pertuzumab and XTrastuzumab heavy chains; 9% intact XTrastuzumab antibodies (both heavy and light chains originating from XTrastuzumab) with the formation of the heavy chain hole-hole association; 4% XTrastuzumab heavy chain hole-hole association combined with Pertuzumab light chains only; and 3% XTrastuzumab heavy chain hole-hole association with 1× XTrastuzumab light chain and 1× Pertuzumab light chain. The 1:1:1:2 plasmid ratio where the molar ratio of the crossed Trastuzumab light chain (XHerLC) was expressed 2-fold, showed approximately 81% of bispecific antibody with the expected molecular weight of approximately 148 kDa as detected by Q-TOF MS; 1% containing 2× Pertuzumab light chains paired with Pertuzumab and XTrastuzumab heavy chains; 16% intact XTrastuzumab antibodies (both heavy and light chains originating from XTrastuzumab) with the formation of the heavy chain hole-hole association; XTrastuzumab heavy chain hole-hole association combined with Pertuzumab light chains only were not detected; and 1% XTrastuzumab heavy chain hole-hole association with 1× XTrastuzumab light chain and 1× Pertuzumab light chain.

The 1:1:1:4 plasmid ratio where the molar ratio of the crossed Trastuzumab light chain was expressed 4-fold, showed approximately 64% of bispecific antibody with the expected molecular weight of approximately 148 kDa as detected by Q-TOF MS; 2× Pertuzumab light chains paired with Pertuzumab and XTrastuzumab heavy chains was not detected, however, 12% 2× XTrastuzumab light chains paired with Pertuzumab and XTrastuzumab heavy chains was detected for the first time at this ratio; 24% intact XTrastuzumab antibodies (both heavy and light chains originating from XTrastuzumab) with the formation of the heavy chain hole-hole association; XTrastuzumab heavy chain hole-hole association combined with Pertuzumab light chains only were not detected; XTrastuzumab heavy chain hole-hole association with 1× XTrastuzumab light chain and 1× Pertuzumab light chain were not detected.

The 1:1:1:8 plasmid ratio where the molar ratio of the crossed Trastuzumab light chain was expressed 8-fold, showed approximately 45% of bispecific antibody with the expected molecular weight of approximately 148 kDa as detected by Q-TOF MS; 2× Pertuzumab light chains paired with Pertuzumab and XTrastuzumab heavy chains was not detected, however, 28% 2× XTrastuzumab light chains paired with Pertuzumab and XTrastuzumab heavy chains was detected for the first time at this ratio; 27% intact XTrastuzumab antibodies (both heavy and light chains originating from XTrastuzumab) with the formation of the heavy chain hole-hole association; XTrastuzumab heavy chain hole-hole association combined with Pertuzumab light chains only were not detected; XTrastuzumab heavy chain hole-hole association with 1× XTrastuzumab light chain and 1× Pertuzumab light chain were not detected.

TABLE 10

CrossMab-XTra Her2GlyMab - Q-TOF analysis and quantification of the by-product profile of the Her2GlyMab antibody constructs comparing the optimization plasmid titration of the crossed Trastuzumab light chain (XHer LC).

| Detected protein species in MS | CrossMab-XTra Her2GlyMab 1:1:1:1 | CrossMab-XTra Her2GlyMab 1:1:1:2 | CrossMab-XTra Her2GlyMab 1:1:1:4 | CrossMab-XTra Her2GlyMab 1:1:1:8 |
|---|---|---|---|---|
| 1 × XHer HC; 1 × Per HC; 2 × XHer LC | N.D. | N.D. | ~12% | ~28% |
| 2 × XHer HC; 2 × XHer LC | ~9% | ~16% | ~24% | ~27% |
| CrossMab-XTra Her2GlyMab (100%) | ~73% | ~81% | ~64% | ~45% |
| 2 × XHer HC; 1 × XHer LC; 1 × Per HC | ~3% | ~1% | N.D. | N.D. |
| 1 × XHer HC; 1 × Per HC; 2 × Per LC | ~11% | ~1% | N.D. | N.D. |
| 2 × XHer HC; 2 × Per LC | ~4% | N.D. | N.D. | N.D. |

N.D.—Not Detected

CrossMab-XPer

After Protein A purification of cell culture supernatants the construct showed at a 1:1:1:1 equimolar plasmid ratio approximately 85% of bispecific antibody with the expected molecular weight of approximately 148 kDa as detected by Q-TOF MS; 2% containing 2× XPertuzumab light chains paired with XPertuzumab and Trastuzumab heavy chains; 1% intact Trastuzumab antibodies (both heavy and light chains originating from Trastuzumab) with the formation of the heavy chain hole-hole association; 12% 2× Trastuzumab light chains paired with XPertuzumab and Trastuzumab heavy chains. No further species were detected.

The 1:1:1:2 plasmid ratio where the molar ratio of the crossed Pertuzumab light chain (XPerLC) was expressed 2-fold, showed approximately 89% of bispecific antibody with the expected molecular weight of approximately 148 kDa as detected by Q-TOF MS; 7% containing 2× XPertuzumab light chains paired with XPertuzumab and Trastuzumab heavy chains; intact Trastuzumab antibodies (both heavy and light chains originating from Trastuzumab) with the formation of the heavy chain hole-hole association were not detected; 4% 2× Trastuzumab light chains paired with XPertuzumab and Trastuzumab heavy chains.

The 1:1:1:4 plasmid ratio where the molar ratio of the crossed Pertuzumab light chain (XPerLC) was expressed 4-fold, showed approximately 74% of bispecific antibody with the expected molecular weight of approximately 148 kDa as detected by Q-TOF MS; 25% containing 2× XPertuzumab light chains paired with XPertuzumab and Trastuzumab heavy chains; intact Trastuzumab antibodies (both heavy and light chains originating from Trastuzumab) with the formation of the heavy chain hole-hole association were not detected; 1% 2× Trastuzumab light chains paired with XPertuzumab and Trastuzumab heavy chains.

The 1:1:1:8 plasmid ratio where the molar ratio of the crossed Pertuzumab light chain (XPerLC) was expressed 8-fold, showed approximately 52% of bispecific antibody with the expected molecular weight of approximately 148 kDa as detected by Q-TOF MS; 48% containing 2× XPertuzumab light chains paired with XPertuzumab and Trastuzumab heavy chains; intact Trastuzumab antibodies (both heavy and light chains originating from Trastuzumab) with the formation of the heavy chain hole-hole association were not detected; 2× Trastuzumab light chains paired with XPertuzumab and Trastuzumab heavy chains were not detected.

CrossMab-CDRG

Figure 12:
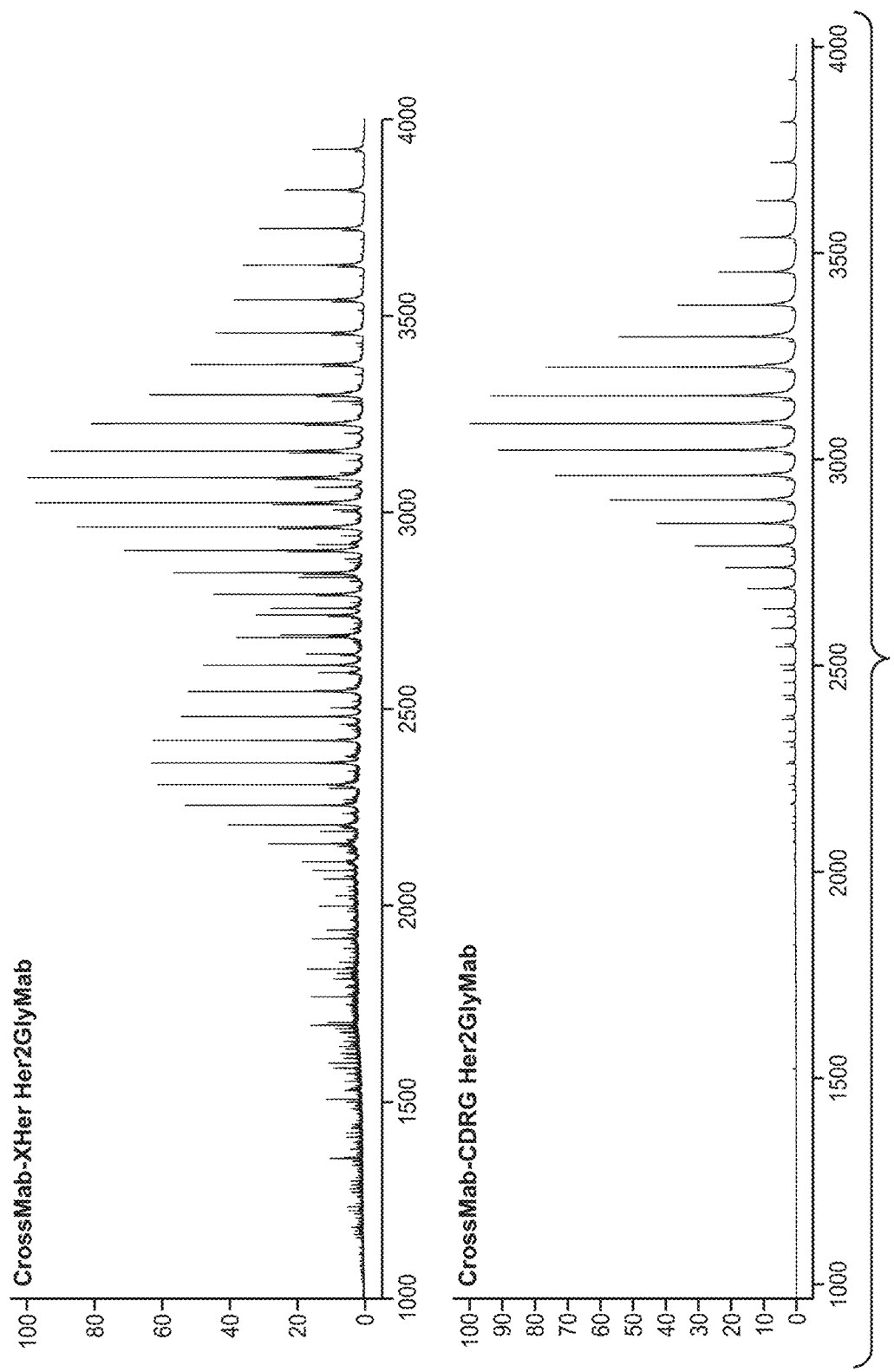
FIG. 12: Q-TOF mass spectrometry comparison of the spectra of CrossMab-XTra (top, SEQ ID NOs 119, 120, 121, 122) and CrossMab-CDRG (bottom, SEQ ID NOs 109, 110, 111, 112) estimating the integrity and purity of the antibody molecules.

After Protein A purification of cell culture supernatants the construct showed at a 1:1:1:1 equimolar plasmid ratio approximately 95% of bispecific antibody with the expected molecular weight of approximately 148 kDa as detected by Q-TOF MS and 5% containing 2× XPertuzumab light chains paired with XPertuzumab and Trastuzumab (HerCDRG) heavy chains. No further species were detected, therefore, further optimization of the plasmid ratios was not performed. The MS spectra performed on the antibodies CrossMab-XHer and CrossMab-CDRG to compare the byproduct profile can be seen in FIG. 12.

TABLE 11

CrossMab-XPer Her2GlyMab - Q-TOF analysis and quantification of the by-product profile of the Her2GlyMab antibody constructs comparing the optimization plasmidtitration of the crossed Trastuzumab light chain (XPer LC).

| Detected protein species in MS | CrossMab-XPer Her2GlyMab 1:1:1:1 | CrossMab-XPer Her2GlyMab 1:1:1:2 | CrossMab-XPer Her2GlyMab 1:1:1:4 | CrossMab-XPer Her2GlyMab 1:1:1:8 |
|---|---|---|---|---|
| 1 x Her HC; 1 x XPer HC; 2 x XPer LC | ~2% | ~7% | ~25% | ~48% |
| 2 x Her HC; 2 x Her LC | ~1% | n.d. | n.d. | n.d. |
| CrossMab-XPer Her2GlyMab (100%) | ~85% | ~89% | ~74% | ~52% |
| 1 x Her HC; 1 x XPer HC; 2 x Her LC | ~12% | ~4% | ~1% | n.d. |

N.D.—Not Detected.

TABLE 12

CrossMab-CDRG Her2GlyMab - Q-TOF analysis and quantification of the by-product profile of the Her2GlyMab antibody construct detecting the presence of mispaired antibody heavy and light chains.

| Detected protein species in MS | CrossMab-CDRG Her2GlyMab 1:1:1:1 |
|---|---|
| 2 x XPer HC; 2 x XPer LC | N.D. |
| 2 x HerCDRG HC; 2 x HerCDRG LC | N.D. |
| CrossMab-CDRG Her2GlyMab (100%) | ~95% |
| 1 x HerCDRG HC; 1 x XPer HC; 2 x XPer LC | ~5% |

N.D.—Not Detected

Example 8: Simultaneous Binding of Bispecific Antibodies to Both Antigens

The binding of the bispecific antibody was analyzed via BIAcore as described above.

In separate assay format samples (CrossMabXPer as well as for OAscFab1 and OAscFab2) were proven to be functional for Trastuzumab as well as Pertuzumab specificity. CrossMabXPer showed kinetic constants and resulting affinities in the same order of magnitude as the positive controls. Except for a slightly reduced $k_a$-rate constant for the Trastuzumab mediated binding OAscFab1 and OAscFab2 showed kinetic constants and resulting affinities in the same order of magnitude as the positive controls i.e the parental Mabs.

Partly bivalent binding of the positive controls—depending on the ligand density on the CM5—Chip may cause the variation of the dissociation rate constants in the two experiments depicted in this example.

TABLE 13

SPR analysis of the Her2GlyMab affinities - The association and dissociation rates of the antibodies were measure using a BIAcoreT100 with a CM5-Chip at 25° C.

| Experiment | T = 25° C. analyzed function | analyte | $k_a$ [$M^{-1} \cdot s^{-1}$] | $k_d$ [$s^{-1}$] | $t(½)$ [min] | $K_D$ [M] |
|---|---|---|---|---|---|---|
| UJ2530 | "Trastuzumab" | Trastuzumab | 3.9E+05 | 8.7E−05 | 132.5 | 2.2E−10 |
| UJ2530 | "Trastuzumab" | Pertuzumab | no binding as expected | | | |
| UJ2530 | "Trastuzumab" | CrossMabXPer | 1.0E+05 | 7.6E−05 | 151.9 | 7.4E−10 |
| UJ2530 | "Pertuzumab" | Trastuzumab | no binding as expected | | | |
| UJ2530 | "Pertuzumab" | Pertuzumab | 4.7E+05 | 9.8E−05 | 118.1 | 2.1E−10 |
| UJ2530 | "Pertuzumab" | CrossMabXPer | 2.0E+05 | 1.8E−04 | 66.0 | 8.7E−10 |
| UJ2530_b | "Trastuzumab" | Trastuzumab | 7.0E+05 | 3.0E−05 | 382.9 | 4.3E−11 |
| UJ2530_b | "Trastuzumab" | Pertuzumab | no binding as expected | | | |
| UJ2530_b | "Trastuzumab" | OAscFab1 | 1.6E+04 | 8.7E−05 | 133.5 | 5.4E−09 |
| UJ2530_b | "Trastuzumab" | OAscFab2 | 1.8E+04 | 1.1E−04 | 100.6 | 6.2E−09 |
| UJ2530_b | "Pertuzumab" | Trastuzumab | no binding as expected | | | |
| UJ2530_b | "Pertuzumab" | Pertuzumab | 2.4E+05 | 2.6E−04 | 44.8 | 1.1E−09 |
| UJ2530_b | "Pertuzumab" | OAscFab1 | 1.2E+05 | 2.6E−04 | 44.3 | 2.2E−09 |
| UJ2530_b | "Pertuzumab" | OAscFab2 | 1.7E+05 | 2.6E−04 | 44.8 | 1.5E−09 |

Example 9: In Vitro Evaluation of 1+1 Herceptarg CrossMAb and Glyocoengineered Herceptarg Crossmab Proliferation Inhibition Assay AlamarBlue® (Invitrogen) was used for the measurement of the metabolic activity and proliferation of (A) BT474 and (B) N87 cells after a 5 day incubation in presence of HER2 CrossMab (CrossMab-XTra Her2GlyMab, SEQ ID NOs 119, 120, 121, 122), Trastuzumab, Pertuzumab or the combination of Trastuzumab/Pertuzumab. The bioreduction of the dye reduces the amount of the oxidized form (blue) and concomitantly increases the fluorescent intermediate (red).

Target cells were harvested, washed, resuspended in RPMI 1640 (Gibco)+10% FCS+1% GlutaMAX™ (Gibco) and plated at a concentration of $1\times10^4$ cells/well. Cells were incubated for 3 hours in the cell incubator before respective antibody dilutions were added. Plates were gently shaked and incubated for 5 days in the cell incubator.

25 µl/well of Alamar Blue were added to the plate and incubated for 7 h in the incubator. Absorbance was monitored at 584 nm and 612 nm in a Wallac Victor3 1420 Multilabel Counter. For calculation of the percentage of proliferation inhibition, non-treated controls samples were included in the assay and defined as 100% proliferation. The average percentage of proliferation inhibition of the triplicates of each experiment was calculated.

Figure 13A:
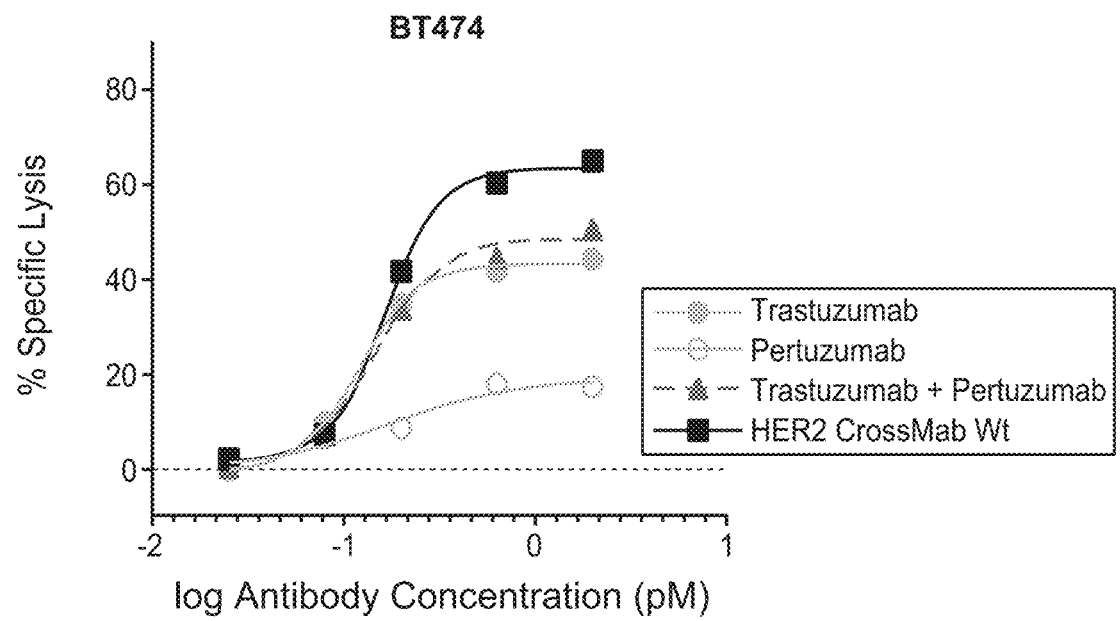
FIGS. 13A and 13B: Proliferation inhibition by non-glycoengineered HER2 CrossMab (SEQ ID NOs 119, 120, 121, 122) after 5 days of incubation as measured in an AlamarBlue® assay. (13A) BT474 cells (13B) N87 cells.
Figure 13B:
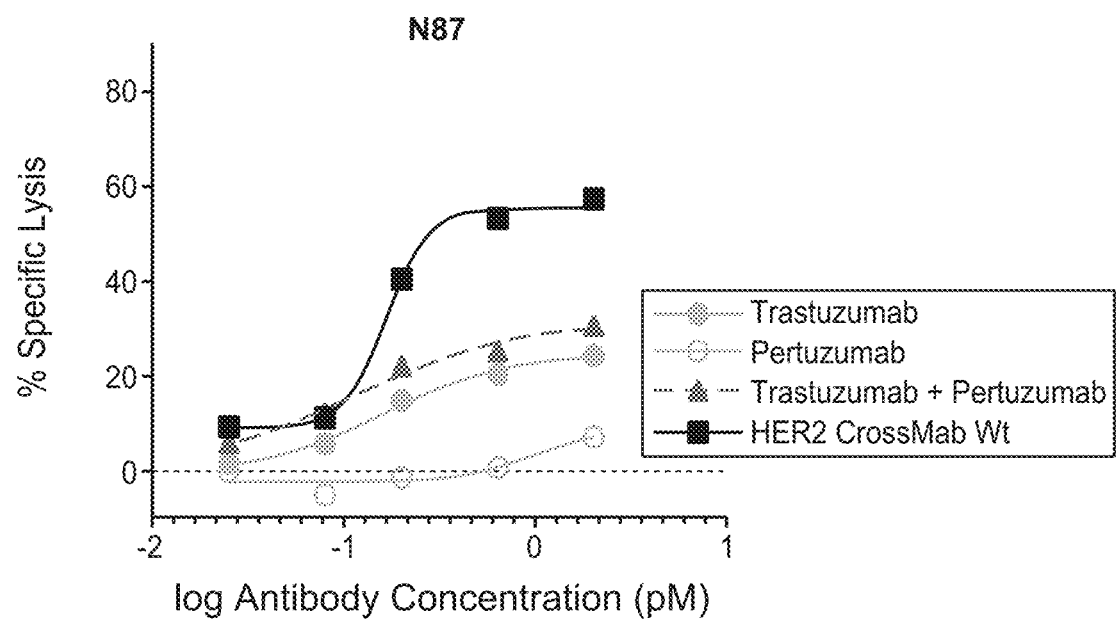

Results are shown in FIGS. 13A and 13B.

ADCC Assay

ADCC mediated by HER2 CrossMab (CrossMab-XTra Her2GlyMab, SEQ ID NOs 119, 120, 121, 122), Trastuzumab, Pertuzumab or the combo of Trastuzumab/Pertuzumab was assessed on KPL-4 (A), T47D (B) and Calu-3 (C) cells.

Target cells were harvested, washed, resuspended in AIM V® medium (Life Technologies), and plated at a concentration of $3\times10^4$ cells/well. The respective antibody dilutions were added in triplicates to the cells and incubated for 10 min before addition of the effector cells (peripheral blood mononuclear effector cells [PBMCs]). Effector (E) and target (T) cells were then incubated for 4 h at 37° C. at an E:T ratio of 25:1 (triplicates for all samples). Lactate dehydrogenase (LDH) release was measured using the LDH Cytotoxicity Detection Kit (Roche Applied Science). ADCC was calculated using the following formula:

$$\text{Percentage } ADCC = \left(\left[\frac{\text{sample release} - \text{spontaneous release}}{\text{maximal release} - \text{spontaneous release}}\right]\right) \times 100.$$

Figure 14A:
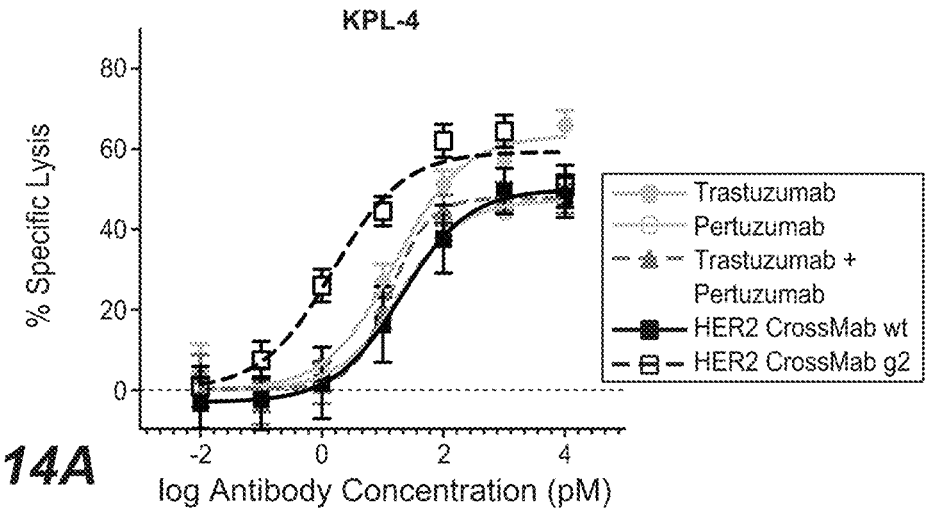
FIGS. 14A-14C: ADCC induced by different HER2 specific antibodies using (14A) KPL-4, (14B) T47D and (14C) Calu-3 as target cells (E:T=25:1, effectors human PBMCs, incubation time 4 h). "HER2 crossmab wt": SEQ ID NOs 119, 120, 121, 122, non glycoengineered; "HER2 crossmab g2": SEQ ID NOs 119, 120, 121, 122, glycoengineered.
Figure 14B:
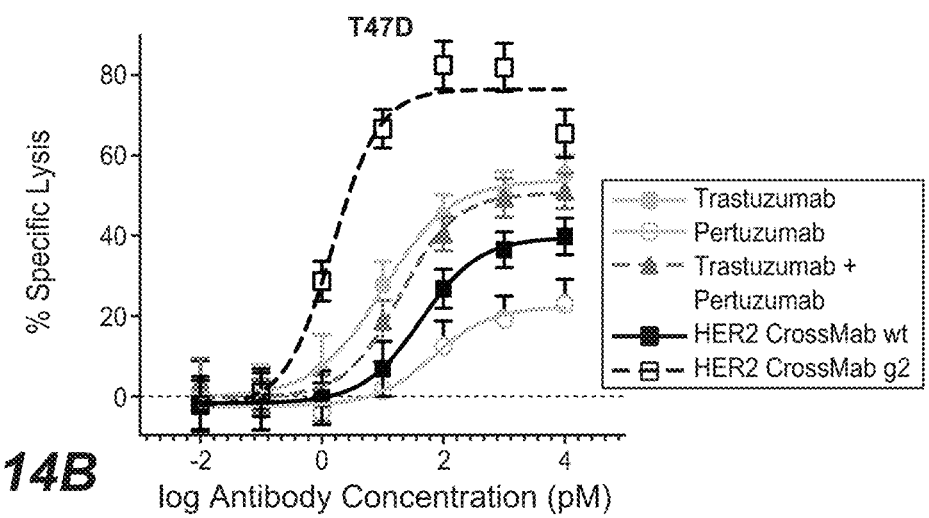
Figure 14C:
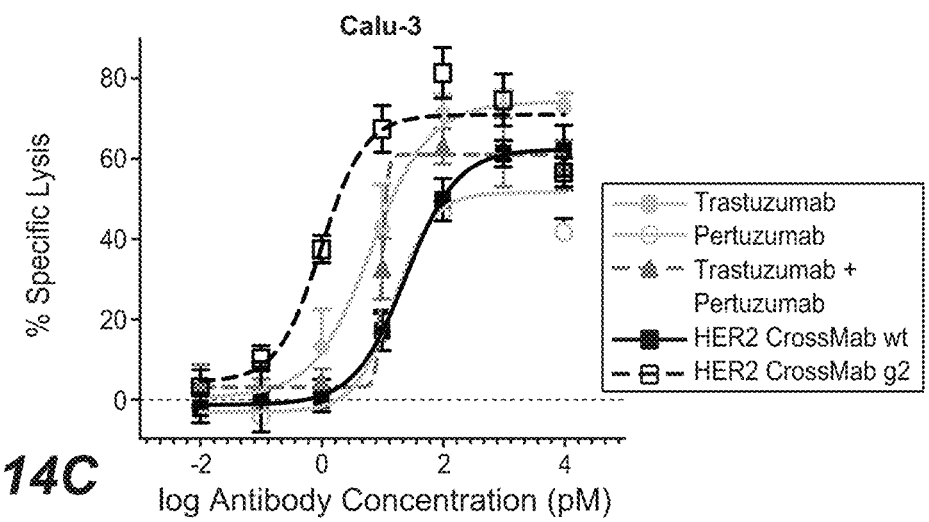
Figure 15A:
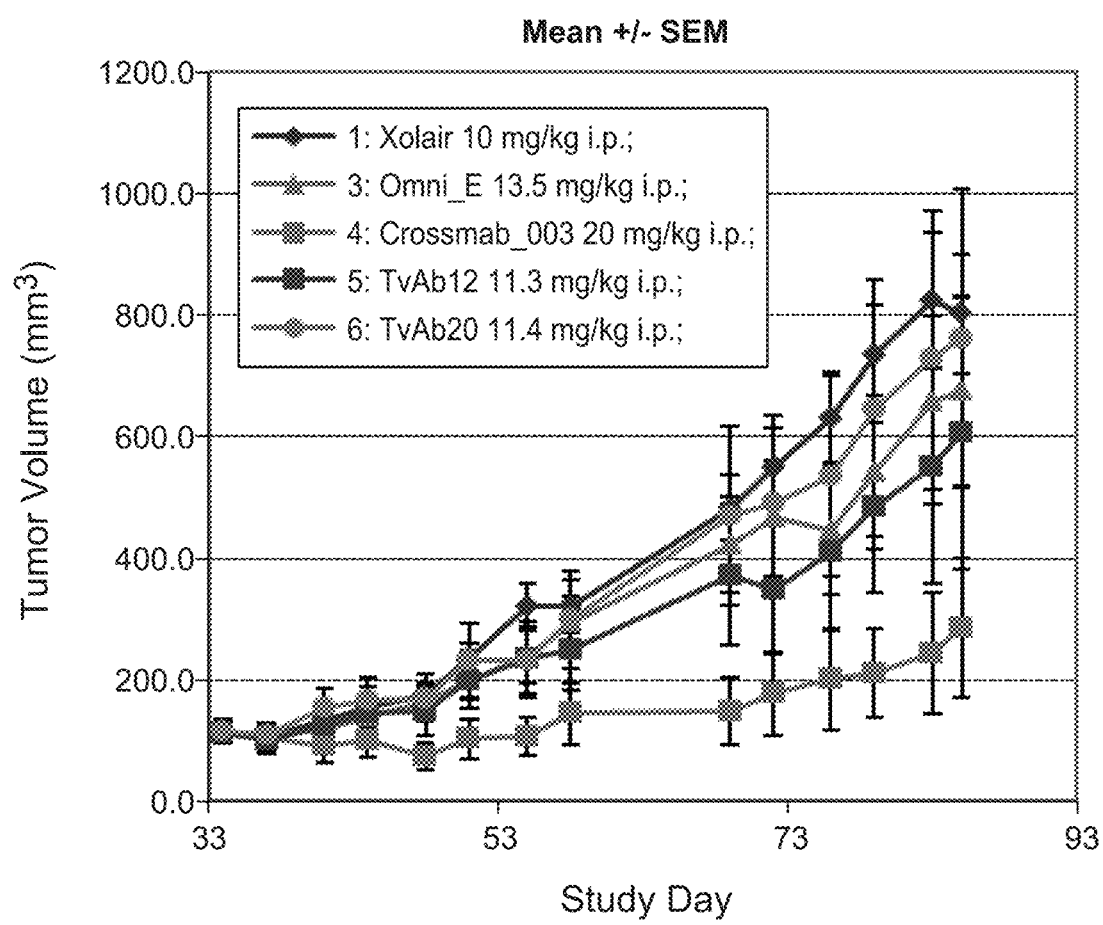
FIGS. 15A-15C: Antitumor activity of different anti-Her2 antibodies in the Calu3 non-small cell lung cancer xenograft (Experiment: BispecHer2_PZ_Calu3_001). SCID beige mice with Calu3 xenograft tumors were treated i.p. once weekly at the indicated dosages for 7 weeks. XOLAIR® a humanized IgG1 antibody targeting human IgE was used as a control. Statistical analysis based on medians at endpoint (day 85) reveals that compared to XOLAIR® the bispecific HER2 antibodies suppressed tumor growth by 87.5% (s.); OmniE (SEQ ID NOs 145, 146) by 43.7% (n.s.); Crossmab_003 (SEQ ID NOs 119, 120, 121, 122, non glycoengineered) by 92.1% (s.); TvAb12 (SEQ ID NOs 123 and 124) by 59.8% (n.s.) and TvAb20 (SEQ ID NOs 131 and 132) by 12.6% (n.s.). Tumor growth curves are depicted as mean+/−SEM (n=8 in each group).
Figure 15B:
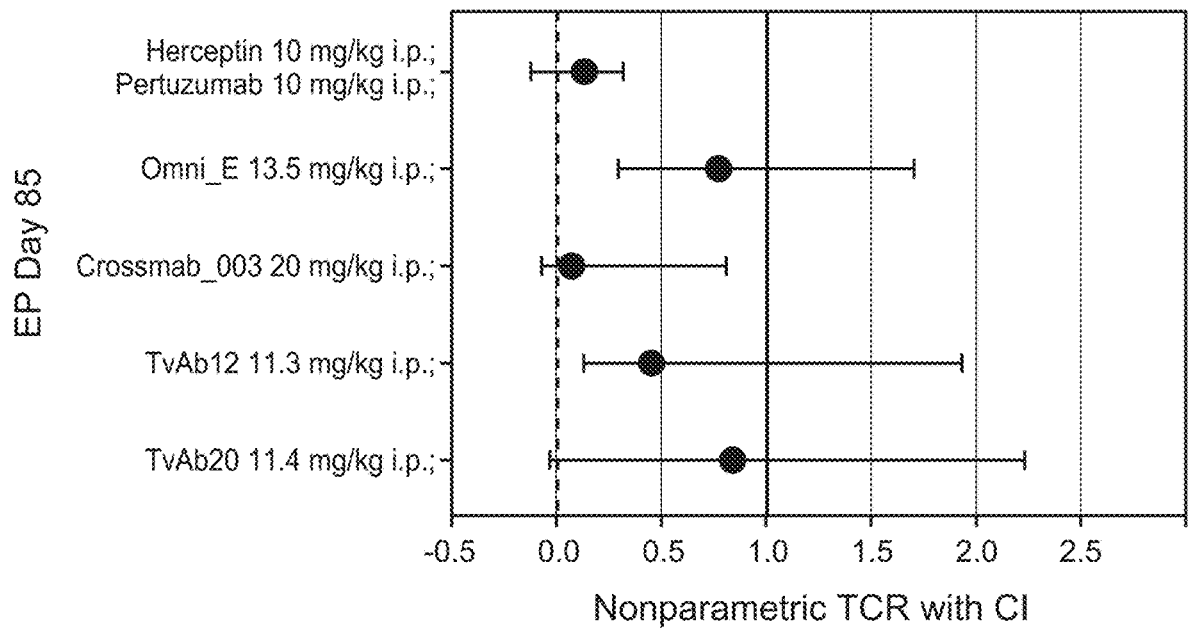
Figure 15C:
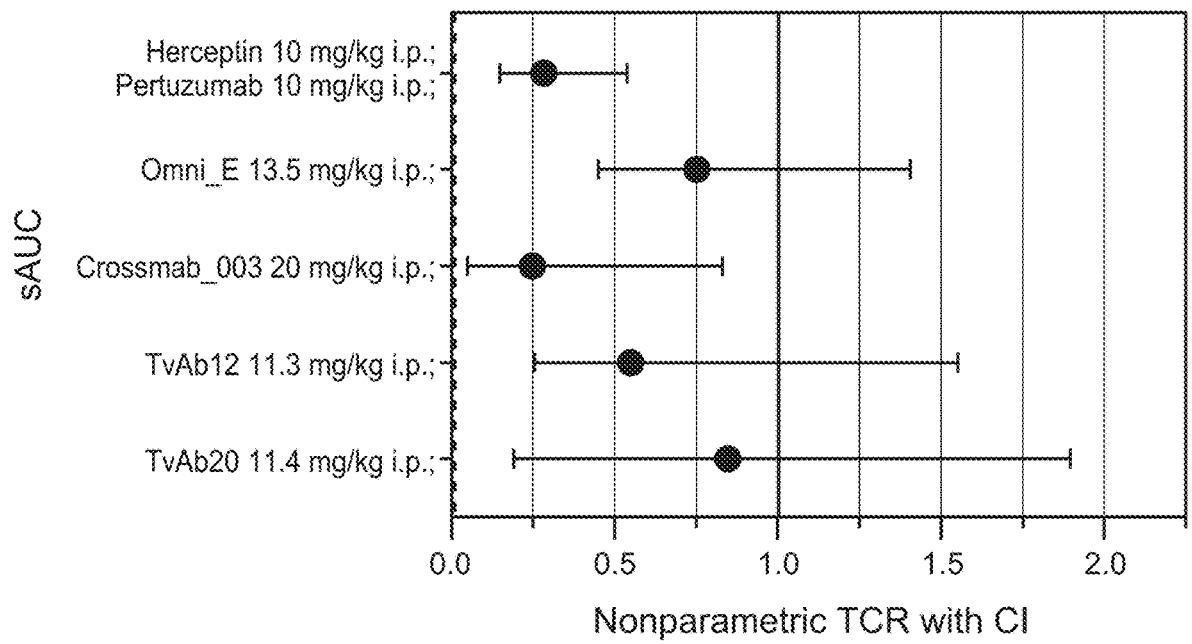

Spontaneous release, corresponding to target cells incubated with effector cells without antibody, was defined as 0% cytotoxicity, with maximal release (target cells lysed with 1% Triton X-100) defined as 100% cytotoxicity. The average percentage of ADCC and standard deviations of the triplicates of each experiment were calculated. Results are shown in FIGS. 14A-14C.

Example 10: In Vivo Characterization of HER2 CrossMab: Effect of Bispecific Antibodies Targeting HER2 on Tumor Growth in Calu3 Lung Cancer and KPL4 Breast Cancer Xenograft In Vitro Cultured Cells—Calu3

This human lung adenocarcinoma cancer cell line has been established from a human caucasian male with lung cancer. Cells were obtained from Chugai Pharmaceuticals Co., Ltd. and passaged in house for working cell bank. Tumor cells are routinely cultured in RPMI medium (PAN Biotech, Germany) supplemented with 10% fetal bovine serum glutamine (PAN Biotech, Germany) at 37° C. in a water-saturated atmosphere at 5% CO2. Culture passage is performed with trypsin/EDTA 1×(PAN) splitting twice/week. Cell passage P6 is used for in vivo study.

In Vitro Cultured Cells—KPL-4

This human breast cancer cell line has been established from the malignant pleural effusion of a breast cancer patient with an inflammatory skin metastasis. Cells have been provided by Professor J. Kurebayashi (Kawasaki Medical School, Kurashiki, Japan). Tumor cells are routinely cultured in DMEM medium (PAN Biotech, Germany) supplemented with 10% fetal bovine serum (PAN Biotech, Germany) and 2 mM L-glutamine (PAN Biotech, Germany) at 37° C. in a water-saturated atmosphere at 5% CO2. Culture passage is performed with trypsin/EDTA 1×(PAN) splitting twice/week. Cell passage P6 is used for in vivo study.

Animals

Female SCID beige (C.B.-17) mice; age 10-12 weeks; body weight 18-20 g (Charles River Germany, Sulzfeld) or female BALB/C nu/nu mice; age 8-10 weeks; body weight >20 g (Bomholtgard, Denmark) are maintained under specific-pathogen-free condition with daily cycles of 12 h light/12 h darkness according to international guidelines (GV-Solas; Felasa; TierschG). After arrival animals are housed in the quarantine part of the animal facility for one week to get accustomed to new environment and for observation. Continuous health monitoring is carried out on regular basis. Diet food (Alltromin) and water (acidified pH 2.5-3) are provided ad libitum. The experimental study was reviewed and approved by local government; registration no. 55.2-1-54-2531.2-3-08 Scid-beige orthotop rodent breast cancer model and 211-2531.2-16/00.1.2.2 subcutan tumor model.

Tumor Cell Injection

At the day of injection tumor cells are harvested (trypsin-EDTA) from culture flasks (Greiner TriFlask) and transferred into 50 ml culture medium, washed once and resuspended in PBS. After an additional washing step with PBS and filtration (cell strainer; Falcon Ø 100 μm) the final cell titer is adjusted to 1.5×108/ml. Tumor cell suspension is carefully mixed with transfer pipette to avoid cell aggregation. Anesthesia is performed using a Stephens inhalation unit for small animals with preincubation chamber (plexiglas), individual mouse nose-mask (silicon) and not flammable or explosive anesthesia compound Isoflurane (Pharmacia-Upjohn, Germany) in a closed circulation system. Two days before injection, coat of the SCID beige mice are shaved. For subcutaneous injection of Calu3 cells, skin of anaesthetized animals is carefully lifted up with an anatomic forceps and 100 μl cell suspension (=5.0×10e6 cells) is injected subcutaneously in the right flank of the animals. Cell suspension is filled into a 1.0 ml tuberculin syringe (Braun, Melsungen) using a wide injection needle (0.45×25 mm). KPL-4 cells (3×10e6 cells) are injected orthotopically in a volume of 20 μl into the right penultimate inguinal mammary fat pad of each anesthetized mouse. For the orthotopic implantation, the cell suspension is injected through the skin under the nipple using a using a Hamilton microliter syringe and a 30G×½" needle.

Monitoring

Animals are controlled daily for detection of clinical symptoms of adverse effects. For monitoring throughout the experiment the body weight of the animals is documented two times weekly and the tumor volume is measured by caliper twice weekly. Tumor volume was calculated according to NCI protocol (Tumor weight=½ab$^2$, where "a" and "b" are the long and the short diameters of the tumor, respectively). Termination criteria were the critical tumor mass (up to 1.7 g or Ø>1.5 cm), body weight loss more than 20% from baseline, tumor ulceration or poor general condition of the animals. Study exclusion criteria for the animals are described and approved in the corresponding "Tierversuchsanzeige".

Treatment of Animals

Mice were randomized for tumor volume, for KPL-4 a mean of 80 mm$^3$, for Calu3 a mean of 100 mm$^3$. Mice were treated once weekly with a volume of 10 ml/kg intra peritoneal. For combination treatment Trastuzumab was given first and Pertuzumab was given 24 hrs thereafter. Results are shown in tables 14 to 17 and FIGS. 15A-15C to 18A-18C.

TABLE 14

BispecHer2_Pz_Calu3_001 (FIGS. 15A-15C): CrossMAb_003 non-ge: non glycoengineered CrossMab-XTra Her2GlyMab (SEQ ID NOs 119, 120, 121, 122), negative control: anti-IgE antibody (Omalizumab), Herceptarg 2 + 2 OmniE: Pertuzumab antibody with the Trastuzumab scFV added onto the c-terminus of the heavy chains. The trastuzumab scFv contains a stabilizing disulphide bond between VH 105-VL 43 (SEQ ID NOs: 145, 146), TvAb12 and TvAb20: scFv 2 + 2 HER2 bispecific antibodies, see example 2.

| Group | No of animals | Compound | Dose (mg/kg) | Route/Mode of administration | No of treatments | Cumulative dose (mg/kg) |
|---|---|---|---|---|---|---|
| 1 | 8 | negative control | 10 | i.p. once weekly | 7 | 70 |
| 2 | 8 | Trastuzumab + | 10 | i.p. once weekly | 7 | 70 |
|   |   | Pertuzumab | 10 | i.p. once weekly | 7 | 70 |
| 3 | 8 | Herceptarg 2 + 2 OmniE | 13.5 | i.p. once weekly | 7 | 94.5 |
| 4 | 8 | CrossMAb_003 non-ge | 20 | i.p. once weekly | 7 | 140 |
| 5 | 8 | TvAb12 | 11.3 | i.p. once weekly | 7 | 79.1 |
| 6 | 8 | TvAb20 | 11.4 | i.p. once weekly | 7 | 79.8 |

TABLE 15

Figure 16A:
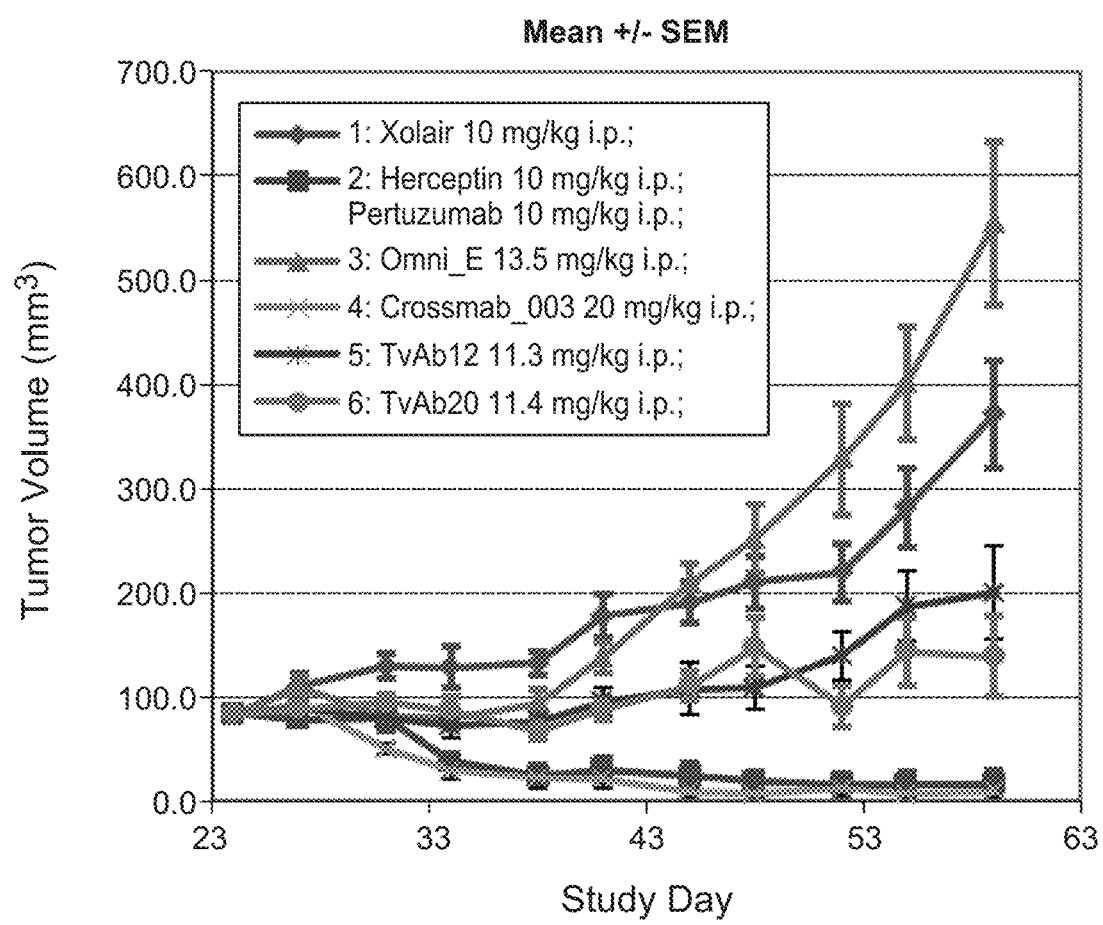
FIGS. 16A-16C: Antitumor activity of different anti-Her2 antibodies in the KPL-4 breast cancer xenograft (Experiment: Bispec.Her2_PZ_KPL-4_002). SCID beige mice with KPL-4 xenograft tumors were treated i.p. once weekly at the indicated dosages for 5 weeks. XOLAIR® a humanized IgG1 antibody targeting human IgE was used as a control. Statistical analysis based on medians at endpoint (day 59) reveals that compared to XOLAIR® the bispecific HER2 antibodies suppressed tumor growth by 120.8% (s.); Crossmab_003 (SEQ ID NOs 119, 120, 121, 122, non glycoengineered) by 120.6% (s.); TvAb12 (SEQ ID NOs 123 and 124) by 70.1% (s.); TvAb20 (SEQ ID NOs 131 and 132) by 83.4% (s) OmniE (SEQ ID NOs 145, 146) had no significant effect on tumor growth. Tumor growth curves are depicted as mean+/−SEM (n=9 in each group).
Figure 16B:
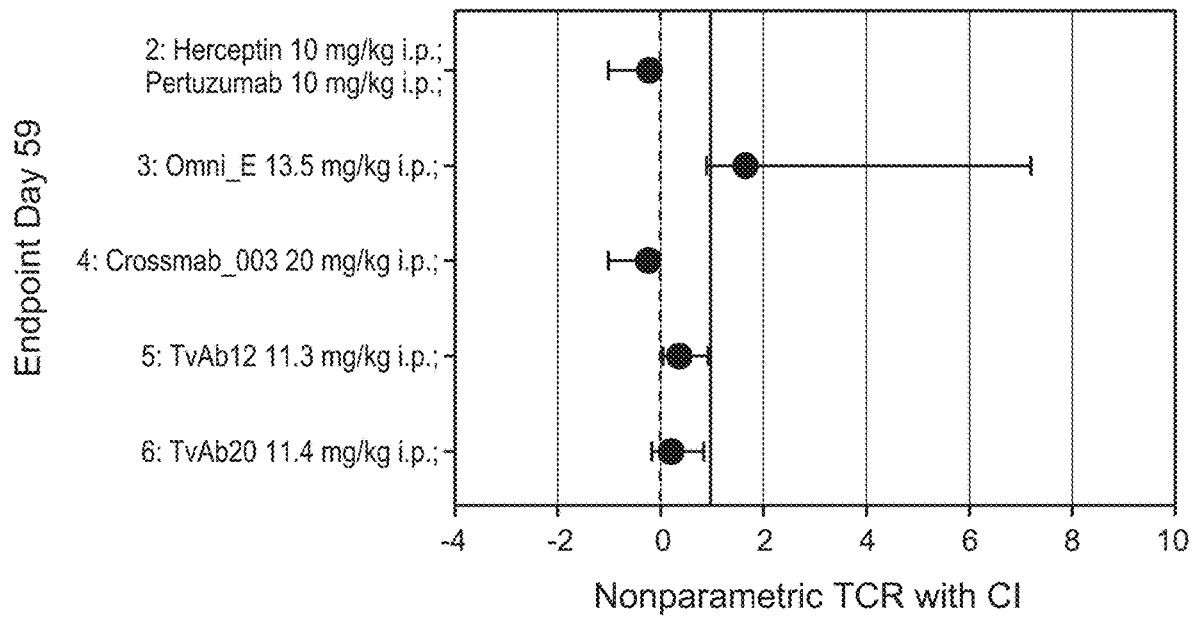
Figure 16C:
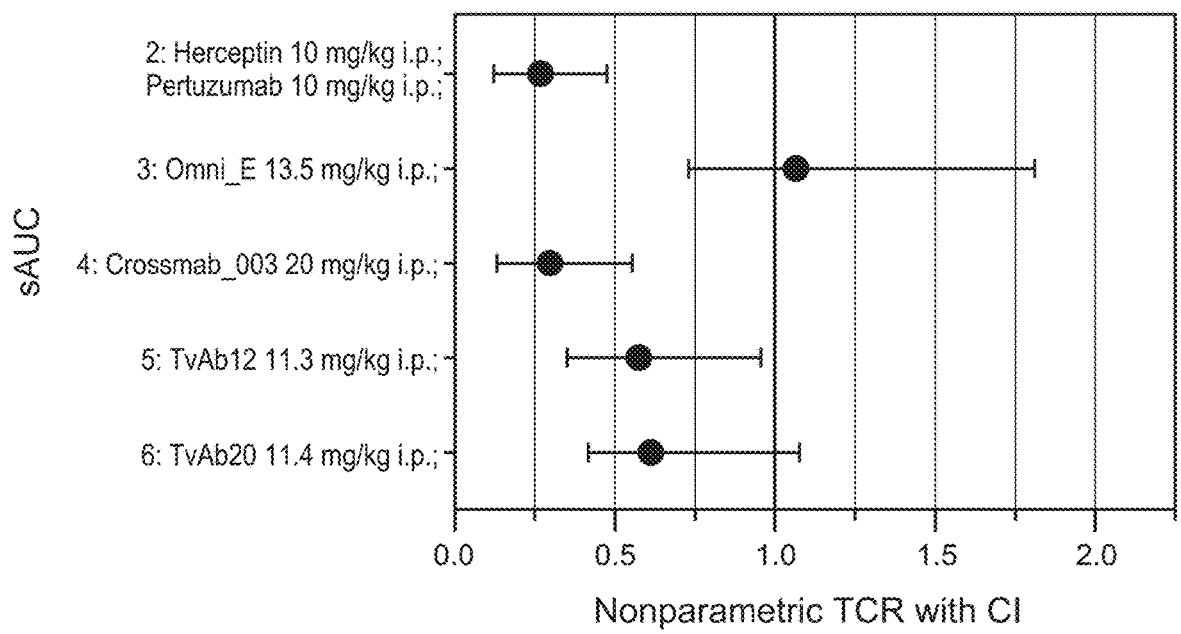

BispecHER2_PZ_KPL-4_002 (FIGS. 16A-16C): CrossMAb_003 non-ge: non glycoengineered CrossMab-XTra Her2GlyMab (SEQ ID NOs 119, 120, 121, 122), negative control: anti-IgE antibody (Omalizumab), Herceptarg 2 + 2 OmniE: Pertuzumab antibody with the Trastuzumab scFV added onto the c-terminal of the heavy chains. The trastuzumab scFv contains a stabilizing disulphide bond between VH 105-VL 43 (SEQ ID NOs: 145, 146), TvAb12 and TvAb20: scFv 2 + 2 HER2 bispecific antibodies, see example 2.

| Group | No of animals | Compound | Dose (mg/kg) | Route/Mode of administration | No of treatments | Cumulative dose (mg/kg) |
|---|---|---|---|---|---|---|
| 1 | 9 | Negative control | 10 | i.p. once weekly | 5 | 50 |
| 2 | 9 | Trastuzumab + | 10 | i.p. once weekly | 5 | 50 |
|   |   | Pertuzumab | 10 | i.p. once weekly |   | 50 |
| 3 | 9 | Herceptarg 2 + 2 OmniE | 13.5 | i.p. once weekly | 5 | 67.5 |
| 4 | 9 | CrossMAb_003 non-ge | 20 | i.p. once weekly | 5 | 100 |
| 5 | 9 | TvAb12 | 11.3 | i.p. once weekly | 5 | 56.5 |
| 6 | 9 | TvAb20 | 11.42 | i.p. once weekly | 5 | 57.1 |

TABLE 16

Figure 17A:
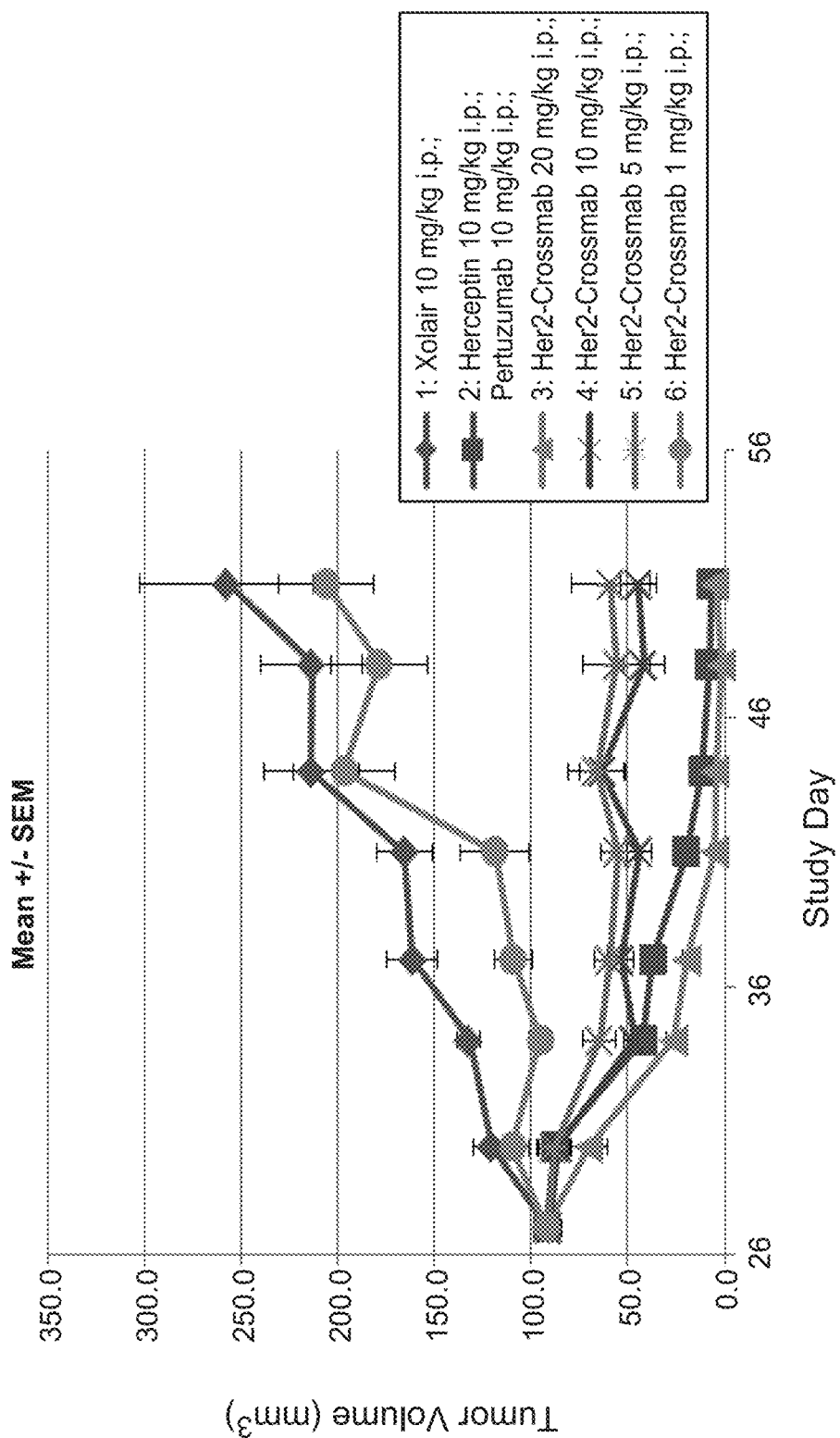
FIGS. 17A-17C: Antitumor activity of anti-Her2_005 crossmab antibody (SEQ ID NOs 119, 120, 121, 122, non glycoengineered) in the KPL-4 breast cancer xenograft (Experiment: Bispec.Her2_PZ_KPL-4_003). SCID beige mice with KPL-4 xenograft tumors were treated i.p. once weekly with escalating dosages of the crossmab ranging from 1 to 20 mg/kg for 5 weeks. XOLAIR® a humanized IgG1 antibody targeting human IgE was used as a control. Statistical analysis based on medians at endpoint (day 70) reveals that compared to XOLAIR® the bispecific HER2 antibodies suppressed tumor growth by 121.8% (s.); The Her2 crossmab_005 suppressed tumor growth at a dosage of 1 mg/kg by 25.1% (n.s.); at 5 mg/kg by 112.3% (s.); at 10 mg/kg by 109.5% (s.) and by 20 mg/kg by 121.8% (s.). Tumor growth curves are depicted as mean+/−SEM (n=10 in each group).
Figure 17B:
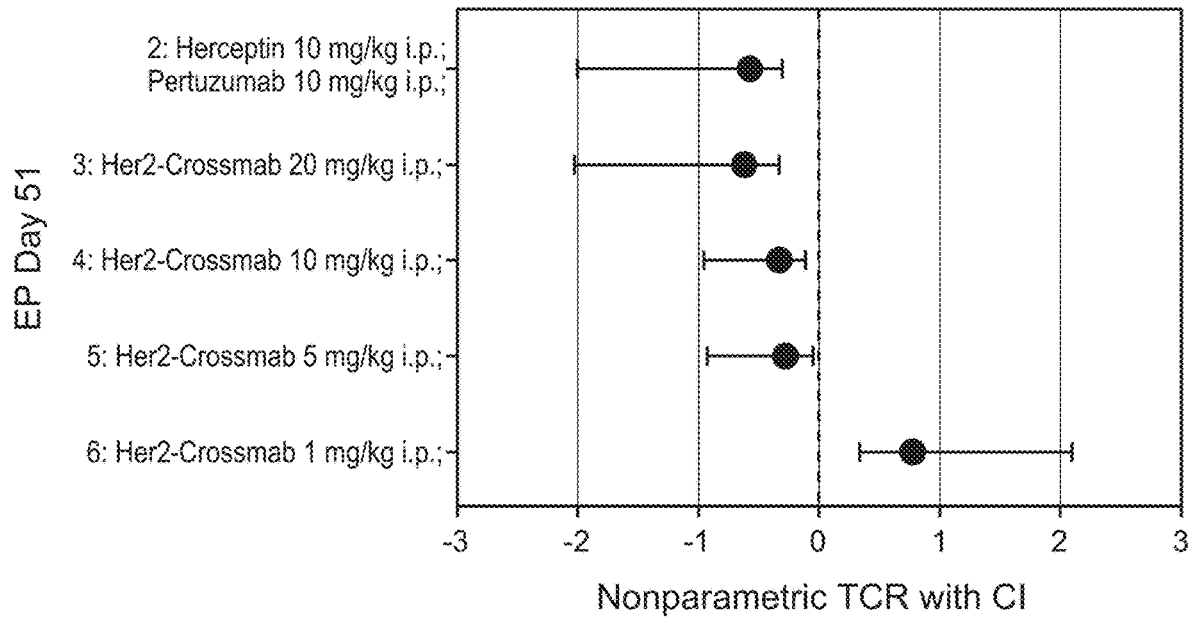
Figure 17C:
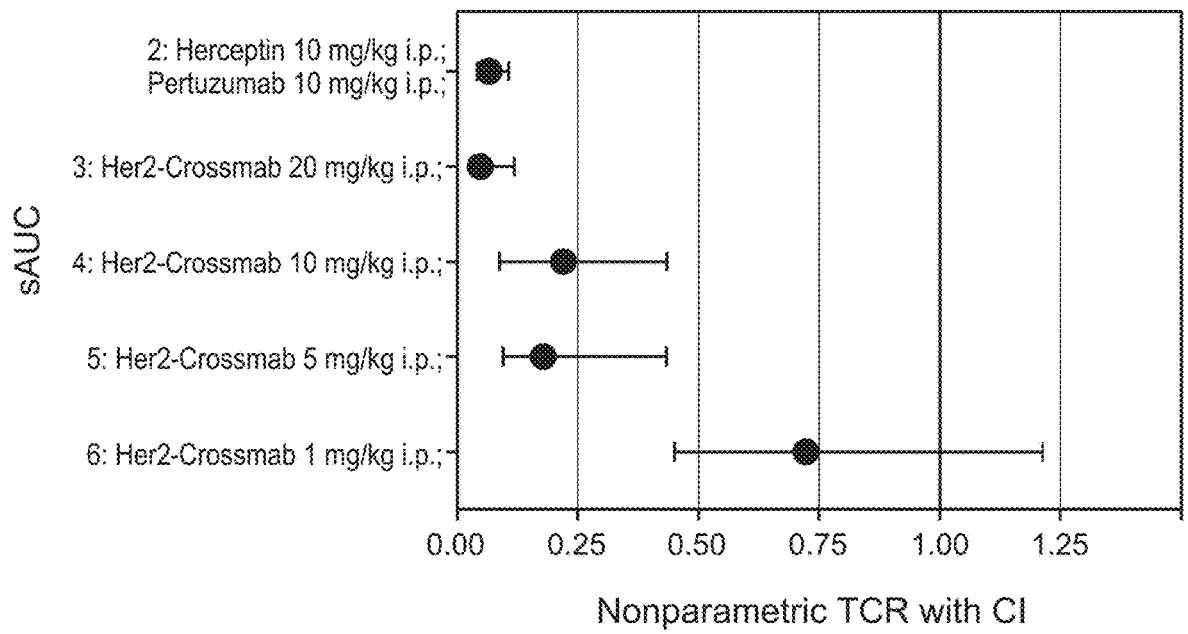
Figure 18A:
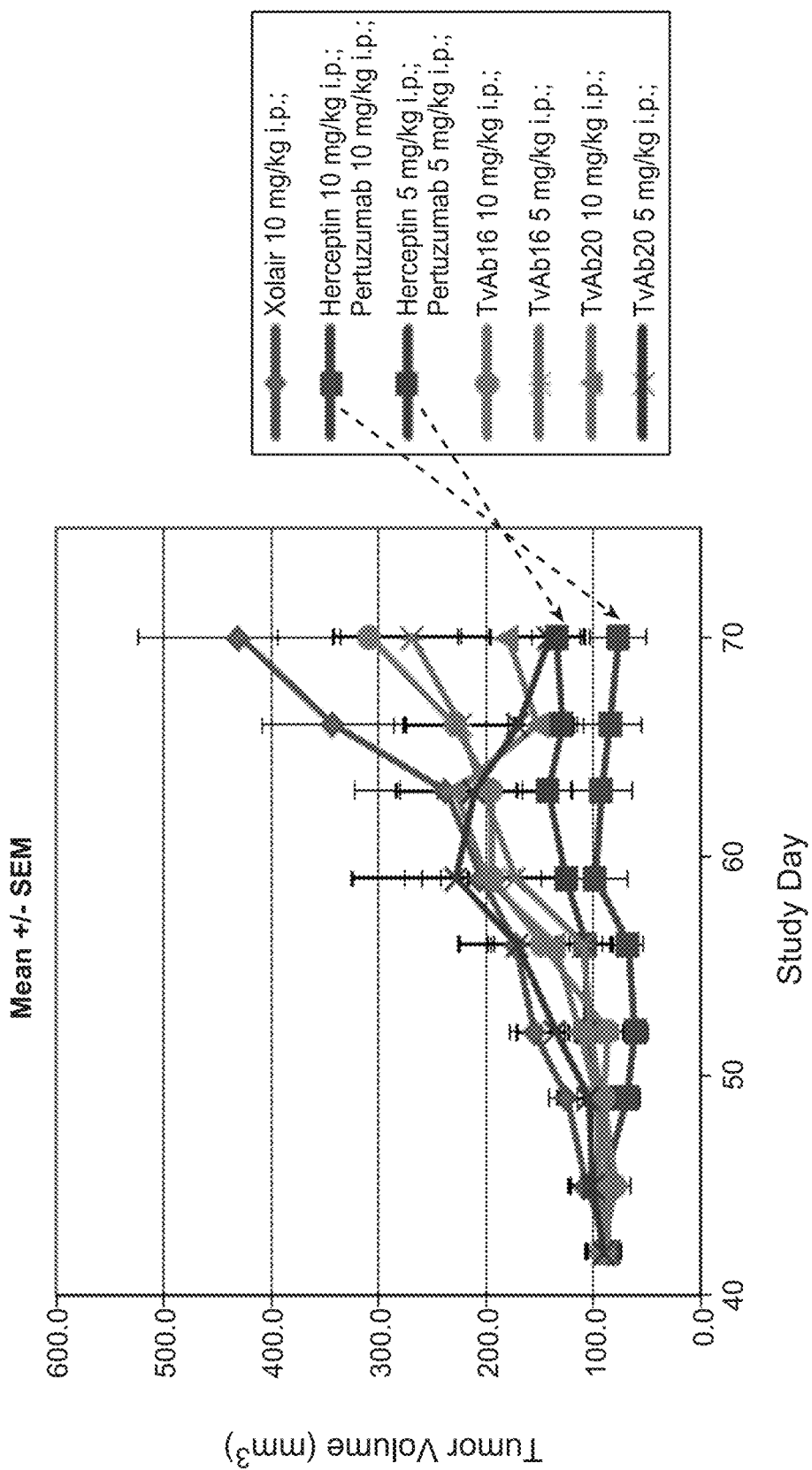
FIGS. 18A-18C: Antitumor activity of different anti-Her2 antibodies in the KPL-4 breast cancer xenograft (Experiment: Bispec.Her2_PZ_KPL-4_009). SCID beige mice with KPL-4 xenograft tumors were treated i.p. once weekly with the different compounds for 4 weeks. XOLAIR® a humanized IgG1 antibody targeting human IgE was used as a control. Statistical analysis based on medians at endpoint (day 70) reveals that compared to XOLAIR® the bispecific HER2 antibodies (each dosed at 5 mg/kg) suppressed tumor growth by 83.2% (s.) and both given at a dosage of 10 mg/kg each by 109.5% (s.). TvAb 16 (SEQ ID NOs 127 and 128) given at two different dosages (5 mg/kg and 10 mg/kg) had no significant anti-tumoral effect. TvAb20 (SEQ ID NOs 131 and 132), at a dosage of 5 mg/kg, suppressed tumor growth by 75.3% (s.) and at a dosage of 10 mg/kg by 59.8% (n.s.). Tumor growth curves are depicted as mean+/−SEM (n=10 in each group).
Figure 18B:
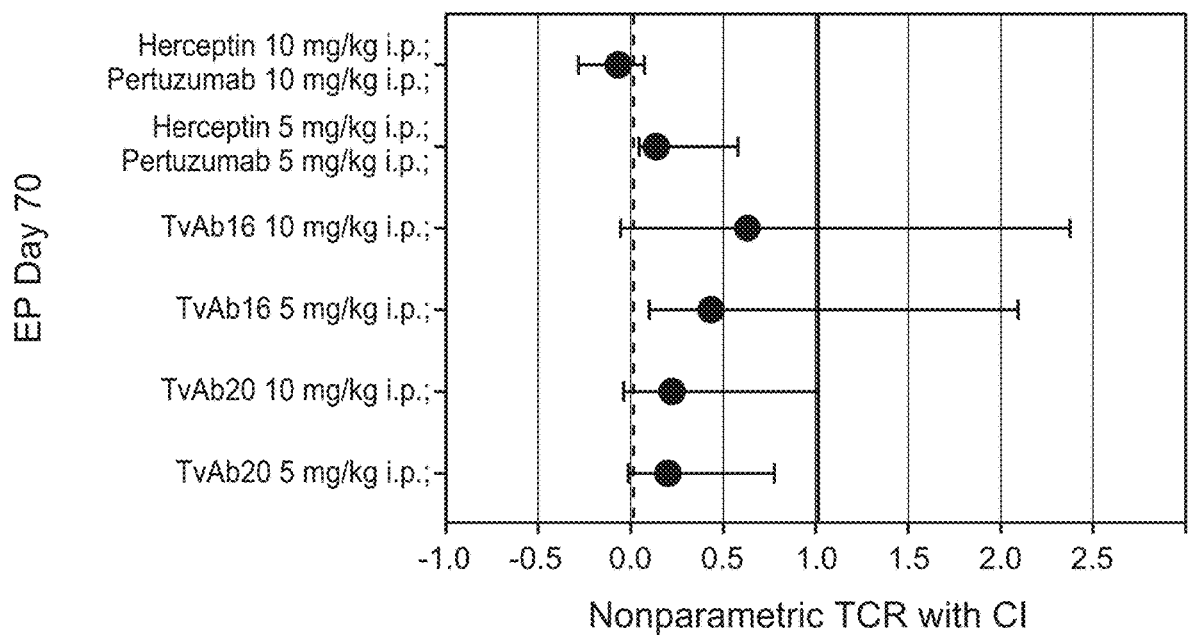
Figure 18C:
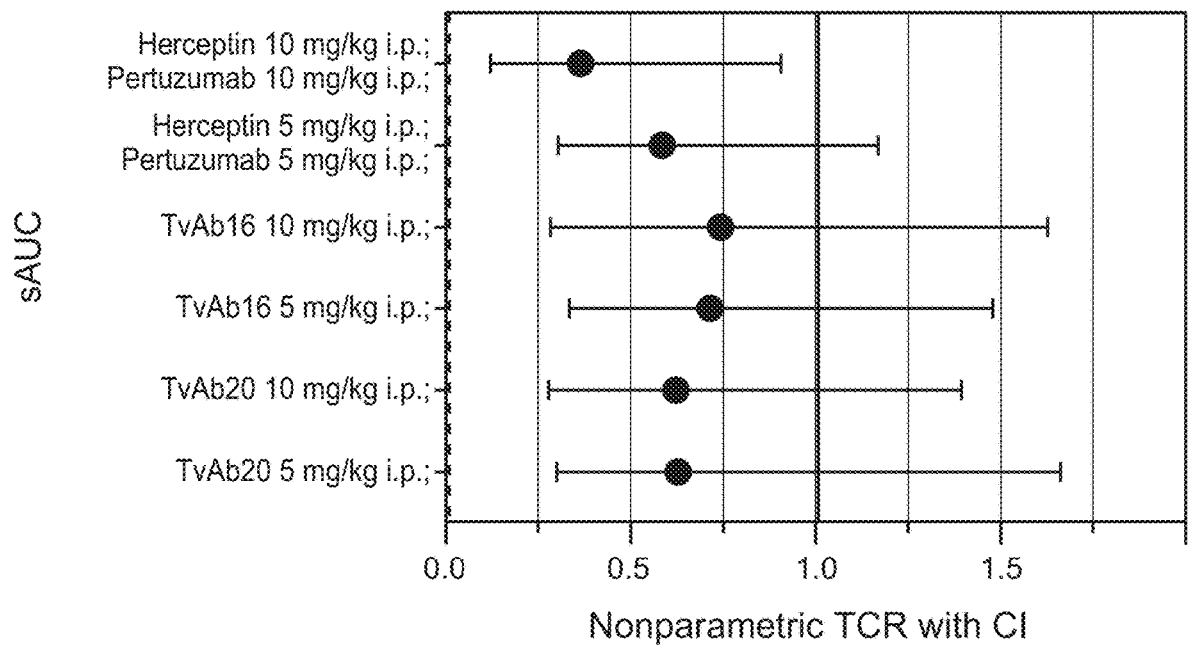

Bispec.HER2_PZ_KPL-4_003 (FIGS. 17A-17C): CrossMAb_005 non glycoengineered CrossMab-XTra Her2GlyMab (SEQ ID NOs 119, 120, 121, 122), negative control: anti-IgE antibody (Omalizumab).

| Group | No of animals | Compound | Dose (mg/kg) | Route/Mode of administration | No of treatments | Cumulative dose (mg/kg) |
|---|---|---|---|---|---|---|
| 1 | 10 | Negative control | 10 | i.p. once weekly | 5 | 50 |
| 2 | 10 | Trastuzumab + | 10 | i.p. once weekly | 5 | 50 |
|   |   | Pertuzumab | 10 | i.p. once weekly |   | 50 |
| 3 | 10 | Her2_Crossmab_005 | 20 | i.p. once weekly | 5 | 100 |
| 4 | 10 | Her2_Crossmab_005 | 10 | i.p. once weekly | 5 | 50 |
| 5 | 10 | Her2_Crossmab_005 | 5 | i.p. once weekly | 5 | 25 |
| 6 | 10 | Her2_Crossmab_005 | 1 | i.p. once weekly | 5 | 5 |

TABLE 17

Exploratory_PZ_KPL-4_009 (FIGs. 18A-18C): negative control: anti-IgE antibody (Omalizumab), TvAb16 and TvAb20: scFv 2 + 2 HER2 bispecific antibodies, see example 2.

| Group | No of animals | Compound | Dose (mg/kg) | Route/Mode of administration | No of treatments | Cumulative dose (mg/kg) |
|---|---|---|---|---|---|---|
| 1 | 10 | Negative control | 10 | i.p. once weekly | 4 | 40 |
| 2 | 10 | Trastuzumab + | 10 | i.p. once weekly | 4 | 40 |
|   |   | Pertuzumab | 10 | i.p. once weekly | 4 | 40 |
| 3 | 10 | Trastuzumab + | 5 | i.p. once weekly | 4 | 20 |
|   |   | Pertuzumab | 5 | i.p. once weekly | 4 | 20 |
| 4 | 10 | TvAb16 | 10 | i.p. once weekly | 4 | 40 |
| 5 | 10 | TvAb16 | 5 | i.p. once weekly | 4 | 20 |
| 6 | 10 | TvAb20 | 10 | i.p. once weekly | 4 | 40 |
| 7 | 10 | TvAb20 | 5 | i.p. once weekly | 4 | 20 |

Example 11: Generation of a Common Light Chain for Trastuzumab and Pertuzumab

Gene Synthesis

Desired gene segments, where required, were either generated by PCR using appropriate templates or were synthesized at Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow subcloning into the respective expression vectors. All constructs were designed with a 5'-end DNA sequence coding for a leader peptide which targets proteins for secretion in eukaryotic cells. SEQ ID NOs: 155, 156, and 157 give exemplary leader peptides.

Cloning of Antigen Expression Vectors

A DNA fragment encoding amino acids 1 to 629 of matured Tyrosine kinase-type cell surface receptor HER2 (Her2, Uniprot: P04626) was cloned in frame into a mammalian recipient vector containing an N-terminal leader sequence. In addition, the construct contains a C-terminal avi-tag allowing specific biotinylation during co-expression with Bir A biotin ligase and a His-tag used for purification by immobilized-metal affinity chromatography (IMAC) (SEQ ID NOs 1 and 2).

The antigen expression is generally driven by an MPSV promoter and transcription is terminated by a synthetic polyA signal sequence located downstream of the CDS. In addition to the expression cassette, each vector contains an EBV oriP sequence for autonomous replication in EBV-EBNA expressing cell lines.

Production and Purification of Antigens and Antibodies

Both antigens and antibodies were transiently transfected into HEK 293 cells, stably expressing the EBV-derived protein EBNA. A simultaneously co-transfected plasmid encoding biotin ligase Bir A allowed avi tag-specific biotinlylation in vivo. The proteins were then purified using a protein A column followed by gel filtration.

Design of Trastuzumab/Pertuzumab Common Light Chains

For the generation of a common light chain (CLC) for Trastuzumab and Pertuzumab, the individual light chains (LC) were analyzed and compared. Sequence analysis revealed that both variable domains originate from the same germline sequence. Given that the Trastuzumab LCDR3 in general and residue H91 in particular interact specifically with the Trastuzumab-specific epitope on Her2, the first attempt to create a Trastuzumab/Pertuzumab CLC was done as follows: Either the complete LCDR3 region or only residue H91 of Trastuzumab substituted the corresponding positions in the Pertuzumab LC. As a result, a hybrid LC construct was created encoding Pertuzumab-derived LCDR1 and 2 but harboring Trastuzumab-derived LCDR3 amino acid residues. The resulting CLCs, named either "Pertuzumab (Tras.L3) LC" (DNA sequence of variable domains listed as SEQ ID NO: 25) or "Pertuzumab (Tras.Y91H) LC" (SEQ ID NO: 27), were co-expressed with either the Trastuzumab or the Pertuzumab HC. The resulting four antibodies (protein sequence of variable domains listed as SEQ ID NOs: 22 and 26, "Pertuzumab HC" x "Pertuzumab (Tras.L3) LC"; SEQ ID NO: 92 and 26, "Trastuzumab HC" x "Pertuzumab (Tras.L3) LC"; SEQ ID NOs: 22 and 28, "Pertuzumab HC" x "Pertuzumab (Trast.Y91H) LC"; SEQ ID NO: 92 and 28, "Trastuzumab HC" x "Pertuzumab (Tras.Y91H) LC") were purified from mammalian-derived cell culture supernatant and binding to Her2 was measured and compared with the respectiv parental antibodies (SEQ ID NOs: 22 and 24, "Pertuzumab HC" x "Pertuzumab LC"; SEQ ID NO: 92 and 82, "Trastuzumab HC" x "Trastuzumab LC") by SPR.

Affinity-Determination by SPR Using BioRad's ProteOn XPR36 Biosensor

The Affinity ($K_D$) of the new antibody chain combinations was measured using surface plasmon resonance using a ProteOn XPR36 instrument (Biorad) at 25° C. In a first step, 6500 RU of anti-human IgG (Sigma 12136, polyclonal goat antibody) recognizing hu IgG (Fc-specific) was immobilized on all 6 channels of a GLM chip by Amine coupling (NaAcetate pH4, 30 µl/min, 300 s) (vertical orientation).

Each antibody was diluted with PBST (10 mM phosphate, 150 mM sodium chloride pH 7.4, 0.005% Tween 20) to 2 µg/ml, and then injected for 60 s at 30 µl/minute to achieve immobilization levels of about 400 response units (RU) in vertical orientation. Injection of Her2: For one-shot kinetics measurements, injection direction was changed to horizontal orientation, three-fold dilution series of purified Her2 (varying concentration ranges between 300 and 3.7 nM) were injected simultaneously at 100 µl/min along separate channels 1-5, with association times of 180 s, and dissociation times of 600 s. Buffer (PBST) was injected along the sixth channel to provide an "in-line" blank for referencing. Regeneration was performed by two pulses of 10 mM glycine pH 1.5 and 50 mM NaOH for 30 s at 100 µl/min (horizontal orientation). Association rate constants ($k_{on}$) and dissociation rate constants ($k_{off}$) were calculated using a simple one-to-one Langmuir binding model in ProteOn Manager v3.1 software by simultaneously fitting the association and dissociation sensorgrams. The equilibrium dissociation constant ($K_D$) was calculated as the ratio $k_{off}/k_{on}$.

Figure 19:
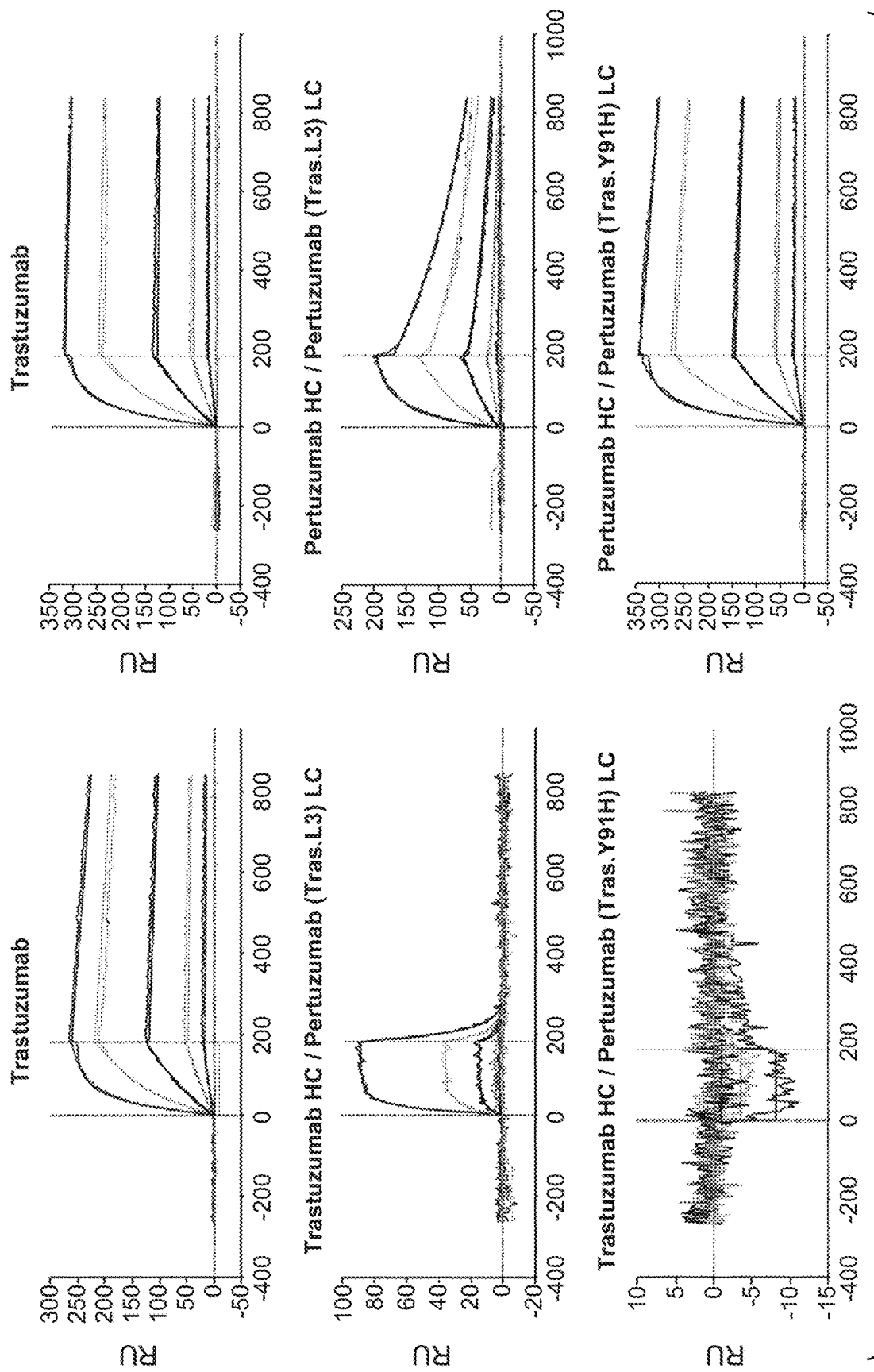
FIG. 19: SPR analysis of initial Pertuzumab/Trastuzumab hybrid light chains. SPR-based kinetic analyses of Pertuzumab, Trastuzumab, and sequence combinations with the initial Pertuzumab hybrid LCs harboring amino acid residues of the Trastuzumab LCDR3 region. Smooth lines represent a global fit of the data to a 1:1 interaction model. PertuzumabTrasL3: SEQ ID No: 26, PertuzumabTras Y91H: SEQ ID No: 28.

As expected, both control antibodies Trastuzumab and Pertuzumab recognized Her2 with their known affinities in the low nanomolar or sub-nanomolar range. However, while the affinity of Pertuzumab HC in combination with the newly designed "Pertuzumab (Tras.Y91H) LC" was slightly reduced, the same light chain in combination with Trastuzumab HC did not yield any detectable binding. This indicates that a single Trastuzumab-derived point mutation (Y91H) in the Pertuzumab LC is not sufficient translate binding to Her2 in this chain combination. This is in contrast to the second CLC variant "Pertuzumab LC (Trast. L3)" which resulted in weak binding when combined with Trastuzumab HC, while binding was was reduced but clearly visible when co-expressed with the Pertuzumab HC. A summary of the kinetic and thermodynamic measurements is given in FIG. 19 and table 18. Based on this finding, the CLC "Pertuzumab LC (Trast. L3)" was further modified in order to restore Her2 binding in combination with Trastuzumab HC while affecting the affinity as little as possible when co-expressed with Pertuzumab HC.

TABLE 18

Kinetic and Thermodynamic parameters of Trastuzumab, Pertuzumab, and hybrid molecules thereof

| Clone | ka [1/Ms] | kd [1/s] | KD [M] |
| --- | --- | --- | --- |
| Trastuzumab | 1.01E+05 | 2.24E−04 | 2.21E−09 |
| Pertuzumab | 8.08E+04 | 6.69E−05 | 1.47E−10 |
| Pertuzumab HC Pertuzumab (Tras.L3) LC | 6.47E+04 | 1.73E−03 | 2.67E−08 |
| Pertuzumab HC Pertuzumab(Tras.Y91H) LC | 8.99E+04 | 1.98E−04 | 2.21E−09 |
| Trastuzumab HC Pertuzumab(Tras.L3) LC | 4.19E+04 | 0.05 | 1.09E−06 |
| Trastuzumab HC Pertuzumab(Tras.Y91H) LC | N/A | N/A | N/A |

Example 12: Affinity-Improvement of the Common Light Chain

Introduction and Characterization of Additional Trastuzumab-Specific LCDR Residues into the Pertuzumab (Tras.L3) LC Based on the results of the previous SPR measurement, binding of the designed CLC "Pertuzumab (Trast. L3) LC" in combination with the Pertuzumab HC led to a reduced but still well detectable binding. In contrast, co-expression of the CLC with Trastuzumab HC resulted in a very weak affinity in the micromolar range and was significantly reduced compared to the parental Trastuzumab antibody.

In order to further evolve the generation of a CLC and improve the binding in combination with the Trastuzumab HC, additional Trastuzumab-specific amino acid of the LCDR1, 2, and 3 as well in framework 3 region that are specific for Trastuzumab were individually introduced into the sequence of the previously designed "Pertuzumab (Trast.L3) LC" (DNA sequence of variable domains listed as SEQ ID NO: 31, 33, 35, 37, 39, 41, 43, 45, 47, 49, and 51). The resulting constructs (protein sequence of variable domains listed as SEQ ID NO: 32, 34, 36, 38, 40, 42, 44, 46, 48, 50, and 52) were co-expressed with the Trastuzumab HC (SEQ ID NO: 92) or the Pertuzumab HC (SEQ ID NO: 22) and purified from mammalian-derived cell culture supernatant. Binding to Her2 was measured and compared with the respective parental antibodies.

Affinity-Determination of the "Pertuzumab (Trast.L3) LC" Variants by SPR

The Affinity ($K_D$) of the new antibody chain combinations was measured by surface plasmon resonance using a ProteOn XPR36 instrument (Biorad) and was performed as described before. A summary of the kinetic and thermodynamic measurements is given in table 19. Interestingly, none of the additional single mutations in the "Pertuzumab (Tras.L3) LC" variants significantly affected the affinity when combined with the Pertuzumab and the affinity was comparable to "Pertuzumab HC" x "Pertuzumab (Tras.L3) LC". However, combination of the "Pertuzumab (Tras.L3) LC" variants with the Trastuzumab HC resulted in significant differences. While back mutations to the Pertuzumab sequence in the LCDR3 region (P94Y and T96Y) (protein sequence of variable domains listed as SEQ ID NOs: 50 and 52) completely abolished binding to Her2, introduction of Pertuzumab-specific mutations (SEQ ID NOs: 32, 34, 36, 38, 40, 42, 44, 46, and 48) yielded an equal or improved affinity compared to the initial combination "Trastuzumab HC" x "Pertuzumab (Tras.L3) LC". In particular, introduction of the mutations I31T, G32A, Y53F, and G66R led to the most significant improvement in binding.

Simultaneous Introduction of Most Significant Trastuzumab-Specific Residues into the "Pertuzumab (Tras.L3) LC"

Based on the binding measurement described above, introduction of the 4 most relevant Trastuzumab-specific mutations into the "Pertuzumab (Tras.L3) LC" was combined. The protein sequences of the variable domains containing either the individual mutations are listed as SEQ ID NOs: 36, 40, 42, and 48.) The chain containing the "quadruple mutation" was named "Pertuzumab (Tras.L3) (QM) LC" (SEQ ID NOs: 54).

Affinity-Determination of the "Pertuzumab (Trast.L3)(QM) LC" by SPR

Figure 20:
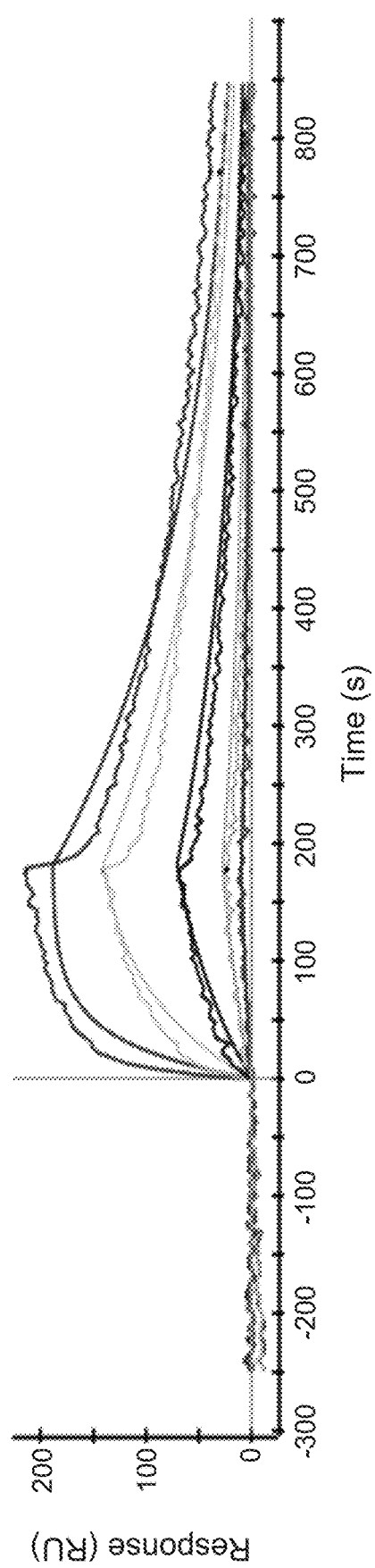
FIG. 20: SPR analysis of the Pertuzumab and Trastuzumab HCs in combination with the newly identified common light chain Pertuzumab (Tras.L3)(QM), SEQ ID No: 54. Shown is the binding of both antibodies to Her2 at different concentrations. Smooth lines represent a global fit of the data to a 1:1 interaction model.
Figure 20:
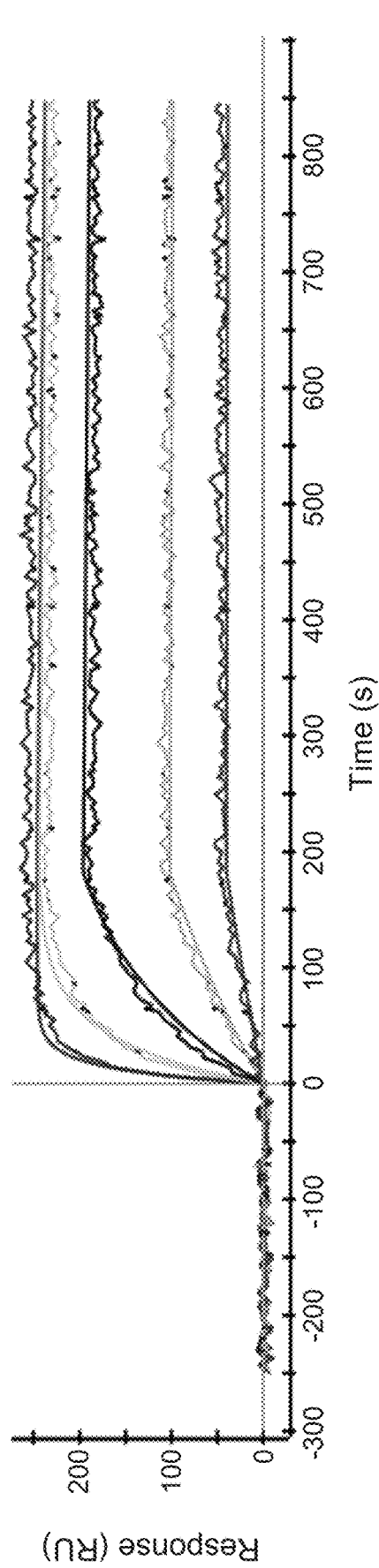

In order to characterize the new "Pertuzumab (Tras.L3) (QM) LC" and to determine the binding affinity when combined with either Pertuzumab HC or Trastuzumab HC, a further SPR experiment was performed. The Affinity ($K_D$) of the new antibody chain combinations was measured using a ProteOnPROTEON™ XPR36 instrument (Biorad) and was performed as described before. A summary of the kinetic and thermodynamic measurements is given in FIG. 20 and table 20.

Similar to the individual mutations that were introduced and characterized before, the affinity of the antibody comprising the Pertuzumab HC and the "Pertuzumab (Tras.L3) (QM) LC" did not significantly decrease compared to the initial chain combination "Pertuzumab HC" x "Pertuzumab (Tras.L3) LC". For both chain combinations, the affinity was in the range of 26 to 34 nM. Interestingly, the combination of the "Trastuzumab HC" with the "Pertuzumab (Tras.L3) (QM) LC" leads to a very strong improvement of the affinity to Her2. Furthermore, its affinity of 200 pM is even better than the measured affinity of the parental antibody Trastuzumab (2.2 nM). Given that the combination of "Pertuzumab (Tras.L3) (QM) LC" with Trastuzumab HC fully restores (or even exceeds) binding to Her2 and considering that the combination with the Pertuzumab HC diminishes but not abrogates binding to Her2, it was apparent to use the "Pertuzumab (Tras.L3) (QM) LC" as a CLC for both Her2 specificities and restore binding to the Pertuzumab-specific epitope by affinity-maturation of the Pertuzumab HC.

TABLE 19

Kinetic and thermodynamic parameters of antibodies comprising either a Trastuzumab or Pertuzumab HC in combination of additional CLC hybrid molecules

| | Pertuzumab HC | | | Trastuzumab HC | | |
|---|---|---|---|---|---|---|
| Clone | ka [1/Ms] | kd [1/s] | KD [M] | ka [1/Ms] | kd [1/s] | KD [M] |
| Tras.L3 (K24R) | 4.57E+05 | 2.11E−03 | 4.62E−09 | 3.77E+05 | 2.52E−02 | 6.68E−08 |
| Tras.L3 (S30N) | 5.30E+05 | 1.80E−03 | 3.40E−09 | 3.96E+05 | 2.56E−03 | 6.46E−08 |
| Tras.L3 (I31T) | 4.31E+05 | 1.75E−03 | 4.06E−09 | 4.73E+05 | 3.41E−03 | 7.21E−09 |
| Tras.L3 (I31V) | 4.40E+05 | 1.92E−03 | 4.35E−09 | 4.13E+05 | 1.16E−02 | 2.80E−08 |
| Tras.L3 (G32A) | 5.11E+05 | 1.87E−03 | 3.66E−09 | 6.75E+05 | 2.68E−03 | 3.97E−09 |
| Tras.L3 (Y53F) | 3.16E+05 | 2.54E−03 | 8.03E−09 | 3.81E+05 | 1.71E−02 | 4.49E−08 |
| Tras.L3 (R54L) | 4.64E+05 | 2.26E−03 | 4.87E−09 | 4.16E+05 | 2.97E−02 | 7.15E−08 |

TABLE 19-continued

Kinetic and thermodynamic parameters of antibodies comprising either a Trastuzumab or Pertuzumab HC in combination of additional CLC hybrid molecules

| Clone | Pertuzumab HC | | | Trastuzumab HC | | |
|---|---|---|---|---|---|---|
| | ka [1/Ms] | kd [1/s] | KD [M] | ka [1/Ms] | kd [1/s] | KD [M] |
| Tras.L3 (T56S) | 4.43E+05 | 2.45E−03 | 5.52E−09 | 4.70E+05 | 2.32E+02 | 4.94E−08 |
| Tras.L3 (G66R) | 3.58E+05 | 2.47E−03 | 6.91E−09 | 5.14E+05 | 5.58E−03 | 1.09E−08 |
| Tras.L3 (T94Y) | 8.05E+05 | 6.30E−04 | 7.82E−10 | N/A | N/A | N/A |
| Tras.L3 (P96Y) | 3.44E+05 | 9.70E−04 | 2.82E−09 | N/A | N/A | N/A |
| Tras.L3 | 4.22E+05 | 2.09E−03 | 4.96E−09 | 3.25E+05 | 2.36E−02 | 7.25E−08 |

TABLE 20

Kinetic and thermodynamic parameters of antibodies comprising either a Trastuzumab or Pertuzumab HC and the final CLC

| Clone | ka [1/Ms] | kd [1/s] | KD [M] |
|---|---|---|---|
| Pertuzumab HC Pertuzumab (Tras.L3)(QM) LC | 9.46E+04 | 3.24E−03 | 3.42E−08 |
| Trastuzumab HC Pertuzumab (Tras.L3)(QM) LC | 2.69E+05 | 5.42E−05 | 2.02E−10 |

Example 13: Affinity Maturation of the Pertuzumab Heavy Chain

Generation of Pertuzumab-Based H1/H3 and H2 Affinity Maturation Libraries

Generation of affinity-matured Pertutzumab-derived heavy chains was carried out by phage display using standard protocols (Silacci et al, 2005).

For the generation of Pertuzumab-derived HCs with improved affinity when jointly expressed with "Pertuzumab (Tras.L3) (QM) LC" a maturation library randomized in CDR1 and 3 or in CDR2 was generated. The sequence of the Pertuzumab HC (SEQ ID NO: 22) and of the "Pertuzumab (Tras.L3) (QM) LC" (SEQ ID NO: 54) was cloned into a phagemid and used as a template for the randomization. For the generation of the Pertuzumab HC affinity maturation library randomized in CDR1 and 3, three fragments were assembled by "splicing by overlapping extension" (SOE) PCR and cloned into the phage vector. The following primer combinations were used to generate the library fragments: fragment 1 (LMB3 (SEQ ID NO: 147) and AM_omni_H1_TN-ba (SEQ ID NO: 148), fragment 2 (RJH108 (omni_3'H1_fo) (SEQ ID NO: 149) and RJH109 (omni_5'H3_re) (SEQ ID NO: 150), and fragment 3 (AM_omni_H3_TN_fo (SEQ ID NO: 151) and RJH99 (SEQ ID NO: 152). After assembly of sufficient amounts of full length randomized fragment, it was digested with MunI/NheI alongside with identically treated acceptor phagemid vector. 6 ug of Fab library insert were ligated with 24 ug of phagemid vector. Purified ligations were used for 60 transformations resulting in 6×10 exp9 transformants. Phagemid particles displaying the Pertuzumab affinity maturation library were rescued and purified by PEG/NaCl purification to be used for selections.

The generation of the CDR2-randomized Pertuzumab HC affinity maturation library was done similarly, but only 2 fragments were generated, assembled and cloned into the phagemid using the same restriction enzymes as before. The following primer combinations were used to generate the library fragments: fragment 1 (LMB3 (SEQ ID NO: 147) and RJH110 (omni_5'H2_ba) (SEQ ID NO: 153) and fragment 2 (AM_omni_h2_TN_fo (SEQ ID NO: 154) and RJH99 (SEQ ID NO:152). Purified ligations were used for 60 transformations resulting in 4×10 exp9 transformants. Phagemid particles displaying the Pertuzumab affinity maturation library were rescued and purified by PEG/NaCl purification to be used for selections.

TABLE 21 a)

Primer combinations for the generation of the CDR1 and 3-randomized Pertuzumab affinity-maturation library Pertuzumab HC affinity maturation (CDR1 and 3)

| fragment | 5'Primer | 3'Primer |
|---|---|---|
| PCR1 | LMB3 | AM_omni_H1_TN-ba |
| PCR2 | RJH108 (omni_3'H1_fo) | RJH109 (omni_5'H3_re) |
| PCR3 | AM_omni_H3_TN_fo | RJH99 |

TABLE 21 b

Primer sequences for the generation of the CDR1 and 3-randomized Pertuzumab affinity-maturation library Pertuzumab HC affinity maturation (CDR1 and 3)

| SEQ ID | Name | Sequence |
|---|---|---|
| 147 | LMB3 | CAGGAAACAGCTATGACCATGATTAC |
| 148 | AM_omni_H1_TN-ba | CCGGTGCCTGACGAACCCAATCCAT4 3 2 1 AAAGGTAAAACCGCTTGCTGCACAGCTC<br>1 T = 60%, S/G/R/N/D = 20% (4% each), rest = 20% (1.7% each)<br>2 D = 60%, S/N/T/A/R/E/Q/G = 30% (3.8% each), rest = 10% (1.1% each) |

TABLE 21 b-continued

Primer sequences for the generation of the CDR1 and 3-randomized Pertuzumab affinity-maturation library
Pertuzumab HC affinity maturation (CDR1 and 3)

| SEQ ID | Name | Sequence |
|---|---|---|
| | | 3 Y = 60%, F/S/H/N/D/T = 30% (5.0% each), rest = 10% (0.9%)<br>4 T = 60%, A/G/V/S/P/D/N = 30% (4.3% each), rest = 10% (1.0%) |
| 149 | RJH108 (omni_3'H1_fo) | ATGGATTGGGTTCGTCAGGCACCGGGTAAAGG |
| 150 | RJH109 (omni_5'H3_re) | ATTACGTGCACAATAATACACTGCGGTATCCTC |
| 151 | AM_omni_H3_TN_fo | TACCGCAGTGTATTATTGTGCACGT4a 5 5a 6 7 TTC8<br>TTTGATTATTGGGGTCAGGGCACCCTGGTTAC<br>4a N = 60%, G/D/E/Q/V/S/A/P/R/L/T/Y = 40% (3.3% each)<br>5 L = 60%, G/Y/S/A/D/T/R/P/V/N/W/F/I/E = 40% (2.9% each)<br>5a G = 60%, Y/S/A/D/T/R/P/L/V/N/W/F/I/E = 40% (2.9% each)<br>6 P = 60%, G/Y/S/A/D/T/R/L/V/N/W/F/I/E = 40% (2.9% each)<br>7 S = 60%, G/Y/P/A/D/T/R/L/V/N/W/F/I/E = 40% (2.9% each)<br>8 Y = 60%, G/A/P/W/S/D/T/F/R/K/H = 40% (3.6% each) |
| 152 | RJH99 | GGCTGAGACTCCTCAAGAGAAGGATTAG |

TABLE 22 a)

Primer combinations for the generation of the CDR2-randomized Pertuzumab affinity-maturation library
Pertuzumab HC affinity maturation (CDR2)

| fragment | 5'Primer | 3'Primer |
|---|---|---|
| PCR1 | LMB3 | RJH110(omni_5'H2_ba) |

Table 22 b

Primer combinations for the generation of the CDR2-randomized Pertuzumab affinity-maturation library
Pertuzumab HCaffinity maturation (CDR2)

| SEQ ID | Name | Sequence |
|---|---|---|
| 153 | RJH110(omni_5'H2_ba) | ATTAACATCTGCAACCCATTCCAGACCTTTAC |
| 154 | AM_onmi_h2_TN_fo | GGTCTGGAATGGGTTGCAGATGTTAAT9 10 11 12 GGT<br>13 ATT14 AAC15 CGTTTTAAAGGTCGTTTTACCCTGAG<br>9 P = 60%, G/A/S/T/D/N/F/Y = 30% (3.8% each), rest = 10% (1.0% each)<br>10 N = 60%, S/D/G/T/R/A = 30% (5.0% each), rest = 10% (0.8%)<br>11 S = 60%, G = 10%, rest = 30% (1.8% each) |

Selection of Affinity Matured Pertuzumab HC-Derived Clones

Selections against the extracellular domain (ECD) of human Her2 were carried out using HEK293-expressed protein. The antigen was enzymatically biotinylated by co-expression of the biotin ligase Bir A via an N-terminal avi-tag Panning rounds were performed in solution according to the following pattern: 1. binding of ~$10^{12}$ phagemid particles to 10 nM biotinylated Her2 ECD for 0.5 h in a total volume of 1 ml, 2. capture of biotinylated Her2 ECD and specifically bound phage particles by addition of 5.4×$10^7$ streptavidin-coated magnetic beads for 10 min, 3. washing of beads using 5×1 ml PBS/Tween20 and 5×1 ml PBS, 4. elution of phage particles by addition of 1 ml 100 mM TEA for 10 min and neutralization by adding 500 µl 1M Tris/HCl pH 7.4, 5. re-infection of exponentially growing E. coli TG1 bacteria, and 6. infection with helper phage VCSM13 and subsequent PEG/NaCl precipitation of phagemid particles to be used in subsequent selection rounds. Selections were carried out over 3 rounds using decreasing (from 20×$10^{-9}$M to 1×$10^{-9}$M) antigen concentrations. In round 2 and 3, capture of antigen:phage complexes was performed using neutravidin plates instead of streptavidin beads. In addition, neutravidin plates were washed for 3 h in 21 PBS. Specific binders were identified by ELISA as follows: 100 µl of 30 nM biotinylated Her2 ECD per well were coated on neutravidin plates. Fab-containing bacterial supernatants were added and binding Fabs were detected via their Flag-tags by using an anti-Flag/HRP secondary antibody. ELISA-positive clones were bacterially expressed as soluble Fab fragments in 96-well format and supernatants were subjected to a kinetic screening experiment by SPR-analysis using PRO-TEON™ XPR36.

Affinity-Determination of Affinity-Matured Pertuzumab HC Variants by SPR

The Affinity ($K_D$) of the new Pertuzumab HC variants was measured by surface plasmon resonance. In a first step, 7000

RU of polyclonal anti-human Fab antibody were immobilized on all 6 channels of a GLM chip by Amine coupling (NaAcetate pH4.5, 30 µl/min, 300 s) (vertical orientation).

Figure 21:
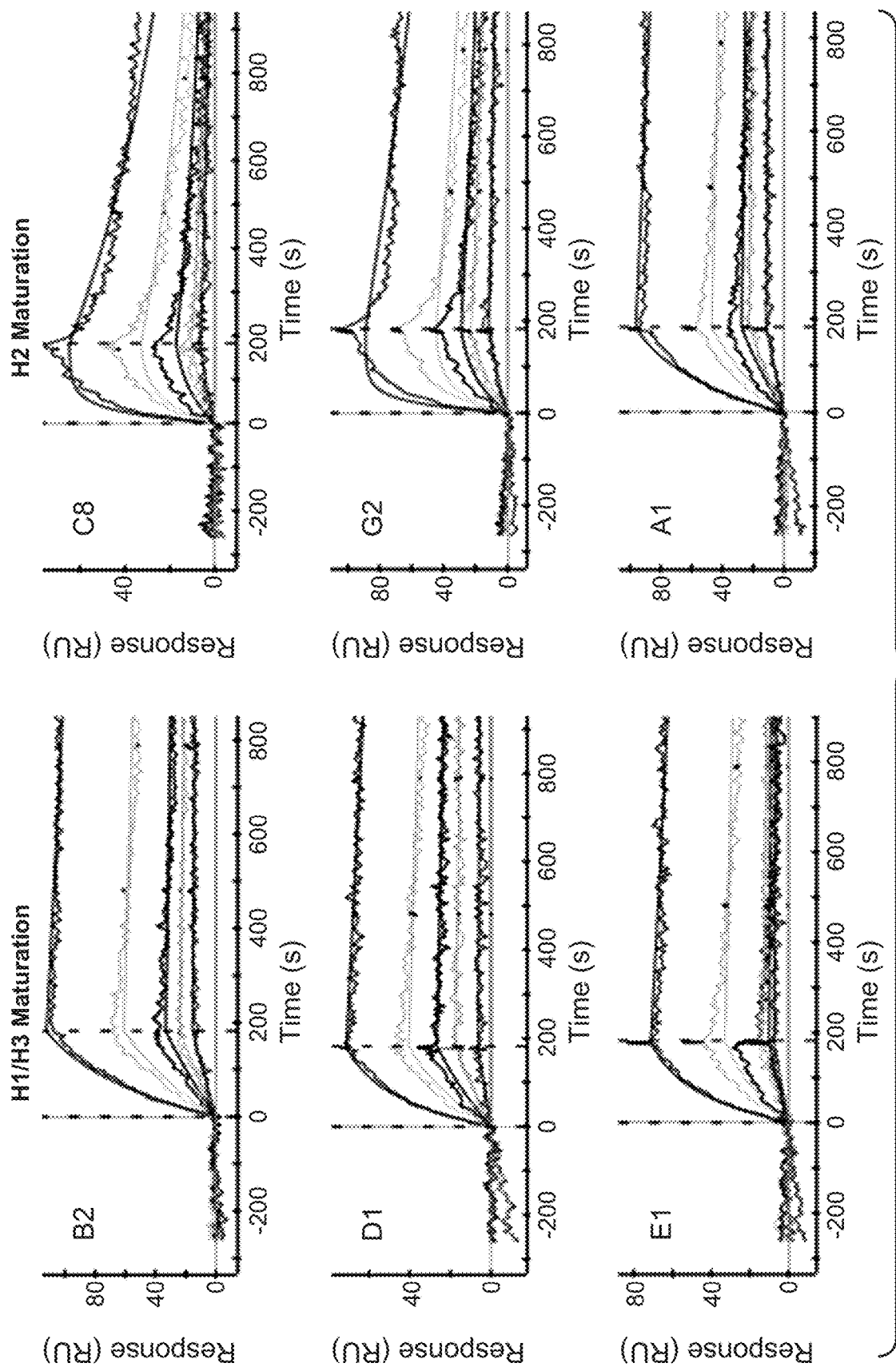
FIG. 21: Characterization of the affinity-matured Pertuzumab clones identified by phage display. SPR analysis of the identified affinity-matured clones. Shown is the binding of bacterial Fabs to Her2 at different concentrations. Smooth lines represent a global fit of the data to a 1:1 interaction model. B2: SEQ ID No: 66, D1: SEQ ID No: 62, E1: SEQ ID No: 68, C8: SEQ ID No: 72, G2: SEQ ID No: 70, A1: SEQ ID No: 74.

Each antibody-containing bacterial supernatant was filtered and 3-fold diluted with PBS, and then injected for 180 s at 30 µl/minute to achieve immobilization levels of between 100 and 400 response units (RU) in vertical orientation. Injection of Her2: For one-shot kinetics measurements, injection direction was changed to horizontal orientation, two-fold dilution series of purified Her2 (varying concentration ranges between 100 and 6.25 nM) were injected simultaneously at 100 µl/min along separate channels 1-5, with association times of 180 s, and dissociation times of 1000 s. Buffer (PBST) was injected along the sixth channel to provide an "in-line" blank for referencing. Regeneration was performed by two pulses of 10 mM glycine pH 1.5 and 50 mM NaOH for 30 s at 100 µl/min (horizontal orientation). Association rate constants ($k_{on}$) and dissociation rate constants ($k_{off}$) were calculated using a simple one-to-one Langmuir binding model in ProteOn Manager v3.1 software by simultaneously fitting the association and dissociation sensorgrams. The equilibrium dissociation constant ($K_D$) was calculated as the ratio $k_{off}/k_{on}$. Clones expressing Fabs with the highest affinity constants were identified and the heavy chains of the corresponding phagemids were sequenced. The thermodynamic measurement of the most affine Pertuzumab HC variants (protein sequence of variable domains listed as SEQ ID NOs: 62, 66, 68, 70, 72, and 74) is summarized in table 23 and FIG. 21.

TABLE 23

Affinity of selected affinity matured Pertuzumab clone variants in combination with the common light chain (CLC)

| Pertuzumab heavy chain | affinity (nM) |
| --- | --- |
| Pertuzumab | 34 |
| Aff. mat. clone D1 | 1 |
| Aff. mat. clone B2 | 1 |
| Aff. mat. clone E1 | 0.5 |
| Aff. mat. clone G2 | 1 |
| Aff. mat. clone C8 | 3 |
| Aff. mat. clone A1 | 1 |

Figure 22:
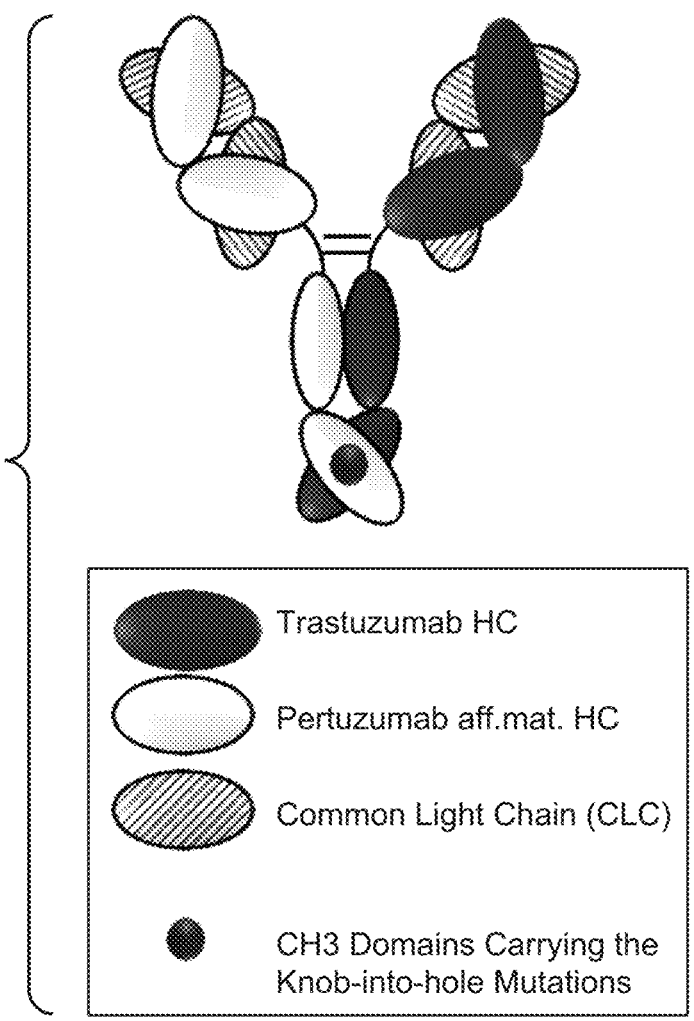
FIG. 22: Schematic drawing of the bi-specific HER2 antibodies with a common light chain.
Figure 23A:
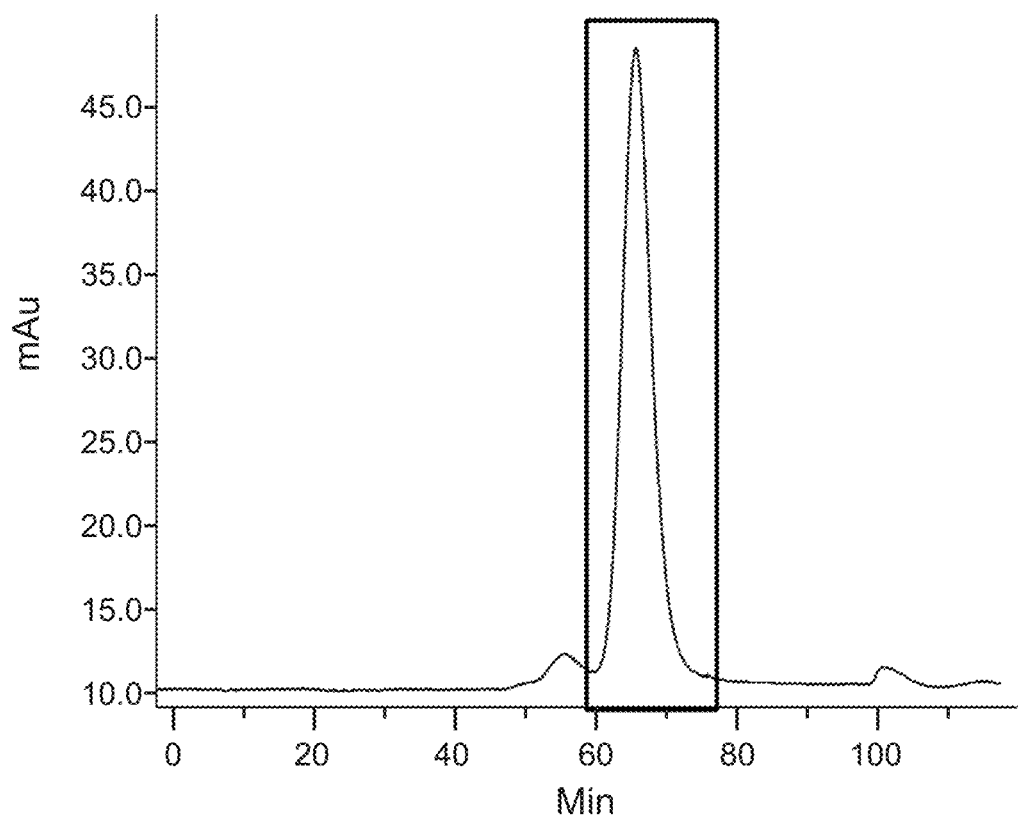
FIGS. 23A-23C: Purification and analytical characterization of the bi-specific HER2 antibodies with a common light chain. The purification method involved an affinity step (protein A) followed by size exclusion chromatography (Superdex 200, GE Healthcare). The final product was analyzed and characterized by analytical size exclusion chromatography (Superdex 200 column) (23A): comprising D1der (SEQ ID NO: 64), (23B): comprising G2 (SEQ ID NO: 70), (23C): comprising E1 (SEQ ID NO: 68).
Figure 23A:
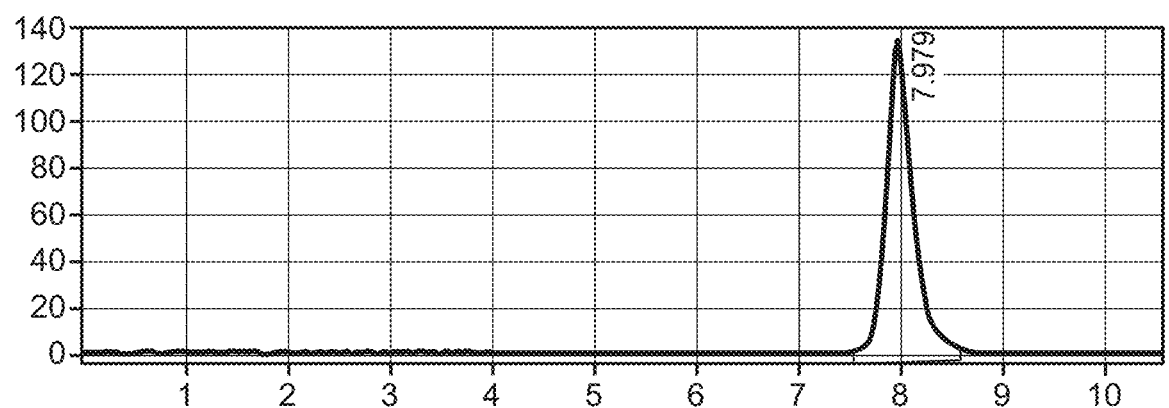
Figure 23B:
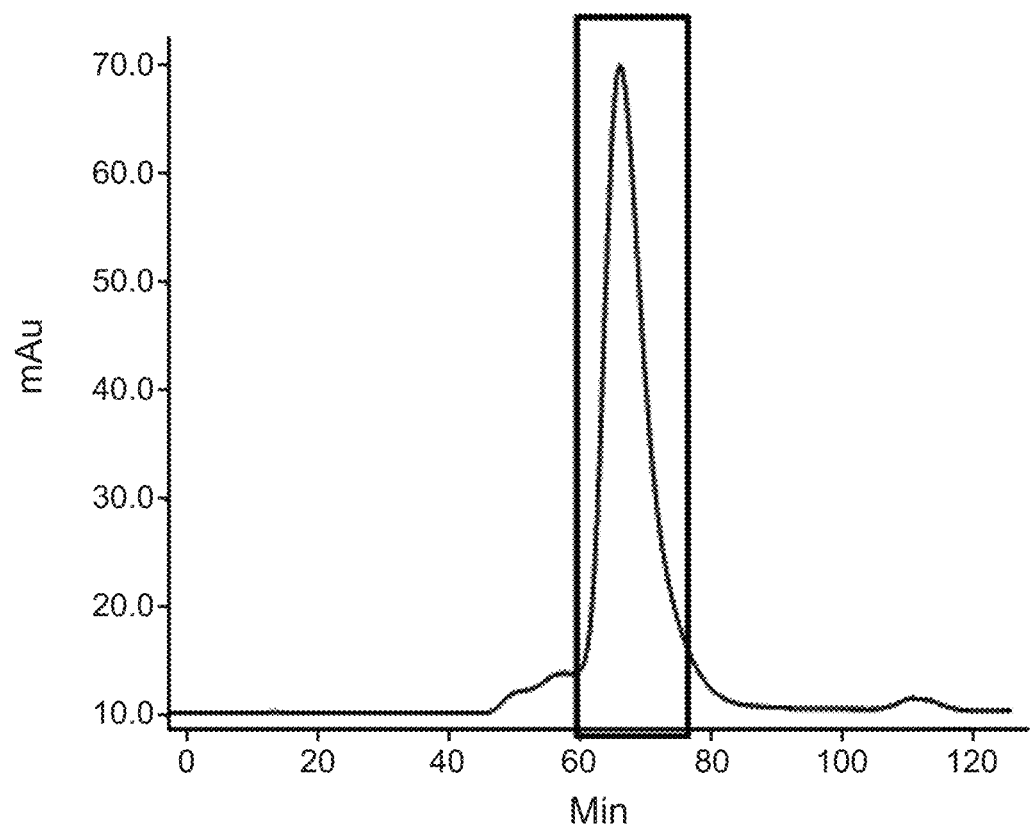
Figure 23B:
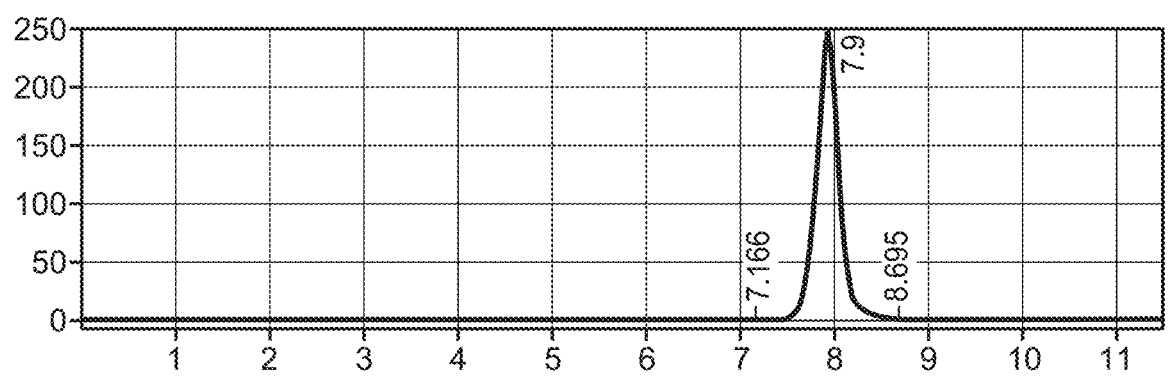
Figure 23C:
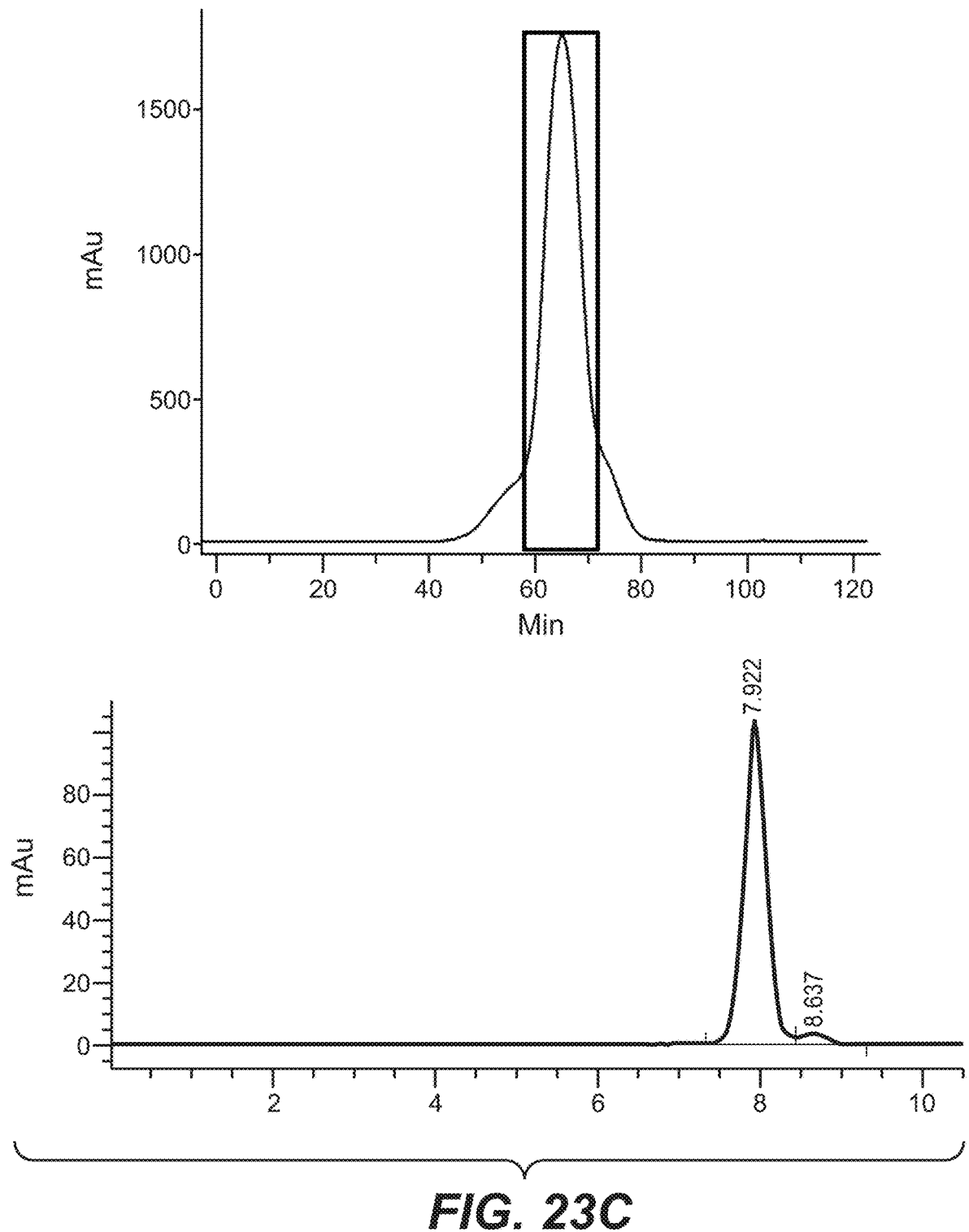

Example 14: Characterization of the Trastuzumab/Pertuzumab Bispecific Antibodies Generation of the Trastuzumab/Pertuzumab Bi-Specific Anti-Her Antibodies with a CLC In the following step, the affinity-matured Pertuzumab HC as well as the Trastuzumab HC were expressed in combination with the CLC named "Pertuzumab (Tras.L3) (QM) LC" in a bispecific antibody format. For the generation of such bispecific antibodies with a CLC, heterodimerization of the 2 different HCs was achieved by application of the knob-into-hole technology. Variable domains of the Pertuzumab affinity-matured clones E1 and G2 (protein sequence of variable domains listed as SEQ ID NOs: 68 and 70) as well as a clone "D1-derived" (D1-der) sequence (SEQ ID NOs: 64) were cloned into a human IgG1 HC containing the "hole" mutations in domain CH3. A schematic overview of the bispecific antibody with a CLC is shown in FIG. 22. Affinity-maturation clone "D1-der" combines the CDR1 and 3 mutations of clone D1 (SEQ ID NOs: 62) with additional CDR2 mutations found in other selected clones. The variable domain of the Tratuzumab HC (SEQ ID NO: 92) was cloned into a human IgG1 HC harboring the "knob" mutations in domain CH3. The resulting constructs, called "Herceptarg" constructs, were co-expressed and purified from mammalian-derived cell culture supernatant. A summary of the analytical data for all three bi-specific antibodies is shown clones in FIGS. 23A-23C and table 24.

TABLE 24

Production of HER2 antibody with common light chain

| Antibody | yield/liter (mg/l) | % Monomer |
| --- | --- | --- |
| Herceptarg CLC G2 | 41.3 | 100 |
| Herceptarg CLC E1 | 72.1 | 96 |
| Herceptarg CLC D1-der. | 20.1 | 100 |

Generation of Her2 Knock-Out Antigen Variants

In order to analyze and characterize binding of the Herceptarg bi-specific antibodies to each of both epitopes on Her2, Her2 knock-out variants were designed. In these variants, either of the two specific epitopes was deleted by mutation of the amino acids that interact with the respective antibody chains.

For expression and purification, the respective DNA fragments were fused in frame to an N-terminal leader sequence and a C-terminal human IgG1 Fc coding fragment serving as solubility- and purification tag. An avi-tag at the C-terminal end of the Fc fragment allowed in vivo biotinylation. In order to express the antigen in a monomeric form, these Fc chains contained the "knob" mutations (SEQ ID NOs: 5 and 6, Her2 ECD-Fc(knob); SEQ ID NOs: 7 and 8, Her2 ECD (Pertuzumab KO)-Fc(knob); SEQ ID NOs: 9 and 10, Her2 ECD (Trastuzumab KO)-Fc(knob)) and was co-expressed in combination with an "Fc-hole" counterpart (SEQ ID NOs: 3 and 4).

Affinity-Determination of the Herceptarg Bi-Specific Antibodies by SPR

The Affinity ($K_D$) of the new bi-specific antibodies to each of their epitopes in her2 was measured by SPR using a ProteOn XPR36 instrument (Biorad) at 25° C. In a first step, 11000 RU of a polyclonal goat anti-human IgG (Sigma 121360 recognizing human IgG (Fc-specific) was immobilized on all 6 channels of a GLM chip by Amine coupling (NaAcetate pH4, 30 µl/min, 300 s) (vertical orientation).

Figure 24:
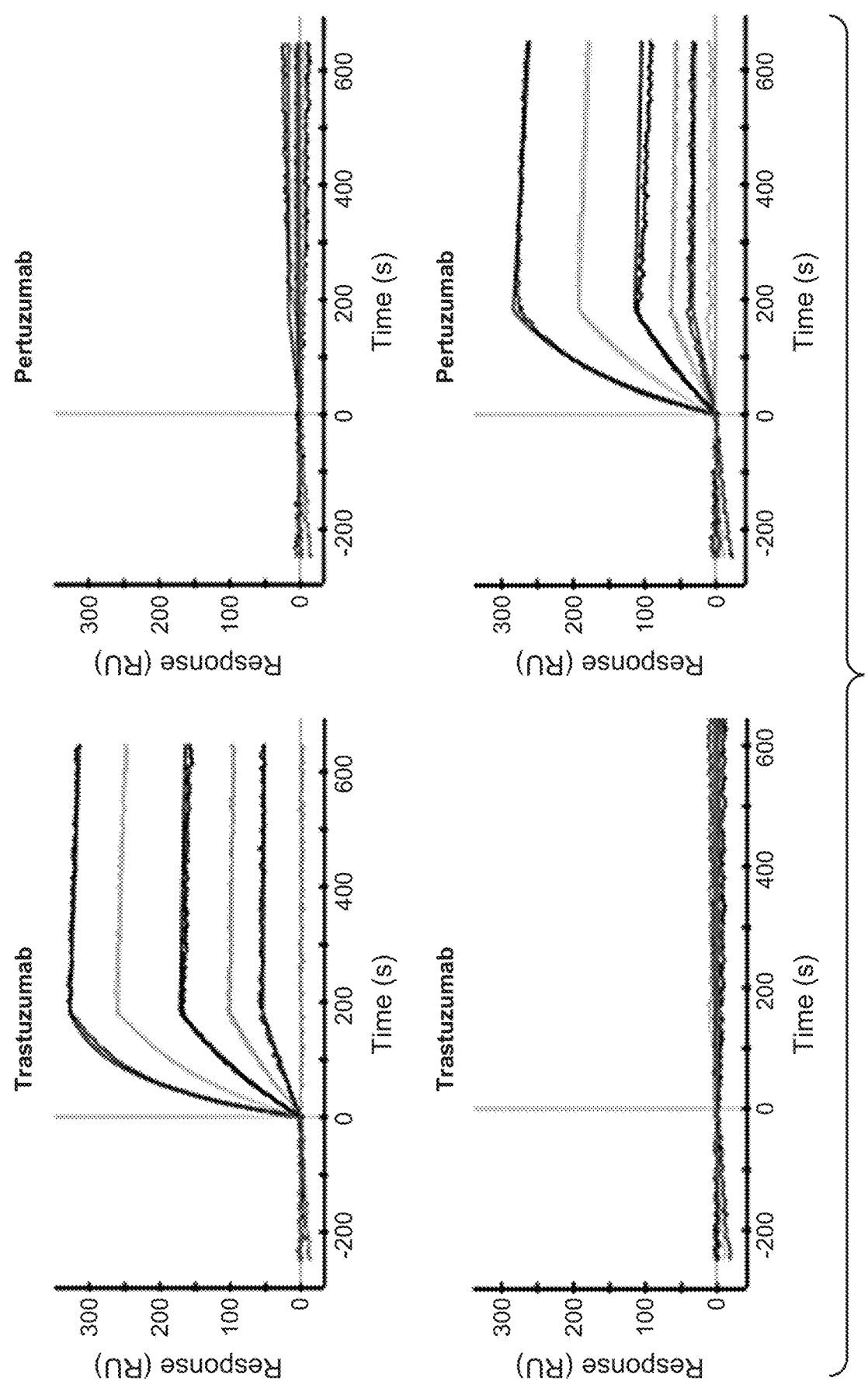
FIG. 24: SPR analysis of the Her2 knock-out variants. Shown are the sensograms of Trastuzumab and Pertuzumab binding to both knock-out variants. Smooth lines represent a global fit of the data to a 1:1 interaction model.

Each antibody was diluted with PBST (10 mM phosphate, 150 mM sodium chloride pH 7.4, 0.005% Tween 20) to 2 µg/ml, and then injected for 60 s at 30 µl/minute to achieve immobilization levels of about 400 response units (RU) in vertical orientation. Injection of Her2: For one-shot kinetics measurements, injection direction was changed to horizontal orientation, two-fold dilution series of purified monovalent Her2-Fc protein constructs (varying concentration ranges between 100 and 6.25 nM) were injected simultaneously at 100 µl/min along separate channels 1-5, with association times of 180 s, and dissociation times of 600 s. Buffer (PBST) was injected along the sixth channel to provide an "in-line" blank for referencing. Regeneration was performed by two pulses of 10 mM glycine pH 1.5 and 50 mM NaOH for 30 s at 100 µl/min (horizontal orientation). Association rate constants ($k_{on}$) and dissociation rate constants ($k_{off}$) were calculated using a simple one-to-one Langmuir binding model in PROTEON™ Manager v3.1 software by simultaneously fitting the association and dissociation sensorgrams. The equilibrium dissociation constant ($K_D$) was calculated as the ratio $k_{off}/k_{on}$. All antibodies including Trastuzumab, Pertuzumab as well as three bi-specific Herceptarg constructs comprising the affinity-matured Pertuzumab HCs, the Trastuzumab HC, and the CLC "Pertuzumab (Trast.L3) (QM)" were tested for binding to both Her2 knock-out variants. As expected, both Trastuzumab and Pertuzumab bind to their respective Her2 epitope with the excepted affinity. Binding to their corresponding knock-out variant was abolished (FIG. 24). These results demonstrate that the use of Her2 knock-out epitope variants allows dissecting the binding of the bispecific antibodies and analyzing the individual affinity of both specificities. Determination of the individual $K_D$ values of each Herceptarg clone variant revealed a constant binding affinity to the Trastuzumab epitope in the expected range of 0.6 to 1.8 nM. In contrast, binding to the Pertuzumab epitope depends on the affinity-matured Pertuzumab HC. Among the three Herceptarg clone variants, clone "D1-der" was found to have the highest affinity (0.16 nM). A summary of the Thermodynamic data is shown in table 25. In summary, this experiment confirms that we were able to generate a bi-specific antibody with a CLC and specific for the epitopes Trastuzumab and Pertuzumab.

Binding Analysis of the Herceptarg Clone Variants to KPL-4 Cells

Figure 25:
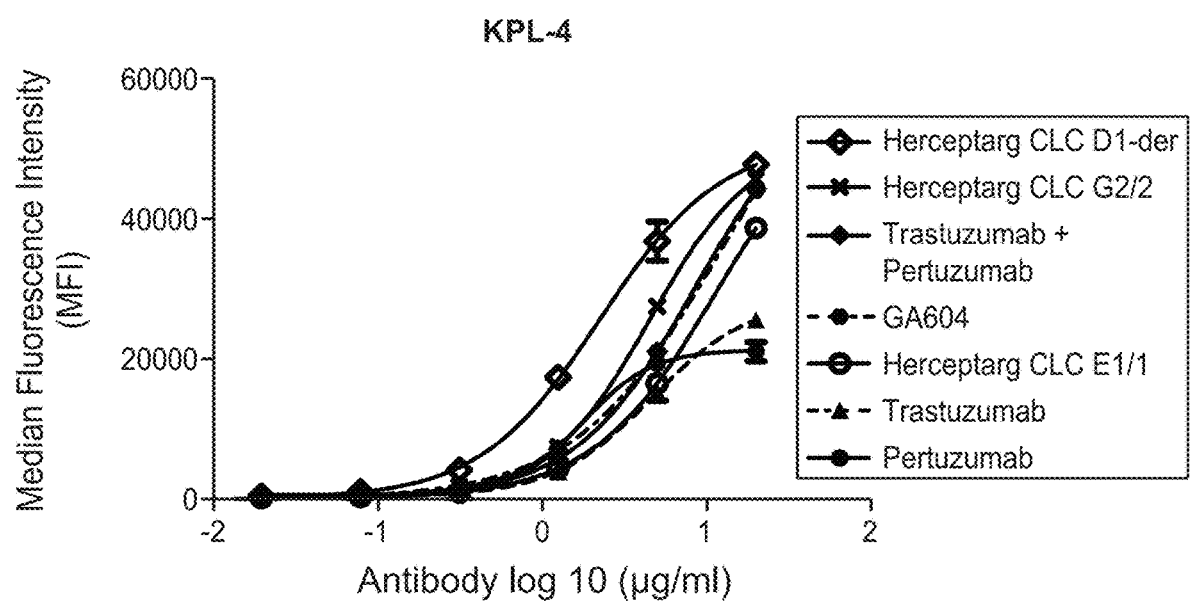
FIG. 25: Binding of bi-specific HER2 antibodies with a common light chain clone variants to KPL-4 cells. KPL-4 cells were stained with increasing concentrations of the indicated antibodies. The antibodies were detected with a FITC labeled anti-human secondary and the fluorescence was determined by flow cytometry. "Herceptarg CLC D1-der": SEQ ID NOs 64, 54, 92, "Herceptarg CLC G2/2": SEQ ID NOs 70, 54, 92, "Herceptarg CLC E1/1": SEQ ID NOs 68, 54, 92; "GA 604": SEQ ID NOs 109, 110, 111, 112.

KPL-4 cells were harvested and resuspended in FACS buffer. 0.2 Mio cells were seeded into a 96 well round bottom plate. The plate was centrifuged at 400 g for 3 min to pellet the cells. The supernatant was removed and the cells were resuspended in 40 µl of the diluted antibodies. The plate was incubated for 30 min at 4° C. to allow binding of the antibodies. To remove unbound antibodies the cells were centrifuged again and washed twice with FACS buffer. To detect the antibodies the cells were resuspended in 12 µl diluted secondary goat anti-human Fc specific FITC-labeled secondary antibody (Jackson ImmunoResearch #109-096-098) and incubated again for 30 min at 4° C. Afterwards the cells were washed twice with FACS buffer, resuspended in 200 µl FACS buffer and the fluorescence was measured with BD CantoII. Results are shown in FIG. 25.

TABLE 25

Affinity of selected bi-specific antibodies affinity matured Pertuzumab clone variants in combination with the CLC

| clone | KD (nM) Trastuzumab Epitope | KD (nM) Pertuzumab Epitope |
|---|---|---|
| Trastuzumab | 2.17 | N/A |
| Pertuzumab | N/A | 0.62 |
| Herceptarg E1 | 0.72 | 1.32 |
| Herceptarg G2 | 1.82 | 9.65 |
| Herceptarg D1-derived | 0.6 | 0.16 |
| Herceptarg crossmab | 0.8 | 0.84 |

TABLE 26

Proliferation inhibition of various cell types (IC50 values with confidence interval)

| cell line | Trastuzumab | Pertuzumab | Trastuzumab + Pertuzumab | Herceptarg CLC E1/1 |
|---|---|---|---|---|
| BT474 | 110.8 (96.7-127.0) | 205.4 (156-270.7) | 222.3 (176.5-280.1) | 114.1 (106-122.7) |
| N87 | 83.13 (59.7-115.7) | 205.8 (126.3-335) | 312.9 (156.5-625.6) | 136.5 (126.6-147) |
| SkBr3 | 73.73 (43.54-124.8) | nd | 55.63 (25.97-119.2) | 69.01 (55.78-85.4) |

| cell line | Herceptarg CLC D1-der | Herceptarg CLC G2/2 | GA604 |
|---|---|---|---|
| BT474 | 78.38 (69.03-89) | 89.99 (82.3-98.4) | 125.4 (113.6-138.4) |
| N87 | 92.7 (80.7-106.5) | 119.1 (107.6-132) | 109.6 (98.3-122.2) |
| SkBr3 | 47.54 (26.61-84.9) | 92.59 (70.1-122.3) | 59.84 (50.2-71.4) |

Proliferation Inhibition Mediated by the Herceptarg Binding Variants

Figure 26A:
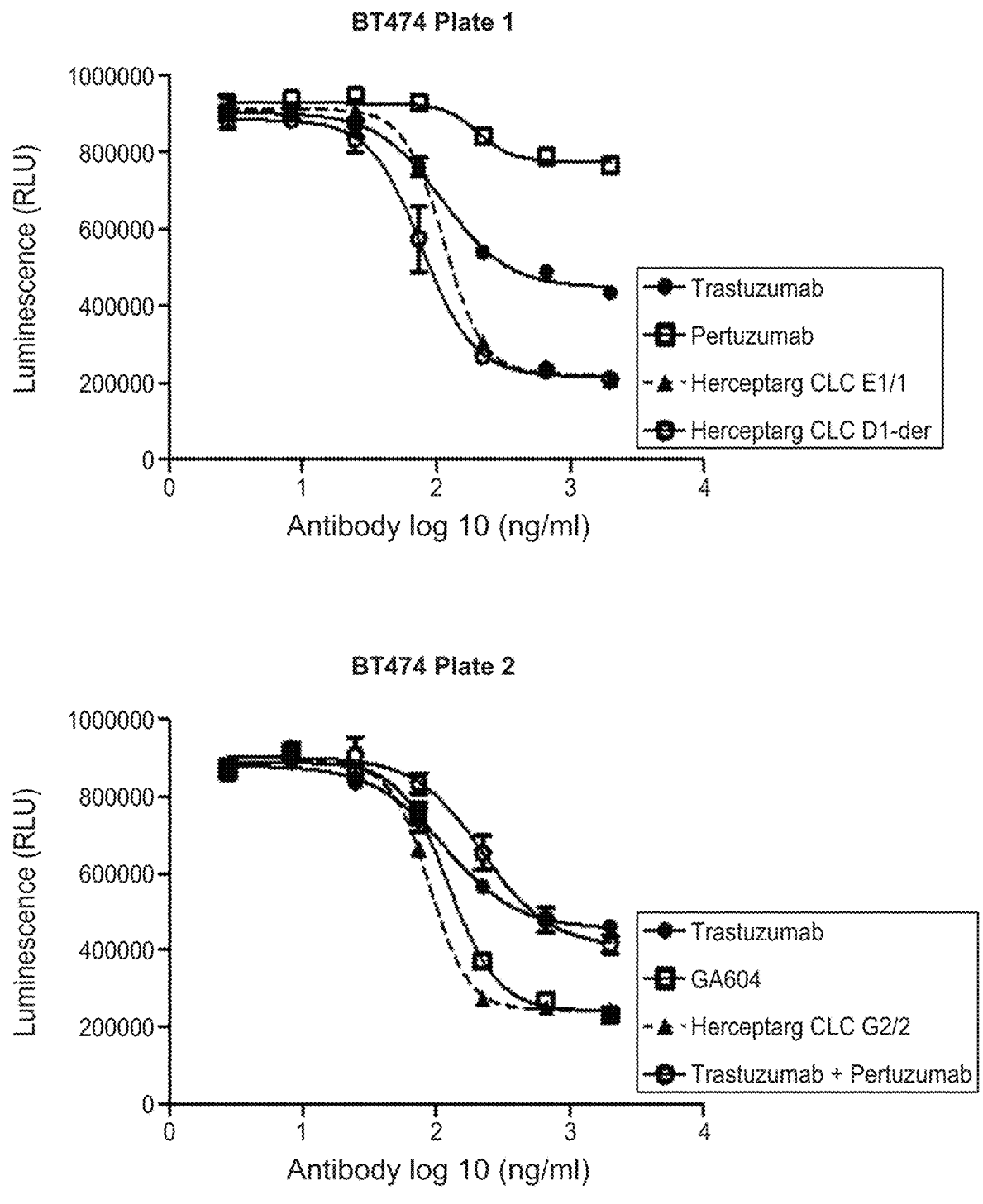
FIGS. 26A-26C: Proliferation inhibition of BT474, N87, and SkBr3 cells with bi-specific HER2 antibodies with common light chain clone variants. BT474 (26A), N87 (26B), and SkBr3 (26C) cells were treated with the three different Herceptarg variants. As controls Trastuzumab, Pertuzumab and the combination of both were included. After 5 days, proliferation inhibition was determined with Cell-Titer Glo. "Herceptarg CLC D1-der": SEQ ID NOs 64, 54, 92, "Herceptarg CLC G2/2": SEQ ID NOs 70, 54, 92, "Herceptarg CLC E1/1": SEQ ID NOs 68, 54, 92; "GA 604": SEQ ID NOs 109, 110, 111, 112.
Figure 26B:
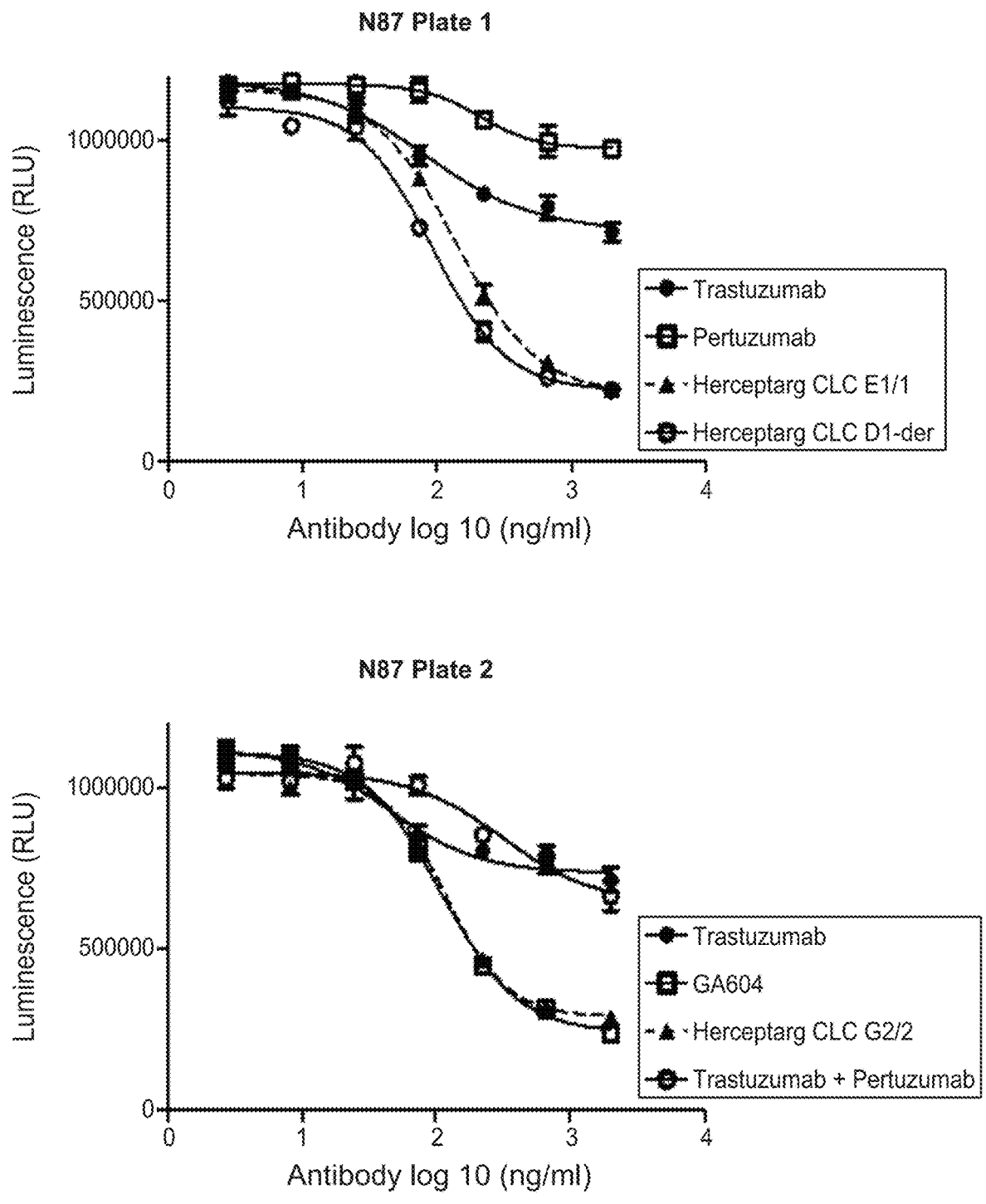
Figure 26C:
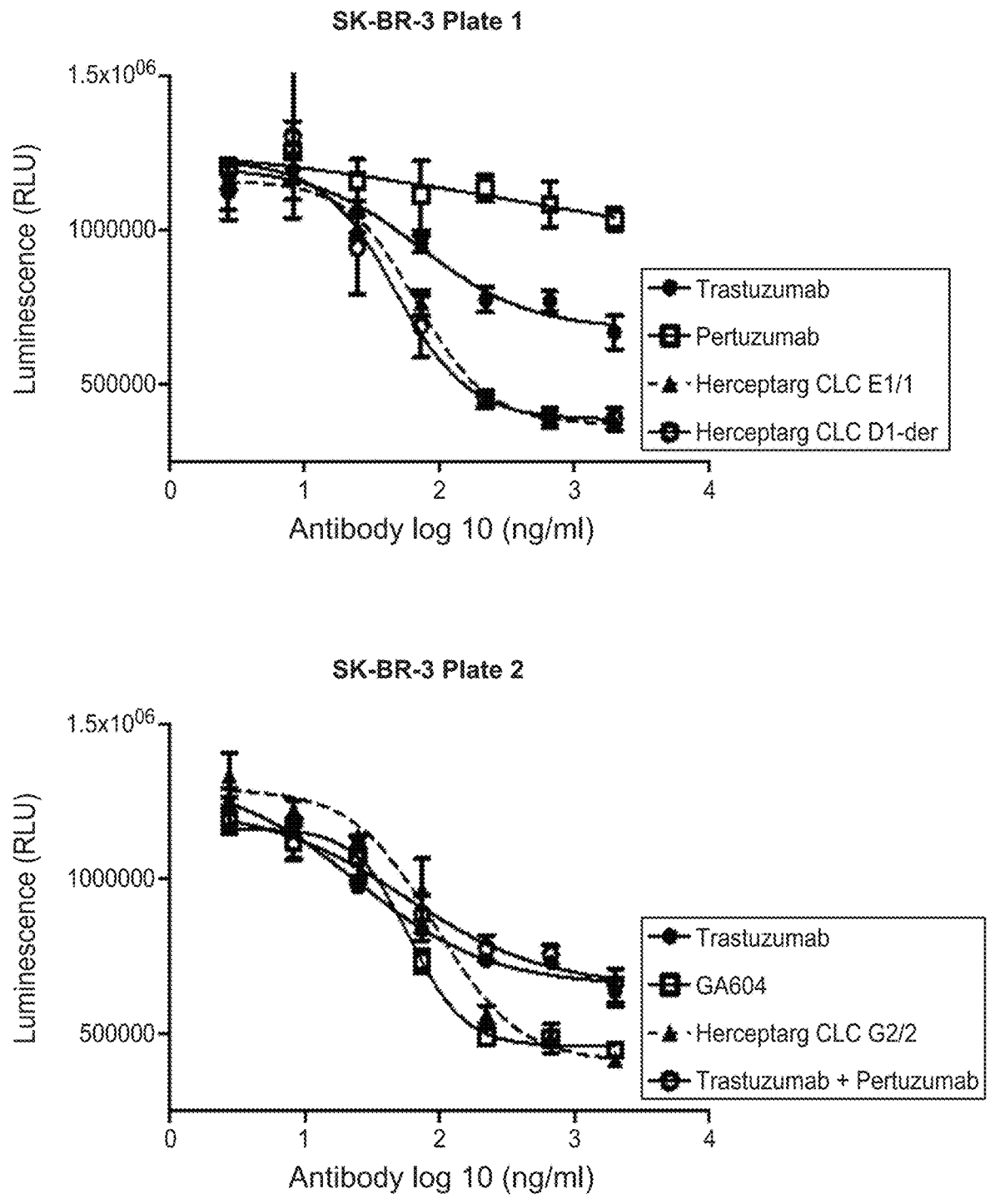

Target cells were harvested, washed, resuspended in RPMI 1640 (Gibco)+10% FCS+1% GlutaMAX™ (Gibco) and plated at a concentration of $5 \times 10^3$ cells/well. Cells were incubated for 4 hours in the cell incubator before respective antibody dilutions were added. Plates were gently shaked and incubated for 5 days in the cell incubator. The plates were equilibrated to room temperature and 100 µl/well of the freshly prepared CELLTITER GLO® (Promega) substrate were added to each well Luminescence was measured in a Wallac Victor3 1420 Multilabel Counter. Results are shown in Table 26 and FIGS. 26A-26C.

Herceptarg Clones-Mediated Antibody-Dependent Cell-Mediated Cytotoxicity (ADCC)

Target cells were harvested, washed, resuspended in AIM V® medium (Life Technologies), and plated at a concentration of $3 \times 10^4$ cells/well. The respective antibody dilutions were added in triplicates to the cells and incubated for 10 min before addition of the effector cells (peripheral blood mononuclear effector cells [PBMCs]). Effector (E) and target (T) cells were then incubated for the indicated time at 37° C. at the indicated E:T ratio (triplicates for all samples). Lactate dehydrogenase (LDH) release was measured using the LDH Cytotoxicity Detection Kit (Roche Applied Science). ADCC was calculated using the following formula:

$$\text{Percentage } ADCC = \left(\left[\frac{\text{sample release} - \text{spontaneous release}}{\text{maximal release} - \text{spontaneous release}}\right]\right) \times 100.$$

Figure 27A:
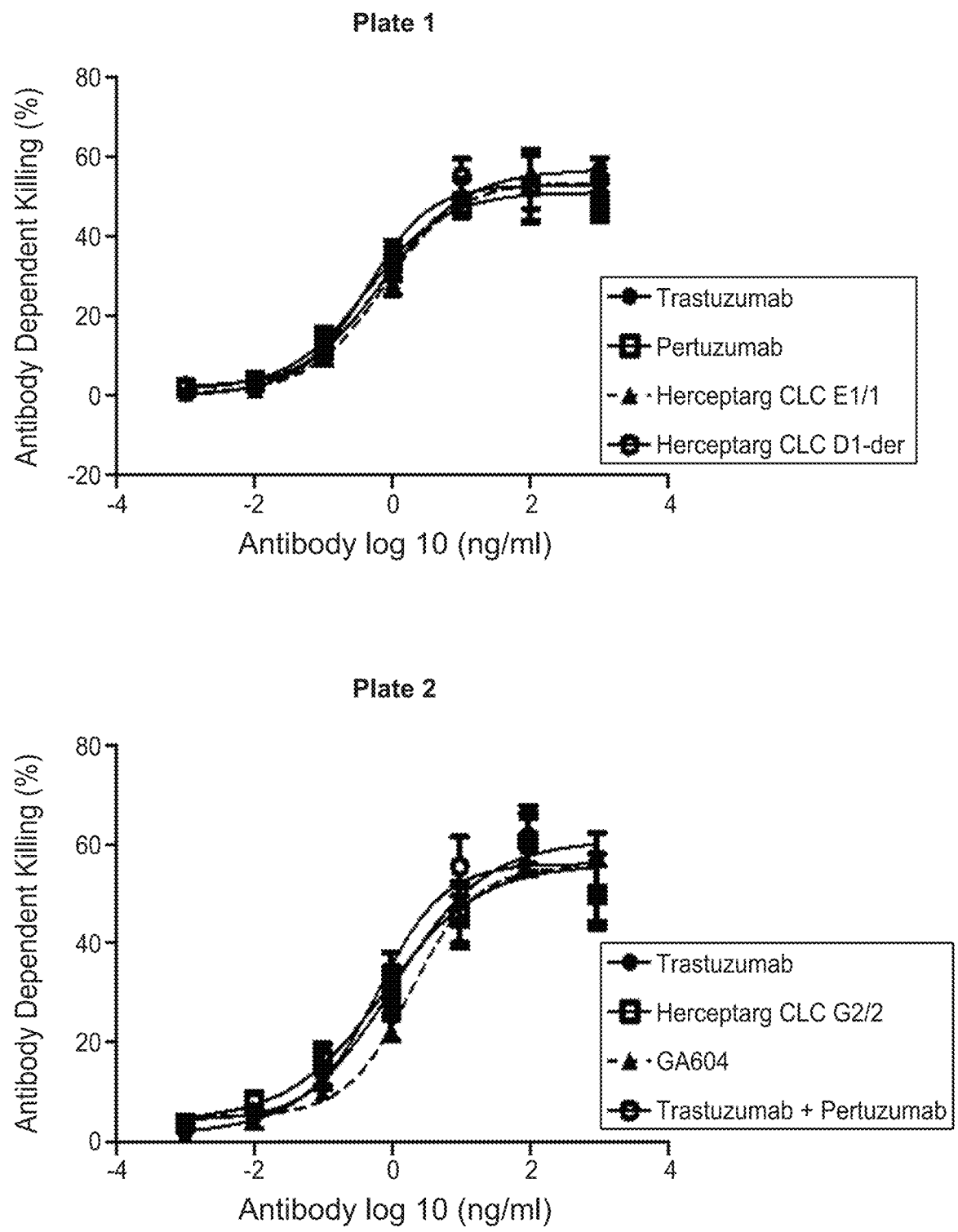
FIGS. 27A and 27B: Killing of KPL-4 cells and MDA-MB 231 with bi-specific HER2 antibodies with common light chain variants. (27A) Antibody dependent killing of KPL-4 cells with PBMCs (E:T 25:1) or was determined by measuring LDH release after 4 h. (27B) Antibody dependent killing of MDA-MB 231 cells with PBMCs (E:T 5:1) was determined by measuring LDH release after 24 h. "Herceptarg CLC D1-der": SEQ ID NOs 64, 54, 92, "Herceptarg CLC G2/2": SEQ ID NOs 70, 54, 92, "Herceptarg CLC E1/1": SEQ ID NOs 68, 54, 92; "GA 604": SEQ ID NOs 109, 110, 111, 112.
Figure 27B:
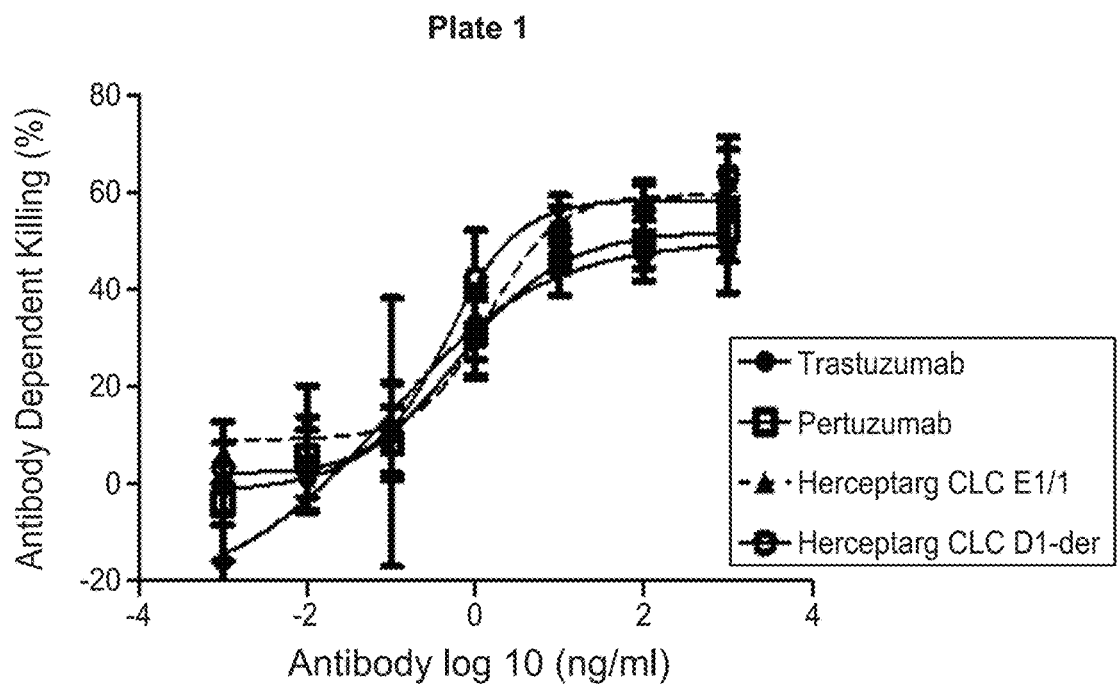
Figure 27B:
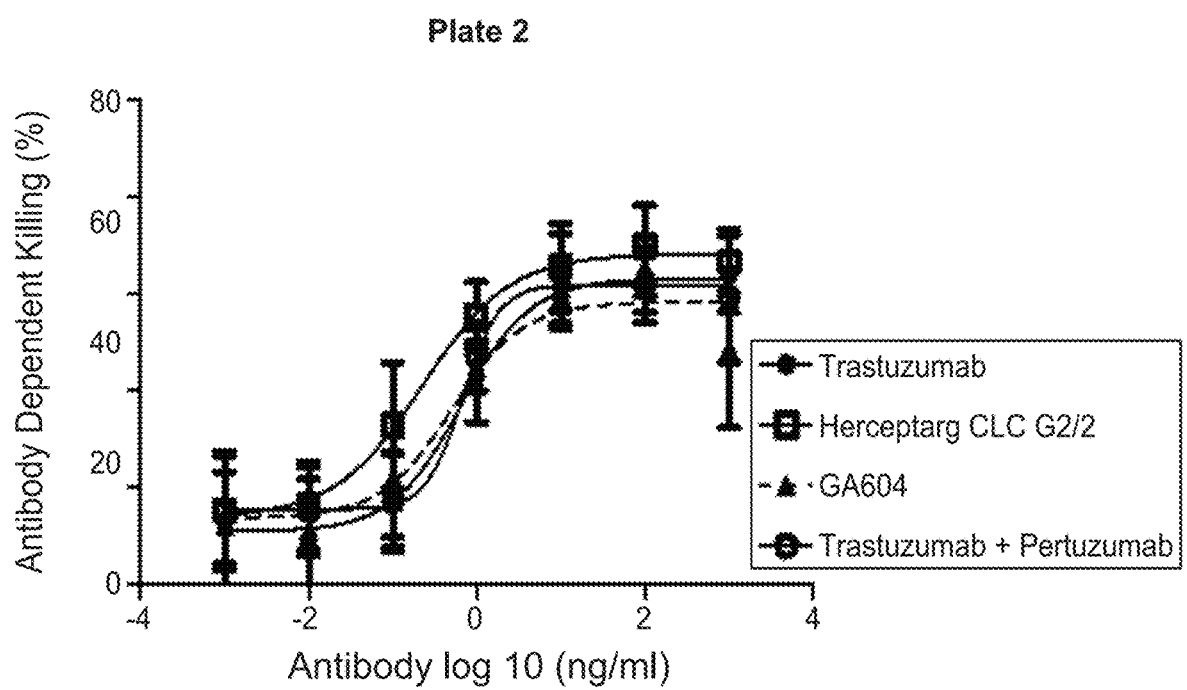

Spontaneous release, corresponding to target cells incubated with effector cells without antibody, was defined as 0% cytotoxicity, and maximal release (target cells lysed with 1% Triton X-100) was defined as 100% cytotoxicity. The average percentage of ADCC and standard deviations of the triplicates of each experiment were calculated. Results are shown in FIGS. 27A and 27B.

TABLE 27

Leader Peptides

| SEQ ID | Protein sequence |
|---|---|
| 155 | MDWTWRILFLVAAATGAHS |
| 156 | MDMRVPAQLLGLLLLWFPGARC |
| 157 | MGWSCIILFLVATATGVHS |

Example 15: Proliferation Assay $1 \times 10^4$ BT-474 cells/well were cultured in RPMI/10% FCS in a 96-well flat bottom plate. After 24 hrs growth medium was removed and titrated amounts of indicated antibodies were added (premixed in culture medium) to a final volume of 100 µl.

To determine the number of viable cells in culture, the CellTiter-Glo Luminescent Cell Viability Assay was performed by quantifying the present ATP levels as an indicator of metabolically active cells. Thus, after six days of culture, 100 µl CellTiter-Glo Reaction Mix (Promega, cat. no. #G7571) was added to the cells, shook for 2 min before 75 µl of the lysate was transferred to a separate 96-well flat bottom titer plate (Costar, cat. no. #3917). After additional mixing, luminescence was assed according to the manufacturer's instructions using a Tecan Infinite Reader.

Figure 28:
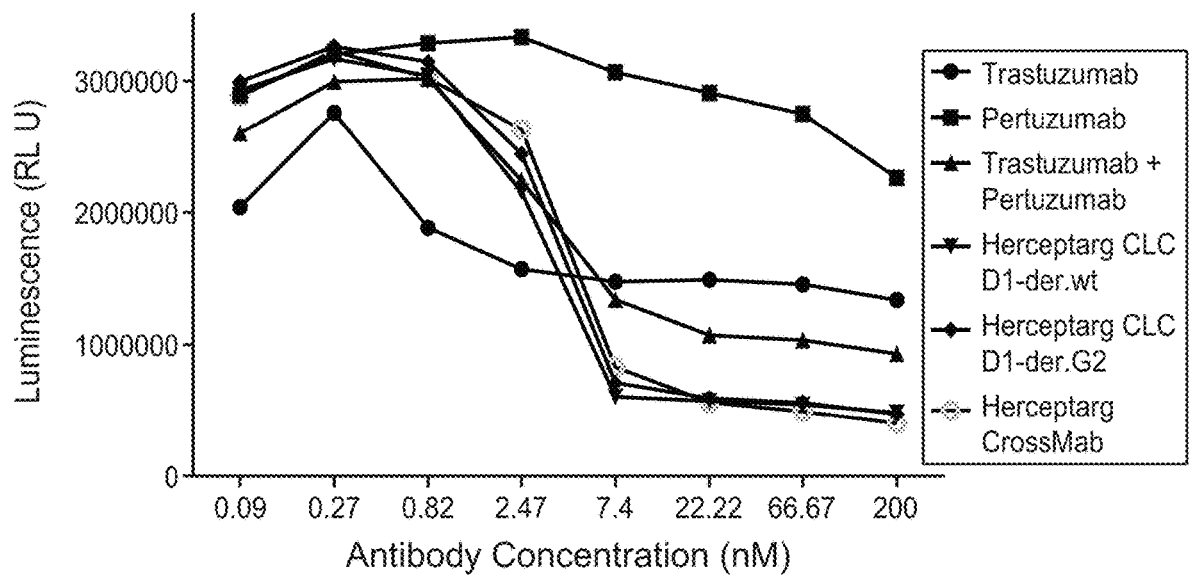
FIG. 28: Proliferation inhibition of BT474 cells with bi-specific HER2 antibodies with common light chain clone variants. BT474 cells were treated with the different Herceptarg variants. As controls Trastuzumab, Pertuzumab and the combination of both were included. After 6 days, proliferation inhibition was determined with CellTiter Glo. "Herceptarg CLC D1-der wt": SEQ ID NOs 64, 54, 92, Herceptarg CLC D1-der G2": SEQ ID NOs 64, 54, 92 (glycoengineered variant) "Herceptarg CrossMab": SEQ ID NOs 109, 110, 111, 112.

Results are shown in table 28 and FIG. 28.

In the proliferation assay it was shown that the bispecific Her2 antibodies inhibited proliferation of BT-474 cells more potently than Pertuzumab or Trastuzumab alone or in combination. The following bispecific Her2 antibodies were tested: Herceptarg CLC D1-der wt": SEQ ID NOs 64, 54, 92, Herceptarg CLC D1-der G2": SEQ ID NOs 64, 54, 92 (glycoengineered variant) "Herceptarg CrossMab": SEQ ID NOs 109, 110, 111, 112.

TABLE 28

IC50 BT474 proliferation assay

| Antibody treatment | IC50 Proliferation [nM] |
|---|---|
| Trastuzumab | n.d. |
| Pertuzumab | n.d. |
| Trastuzumab + Pertuzumab | 6.20 |
| Herceptarg CLC D1-der. wt | 3.31 |
| Herceptarg CLC D1-der. G2 | 3.93 |
| Herceptarg CrossMab | 4.75 |

Example 16: C1q FACS Binding Assay $3 \times 10^5$ BT-474 cells were incubated with 10 ug/ml of indicated antibody on ice. The following bispecific Her2 antibodies were tested: Herceptarg CLC D1-der wt": SEQ ID NOs 64, 54, 92, Herceptarg CLC D1-der G2": SEQ ID NOs 64, 54, 92 (glycoengineered variant) "Herceptarg CrossMab": SEQ ID NOs 109, 110, 111, 112.

After 30 min, 10 ug/ml C1q (Sigma, C1740) was added and additionally incubated for 20 min After washing, cells were counterstained with commercial PE-labeled anti-C1q antibody (Cedarlane, CL7611PE-SP). After further incubation (30 min, ice), cells were washed twice and analyzed on a FACS CANTO™ II.

Figure 29:
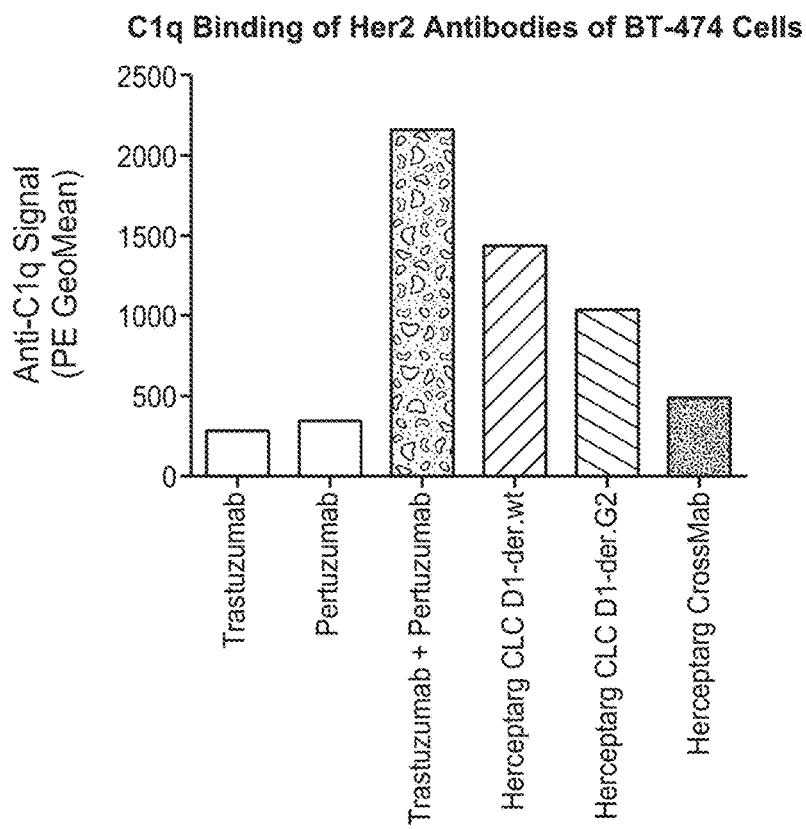
FIG. 29: C1q binding of Her2 antibodies on BT-474 cells. BT474 cells were incubated with the three Herceptarg variants. As controls Trastuzumab, Pertuzumab and the combination of both were included. "Herceptarg CLC D1-der wt": SEQ ID NOs 64, 54, 92, Herceptarg CLC D1-der G2": SEQ ID NOs 64, 54, 92 (glycoengineered variant) "Herceptarg CrossMab": SEQ ID NOs 109, 110, 111, 112.

Results are shown in FIG. 29 and table 29. This C1q assay illustrates the binding of recombinant complement factor C1q to different Her antibodies on BT-474 cells. It was shown that the highest C1q binding resulted upon treatment with the combination of Trastuzumab and Pertuzumab, followed by the two CLC bispecific Her2 antibodies. Treatment with the Crossmab resulted only in a slightly elevated C1q binding.

TABLE 29

C1q binding assay

| antibody/antibodies | PE-signal (geomean) |
|---|---|
| trastuzumab | 282 |
| pertuzumab | 344 |
| combination of trastuzumab and pertuzumab | 2157 |
| bispecific anti-HER2 antibody, common light chain | 1439 |
| bispecific anti-HER2 antibody, common light chain, glycoengineered | 1036 |
| bispecific anti-HER2 antibody, CrossMab format | 489 |

Example 17: LDH Assay with Baby Rabbit Complement (BRC)

CHO-K1 Nxre19 cells (IL15R transfected CHO-K1) were seeded at 10,000 cells/well on 96-well flat bottom cell culture plates (NUNC, 100 µL/well) and cultivated overnight. IL15-Fc fusion polypeptide was added (25 µL/well in 5-fold end-concentration) and incubated for one hour. Thereafter, one vial of Baby Rabbit complement (Cedarlane, Cat. No. CL3441) was reconstituted with 1 mL of Aqua bidest. The complement solution was diluted with medium and 25 µL added to the wells. After four hours the plates were centrifuged at 200 g and 100 µL/well were transferred to another 96-well flat bottom plate. Thereafter 100 µL of LDH reaction mix (Cytotoxicity Detection Kit, Roche Diagnostic GmbH, Mannheim, Germany) was added. After an incubation time of 20 min at 37° C. optical density (OD) was measured at 492/690 nm on a Tecan Sunrise reader.

TABLE 30

LDH assay with BRC

| | signal [OD] | |
|---|---|---|
| sample | BRC 1/40 | BRC 1/30 |
| 9000 ng/ml IL15-Fc-fusion with HUC | 11.3 | 12.3 |
| 3000 ng/ml IL15-Fc-fusion with HUC | 12.3 | 17.0 |
| 1000 ng/ml IL15-Fc-fusion with HUC | 10.2 | 13.6 |
| 333.3 ng/ml IL15-Fc-fusion with HUC | 7.8 | 12.2 |
| 111.1 ng/ml IL15-Fc-fusion with HUC | 8.3 | 13.0 |
| 37.04 ng/ml IL15-Fc-fusion with HUC | 14.9 | 19.7 |
| 12.35 ng/ml IL15-Fc-fusion with HUC | 43.2 | 53.0 |
| 4.12 ng/ml IL15-Fc-fusion with HUC | 41.5 | 63.8 |
| 0 ng/ml IL15-Fc-fusion with HUC | 42.4 | 48.4 |

It can be seen that BRC has a low background toxicity and shows dose dependent complement toxicity.

Example 18: CDC (Complement Dependent Cytotoxicity) Activation on BT-474 Cells (LDH Release)

$1 \times 10^4$ cells/well were incubated with 10 µg/ml of the indicated antibodies for 30 min at 37° C. in 150 µl. The following bispecific Her2 antibodies were tested: Herceptarg CLC D1-der wt": SEQ ID NOs 64, 54, 92, Herceptarg CLC D1-der G2": SEQ ID NOs 64, 54, 92 (glycoengineered variant) "Herceptarg CrossMab": SEQ ID NOs 109, 110, 111, 112.

Then 50 µl Baby Rabbit Complement (Cedarlane, cat. no. CL3441, batch no. 6312) was added and incubated for further 2 hrs. Then, the s/n was transferred and mixed with 50 µl LDH Reaction Mix (Roche) and, after a further incubation of 15 min, extinktion (Ex.) at 490/620 nm was analyzed on a Tecan Sunrise Reader. The specific antibody dependent toxicity (mean+/−SD of n=4) on BT-474 cell was calculated as follows:

(Ex. sample−Ex. spontaneous lysis/Ex. maximal lysis−spontaneous lysis)×100.

Figure 30:
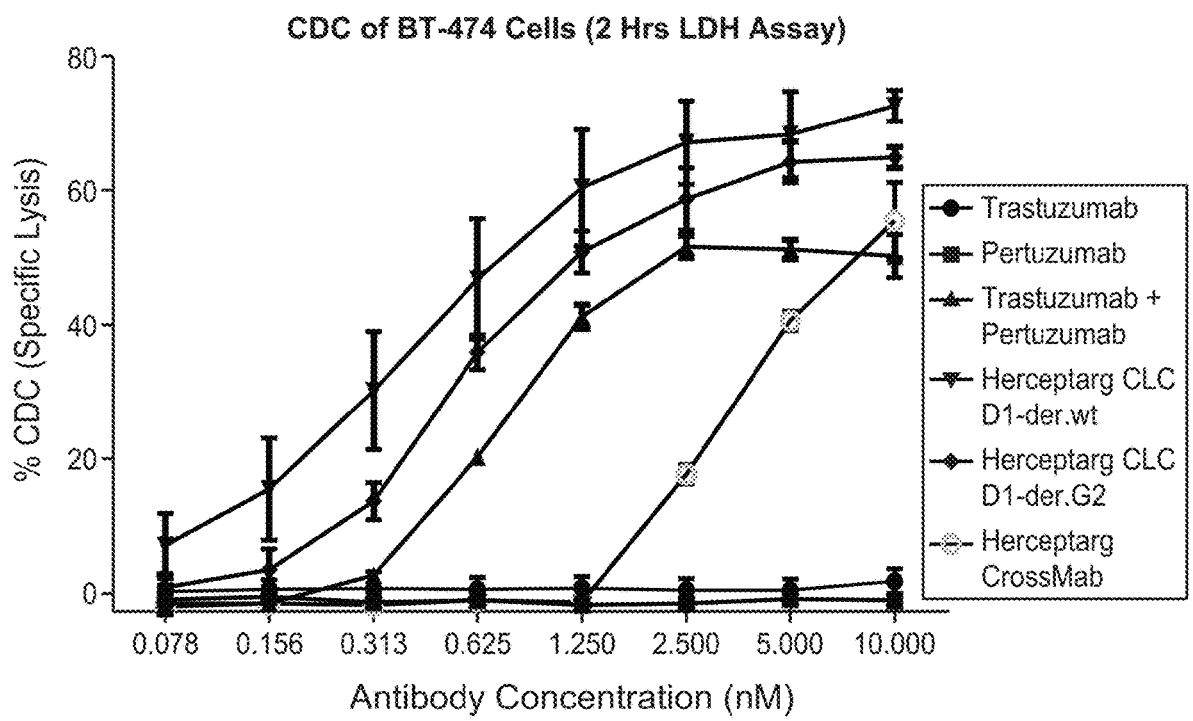
FIG. 30: CDC activation on BT-474 cells (LDH release). BT474 cells were incubated with the three Herceptarg variants. As controls Trastuzumab, Pertuzumab and the combination of both were included. "Herceptarg CLC D1-der wt": SEQ ID NOs 64, 54, 92, Herceptarg CLC D1-der G2": SEQ ID NOs 64, 54, 92 (glycoengineered variant) "Herceptarg CrossMab": SEQ ID NOs 109, 110, 111, 112.

Results are shown in FIG. 30.

This CDC assay shows the release of LDH as a marker for dying/dead cells upon treatment of different anti-Her2 antibodies (formats, combination) in the presence of baby rabbit complement. Here, the combination of Trastuzumab and Pertuzumab resulted in a significant induction of CDC, whereas the parental antibodies alone did not. Surprisingly, both CLC Herceptarg variants provoked even superior CDC effects, whereas the Herceptarg Crossmab treatment results in a CDC reaction less effective than the combination of the parental antibodies.

Example 19: CDC (Complement Dependent Cytotoxicity)-Mediated Killing of BT-474 Cells (ACEA)

$1 \times 10^4$ BT-474 cells/well were seeded on 96-well E-Plates (ACEA Biosciences Inc.) and grown overnight in an Xcelligence device. Growth medium was removed and cells were washed once with serum-free AIM-V medium (Gibco). 50 µl/well AIM-V medium and 50 µl antibody in AIM-V (3-fold end concentration) were added and incubated for 20 min. 50 µl Baby Rabbit Complement (Cedarlane) was added and CellIndex (CI; as representative for the viability of the cells) was measured every 5 minutes (see curve). The following bispecific Her2 antibodies were tested: Herceptarg CLC D1-der wt": SEQ ID NOs 64, 54, 92, Herceptarg CLC D1-der G2": SEQ ID NOs 64, 54, 92 (glycoengineered variant) "Herceptarg CrossMab": SEQ ID NOs 109, 110, 111, 112.

Specific CDC was calculated according following formula, whereas CI is the normalized cell index:

$$\% \, CDC = \frac{CI \, \text{Complement control} - CI \, \text{sample}}{CI \, \text{Complement control}} \times 100$$

At two representative time points (1 hr and 2 hrs after starting the reaction, specific lysis (=CDC-induced cell death) was calculated and shown in the diagram (mean+/SEM of n=4).

Figure 31A:
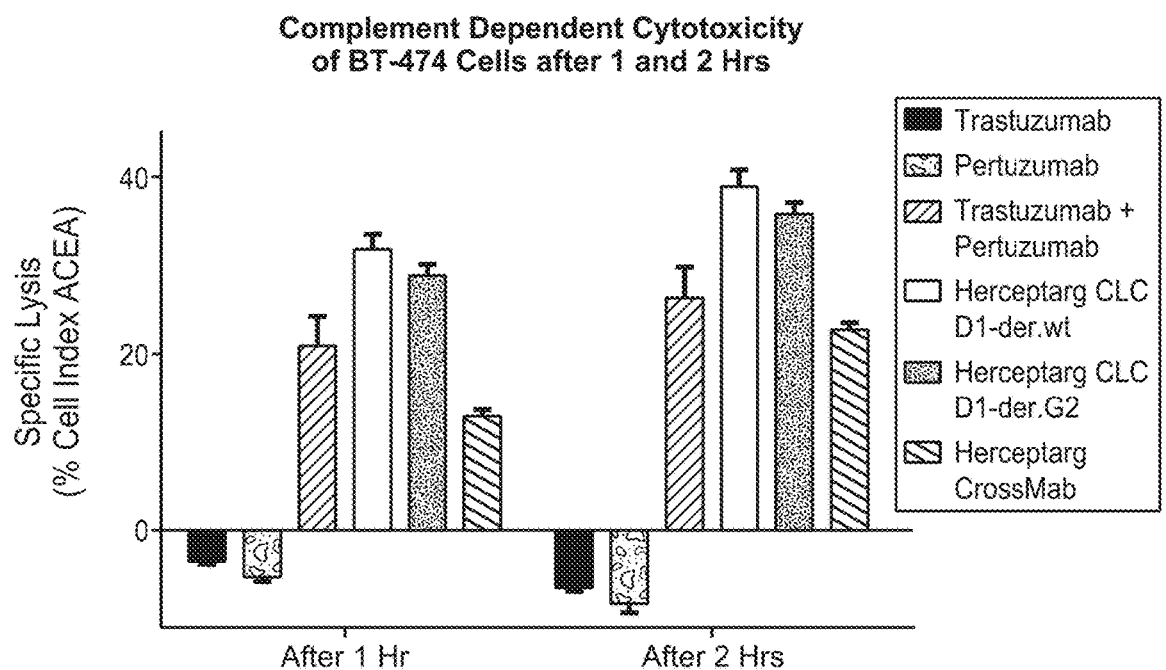
FIGS. 31A and 31B: CDC mediated killing of BT-474 cells (ACEA). BT474 cells were incubated with the three Herceptarg variants. As controls Trastuzumab, Pertuzumab and the combination of both were included. "Herceptarg CLC D1-der wt": SEQ ID NOs 64, 54, 92, Herceptarg CLC D1-der G2": SEQ ID NOs 64, 54, 92 (glycoengineered variant) "Herceptarg CrossMab": SEQ ID NOs 109, 110, 111, 112.
Figure 31B:
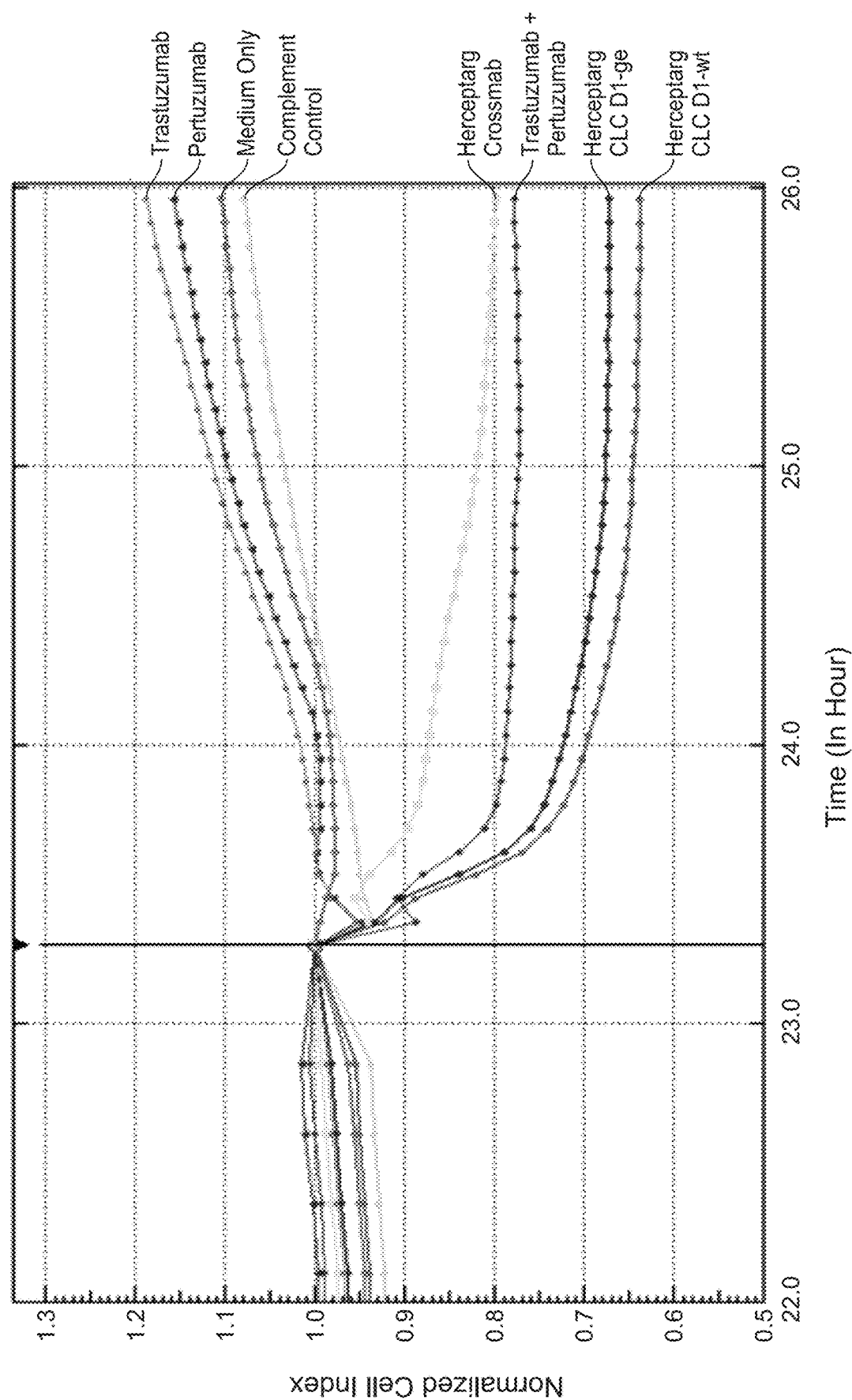

Results are shown in FIGS. 31A and 31B and table 31. This CDC assay illustrates a change in the cell index as a marker for dying/dead cells upon treatment with different anti-Her2 antibodies (formats, combination) in the presence of baby rabbit complement: Here, the combination of Trastuzumab and Pertuzumab resulted in a significant induction of CDC, whereas the parental antibodies alone did not. Surprisingly, both CLC Herceptarg variants provoked even superior CDC effects, whereas the Herceptarg Crossmab treatment results in a CDC reaction less effective than the combination of the parental antibodies.

One possible reason for the superiority of Herceptarg CLC D1-der may be the slightly higher affinity to the Trastuzumab epitope as well as the significantly higher affinity to the Pertuzumab epitope (see also table 25).

TABLE 31

CDC (complement dependent cytotoxicity)-mediated killing of BT-474 cells (ACEA)

| antibody/antibodies | specific lysis [% cell index ACEA] | |
|---|---|---|
|  | 1 hour | 2 hours |
| trastuzumab | −3.5 ± 0.6 | −6.5 ± 0.8 |
| pertuzumab | −5.3 ± 1.0 | −8.3 ± 2.1 |
| combination of trastuzumab and pertuzumab | 20.9 ± 6.7 | 26.3 ± 7.0 |
| bispecific anti-HER2 antibody, common light chain (D1 der) | 31.8 ± 3.4 | 38.9 ± 3.7 |
| bispecific anti-HER2 antibody, common light chain, glycoengineered (D1 der) | 28.8 ± 2.6 | 35.8 ± 2.6 |
| bispecific anti-HER2 antibody, CrossMab format | 12.9 ± 1.4 | 22.7 ± 1.6 |

Example 20: Mouse Xenograft Studies

Cell Line KPL4

This human breast cancer cell line has been established from the malignant pleural effusion of a breast cancer patient with an inflammatory skin metastasis. Cells have been provided by Professor J. Kurebayashi (Kawasaki Medical School, Kurashiki, Japan). Tumor cells were routinely cultured in DMEM medium (PAN Biotech, Germany) supplemented with 10% fetal bovine serum (PAN Biotech, Germany) and 2 mM L-glutamine (PAN Biotech, Germany) at 37° C. in a water-saturated atmosphere at 5% CO2. Culture passage was performed with trypsin/EDTA 1×(PAN) splitting twice/week. Cell passage P6 was used for in vivo study.

Mice

Female SCID beige (C.B.-17) mice; age 10-12 weeks; body weight 18-20 g (Charles River Germany, Sulzfeld); body weight >20 g are maintained under specific-pathogen-free condition with daily cycles of 12 h light/12 h darkness according to international guidelines (GV-Solas; Felasa; TierschG). After arrival animals were housed in the quarantine part of the animal facility for one week to get accustomed to new environment and for observation. Continuous health monitoring was carried out on regular basis. Diet food (Alltromin) and water were provided ad libitum. The experimental study was reviewed and approved by local government.

Tumor Cell Injection

At the day of injection tumor cells were harvested (trypsin-EDTA) from culture flasks (Greiner TriFlask) and transferred into 50 ml culture medium, washed once and resuspended in PBS. After an additional washing step with PBS and filtration (cell strainer; Falcon Ø 100 µm) the final cell titer was adjusted to 1.5×10e8/ml. Tumor cell suspension was carefully mixed with transfer pipette to avoid cell aggregation. Anesthesia was performed using a Stephens inhalation unit for small animals with preincubation chamber (plexiglas), individual mouse nose-mask (silicon) and not flammable or explosive anesthesia compound Isoflurane (Pharmacia-Upjohn, Germany) in a closed circulation system. Two days before injection, coat of the SCID beige mice were shaved and KPL-4 cells (3×10e6 cells) were injected orthotopically in a volume of 20 μl (using a Hamilton microliter syringe and a 30G×½" needle) into the right penultimate inguinal mammary fat pad of each anesthetized mouse. The cell suspension was injected through the skin under the nipple.

Monitoring

Animals were controlled daily for detection of clinical symptoms of adverse effects. For monitoring throughout the experiment the body weight of the animals was documented two times weekly and the tumor volume was measured by caliper twice weekly. Tumor volume was calculated according to NCI protocol (Tumor weight=½ab2, where "a" and "b" are the long and the short diameters of the tumor, respectively). Termination criteria were the critical tumor mass (up to 1.7 g or Ø>1.5 cm), body weight loss more than 20% from baseline, tumor ulceration or poor general condition of the animals. Study exclusion criteria for the animals are described and approved in the corresponding "Tierversuchsanzeige".

Treatment

Mice were randomized for tumor volume of 80 mm³ and subsequently treated once weekly with a volume of 10 ml/kg intra peritoneal. For combination treatment HERCEPTIN© was given first and PERJETA© was given 24 hrs thereafter.

Figure 32:
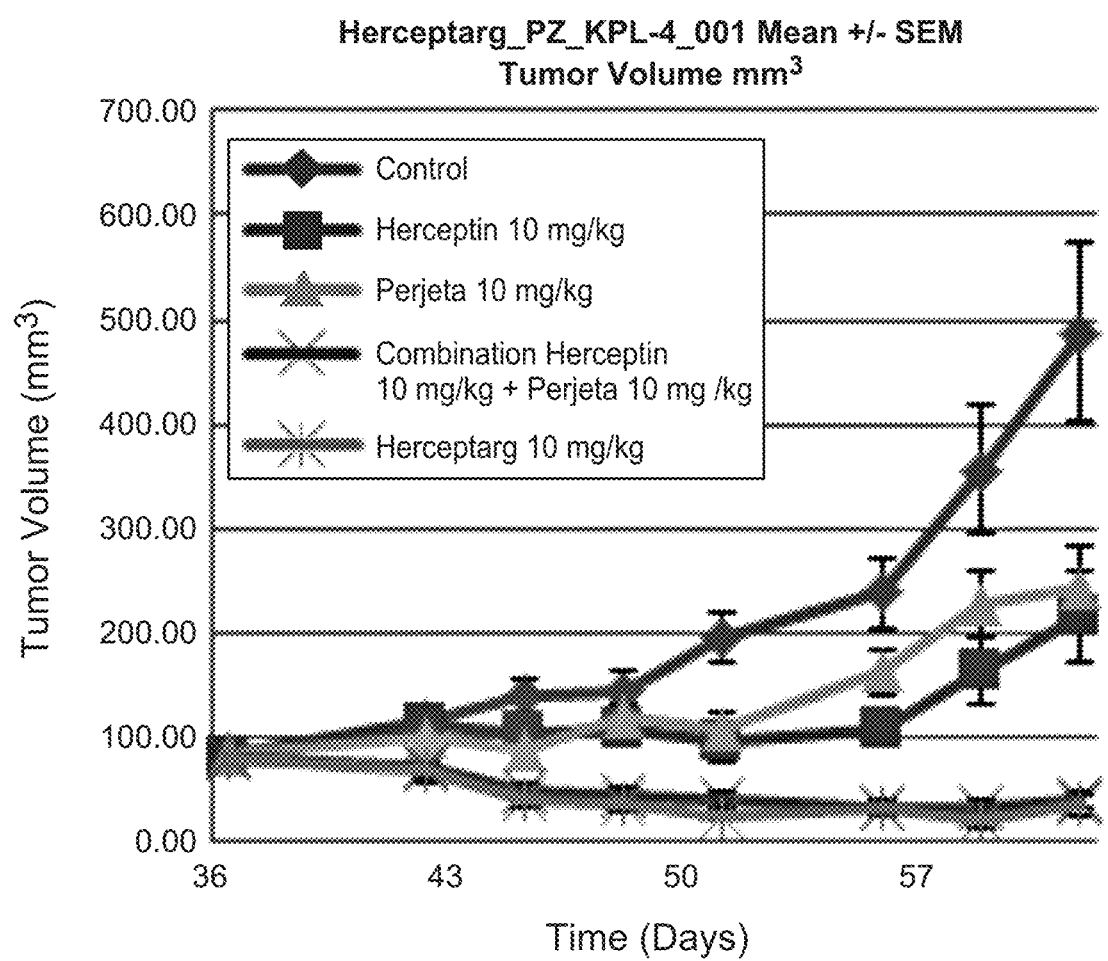
FIG. 32: In vivo activity of bispecific antibodies. Tumor volume in mouse xenograft models after treatment with different Her2 bispecific molecules (10 mg/kg) was compared to treatment with Trastuzumab, Pertuzumab and the combination of both. "Herceptarg": SEQ ID NOs 64, 54, 92. "Control": XOLAIR®, a non Her2 binding antibody.

The following bispecific Her2 antibodies was tested: Herceptarg CLC-D1-der: SEQ ID NOs 64, 54, 92. Results are shown in FIG. 32.

| Group | No of animals | Compound | Dose (mg/kg) | Route/Mode of administration |
|---|---|---|---|---|
| 1 | 9 | Control (XOLAIR ®) | 10 | i.p. once weekly |
| 2 | 9 | HERCEPTIN © | 10 | i.p. once weekly |
| 3 | 9 | PERJETA © | 10 | i.p. once weekly |
| 4 | 9 | HERCEPTIN © plus PERJETA © | 10 plus 10 | i.p. once weekly |
| 5 | 8 | Herceptarg CLC-D1-der | 10 | i.p. once weekly |

TABLE 32

Parent sequences of Pertuzumab and Trastuzumab

| SEQ ID NO | Name | Sequence |
|---|---|---|
| | Pertuzumab wt (parent) sequences | |
| 22 | Pertuzumab wt VH (10289) | EVQLVESGGGLVQPGGSLRLSCAASGFTFTDYTMDWVRQAPG KGLEWVADVNPNSGGSIYNQRFKGRFTLSVDRSKNTLYLQMN SLRAEDTAVYYCARNLGPSFYFDYWGQGTLVTVSS |
| 21 | Pertuzumab wt VH (10289)DNA | GAGGTGCAGCTGGTCGAGTCTGGCGGCGGACTGGTGCAGCC TGGCGGCAGCCTGAGACTGAGCTGCGCCGCCAGCGGCTTCA CCTTCACCGACTACACCATGGACTGGGTGCGGCAGGCCCCT GGCAAGGGCCTGGAATGGGTGGCCGACGTGAACCCCAACAG CGGCGGCAGCATCTACAACCAGCGGTTCAAGGGCCGGTTCA CCCTGAGCGTGGACAGAAGCAAGAACACCCTGTACCTCCAG ATGAACAGCCTGCGGGCCGAGGACACCGCCGTGTACTACTG CGCCCGGAACCTGGGCCCCAGCTTCTACTTCGACTACTGGGG CCAGGGCACCCTGGTGACCGTGAGCAGCGCTAGCACCAAGG GCCCATCGGTCTTCCCCCTGGCACCCTCCTCCAAGAGCACCT CTGGGGGCACAGCGGCCCTGGGCTGCCTGGTCAAGGACTAC TTCCCCGAACCGGTGACGGTGTCGTGGAACTCAGGCGCCCT GACCAGCGGCGTGCACACCTTCCCGGCTGTCCTACAGTCCTC AGGACTCTACTCCCTCAGCAGC |
| 14 | Pertuzumab wt VH CDR1 | GFTFTDYTMD |
| 15 | Pertuzumab wt VH CDR2 | DVNPNSGGSIYNQRFKG |
| 16 | Pertuzumab wt VH CDR3 | NLGPSFYFDY |
| 114 | Pertuzumab wt CH1 | ASTKGPSVFPLAPSSKSTSGGTAALGCLVKDYFPEPVTVSWN SGALTSGVHTFPAVLQSSGLYSLSSVVTVPSSSLGTQTYICNV NHKPSNTKVDKKV |
| 24 | Pertuzumab wt VL (10290) | DIQMTQSPSSLSASVGDRVTITCKASQDVSIGVAWYQQKPGKA PKLLIYSASYRYTGVPSRFSGSGSGTDFTLTISSLQPEDFATYYC QQYYIYPYTFGQGTKVEIK |
| 23 | Pertuzumab wt VL (10290)DNA | GACATCCAGATGACCCAGAGCCCCAGCAGCCTGAGCGCCAG CGTGGGCGACAGAGTGACCATCACCTGCAAGGCCAGCCAGG ACGTGTCCATCGGCGTGGCCTGGTATCAGCAGAAGCCCGGC AAGGCCCCCAAGCTGCTGATCTACAGCGCCAGCTACCGGTA |

TABLE 32-continued

Parent sequences of Pertuzumab and Trastuzumab

| SEQ ID NO | Name | Sequence |
|---|---|---|
| | | CACAGGCGTGCCCAGCCGGTTCAGCGGCAGCGGCTCCGGCA CCGACTTCACCCTGACCATCAGCAGCCTGCAGCCCGAGGAC TTCGCCACCTACTACTGCCAGCAGTACTACATCTACCCCTAC ACCTTCGGCCAGGGCACCAAGGTGGAGATCAAG |
| 11 | Pertuzumab wt VL CDR1 | KASQDVSIGVA |
| 12 | Pertuzumab wt VL CDR2 | SASYRYT |
| 13 | Pertuzumab wt VL CDR3 | QQYYIYPYT |
| 113 | Pertuzumab wt CL | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |

Trastuzumab wt (parent) sequences

| SEQ ID NO | Name | Sequence |
|---|---|---|
| 82 | Trastuzumab VL (4245) | DIQMTQSPSSLSASVGDRVTITCRASQDVNTAVAWYQQKPGKA PKLLIYSASFLYSGVPSRFSGSRSGTDFTLTISSLQPEDFATYYCQ QHYTTPPTFGQGTKVEIK |
| 81 | Trastuzumab VL(4245)DNA | GACATCCAGATGACCCAGAGCCCAAGCTCTCTGTCTGCCTCT GTGGGCGACAGAGTGACCATCACCTGCAGAGCCAGCCAGGA CGTGAACACAGCCGTGGCCTGGTATCAGCAGAAGCCAGGCA AGGCCCCCAAAGCTGCTGATCTACAGCGCCAGCTTCCTGTACA GCGGCGTGCCAAGCAGATTCAGCGGCAGCAGAAGCGGCACA GACTTCACCCTGACCATCAGCAGCCTGCAGCCAGAGGACTT CGCCACCTACTACTGCCAGCAGCACTACACCACCCCACCAA CCTTCGGACAGGGCACCAAGGTGGAGATCAAG |
| 17 | Trastuzumab wt VL CDR1 | RASQDVNTAVA |
| 18 | Trastuzumab wt VL CDR2 | SASFLYS |
| 19 | Trastuzumab wt VL CDR3 | QQHYTTPPT |
| 116 | Trastuzumab wt CL | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |
| 92 | Trastuzumab VH (1345) | EVQLVESGGGLVQPGGSLRLSCAASGFNIKDTYIHWVRQAPGK GLEWVARIYPTNGYTRYADSVKGRFTISADTSKNTAYLQMNSL RAEDTAVYYCSRWGGDGFYAMDYWGQGTLVTVSS |
| 91 | Trastuzumab VH (11345)DNA | GAAGTGCAATTGGTGGAAAGCGGCGGCGGCCTGGTGCAACC GGGCGGCAGCCTGCGTCTGAGCTGCGCGGCCTCCGGATTTA ACATAAAGGACACATACATCCACTGGGTGCGCCAAGCACCT GGGAAGGGTCTCGAGTGGGTGGCTCGGATTTACCCAACAAA TGGCTACACCAGGTATGCGGATAGCGTGAAAGGCCGTTTTA CCATTTCAGCTGATACTTCGAAGAACACCGCCTATCTGCAAA TGAACAGCCTGCGTGCGGAAGATACGGCCGTGTATTATTGCT CGCGTTGGGGAGGAGACGGGTTCTATGCTATGGATTACTGG GGCCAAGGCACCCTGGTGACGGTTAGCTCA |
| 20 | Trastuzumab wt VH CDR1 | GFNIKDTYIH |
| 29 | Trastuzumab wt VH CDR2 | RIYPTNGYTRYADSVKG |
| 30 | Trastuzumab wt VH CDR3 | WGGDGFYAMDY |
| 115 | Trastuzumab wt CH1 | ASTKGPSVFPLAPSSKSTSGGTAALGCLVKDYFPEPVTVSWN SGALTSGVHTFPAVLQSSGLYSLSSVVTVPSSSLGTQTYICNV NHKPSNTKVDKKV |

TABLE 33

Sequences of antibodies with common light chain

| SEQ ID NO | Name | Sequence |
|---|---|---|
| | Pertuzumab / Trastuzumab hybrid light chains | |
| 26 | Pertuzumab VL (Trast. L3) (10403) | DIQMTQSPSSLSASVGDRVTITCKASQDVSIGVAWYQQKPGKA PKLLIYSASYRYTGVPSRFSGSGSGTDFTLTISSLQPEDFATYYC QQHYTTPPTFGQGTKVEIK |
| 25 | Pertuzumab VL (Trast. L3) (10403)DNA | GACATCCAGATGACCCAGAGCCCCAGCAGCCTGAGCGCCAG CGTGGGCGACAGAGTGACCATCACATGCAAGGCCAGCCAGG ACGTGTCCATCGGCGTGGCCTGGTATCAGCAGAAGCCCGGC AAGGCCCCCAAGCTGCTGATCTACAGCGCCAGCTACCGGTA CACCGGCGTGCCCAGCAGATTCAGCGGCAGCGGCTCCGGCA CCGACTTCACCCTGACCATCAGCAGCCTGCAGCCCGAGGAC TTCGCCACCTACTACTGCCAGCAGCACTACACCACCCCCCCC ACCTTCGGCCAGGGCACCAAGGTGGAAATCAAG |
| 28 | Pertuzumab VL (Trast. H91) (10404) | DIQMTQSPSSLSASVGDRVTITCKASQDVSIGVAWYQQKPGKA PKLLIYSASYRYTGVPSRFSGSGSGTDFTLTISSLQPEDFATYYC QQHYIYPYTFGQGTKVEIK |
| 27 | Pertuzumab VL (Trast. H91) (10404)DNA | GACATCCAGATGACCCAGAGCCCCAGCAGCCTGAGCGCCAG CGTGGGCGACAGAGTGACCATCACCTGCAAGGCCAGCCAGG ACGTGTCCATCGGCGTGGCCTGGTATCAGCAGAAGCCCGGC AAGGCCCCCAAGCTGCTGATCTACAGCGCCAGCTACCGGTA CACAGGCGTGCCCAGCCGGTTCAGCGGCAGCGGCTCCGGCA CCGACTTCACCCTGACCATCAGCAGCCTGCAGCCCGAGGAC TTCGCCACCTACTACTGCCAGCAGCACTACATCTACCCCTAC ACCTTCGGCCAGGGCACCAAGGTGGAGATCAAG |
| 32 | Pertuzumab VL (Tras.L3) K24R (10949) | DIQMTQSPSSLSASVGDRVTITCRASQDVSIGVAWYQQKPGKA PKLLIYSASYRYTGVPSRFSGSGSGTDFTLTISSLQPEDFATYYC QQHYTTPPTFGQGTKVEIK |
| 31 | Pertuzumab VL (Tras.L3) K24R (10949)DNA | GACATCCAGATGACCCAGAGCCCCAGCAGCCTGAGCGCCAG CGTGGGCGACAGAGTGACCATCACATGCCGGGCCAGCCAGG ACGTGTCCATCGGCGTGGCCTGGTATCAGCAGAAGCCCGGC AAGGCCCCCAAGCTGCTGATCTACAGCGCCAGCTACCGGTA CACCGGCGTGCCCAGCAGATTCAGCGGCAGCGGCTCCGGCA CCGACTTCACCCTGACCATCAGCAGCCTGCAGCCCGAGGAC TTCGCCACCTACTACTGCCAGCAGCACTACACCACCCCCCCC ACCTTCGGCCAGGGCACCAAGGTGGAAATCAAG |
| 34 | Pertuzumab VL (Tras.L3) S30N (10950) | DIQMTQSPSSLSASVGDRVTITCKASQDVNIGVAWYQQKPGKA PKLLIYSASYRYTGVPSRFSGSGSGTDFTLTISSLQPEDFATYYC QQHYTTPPTFGQGTKVEIK |
| 33 | Pertuzumab VL(Tras.L3) S30N (10950)DNA | GACATCCAGATGACCCAGAGCCCCAGCAGCCTGAGCGCCAG CGTGGGCGACAGAGTGACCATCACATGCAAGGCCAGCCAGG ACGTGAACATCGGCGTGGCCTGGTATCAGCAGAAGCCCGGC AAGGCCCCCAAGCTGCTGATCTACAGCGCCAGCTACCGGTA CACCGGCGTGCCCAGCAGATTCAGCGGCAGCGGCTCCGGCA CCGACTTCACCCTGACCATCAGCAGCCTGCAGCCCGAGGAC TTCGCCACCTACTACTGCCAGCAGCACTACACCACCCCCCCC ACCTTCGGCCAGGGCACCAAGGTGGAAATCAAG |
| 36 | Pertuzumab VL (Tras.L3) I31T (10951) | DIQMTQSPSSLSASVGDRVTITCKASQDVSTGVAWYQQKPGKA PKLLIYSASYRYTGVPSRFSGSGSGTDFTLTISSLQPEDFATYYC QQHYTTPPTFGQGTKVEIK |
| 35 | Pertuzumab VL (Tras.L3) I31T (10951)DNA | GACATCCAGATGACCCAGAGCCCCAGCAGCCTGAGCGCCAG CGTGGGCGACAGAGTGACCATCACATGCAAGGCCAGCCAGG ACGTGTCCACCGGCGTGGCCTGGTATCAGCAGAAGCCCGGC AAGGCCCCCAAGCTGCTGATCTACAGCGCCAGCTACCGGTA CACCGGCGTGCCCAGCAGATTCAGCGGCAGCGGCTCCGGCA CCGACTTCACCCTGACCATCAGCAGCCTGCAGCCCGAGGAC TTCGCCACCTACTACTGCCAGCAGCACTACACCACCCCCCCC ACCTTCGGCCAGGGCACCAAGGTGGAAATCAAG |
| 38 | Pertuzumab VL (Tras.L3) I31V (10952) | DIQMTQSPSSLSASVGDRVTITCKASQDVSVGVAWYQQKPGKA PKLLIYSASYRYTGVPSRFSGSGSGTDFTLTISSLQPEDFATYYC QQHYTTPPTFGQGTKVEIK |
| 37 | Pertuzumab VL (Tras.L3) I31V (10952)DNA | GACATCCAGATGACCCAGAGCCCCAGCAGCCTGAGCGCCAG CGTGGGCGACAGAGTGACCATCACATGCAAGGCCAGCCAGG ACGTGTCCGTCGGCGTGGCCTGGTATCAGCAGAAGCCCGGC AAGGCCCCCAAGCTGCTGATCTACAGCGCCAGCTACCGGTA |

TABLE 33-continued

Sequences of antibodies with common light chain

| SEQ ID NO | Name | Sequence |
|---|---|---|
| | | CACCGGCGTGCCCAGCAGATTCAGCGGCAGCGGCTCCGGCA CCGACTTCACCCTGACCATCAGCAGCCTGCAGCCCGAGGAC TTCGCCACCTACTACTGCCAGCAGCACTACACCACCCCCCCC ACCTTCGGCCAGGGCACCAAGGTGGAAATCAAG |
| 40 | Pertuzumab VL (Tras.L3) G32A (10953) | DIQMTQSPSSLSASVGDRVTITCKASQDVSIAVAWYQQKPGKA PKLLIYSASYRYTGVPSRFSGSGSGTDFTLTISSLQPEDFATYYC QQHYTTPPTFGQGTKVEIK |
| 39 | Pertuzumab VL (Tras.L3) G32A (10953)DNA | GACATCCAGATGACCCAGAGCCCCAGCAGCCTGAGCGCCAG CGTGGGCGACAGAGTGACCATCACATGCAAGGCCAGCCAGG ACGTGTCCATCGCCGTGGCCTGGTATCAGCAGAAGCCCGGC AAGGCCCCCAAGCTGCTGATCTACAGCGCCAGCTACCGGTA CACCGGCGTGCCCAGCAGATTCAGCGGCAGCGGCTCCGGCA CCGACTTCACCCTGACCATCAGCAGCCTGCAGCCCGAGGAC TTCGCCACCTACTACTGCCAGCAGCACTACACCACCCCCCCC ACCTTCGGCCAGGGCACCAAGGTGGAAATCAAG |
| 42 | Pertuzumab VL (Tras.L3) Y53F (10954) | DIQMTQSPSSLSASVGDRVTITCKASQDVSIGVAWYQQKPGKA PKLLIYSASFRYTGVPSRFSGSGSGTDFTLTISSLQPEDFATYYC QQHYTTPPTFGQGTKVEIK |
| 41 | Pertuzumab VL(Tras.L3) Y53F (10954)DNA | GACATCCAGATGACCCAGAGCCCCAGCAGCCTGAGCGCCAG CGTGGGCGACAGAGTGACCATCACATGCAAGGCCAGCCAGG ACGTGTCCATCGGCGTGGCCTGGTATCAGCAGAAGCCCGGC AAGGCCCCCAAGCTGCTGATCTACAGCGCCAGCTTCCGGTA CACCGGCGTGCCCAGCAGATTCAGCGGCAGCGGCTCCGGCA CCGACTTCACCCTGACCATCAGCAGCCTGCAGCCCGAGGAC TTCGCCACCTACTACTGCCAGCAGCACTACACCACCCCCCCC ACCTTCGGCCAGGGCACCAAGGTGGAAATCAAG |
| 44 | Pertuzumab VL (Tras.L3) R54L (10955) | DIQMTQSPSSLSASVGDRVTITCKASQDVSIGVAWYQQKPGKA PKLLIYSASYLYTGVPSRFSGSGSGTDFTLTISSLQPEDFATYYC QQHYTTPPTFGQGTKVEIK |
| 43 | Pertuzumab (Tras.L3) R54L (10955)DNA | GACATCCAGATGACCCAGAGCCCCAGCAGCCTGAGCGCCAG CGTGGGCGACAGAGTGACCATCACATGCAAGGCCAGCCAGG ACGTGTCCATCGGCGTGGCCTGGTATCAGCAGAAGCCCGGC AAGGCCCCCAAGCTGCTGATCTACAGCGCCAGCTACCTGTA CACCGGCGTGCCCAGCAGATTCAGCGGCAGCGGCTCCGGCA CCGACTTCACCCTGACCATCAGCAGCCTGCAGCCCGAGGAC TTCGCCACCTACTACTGCCAGCAGCACTACACCACCCCCCCC ACCTTCGGCCAGGGCACCAAGGTGGAAATCAAG |
| 46 | Pertuzumab (Tras.L3) T56S (10956) | DIQMTQSPSSLSASVGDRVTITCKASQDVSIGVAWYQQKPGKA PKLLIYSASYRYSGVPSRFSGSGSGTDFTLTISSLQPEDFATYYC QQHYTTPPTFGQGTKVEIK |
| 45 | Pertuzumab (Tras.L3) T56S (10956)DNA | GACATCCAGATGACCCAGAGCCCCAGCAGCCTGAGCGCCAG CGTGGGCGACAGAGTGACCATCACATGCAAGGCCAGCCAGG ACGTGTCCATCGGCGTGGCCTGGTATCAGCAGAAGCCCGGC AAGGCCCCCAAGCTGCTGATCTACAGCGCCAGCTACCGGTA CAGCGGCGTGCCCAGCAGATTCAGCGGCAGCGGCTCCGGCA CCGACTTCACCCTGACCATCAGCAGCCTGCAGCCCGAGGAC TTCGCCACCTACTACTGCCAGCAGCACTACACCACCCCCCCC ACCTTCGGCCAGGGCACCAAGGTGGAAATCAAG |
| 48 | Pertuzumab (Tras.L3) G66R (10957) | DIQMTQSPSSLSASVGDRVTITCKASQDVSIGVAWYQQKPGKA PKLLIYSASYRYTGVPSRFSGSRGTDFTLTISSLQPEDFATYYC QQHYTTPPTFGQGTKVEIK |
| 47 | Pertuzumab (Tras.L3) G66R (10957)DNA | GACATCCAGATGACCCAGAGCCCCAGCAGCCTGAGCGCCAG CGTGGGCGACAGAGTGACCATCACATGCAAGGCCAGCCAGG ACGTGTCCATCGGCGTGGCCTGGTATCAGCAGAAGCCCGGC AAGGCCCCCAAGCTGCTGATCTACAGCGCCAGCTACCGGTA CACCGGCGTGCCCAGCAGATTCAGCGGCAGCCGCTCCGGCA CCGACTTCACCCTGACCATCAGCAGCCTGCAGCCCGAGGAC TTCGCCACCTACTACTGCCAGCAGCACTACACCACCCCCCCC ACCTTCGGCCAGGGCACCAAGGTGGAAATCAAG |
| 50 | Pertuzumab (Tras.L3) T94Y (10958) | DIQMTQSPSSLSASVGDRVTITCKASQDVSIGVAWYQQKPGKA PKLLIYSASYRYTGVPSRFSGSGSGTDFTLTISSLQPEDFATYYC QQHYTYPPTFGQGTKVEIK |

TABLE 33-continued

Sequences of antibodies with common light chain

| SEQ ID NO | Name | Sequence |
|---|---|---|
| 49 | Pertuzumab (Tras.L3) T94Y (10958)DNA | ACATCCAGATGACCCAGAGCCCCAGCAGCCTGAGCGCCAGC GTGGGCGACAGAGTGACCATCACATGCAAGGCCAGCCAGGA CGTGTCCATCGGCGTGGCCTGGTATCAGCAGAAGCCCGGCA AGGCCCCCAAGCTGCTGATCTACAGCGCCAGCTACCGGTAC ACCGGCGTGCCCAGCAGATTCAGCGGCAGCGGCTCCGGCAC CGACTTCACCCTGACCATCAGCAGCCTGCAGCCCGAGGACTT CGCCACCTACTACTGCCAGCAGCACTACACCTACCCCCCAC CTTCGGCCAGGGCACCAAGGTGGAAATCAAG |
| 52 | Pertuzumab (Tras.L3) P96Y (10959) | DIQMTQSPSSLSASVGDRVTITCKASQDVSIGVAWYQQKPGKA PKLLIYSASYRYTGVPSRFSGSGSGTDFTLTISSLQPEDFATYYC QQHYTTPYTFGQGTKVEIK |
| 51 | Pertuzumab (Tras.L3) P96Y (10959)DNA | GACATCCAGATGACCCAGAGCCCCAGCAGCCTGAGCGCCAG CGTGGGCGACAGAGTGACCATCACATGCAAGGCCAGCCAGG ACGTGTCCATCGGCGTGGCCTGGTATCAGCAGAAGCCCGGC AAGGCCCCCAAGCTGCTGATCTACAGCGCCAGCTACCGGTA CACCGGCGTGCCCAGCAGATTCAGCGGCAGCGGCTCCGGCA CCGACTTCACCCTGACCATCAGCAGCCTGCAGCCCGAGGAC TTCGCCACCTACTACTGCCAGCAGCACTACACCACCCCCTAC ACCTTCGGCCAGGGCACCAAGGTGGAAATCAAG |
| 54 | Pertuzumab (Tras.L3)(QM) (11055) | DIQMTQSPSSLSASVGDRVTITCKASQDVSTAVAWYQQKPGKA PKLLIYSASFRYTGVPSRFSGSRSGTDFTLTISSLQPEDFATYYCQ QHYTTPPTFGQGTKVEIK |
| 53 | Pertuzumab (Tras.L3)(QM) (11055)DNA | GACATCCAGATGACCCAGAGCCCCAGCAGCCTGTCTGCCAG CGTGGGCGACAGAGTGACCATCACATGCAAGGCCAGCCAGG ACGTGTCCACAGCCGTGGCCTGGTATCAGCAGAAGCCTGGC AAGGCCCCCAAGCTGCTGATCTACAGCGCCAGCTTCCGGTA CACCGGCGTGCCCAGCAGATTCAGCGGCAGCAGATCCGGCA CCGACTTCACCCTGACCATCAGCTCCCTGCAGCCCGAGGACT TCGCCACCTACTACTGCCAGCAGCACTACACCACCCCCCCCA CATTTGGCCAGGGCACCAAGGTGGAAATCAAG |
| 89 | Pertuzumab (Tras.L3)(QM)- CDR1 | KASQDVSTAVA |
| 90 | Pertuzumab (Tras.L3)(QM)- CDR2 | SASFRYT |
| 19 | Pertuzumab (Tras.L3)(QM)- CDR3 | QQHYTTPPT |

Pertuzumab / Trastuzumab hybrid light chain affinity matured VH clones

| 62 | Pertuzumab aff.mat. clone D1 | EVQLVESGGGLVQPGGSLRLSCAASGFTFNDYTMDWVRQAPG KGLEWVADVNPNSGGSIYNQRFKGRFTLSVDRSKNTLYLQMN SLRAEDTAVYYCARNLGPFFYFDYWGQGTLVTVSS |
| 61 | Pertuzumab aff.mat. clone D1 DNA | GAGGTGCAATTGGTTGAAAGCGGTGGTGGTCTGGTTCAGCC TGGTGGTAGCCTGCGTCTGAGCTGTGCAGCAAGCGGTTTTAC CTTTAACGATTATACCATGGATTGGGTTCGTCAGGCACCGGG TAAAGGTCTGGAATGGGTTGCAGATGTTAATCCGAATAGCG GTGGTAGCATTTATAACCAGCGTTTTAAAGGTCGTTTTACCC TGAGCGTTGATCGTAGCAAAAATACCCTGTATCTGCAAATG AATAGTCTGCGTGCAGAGGATACCGCAGTGTATTATTGTGCA CGTAACCTGGGTCCGTTCTTCTACTTTGATTATTGGGGTCAG GGCACCCTGGTTACCGTTAGCAGC |
| 55 | Pertuzumab aff.mat. clone D1- VH CDR1 | GFTFNDYTMD |
| 15 | Pertuzumab aff.mat. clone D1- VH CDR2 | DVNPNSGGSIYNQRFKG |
| 56 | Pertuzumab aff.mat. clone D1- VH CDR3 | NLGPFFYFDY |

TABLE 33-continued

Sequences of antibodies with common light chain

| SEQ ID NO | Name | Sequence |
|---|---|---|
| 64 | Pertuzumab aff.mat. clone D1-derived | EVQLVESGGGLVQPGGSLRLSCAASGFTFNDYTMDWVRQAPG KGLEWVADVNPNSGGSIVNRRFKGRFTLSVDRSKNTLYLQMN SLRAEDTAVYYCARNLGPFFYFDYWGQGTLVTVSS |
| 63 | Pertuzumab aff.mat. clone D1-derived, DNA | GAGGTGCAATTGGTTGAAAGCGGTGGTGGTCTGGTTCAGCC TGGTGGTAGCCTGCGTCTGAGCTGTGCAGCAAGCGGTTTTAC CTTTAACGATTATACCATGGATTGGGTTCGTCAGGCACCGGG TAAAGGTCTGGAATGGGTTGCAGATGTTAATCCGAATAGCG GTGGTAGCATTGTTAACCGTCGTTTTAAAGGTCGTTTTACCC TGAGCGTTGATCGTAGCAAAAATACCCTGTATCTGCAAATG AATAGTCTGCGTGCAGAGGATACCGCAGTGTATTATTGTGCA CGTAACCTGGGTCCGTTCTTCTACTTTGATTATTGGGGTCAG GGCACCCTGGTTACCGTTAGCAGC |
| 55 | Pertuzumab aff.mat. clone D1-derived VH CDR 1 | GFTFNDYTMD |
| 77 | Pertuzumab aff.mat. clone D1-derived VH CDR2 | DVNPNSGGSIVNRRFKG |
| 56 | Pertuzumab aff.mat. clone D1- derived VH CDR3 | NLGPFFYFDY |
| 66 | Pertuzumab aff.mat. clone B2 | EVQLVESGGGLVQPGGSLRLSCAASGFTFNDYTMDWFRQAPG KGLEWVADVNPNSGGSIYNQRFKGRFTLSVDRSKNTLYLQMN SLRAEDTAVYYCARNLGPNFYFDYWGQGTLVTVSS |
| 65 | Pertuzumab aff.mat. clone B2, DNA | GAGGTGCAATTGGTTGAAAGCGGTGGTGGTCTGGTTCAGCC TGGTGGTAGCCTGCGTCTGAGCTGTGCAGCAAGCGGTTTTAC CTTTAACGATTATACCATGGATTGGTTTCGTCAGGCACCGGG TAAAGGTCTGGAATGGGTTGCAGATGTTAATCCGAATAGCG GTGGTAGCATTTATAACCAGCGTTTTAAAGGTCGTTTTACCC TGAGCGTTGATCGTAGCAAAAATACCCTGTATCTGCAAATG AATAGTCTGCGTGCAGAGGATACCGCAGTGTATTATTGTGCA CGTAATCTGGGTCCGAACTTCTACTTTGATTATTGGGGTCAG GGCACCCTGGTTACCGTTAGCAGC |
| 55 | Pertuzumab aff.mat. clone B2- VH CDR1 | GFTFNDYTMD |
| 15 | Pertuzumab aff.mat. clone B2- VH CDR2 | DVNPNSGGSIYNQRFKG |
| 57 | Pertuzumab aff.mat. clone B2- VH CDR3 | NLGPNFYFDY |
| 68 | Pertuzumab aff.mat. clone E1 | EVQLVESGGGLVQPGGSLRLSCAASGFTFADYTMDWVRQAPG KGLEWVADVNPNSGGSIYNQRFKGRFTLSVDRSKNTLYLQMN SLRAEDTAVYYCARNLGPWFYFDYWGQGTLVTVSS |
| 67 | Pertuzumab aff.mat. clone E1, DNA | GAGGTGCAATTGGTTGAAAGCGGTGGTGGTCTGGTTCAGCC TGGTGGTAGCCTGCGTCTGAGCTGTGCAGCAAGCGGTTTTAC CTTTGCAGATTATACCATGGATTGGGTTCGTCAGGCACCGGG TAAAGGTCTGGAATGGGTTGCAGATGTTAATCCGAATAGCG GTGGTAGCATTTATAACCAGCGTTTTAAAGGTCGTTTTACCC TGAGCGTTGATCGTAGCAAAAATACCCTGTATCTGCAAATG AATAGTCTGCGTGCAGAGGATACCGCAGTGTATTATTGTGCA CGTAATCTGGGTCCGTGGTTCTACTTTGATTATTGGGGTCAG GGCACCCTGGTTACCGTTAGCAGC |
| 58 | Pertuzumab aff.mat. clone E1- VH CDR1 | GFTFADYTMD |

TABLE 33-continued

Sequences of antibodies with common light chain

| SEQ ID NO | Name | Sequence |
|---|---|---|
| 15 | Pertuzumab aff.mat. clone E1- VH CDR2 | DVNPNSGGSIYNQRFKG |
| 59 | Pertuzumab aff.mat. clone E1- VH CDR3 | NLGPWFYFDY |
| 70 | Pertuzumab aff.mat. clone G2 | EVQLVESGGGLVQPGGSLRLSCAASGFTFTDYTMDWVRQAPG KGLEWVADVNPNSGGYIVNRRFKGRFTLSVDRSKNTLYLQMN SLRAEDTAVYYCARNLGPSFYFDYWGQGTLVTVSS |
| 69 | Pertuzumab aff.mat. clone G2, DNA | GAGGTGCAATTGGTTGAAAGCGGTGGTGGTCTGGTTCAGCC TGGTGGTAGCCTGCGTCTGAGCTGTGCAGCAAGCGGTTTTAC CTTTACCGATTACACAATGGATTGGGTTCGTCAGGCACCGGG TAAAGGTCTGGAATGGGTTGCAGATGTTAATCCGAACTCTG GTGGTTACATTGTTAACCGTCGTTTTAAAGGTCGTTTTACCCT GAGCGTTGATCGTAGCAAAAATACCCTGTATCTGCAAATGA ATAGTCTGCGTGCAGAGGATACCGCAGTGTATTATTGTGCAC GTAATCTGGGTCCGAGCTTCTATTTTGATTATTGGGGTCAGG GCACCCTGGTTACCGTTAGCAGC |
| 14 | Pertuzumab aff.mat. clone G2- VH CDR1 | GFTFTDYTMD |
| 60 | Pertuzumab aff.mat. clone G2- VH CDR2 | DVNPNSGGYIVNRRFKG |
| 16 | Pertuzumab aff.mat. clone G2- VH CDR3 | NLGPSFYFDY |
| 72 | Pertuzumab aff.mat. clone C8 | EVQLVESGGGLVQPGGSLRLSCAASGFTFTDYTMDWVRQAPG KGLEWVADVNPNSGGSIMNRRFKGRFTLSVDRSKNTLYLQMN SLRAEDTAVYYCARNLGPSFYFDYWGQGTLVTVSS |
| 71 | Pertuzumab aff.mat. clone C8, DNA | GAGGTGCAATTGGTTGAAAGCGGTGGTGGTCTGGTTCAGCC TGGTGGTAGCCTGCGTCTGAGCTGTGCAGCAAGCGGTTTTAC CTTTACCGATTACACAATGGATTGGGTTCGTCAGGCACCGGG TAAAGGTCTGGAATGGGTTGCAGATGTTAATCCGAACTCTG GTGGTTCTATTATGAACCGTCGTTTTAAAGGTCGTTTTACCCT GAGCGTTGATCGTAGCAAAAATACCCTGTATCTGCAAATGA ATAGTCTGCGTGCAGAGGATACCGCAGTGTATTATTGTGCAC GTAATCTGGGTCCGAGCTTCTATTTTGATTATTGGGGTCAGG GCACCCTGGTTACCGTTAGCAGC |
| 14 | Pertuzumab aff.mat. clone C8- VH CDR1 | GFTFTDYTMD |
| 75 | Pertuzumab aff.mat. clone C8- VH CDR2 | DVNPNSGGSIMNRRFKG |
| 16 | Pertuzumab aff.mat. clone C8- VH CDR3 | NLGPSFYFDY |
| 74 | Pertuzumab aff.mat. clone A1 | EVQLVESGGGLVQPGGSLRLSCAASGFTFTDYTMDWVRQAPG KGLEWVADVNPNSGGIVNQRFKGRFTLSVDRSKNTLYLQMN SLRAEDTAVYYCARNLGPWFYFDYWGQGTLVTVSS |
| 73 | Pertuzumab aff.mat. clone A1, DNA | GAGGTGCAATTGGTTGAAAGCGGTGGTGGTCTGGTTCAGCC TGGTGGTAGCCTGCGTCTGAGCTGTGCAGCAAGCGGTTTTAC CTTTACCGATTACACAATGGATTGGGTTCGTCAGGCACCGGG TAAAGGTCTGGAATGGGTTGCAGATGTTAATCCGAACTCTG GTGGTTCTATTGTTAACCAGCGTTTTAAAGGTCGTTTTACCCT GAGCGTTGATCGTAGCAAAAATACCCTGTATCTGCAAATGA ATAGTCTGCGTGCAGAGGATACCGCAGTGTATTATTGTGCAC GTAATCTGGGTCCGGTTCTACTTTGATTATTGGGGTCAGG GCACCCTGGTTACCGTTAGCAGC |

TABLE 33-continued

Sequences of antibodies with common light chain

| SEQ ID NO | Name | Sequence |
|---|---|---|
| 14 | Pertuzumab aff.mat. clone A1- VH CDR1 | GFTFTDYTMD |
| 76 | Pertuzumab aff.mat. clone A1- VH CDR2 | DVNPNSGGSIVNQRFKG |
| 59 | Pertuzumab aff.mat. clone A1- VH CDR3 | NLGPWFYFDY |

Trastuzumab Stabilization Variants

| SEQ ID NO | Name | Sequence |
|---|---|---|
| 84 | Trastuzumab VL T31A (6641) | DIQMTQSPSSLSASVGDRVTITCRASQDVNAAVAWYQQKPGK APKLLIYSASFLYSGVPSRFSGSRSGTDFTLTISSLQPEDFATYYC QQHYTTPPTFGQGTKVEIK |
| 83 | Trastuzumab VL T31A (6641) | GATATCCAGATGACCCAGTCTCCATCCTCCCTGTCTGCATCT GTAGGAGACAGAGTCACCATCACTTGCCGGGCAAGTCAGGA CGTGAACGCCGCTGTAGCGTGGTACCAGCAGAAACCAGGTA AGGCACCGAAGCTATTAATTTATAGTGCGAGCTTCCTGTACA GTGGGGTCCCGTCGCGTTTTAGCGGCTCTCGATCCGGCACGG ATTTTACCCTGACCATTAGCAGCCTGCAGCCTGAAGACTTTG CGACATATTATTGCCAACAGCACTACACAACTCCTCCCACCT TTGGCCAGGGTACGAAAGTTGAAATTAAA |
| 103 | Trastuzumab VL T31A (6641)CDR1 | RASQDVNAAVA |
| 18 | Trastuzumab VL T31A (6641)CDR2 | SASFLYS |
| 19 | Trastuzumab VL T31A (6641)CDR3 | QQHYTTPPT |
| 86 | Trastuzumab VL T31V (6642) | DIQMTQSPSSLSASVGDRVTITCRASQDVNVAVAWYQQKPGK APKLLIYSASFLYSGVPSRFSGSRSGTDFTLTISSLQPEDFATYYC QQHYTTPPTFGQGTKVEIK |
| 85 | Trastuzumab VL T31V (6642)DNA | GATATCCAGATGACCCAGTCTCCATCCTCCCTGTCTGCATCT GTAGGAGACAGAGTCACCATCACTTGCCGGGCAAGTCAGGA CGTGAACGTGGCTGTAGCGTGGTACCAGCAGAAACCAGGTA AGGCACCGAAGCTATTAATTTATAGTGCGAGCTTCCTGTACA GTGGGGTCCCGTCGCGTTTTAGCGGCTCTCGATCCGGCACGG ATTTTACCCTGACCATTAGCAGCCTGCAGCCTGAAGACTTTG CGACATATTATTGCCAACAGCACTACACAACTCCTCCCACCT TTGGCCAGGGTACGAAAGTTGAAATTAAAG |
| 104 | Trastuzumab VL T31V (6642)CDR1 | RASQDVNVAVA |
| 18 | Trastuzumab VL T31V (6642)CDR2 | SASFLYS |
| 19 | Trastuzumab VL T31V (6642)CDR3 | QQHYTTPPT |
| 158 | Trastuzumab VL N30S CDR1 | RASQDVSTAVA |
| 94 | Trastuzumab VH (D98N) (6636) | EVQLVESGGGLVQPGGSLRLSCAASGFNIKDTYIHWVRQAPGK GLEWVARIYPTNGYTRYADSVKGRFTISADTSKNTAYLQMNSL RAEDTAVYYCSRWGGNGFYAMDYWGQGTLVTVSS |
| 93 | Trastuzumab VH (D98N) (6636)DNA | GAAGTGCAATTGGTGGAAAGCGGCGGCGGCCTGGTGCAACC GGGCGGCAGCCTGCGTCTGAGCTGCGCGGCCTCCGGATTTA ACATAAAGGACACATACATCCACTGGGTGCGCCAAGCACCT GGGAAGGGTCTCGAGTGGGTGGCTCGGATTTACCCAACAAA |

TABLE 33-continued

Sequences of antibodies with common light chain

| SEQ ID NO | Name | Sequence |
|---|---|---|
| | | TGGCTACACCAGGTATGCGGATAGCGTGAAAGGCCGTTTTA<br>CCATTTCAGCTGATACTTCGAAGAACACCGCCTATCTGCAAA<br>TGAACAGCCTGCGTGCGGAAGATACGGCCGTGTATTATTGCT<br>CGCGTTGGGGAGGAAACGGGTTCTATGCTATGGATTACTGG<br>GGCCAAGGCACCCTGGTGACGGTTAGCTCA |
| 20 | Trastuzumab VH (D98N) (6636)CDR1 | GFNIKDTYIH |
| 29 | Trastuzumab VH (D98N) (6636)CDR2 | RIYPTNGYTRYADSVKG |
| 78 | Trastuzumab VH (D98N) (6636)CDR3 | WGGNGFYAMDY |
| 96 | Trastuzumab VH (D98E) (6637) | EVQLVESGGGLVQPGGSLRLSCAASGFNIKDTYIHWVRQAPGK<br>GLEWVARIYPTNGYTRYADSVKGRFTISADTSKNTAYLQMNSL<br>RAEDTAVYYCSRWGGEGFYAMDYWGQGTLVTVSS |
| 95 | Trastuzumab VH (D98E) (6637)DNA | GAAGTGCAATTGGTGGAAAGCGGCGGCGGCCTGGTGCAACC<br>GGGCGGCAGCCTGCGTCTGAGCTGCGCGGCCTCCGGATTTA<br>ACATAAAGGACACATACATCCACTGGGTGCGCCAAGCACCT<br>GGGAAGGGTCTCGAGTGGGTGGCTCGGATTTACCCAACAAA<br>TGGCTACACCAGGTATGCGGATAGCGTGAAAGGCCGTTTTA<br>CCATTTCAGCTGATACTTCGAAGAACACCGCCTATCTGCAAA<br>TGAACAGCCTGCGTGCGGAAGATACGGCCGTGTATTATTGCT<br>CGCGTTGGGGAGGAGAGGGGTTCTATGCTATGGATTACTGG<br>GGCCAAGGCACCCTGGTGACGGTTAGCTCA |
| 20 | Trastuzumab VH (D98E) (6637)CDR1 | GFNIKDTYIH |
| 29 | Trastuzumab VH (D98E) (6637)CDR2 | RIYPTNGYTRYADSVKG |
| 79 | Trastuzumab VH (D98E) (6637)CDR3 | WGGEGFYAMDY |
| 98 | Trastuzumab VH (D98T) (6638) | EVQLVESGGGLVQPGGSLRLSCAASGFNIKDTYIHWVRQAPGK<br>GLEWVARIYPTNGYTRYADSVKGRFTISADTSKNTAYLQMNSL<br>RAEDTAVYYCSRWGGTGFYAMDYWGQGTLVTVSS |
| 97 | Trastuzumab VH (D98T) (6638)DNA | GAAGTGCAATTGGTGGAAAGCGGCGGCGGCCTGGTGCAACC<br>GGGCGGCAGCCTGCGTCTGAGCTGCGCGGCCTCCGGATTTA<br>ACATAAAGGACACATACATCCACTGGGTGCGCCAAGCACCT<br>GGGAAGGGTCTCGAGTGGGTGGCTCGGATTTACCCAACAAA<br>TGGCTACACCAGGTATGCGGATAGCGTGAAAGGCCGTTTTA<br>CCATTTCAGCTGATACTTCGAAGAACACCGCCTATCTGCAAA<br>TGAACAGCCTGCGTGCGGAAGATACGGCCGTGTATTATTGCT<br>CGCGTTGGGGAGGAACCGGGTTCTATGCTATGGATTACTGG<br>GGCCAAGGCACCCTGGTGACGGTTAGCTCA |
| 20 | Trastuzumab VH (D98T) (6638) CDR1 | GFNIKDTYIH |
| 29 | Trastuzumab VH (D98T) (6638) CDR2 | RIYPTNGYTRYADSVKG |
| 80 | Trastuzumab VH (D98T) (6638) CDR3 | WGGTGFYAMDY |
| 100 | Trastuzumab VH (G99A) (6639) | EVQLVESGGGLVQPGGSLRLSCAASGFNIKDTYIHWVRQAPGK<br>GLEWVARIYPTNGYTRYADSVKGRFTISADTSKNTAYLQMNSL<br>RAEDTAVYYCSRWGGDAFYAMDYWGQGTLVTVSS |

TABLE 33-continued

Sequences of antibodies with common light chain

| SEQ ID NO | Name | Sequence |
|---|---|---|
| 99 | Trastuzumab VH (G99A) (6639)DNA | GAAGTGCAATTGGTGGAAAGCGGCGGCGGCCTGGTGCAACC<br>GGGCGGCAGCCTGCGTCTGAGCTGCGCGGCCTCCGGATTTA<br>ACATAAAGGACACATACATCCACTGGGTGCGCCAAGCACCT<br>GGGAAGGGTCTCGAGTGGGTGGCTCGGATTTACCCAACAAA<br>TGGCTACACCAGGTATGCGGATAGCGTGAAAGGCCGTTTTA<br>CCATTTCAGCTGATACTTCGAAGAACACCGCCTATCTGCAAA<br>TGAACAGCCTGCGTGCGGAAGATACGGCCGTGTATTATTGCT<br>CGCGTTGGGGAGGAGACGCCTTCTATGCTATGGATTACTGG<br>GGCCAAGGCACCCTGGTGACGGTTAGCTCA |
| 20 | Trastuzumab VH (G99A) (6639) CDR1 | GFNIKDTYIH |
| 29 | Trastuzumab VH (G99A) (6639) CDR2 | RIYPTNGYTRYADSVKG |
| 87 | Trastuzumab VH (G99A) (6639) CDR3 | WGGDAFYAMDY |
| 102 | Trastuzumab VH (G99S) (6640) | EVQLVESGGGLVQPGGSLRLSCAASGFNIKDTYIHWVRQAPGK<br>GLEWVARIYPTNGYTRYADSVKGRFTISADTSKNTAYLQMNSL<br>RAEDTAVYYCSRWGGD<u>S</u>FYAMDYWGQGTLVTVSS |
| 101 | Trastuzumab VH (G99S) (6640)DNA | GAAGTGCAATTGGTGGAAAGCGGCGGCGGCCTGGTGCAACC<br>GGGCGGCAGCCTGCGTCTGAGCTGCGCGGCCTCCGGATTTA<br>ACATAAAGGACACATACATCCACTGGGTGCGCCAAGCACCT<br>GGGAAGGGTCTCGAGTGGGTGGCTCGGATTTACCCAACAAA<br>TGGCTACACCAGGTATGCGGATAGCGTGAAAGGCCGTTTTA<br>CCATTTCAGCTGATACTTCGAAGAACACCGCCTATCTGCAAA<br>TGAACAGCCTGCGTGCGGAAGATACGGCCGTGTATTATTGCT<br>CGCGTTGGGGAGGAGACAGCTTCTATGCTATGGATTACTGG<br>GGCCAAGGCACCCTGGTGACGGTTAGCTCA |
| 20 | Trastuzumab VH (G99S) (6640)CDR1 | GFNIKDTYIH |
| 29 | Trastuzumab VH (G99S) (6640)CDR2 | RIYPTNGYTRYADSVKG |
| 88 | Trastuzumab VH (G99S) (6640)CDR3 | WGGDSFYAMDY |

TABLE 34

Antigens

| SEQ ID NO | Name | Sequence |
|---|---|---|
| 2 | Her2 ECD | MGWSCIILFLVATATGVHSTQVCTGTDMKLRLPASPETHLDML<br>RHLYQGCQVVQGNLELTYLPTNASLSFLQDIQEVQGYVLIAHN<br>QVRQVPLQRLRIVRGTQLFEDNYALAVLDNGDPLNNTTPVTGA<br>SPGGLRELQLRSLTEILKGGVLIQRNPQLCYQDTILWKDIFHKN<br>NQLALTLIDTNRSRACHPCSPMCKGSRCWGESSEDCQSLTRTV<br>CAGGCARCKGPLPTDCCHEQCAAGCTGPKHSDCLACLHFNHS<br>GICELHCPALVTYNTDTFESMPNPEGRYTFGASCVTACPYNYLS<br>TDVGSCTLVCPLHNQEVTAEDGTQRCEKCSKPCARVCYGLGM<br>EHLREVRAVTSANIQEFAGCKKIFGSLAFLPESFDGDPASNTAPL<br>QPEQLQVFETLEEITGYLYISAWPDSLPDLSVFQNLQVIRGRILH<br>NGAYSLTLQGLGISWLGLRSLRELGSGLALIHHNTHLCFVHTVP<br>WDQLFRNPHQALLHTANRPEDECVGEGLACHQLCARGHCWG<br>PGPTQCVNCSQFLRGQECVEECRVLQGLPREYVNARHCLPCHP<br>ECQPQNGSVTCFGLEADQCVACAHYKDPPFCVARCPSGVKPDL<br>SYMPIWKFPDEEGACQPCPINCTHSCVDLDDKGCPAEQRASPLT<br>VDEQLYFQGGSGLNDIFEAQKIEWHEARAHHHHHH |

TABLE 34-continued

Antigens

| SEQ ID NO | Name | Sequence |
|---|---|---|
| 1 | Her2 ECD DNA | ACCCAAGTGTGCACCGGCACAGACATGAAGCTGCGGCTCCC
TGCCAGTCCCGAGACCCACCTGGACATGCTCCGCCACCTCTA
CCAGGGCTGCCAGGTGGTGCAGGGAAACCTGGAACTCACCT
ACCTGCCCACCAATGCCAGCCTGTCCTTCCTGCAGGATATCC
AGGAGGTGCAGGGCTACGTGCTCATCGCTCACAACCAAGTG
AGGCAGGTCCCACTGCAGAGGCTGCGGATTGTGCGAGGCAC
CCAGCTCTTTGAGGACAACTATGCCCTGGCCGTGCTAGACAA
TGGAGACCCGCTGAACAATACCACCCCTGTCACAGGGGCCT
CCCCAGGAGGCCTGCGGGAGCTGCAGCTTCGAAGCCTCACA
GAGATCTTGAAAGGAGGGGTCTTGATCCAGCGGAACCCCCA
GCTCTGCTACCAGGACACGATTTTGTGGAAGGACATCTTCCA
CAAGAACAACCAGCTGGCTCTCACACTGATAGACACCAACC
GCTCTCGGGCCTGCCACCCCTGTTCTCCGATGTGTAAGGGCT
CCCGCTGCTGGGGAGAGAGTTCTGAGGATTGTCAGAGCCTG
ACGCGCACTGTCTGTGCCGGTGGCTGTGCCCGCTGCAAGGG
GCCACTGCCCACTGACTGCTGCCATGAGCAGTGTGCTGCCGG
CTGCACGGGCCCCAAGCACTCTGACTGCCTGGCCTGCCTCCA
CTTCAACCACAGTGGCATCTGTGAGCTGCACTGCCCAGCCCT
GGTCACCTACAACACAGACACGTTTGAGTCCATGCCCAATCC
CGAGGGCCGGTATACATTCGGCGCCAGCTGTGTGACTGCCT
GTCCCTACAACTACCTTTCTACGGACGTGGGATCCTGCACCC
TCGTCTGCCCCCTGCACAACCAAGAGGTGACAGCAGAGGAT
GGAACACAGCGGTGTGAGAAGTGCAGCAAGCCCTGTGCCCG
AGTGTGCTATGGTCTGGGCATGGAGCACTTGCGAGAGGTGA
GGGCAGTTACCAGTGCCAATATCCAGGAGTTTGCTGGCTGC
AAGAAGATCTTTGGGAGCCTGGCATTTCTGCCGGAGAGCTTT
GATGGGGACCCAGCCTCCAACACTGCCCCGCTCCAGCCAGA
GCAGCTCCAAGTGTTTGAGACTCTGGAAGAGATCACAGGTT
ACCTATACATCTCAGCATGGCCGGACAGCCTGCCTGACCTCA
GCGTCTTCCAGAACCTGCAAGTAATCCGGGGACGAATTCTG
CACAATGGCGCCTACTCGCTGACCCTGCAAGGGCTGGGCAT
CAGCTGGCTGGGGCTGCGCTCACTGAGGGAACTGGGCAGTG
GACTGGCCCTCATCCACCATAACACCCACCTCTGCTTCGTGC
ACACGGTGCCCTGGGACCAGCTCTTTCGGAACCCGCACCAA
GCTCTGCTCCACACTGCCAACCGGCCAGAGGACGAGTGTGT
GGGCGAGGGCCTGGCCTGCCACCAGCTGTGCGCCCGAGGGC
ACTGCTGGGGTCCAGGGCCCACCCAGTGTGTCAACTGCAGC
CAGTTCCTTCGGGGCCAGGAGTGCGTGGAGGAATGCCGAGT
ACTGCAGGGGCTCCCCAGGGAGTATGTGAATGCCAGGCACT
GTTTGCCGTGCCACCCTGAGTGTCAGCCCCAGAATGGCTCAG
TGACCTGTTTTGGACTGGAGGCTGACCAGTGTGTGGCCTGTG
CCCACTATAAGGACCCTCCCTTCTGCGTGGCCCGCTGCCCCA
GCGGTGTGAAACCTGACCTCTCCTACATGCCCATCTGGAAGT
TTCCAGATGAGGAGGGCGCATGCCAGCCTTGCCCCATCAAC
TGCACCCACTCCTGTGTGGACCTGGATGACAAGGGCTGCCCC
GCCGAGCAGAGAGCCAGCCCTCTGACGGTCGACGAACAGTT
ATATTTTCAGGGCGGCTCAGGCCTGAACGACATCTTCGAGGC
CCAGAAGATCGAGTGGCACGAGGCTCGAGCTCACCACCATC
ACCATCAC |
| 4 | Fc(hole) | DKTHTCPPCPAPELLGGPSVFLFPPKPKDTLMISRTPEVTCVVV
DVSHEDPEVKFNWYVDGVEVHNAKTKPREEQYNSTYRVVSVL
TVLHQDWLNGKEYKCKVSNKALPAPIEKTISKAKGQPREPQVC
TLPPSRDELTKNQVSLSCAVKGFYPSDIAVEWESNGQPENNYK
TTPPVLDSDGSFFLVSKLTVDKSRWQQGNVFSCSVMHEALHNR
FTQKSLSLSPGK |
| 3 | Fc(hole)DNA | GACAAAACTCACACATGCCCACCGTGCCCAGCACCTGAACT
CCTGGGGGGACCGTCAGTCTTCCTCTTCCCCCCAAAACCCAA
GGACACCCTCATGATCTCCCGGACCCCTGAGGTCACATGCGT
GGTGGTGGACGTGAGCCACGAAGACCCTGAGGTCAAGTTCA
ACTGGTACGTGGACGGCGTGGAGGTGCATAATGCCAAGACA
AAGCCGCGGGAGGAGCAGTACAACAGCACGTACCGTGTGGT
CAGCGTCCTCACCGTCCTGCACCAGGACTGGCTGAATGGCA
AGGAGTACAAGTGCAAGGTCTCCAACAAAGCCCTCCCAGCC
CCCATCGAGAAAACCATCTCCAAAGCCAAAGGGCAGCCCCG
AGAACCACAGGTGTGCACCCTGCCCCCATCCCGGGATGAGC
TGACCAAGAACCAGGTCAGCCTCTCGTGCGCAGTCAAAGGC
TTCTATCCCAGCGACATCGCCGTGGAGTGGGAGAGCAATGG
GCAGCCGGAGAACAACTACAAGACCACGCCTCCCGTGCTGG
ACTCCGACGGCTCCTTCTTCCTCGTGAGCAAGCTCACCGTGG
ACAAGAGCAGGTGGCAGCAGGGGAACGTCTTCTCATGCTCC
GTGATGCATGAGGCTCTGCACAACCGCTTCACGCAGAAGAG
CCTCTCCCTGTCTCCGGGTAAA |

TABLE 34-continued

Antigens

| SEQ ID NO | Name | Sequence |
|---|---|---|
| 6 | Her2 ECD-Fc(knob) | TQVCTGTDMKLRLPASPETHLDMLRHLYQGCQVVQGNLELTY
LPTNASLSFLQDIQEVQGYVLIAHNQVRQVPLQRLRIVRGTQLF
EDNYALAVLDNGDPLNNTTPVTGASPGGLRELQLRSLTEILKG
GVLIQRNPQLCYQDTILWKDIFHKNNQLALTLIDTNRSRACHPC
SPMCKGSRCWGESSEDCQSLTRTVCAGGCARCKGPLPTDCCHE
QCAAGCTGPKHSDCLACLHFNHSGICELHCPALVTYNTDTFES
MPNPEGRYTFGASCVTACPYNYLSTDVGSCTLVCPLHNQEVTA
EDGTQRCEKCSKPCARVCYGLGMEHLREVRAVTSANIQEFAG
CKKIFGSLAFLPESFDGDPASNTAPLQPEQLQVFETLEEITGYLYI
SAWPDSLPDLSVFQNLQVIRGRILHNGAYSLTLQGLGISWLGLR
SLRELGSGLALIHHNTHLCFVHTVPWDQLFRNPHQALLHTANR
PEDECVGEGLACHQLCARGHCWGPGPTQCVNCSQFLRGQECV
EECRVLQGLPREYVNARHCLPCHPECQPQNGSVTCFGLEADQC
VACAHYKDPPFCVARCPSGVKPDLSYMPIWKFPDEEGACQPCP
INCTHSCVDLDDKGCPAEQRASPLTVDGGSPTPPTPGGGSADKT
HTCPPCPAPELLGGPSVFLFPPKPKDTLMISRTPEVTCVVVDVSH
EDPEVKFNWYVDGVEVHNAKTKPREEQYNSTYRVVSVLTVLH
QDWLNGKEYKCKVSNKALPAPIEKTISKAKGQPREPQVYTLPP
CRDELTKNQVSLWCLVKGFYPSDIAVEWESNGQPENNYKTTPP
VLDSDGSFFLYSKLTVDKSRWQQGNVFSCSVMHEALHNHYTQ
KSLSLSPGKSGGLNDIFEAQKIEWHE |
| 5 | Her2 ECD-Fc(knob)DNA | ACCCAAGTGTGCACCGGCACAGACATGAAGCTGCGGCTCCC
TGCCAGTCCCGAGACCCACCTGGACATGCTCCGCCACCTCTA
CCAGGGCTGCCAGGTGGTGCAGGGAAACCTGGAACTCACCT
ACCTGCCCACCAATGCCAGCCTGTCCTTCCTGCAGGATATCC
AGGAGGTGCAGGGCTACGTGCTGCTCATCGCTCACAACCAAGTG
AGGCAGGTCCCACTGCAGAGGCTGCGGATTGTGCGAGGCAC
CCAGCTCTTTGAGGACAACTATGCCCTGGCCGTGCTAGACAA
TGGAGACCCGCTGAACAATACCACCCCTGTCACAGGGGCCT
CCCCAGGAGGCCTGCGGGAGCTGCAGCTTCGAAGCCTCACA
GAGATCTTGAAAGGAGGGGTCTTGATCCAGCGGAACCCCCA
GCTCTGCTACCAGGACACGATTTTGTGGAAGGACATCTTCCA
CAAGAACAACCAGCTGGCTCTCACACTGATAGACACCAACC
GCTCTCGGGCCTGCCACCCCTGTTCTCCGATGTGTAAGGGCT
CCCGCTGCTGGGGAGAGAGTTCTGAGGATTGTCAGAGCCTG
ACGCGCACTGTCTGTGCCGGTGGCTGTGCCCGCTGCAAGGG
GCCACTGCCCACTGACTGCTGCCATGAGCAGTGTGCTGCCGG
CTGCACGGGCCCCAAGCACTCTGACTGCCTGGCCTGCCTCCA
CTTCAACCACAGTGGCATCTGTGAGCTGCACTGCCCAGCCCT
GGTCACCTACAACACAGACACGTTTGAGTCCATGCCCAATCC
CGAGGGCCGGTATACATTCGGCGCCAGCTGTGTGACTGCCT
GTCCCTACAACTACCTTTCTACGGACGTGGGATCCTGCACCC
TCGTCTGCCCCCTGCACAACCAAGAGGTGACAGCAGAGGAT
GGAACACAGCGGTGTGAGAAGTGCAGCAAGCCCTGTGCCCG
AGTGTGCTATGGTCTGGGCATGGAGCACTTGCGAGAGGTGA
GGGCAGTTACCAGTGCCAATATCCAGGAGTTTGCTGGCTGC
AAGAAGATCTTTGGGAGCCTGGCATTTCTGCCGGAGAGCTTT
GATGGGGACCCAGCCTCCAACACTGCCCCGCTCCAGCCAGA
GCAGCTCCAAGTGTTTGAGACTCTGGAAGAGATCACAGGTT
ACCTATACATCTCAGCATGGCCGGACAGCCTGCCTGACCTCA
GCGTCTTCCAGAACCTGCAAGTAATCCGGGGACGAATTCTG
CACAATGGCGCCTACTCGCTGACCCTGCAAGGGCTGGGCAT
CAGCTGGCTGGGGCTGCGCTCACTGAGGGAACTGGGCAGTG
GACTGGCCCTCATCCACCATAACACCCACCTCTGCTTCGTGC
ACACGGTGCCCTGGGACCAGCTCTTTCGGAACCCGCACCAA
GCTCTGCTCCACACTGCCAACCGGCCAGAGGACGAGTGTGT
GGGCGAGGGCCTGGCCTGCCACCAGCTGTGCGCCCGAGGGC
ACTGCTGGGTCCAGGGCCCACCCAGTGTGTCAACTGCAGC
CAGTTCCTTCGGGGCCAGGAGTGCGTGGAGGAATGCCGAGT
ACTGCAGGGGCTCCCCAGGGAGTATGTGAATGCCAGGCACT
GTTTGCCGTGCCACCCTGAGTGTCAGCCCCAGAATGGCTCAG
TGACCTGTTTTGGACTGGAGGCTGACCAGTGTGTGGCCTGTG
CCCACTATAAGGACCCTCCCTTCTGCGTGGCCCGCTGCCCCA
GCGGTGTGAAACCTGACCTCTCCTACATGCCCATCTGGAAGT
TTCCAGATGAGGAGGGCGCATGCCAGCCTTGCCCCATCAAC
TGCACCCACTCCTGTGTGGACCTGGATGACAAGGGCTGCCCC
GCCGAGCAGAGAGCCAGCCCTCTGACGGTCGACGGTGGTAG
TCCGACACCTCCGACACCCGGGGGTGGTTCTGCAGACAAAA
CTCACACATGCCCACCGTGCCCAGCACCTGAACTCCTGGGG
GGACCGTCAGTCTTCCTCTTCCCCCCAAAACCCAAGGACACC
CTCATGATCTCCCGGACCCCTGAGGTCACATGCGTGGTGGTG
GACGTGAGCCACGAAGACCCTGAGGTCAAGTTCAACTGGTA
CGTGGACGGCGTGGAGGTGCATAATGCCAAGACAAAGCCGC |

TABLE 34-continued

Antigens

| SEQ ID NO | Name | Sequence |
|---|---|---|
| | | GGGAGGAGCAGTACAACAGCACGTACCGTGTGGTCAGCGTC<br>CTCACCGTCCTGCACCAGGACTGGCTGAATGGCAAGGAGTA<br>CAAGTGCAAGGTCTCCAACAAAGCCCTCCCAGCCCCCATCG<br>AGAAAACCATCTCCAAAGCCAAAGGGCAGCCCCGAGAACCA<br>CAGGTGTACACCCTGCCCCCATGCCGGGATGAGCTGACCAA<br>GAACCAGGTCAGCCTGTGGTGCCTGGTCAAAGGCTTCTATCC<br>CAGCGACATCGCCGTGGAGTGGGAGAGCAATGGGCAGCCGG<br>AGAACAACTACAAGACCACGCCTCCCGTGCTGGACTCCGAC<br>GGCTCCTTCTTCCTCTACAGCAAGCTCACCGTGGACAAGAGC<br>AGGTGGCAGCAGGGGAACGTCTTCTCATGCTCCGTGATGCA<br>TGAGGCTCTGCACAACCACTACACGCAGAAGAGCCTCTCCC<br>TGTCTCCGGGTAAATCCGGAGGCCTGAACGACATCTTCGAG<br>GCCCAGAAGATTGAATGGCACGAG |
| 8 | Her2<br>ECD(pertuzumab<br>KO)-Fc(knob) | TQVCTGTDMKLRLPASPETHLDMLRHLYQGCQVVQGNLELTY<br>LPTNASLSFLQDIQEVQGYVLIAHNQVRQVPLQRLRIVRGTQLF<br>EDNYALAVLDNGDPLNNTTPVTGASPGGLRELQLRSLTEILKG<br>GVLIQRNPQLCYQDTILWKDIFHKNNQLALTLIDTNRSRACHPC<br>SPMCKGSRCWGESSEDCQSLTRTVCAGGCARCKGPLPTDCCHE<br>QCAAGCTGPKHSDCLACLHFNHSGICELHCPALVTYNTDTRES<br>MPNPEGRYRFGASCVTACPYNYLSTDRGSCTLVCPLANQEVTA<br>EDGTQRCEKCSKPCARVCYGLGMEHLREVRAVTSANIQEFAG<br>CKKIFGSLAFLPESFDGDPASNTAPLQPEQLQVFETLEEITGYLYI<br>SAWPDSLPDLSVFQNLQVIRGRILHNGAYSLTLQGLGISWLGLR<br>SLRELGSGLALIHHNTHLCFVHTVPWDQLFRNPHQALLHTANR<br>PEDECVGEGLACHQLCARGHCWGPGPTQCVNCSQFLRGQECV<br>EECRVLQGLPREYVNARHCLPCHPECQPQNGSVTCFGLEADQC<br>VACAHYKDPPFCVARCPSGVKPDLSYMPIWKFPDEEGACQPCP<br>INCTHSCVDLDDKGCPAEQRASPLTVDGGSPTPPTPGGGSADKT<br>HTCPPCPAPELLGGPSVFLFPPKPKDTLMISRTPEVTCVVVDVSH<br>EDPEVKFNWYVDGVEVHNAKTKPREEQYNSTYRVVSVLTVLH<br>QDWLNGKEYKCKVSNKALPAPIEKTISKAKGQPREPQVYTLPP<br>CRDELTKNQVSLWCLVKGFYPSDIAVEWESNGQPENNYKTTPP<br>VLDSDGSFFLYSKLTVDKSRWQQGNVFSCSVMHEALHNHYTQ<br>KSLSLSPGKSGGLNDIFEAQKIEWHE |
| 7 | Her2<br>ECD(pertuzumab<br>KO)-<br>Fc(knob)DNA | ACCCAAGTGTGCACCGGCACAGACATGAAGCTGCGGCTCCC<br>TGCCAGTCCCGAGACCCACCTGGACATGCTCCGCCACCTCTA<br>CCAGGGCTGCCAGGTGGTGCAGGGAAACCTGGAACTCACCT<br>ACCTGCCCACCAATGCCAGCCTGTCCTTCCTGCAGGATATCC<br>AGGAGGTGCAGGGCTACGTGCTCATCGCTCACAACCAAGTG<br>AGGCAGGTCCCACTGCAGAGGCTGCGGATTGTGCGAGGCAC<br>CCAGCTCTTTGAGGACAACTATGCCCTGGCCGTGCTAGACAA<br>TGGAGACCCGCTGAACAATACCACCCCTGTCACAGGGGCCT<br>CCCCAGGAGGCCTGCGGGAGCTGCAGCTTCGAAGCCTCACA<br>GAGATCTTGAAAGGAGGGGTCTTGATCCAGCGGAACCCCCA<br>GCTCTGCTACCAGGACACGATTTTGTGGAAGGACATCTTCCA<br>CAAGAACAACCAGCTGGCTCTCACACTGATAGACACCAACC<br>GCTCTCGGGCCTGCCACCCCTGTTCTCCGATGTGTAAGGGCT<br>CCCGCTGCTGGGGAGAGAGTTCTGAGGATTGTCAGAGCCTG<br>ACGCGCACTGTCTGTGCCGGTGGCTGTGCCCGCTGCAAGGG<br>GCCACTGCCCACTGACTGCTGCCATGAGCAGTGTGCTGCCGG<br>CTGCACGGGCCCCAAGCACTCTGACTGCCTGGCCTGCCTCCA<br>CTTCAACCACAGTGGCATCTGTGAGCTGCACTGCCCAGCCCT<br>GGTCACCTACAACACAGACACGCGGGAGTCCATGCCCAATC<br>CCGAGGGCCGGTATAGATTCGGCGCCAGCTGTGTGACTGCC<br>TGTCCCTACAACTACCTTTCTACGGACCGGGGATCCTGCACC<br>CTCGTCTGCCCCCTGGCCAACCAAGAGGTGACAGCAGAGGA<br>TGGAACACAGCGGTGTGAGAAGTGCAGCAAGCCCTGTGCCC<br>GAGTGTGCTATGGTCTGGGCATGGAGCACTTGCGAGAGGTG<br>AGGGCAGTTACCAGTGCCAATATCCAGGAGTTTGCTGGCTG<br>CAAGAAGATCTTTGGGAGCCTGGCATTTCTGCCGGAGAGCTT<br>TGATGGGGACCCAGCCTCCAACACTGCCCCGCTCCAGCCAG<br>AGCAGCTCCAAGTGTTTGAGACTCTGGAAGAGATCACAGGT<br>TACCTATACATCTCAGCATGGCCGGACAGCCTGCCTGACCTC<br>AGCGTCTTCCAGAACCTGCAAGTAATCCGGGGACGAATTCT<br>GCACAATGGCGCCTACTCGCTGACCCTGCAAGGGCTGGGCA<br>TCAGCTGGCTGGGGCTGCGCTCACTGAGGGAACTGGGCAGT<br>GGACTGGCCCTCATCCACCATAACACCCACCTCTGCTTCGTG<br>CACACGGTGCCCTGGGACCAGCTCTTTCGGAACCCGCACCA<br>AGCTCTGCTCCACACTGCCAACCGGCCAGAGGACGAGTGTG<br>TGGGCGAGGGCCTGGCCTGCCACCAGCTGTGCGCCCGAGGG<br>CACTGCTGGGGTCCAGGGCCCACCCAGTGTGTCAACTGCAG<br>CCAGTTCCTTCGGGGCCAGGAGTGCGTGGAGGAATGCCGAG<br>TACTGCAGGGGCTCCCCAGGGGAGTATGTGAATGCCAGGCAC |

TABLE 34-continued

Antigens

| SEQ ID NO | Name | Sequence |
|---|---|---|
| | | TGTTTGCCGTGCCACCCTGAGTGTCAGCCCCAGAATGGCTCA
GTGACCTGTTTTGGACTGGAGGCTGACCAGTGTGTGGCCTGT
GCCCACTATAAGGACCCTCCCTTCTGCGTGGCCCGCTGCCCC
AGCGGTGTGAAACCTGACCTCTCCTACATGCCCATCTGGAAG
TTTCCAGATGAGGAGGGCGCATGCCAGCCTTGCCCCATCAA
CTGCACCCACTCCTGTGTGGACCTGGATGACAAGGGCTGCCC
CGCCGAGCAGAGAGCCAGCCCTCTGACGGTCGACGGTGGTA
GTCCGACACCTCCGACACCCGGGGGTGGTTCTGCAGACAAA
ACTCACACATGCCCACCGTGCCCAGCACCTGAACTCCTGGG
GGGACCGTCAGTCTTCCTCTTCCCCCCAAAACCCAAGGACAC
CCTCATGATCTCCCGGACCCCTGAGGTCACATGCGTGGTGGT
GGACGTGAGCCACGAAGACCCTGAGGTCAAGTTCAACTGGT
ACGTGGACGGCGTGGAGGTGCATAATGCCAAGACAAAGCCG
CGGGAGGAGCAGTACAACAGCACGTACCGTGTGGTCAGCGT
CCTCACCGTCCTGCACCAGGACTGGCTGAATGGCAAGGAGT
ACAAGTGCAAGGTCTCCAACAAAGCCCTCCCAGCCCCCATC
GAGAAAACCATCTCCAAAGCCAAAGGGCAGCCCCGAGAACC
ACAGGTGTACACCCTGCCCCCATGCCGGGATGAGCTGACCA
AGAACCAGGTCAGCCTGTGGTGCCTGGTCAAAGGCTTCTATC
CCAGCGACATCGCCGTGGAGTGGGAGAGCAATGGGCAGCCG
GAGAACAACTACAAGACCACGCCTCCCGTGCTGGACTCCGA
CGGCTCCTTCTTCCTCTACAGCAAGCTCACCGTGGACAAGAG
CAGGTGGCAGCAGGGGAACGTCTTCTCATGCTCCGTGATGC
ATGAGGCTCTGCACAACCACTACACGCAGAAGAGCCTCTCC
CTGTCTCCGGGTAAATCCGGAGGCCTGAACGACATCTTCGA
GGCCCAGAAGATTGAATGGCACGAG |
| 10 | Her2 ECD(trastuzumab KO)- Fc(knob) | TQVCTGTDMKLRLRPASPETHLDMLRHLYQGCQVVQGNLELTY
LPTNASLSFLQDIQEVQGYVLIAHNQVRQVPLQRLRIVRGTQLF
EDNYALAVLDNGDPLNNTTPVTGASPGGLRELQLRSLTEILKG
GVLIQRNPQLCYQDTILWKDIFHKNNQLALTLIDTNRSRACHPC
SPMCKGSRCWGESSEDCQSLTRTVCAGGCARCKGPLPTDCCHE
QCAAGCTGPKHSDCLACLHFNHSGICELHCPALVTYNTDTFES
MPNPEGRYTFGASCVTACPYNYLSTDVGSCTLVCPLHNQEVTA
EDGTQRCEKCSKPCARVCYGLGMEHLREVRAVTSANIQEFAG
CKKIFGSLAFLPESFDGDPASNTAPLQPEQLQVFETLEEITGYLYI
SAWPDSLPDLSVFQNLQVIRGRILHNGAYSLTLQGLGISWLGLR
SLRELGSGLALIHHNTHLCFVHTVPWDQLFRNPHQALLHTANR
PEDECVGEGLACHQLCARGHCWGPGPTQCVNCSQFLRGQECV
EECRVLQGLPREYVNARHCLPCHPECQPQNGSVTCFGLEARQC
VACAHYKDRRCVARCPSGVKPDLSYMPIWKFPDEEGACQPCPI
NCTHSCVDLDDKGCPAEQRASPLTVDGGSPTPPTPGGGSADKT
HTCPPCPAPELLGGPSVFLFPPKPKDTLMISRTPEVTCVVVDVSH
EDPEVKFNWYVDGVEVHNAKTKPREEQYNSTYRVVSVLTVLH
QDWLNGKEYKCKVSNKALPAPIEKTISKAKGQPREPQVYTLPP
CRDELTKNQVSLWCLVKGFYPSDIAVEWESNGQPENNYKTTPP
VLDSDGSFFLYSKLTVDKSRWQQGNVFSCSVMHEALHNHYTQ
KSLSLSPGKSGGLNDIFEAQKIEWHE |
| 9 | Her2 ECD(trastuzumab KO)- Fc(knob)DNA | ACCCAAGTGTGCACCGGCACAGACATGAAGCTGCGGCTCCC
TGCCAGTCCCGAGACCCACCTGGACATGCTCCGCCACCTCTA
CCAGGGCTGCCAGGTGGTGCAGGGAAACCTGGAACTCACCT
ACCTGCCCACCAATGCCAGCCTGTCCTTCCTGCAGGATATCC
AGGAGGTGCAGGGCTACGTGCTCATCGCTCACAACCAAGTG
AGGCAGGTCCCACTGCAGAGGCTGCGGATTGTGCGAGGCAC
CCAGCTCTTTGAGGACAACTATGCCCTGGCCGTGCTAGACAA
TGGAGACCCGCTGAACAATACCACCCCTGTCACAGGGGCCT
CCCCAGGAGGCCTGCGGGAGCTGCAGCTTCGAAGCCTCACA
GAGATCTTGAAAGGAGGGGTCTTGATCCAGCGGAACCCCCA
GCTCTGCTACCAGGACACGATTTTGTGGAAGGACATCTTCCA
CAAGAACAACCAGCTGGCTCTCACACTGATAGACACCAACC
GCTCTCGGGCCTGCCACCCCTGTTCTCCGATGTGTAAGGGCT
CCCGCTGCTGGGGAGAGAGTTCTGAGGATTGTCAGAGCCTG
ACGCGCACTGTCTGTGCCGGTGGCTGTGCCCGCTGCAAGGG
GCCACTGCCCACTGACTGCTGCCATGAGCAGTGTGCTGCCGG
CTGCACGGGCCCCAAGCACTCTGACTGCCTGGCCTGCCTCCA
CTTCAACCACAGTGGCATCTGTGAGCTGCACTGCCCAGCCCT
GGTCACCTACAACACAGACACGTTTGAGTCCATGCCCAATCC
CGAGGGCCGGTATACATTCGGCGCCAGCTGTGTGACTGCCT
GTCCCTACAACTACCTTTCTACGGACGTGGGATCCTGCACCC
TCGTCTGCCCCCTGCACAACCAAGAGGTGACAGCAGAGGAT
GGAACACAGCGGTGTGAGAAGTGCAGCAAGCCCTGTGCCCG
AGTGTGCTATGGTCTGGGCATGGAGCACTTGCGAGAGGTGA
GGGCAGTTACCAGTGCCAATATCCAGGAGTTTGCTGGCTGC
AAGAAGATCTTTGGGAGCCTGGCATTTCTGCCGGAGAGCTTT |

TABLE 34-continued

| | Antigens | |
|---|---|---|
| SEQ ID NO | Name | Sequence |
| | | GATGGGGACCCAGCCTCCAACACTGCCCCGCTCCAGCCAGA<br>GCAGCTCCAAGTGTTTGAGACTCTGGAAGAGATCACAGGTT<br>ACCTATACATCTCAGCATGGCCGGACAGCCTGCCTGACCTCA<br>GCGTCTTCCAGAACCTGCAAGTAATCCGGGGACGAATTCTG<br>CACAATGGCGCCTACTCGCTGACCCTGCAAGGGCTGGGCAT<br>CAGCTGGCTGGGGCTGCGCTCACTGAGGGAACTGGGCAGTG<br>GACTGGCCCTCATCCACCATAACACCCACCTCTGCTTCGTGC<br>ACACGGTGCCCTGGGACCAGCTCTTTCGGAACCCGCACCAA<br>GCTCTGCTCCACACTGCCAACCGGCCAGAGGACGAGTGTGT<br>GGGCGAGGGCCTGGCCTGCCACCAGCTGTGCGCCCGAGGGC<br>ACTGCTGGGGTCCAGGGCCCACCCAGTGTGTCAACTGCAGC<br>CAGTTCCTTCGGGGCCAGGAGTGCGTGGAGGAATGCCGAGT<br>ACTGCAGGGGCTCCCCAGGGAGTATGTGAATGCCAGGCACT<br>GTTTGCCGTGCCACCCTGAGTGTCAGCCCCAGAATGGCTCAG<br>TGACCTGTTTTGGACTGGAGGCTCGGCAGTGTGTGGCCTGTG<br>CCCACTATAAGGACAGACGGTGCGTGGCCCGCTGCCCCAGC<br>GGTGTGAAACCTGACCTCTCCTACATGCCCATCTGGAAGTTT<br>CCAGATGAGGAGGGCGCATGCCAGCCTTGCCCCATCAACTG<br>CACCCACTCCTGTGTGGACCTGGATGACAAGGGCTGCCCCG<br>CCGAGCAGAGAGCCAGCCCTCTGACGGTCGACGGTGGTAGT<br>CCGACACCTCCGACACCCGGGGGTGGTTCTGCAGACAAAAC<br>TCACACATGCCCACCGTGCCCAGCACCTGAACTCCTGGGGG<br>GACCGTCAGTCTTCCTCTTCCCCCCAAAACCCAAGGACACCC<br>TCATGATCTCCCGGACCCCTGAGGTCACATGCGTGGTGGTGG<br>ACGTGAGCCACGAAGACCCTGAGGTCAAGTTCAACTGGTAC<br>GTGGACGGCGTGGAGGTGCATAATGCCAAGACAAAGCCGCG<br>GGAGGAGCAGTACAACAGCACGTACCGTGTGGTCAGCGTCC<br>TCACCGTCCTGCACCAGGACTGGCTGAATGGCAAGGAGTAC<br>AAGTGCAAGGTCTCCAACAAAGCCCTCCCAGCCCCCATCGA<br>GAAAACCATCTCCAAAGCCAAAGGGCAGCCCCGAGAACCAC<br>AGGTGTACACCCTGCCCCCATGCCGGGATGAGCTGACCAAG<br>AACCAGGTCAGCCTGTGGTGCCTGGTCAAAGGCTTCTATCCC<br>AGCGACATCGCCGTGGAGTGGGAGAGCAATGGGCAGCCGG<br>AGAACAACTACAAGACCACGCCTCCCGTGCTGGACTCCGAC<br>GGCTCCTTCTTCCTCTACAGCAAGCTCACCGTGGACAAGAGC<br>AGGTGGCAGCAGGGGAACGTCTTCTCATGCTCCGTGATGCA<br>TGAGGCTCTGCACAACCACTACACGCAGAAGAGCCTCTCCC<br>TGTCTCCGGGTAAATCCGGAGGCCTGAACGACATCTTCGAG<br>GCCCAGAAGATTGAATGGCACGAG |

TABLE 35

| | Full-length antibody sequences of common light chain antibody "D1 der" | |
|---|---|---|
| SEQ ID NO | Name | Sequence |
| 159 | Trastuzumab VHCH1-Fc KNOB | EVQLVESGGGLVQPGGSLRLSCAASGFNIKDTYIHWVRQAPGK<br>GLEWVARIYPTNGYTRYADSVKGRFTISADTSKNTAYLQMNSL<br>RAEDTAVYYCSRWGGDGFYAMDYWGQGTLVTVSSASTKGPS<br>VFPLAPSSKSTSGGTAALGCLVKDYFPEPVTVSWNSGALTSGV<br>HTFPAVLQSSGLYSLSSVVTVPSSSLGTQTYICNVNHKPSNTKV<br>DKKVEPKSCDKTHTCPPCPAPELLGGPSVFLFPPKPKDTLMISRT<br>PEVTCVVVDVSHEDPEVKFNWYVDGVEVHNAKTKPREEQYNS<br>TYRVVSVLTVLHQDWLNGKEYKCKVSNKALPAPIEKTISKAKG<br>QPREPQVYTLPPCRDELTKNQVSLWCLVKGFYPSDIAVEWESN<br>GQPENNYKTTPPVLDSDGSFFLYSKLTVDKSRWQQGNVFSCSV<br>MHEALHNHYTQKSLSLSPGK |
| 160 | Trastuzumab VHCH1-Fc KNOB DNA | GAAGTGCAATTGGTGGAAAGCGGCGGCGGCCTGGTGCAACCGGG<br>CGGCAGCCTGCGTCTGAGCTGCGCGGCCTCCGGATTTAACATAAA<br>GGACACATACATCCACTGGGTGCGCCAAGCACCTGGGAAGGGTCT<br>CGAGTGGGTGGCTCGGATTTACCCAACAAATGGCTACACCAGGTA<br>TGCGGATAGCGTGAAAGGCCGTTTTACCATTTCAGCTGATACTTCG<br>AAGAACACCGCCTATCTGCAAATGAACAGCCTGCGTGCGGAAGAT<br>ACGGCCGTGTATTATTGCTCGCGTTGGGGAGGAGACGGGTTCTAT<br>GCTATGGATTACTGGGGCCAAGGCACCCTGGTGACGGTTAGCTCA<br>GCTAGCACCAAGGGCCCATCGGTCTTCCCCCTGGCACCCTCCTCCA<br>AGAGCACCTCTGGGGGCACAGCGGCCCTGGGCTGCCTGGTCAAGG<br>ACTACTTCCCCGAACCGGTGACGGTGTCGTGGAACTCAGGCGCCC<br>TGACCAGCGGCGTGCACACCTTCCCGGCTGTCCTACAGTCCTCAGG<br>ACTCTACTCCCTCAGCAGCGTGGTGACCGTGCCCTCCAGCAGCTTG |

TABLE 35-continued

Full-length antibody sequences of common light chain antibody "D1 der"

| SEQ ID NO | Name | Sequence |
|---|---|---|
| | | GGCACCCAGACCTACATCTGCAACGTGAATCACAAGCCCAGCAAC<br>ACCAAGGTGGACAAGAAAGTTGAGCCCAAATCTTGTGACAAAACT<br>CACACATGCCCACCGTGCCCAGCACCTGAACTCCTGGGGGGACCG<br>TCAGTCTTCCTCTTCCCCCCAAAACCCAAGGACACCCTCATGATCT<br>CCCGGACCCCTGAGGTCACATGCGTGGTGGTGGACGTGAGCCACG<br>AAGACCCTGAGGTCAAGTTCAACTGGTACGTGGACGGCGTGGAGG<br>TGCATAATGCCAAGACAAAGCCGCGGGAGGAGCAGTACAACAGC<br>ACGTACCGTGTGGTCAGCGTCCTCACCGTCCTGCACCAGGACTGG<br>CTGAATGGCAAGGAGTACAAGTGCAAGGTCTCCAACAAAGCCCTC<br>CCAGCCCCCATCGAGAAAACCATCTCCAAAGCCAAAGGGCAGCCC<br>CGAGAACCACAGGTGTACACCCTGCCCCCATGCCGGGATGAGCTG<br>ACCAAGAACCAGGTCAGCCTGTGGTGCCTGGTCAAAGGCTTCTAT<br>CCCAGCGACATCGCCGTGGAGTGGGAGAGCAATGGGCAGCCGGA<br>GAACAACTACAAGACCACGCCTCCCGTGCTGGACTCCGACGGCTC<br>CTTCTTCCTCTACAGCAAGCTCACCGTGGACAAGAGCAGGTGGCA<br>GCAGGGGAACGTCTTCTCATGCTCCGTGATGCATGAGGCTCTGCA<br>CAACCACTACACGCAGAAGAGCCTCTCCCTGTCTCCGGGTAAA |
| 161 | Common light chain VLCL | DIQMTQSPSSLSASVGDRVTITCKASQDVSTAVAWYQQKPGKAPKLL<br>IYSASFRYTGVPSRFSGSRSGTDFTLTISSLQPEDFATYYCQQHYTTPPT<br>FGQGTKVEIKRTVAAPSVFIFPPSDEQLKSGTASVVCLLNNFYPREAK<br>VQWKVDNALQSGNSQESVTEQDSKDSTYSLSSTLTLSKADYEKHKV<br>YACEVTHQGLSSPVTKSFNRGEC |
| 162 | Common light chain VLCL-DNA | GACATCCAGATGACCCAGAGCCCCAGCAGCCTGTCTGCCAGCGTGGGCG<br>ACAGAGTGACCATCACATGCAAGGCCAGCCAGGACGTGTCCACAGCCGT<br>GGCCTGGTATCAGCAGAAGCCTGGCAAGGCCCCCAAGCTGCTGATCTACA<br>GCGCCAGCTTCCGGTACACCGGCGTGCCCAGCAGATTCAGCGGCAGCAG<br>ATCCGGCACCGACTTCACCCTGACCATCAGCTCCCTGCAGCCCGAGGACT<br>TCGCCACCTACTACTGCCAGCAGCACTACACCACCCCCCCCACATTTGGC<br>CAGGGCACCAAGGTGGAAATCAAGCGTACGGTGGCTGCACCATCTGTCTT<br>CATCTTCCCGCCATCTGATGAGCAGTTGAAATCTGGAACTGCCTCTGTTGT<br>GTGCCTGCTGAATAACTTCTATCCCAGAGAGGCCAAAGTACAGTGGAAG<br>GTGGATAACGCCCTCCAATCGGGTAACTCCCAGGAGAGTGTCACAGAGC<br>AGGACAGCAAGGACAGCACCTACAGCCTCAGCAGCACCCTGACGCTGAG<br>CAAAGCAGACTACGAGAAACACAAAGTCTACGccTGCGAAGTCACCCAT<br>CAGGGCCTGAGCTCGCCCGTCACAAAGAGCTTCAACAGGGGAGAGTGT |
| 163 | Pertuzumab VHCH1 Fc hole | EVQLVESGGGLVQPGGSLRLSCAASGFTFNDYTMDWVRQAPGKGLE<br>WVADVNPNSGGSIVNRRFKGRFTLSVDRSKNTLYLQMNSLRAEDTA<br>VYYCARNLGPFFYFDYWGQGTLVTVSSASTKGPSVFPLAPSSKSTSG<br>GTAALGCLVKDYFPEPVTVSWNSGALTSGVHTFPAVLQSSGLYSLSS<br>VVTVPSSSLGTQTYICNVNHKPSNTKVDKKVEPKSCDKTHTCPPCPAP<br>ELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVS<br>NKALPAPIEKTISKAKGQPREPQVCTLPPSRDELTKNQVSLSCAVKGF<br>YPSDIAVEWESNGQPENNYKTTPPVLDSDGSFFLVSKLTVDKSRWQQ<br>GNVFSCSVMHEALHNHYTQKSLSLSPGK |
| 164 | Pertuzumab VHCH1 Fc hole DNA | GAAGTTCAGCTGGTTGAAAGCGGTGGTGGTCTGGTTCAGCCTGGT<br>GGTAGCCTGCGTCTGAGCTGTGCAGCAAGCGGTTTTACCTTTAACG<br>ATTATACCATGGATTGGGTTCGTCAGGCACCGGGTAAAGGTCTGG<br>AATGGGTTGCAGATGTTAATCCGAATAGCGGTGGTAGCATTGTTA<br>ACCGTCGTTTTAAAGGTCGTTTTACCCTGAGCGTTGATCGTAGCAA<br>AAATACCCTGTATCTGCAAATGAATAGTCTGCGTGCAGAGGATAC<br>CGCAGTGTATTATTGTGCACGTAACCTGGGTCCGTTCTTCTACTTT<br>GATTATTGGGGTCAGGGCACCCTGGTACCGTTAGCAGCGCTAGC<br>ACCAAGGGCCCAAGCGTGTTCCCTCTGGCCCCCAGCAGCAAGAGC<br>ACAAGCGGCGGAACAGCCGCCCTGGGCTGCCTGGTCAAGGACTAC<br>TTCCCCGAGCCCGTGACAGTGTCCTGGAACAGCGGAGCCCTGACC<br>AGCGGCGTGCACACCTTTCCAGCCGTGCTGCAGAGCAGCGGCCTG<br>TACAGCCTGAGCAGCGTGGTCACAGTGCCTAGCAGCAGCCTGGGC<br>ACCCAGACCTACATCTGCAACGTGAACCACAAGCCCAGCAACACC<br>AAGGTGGACAAGAAGGTGGAGCCCAAGAGCTGCGACAAGACCCA<br>CACCTGTCCCCCTTGTCCTGCCCCTGAGCTGCTGGGCGGACCCAGC<br>GTGTTCCTGTTCCCCCCAAAGCCCAAGGACACCCTGATGATCAGCC<br>GGACCCCCGAAGTGACCTGCGTGGTGGTGGACGTGTCCCACGAGG<br>ACCCTGAAGTGAAGTTCAATTGGTACGTGGACGGCGTGGAGGTGC<br>ACAATGCCAAGACCAAGCCCGGGAGGAACAGTACAACAGCACC<br>TACCGGGTGGTGTCCGTGCTGACCGTGCTGCACCAGGACTGGCTG<br>AACGGCAAAGAGTACAAGTGCAAGGTCTCCAACAAGGCCCTGCCT<br>GCCCCCATCGAGAAAACCATCAGCAAGGCCAAGGGCCAGCCCAG<br>AGAACCCCAGGTGCACCCTGCCCCCAGCAGAGATGAGCTGAC<br>CAAGAACCAGGTGTCCCTGAGCTGTGCCGTCAAGGGCTTCTACCC<br>CAGCGATATCGCCGTGGAGTGGGAGAGCAACGGCCAGCCTGAGA |

TABLE 35-continued

Full-length antibody sequences of common light chain antibody "D1 der"

| SEQ ID NO | Name | Sequence |
|---|---|---|
| | | ACAACTACAAGACCACCCCCCCTGTGCTGGACAGCGACGGCAGCT<br>TCTTCCTGGTGTCCAAACTGACCGTGGACAAGAGCCGGTGGCAGC<br>AGGGCAACGTGTTCAGCTGCAGCGTGATGCACGAGGCCCTGCACA<br>ACCACTACACCCAGAAGTCCCTGAGCCTGAGCCCCGGCAAG |

The invention claimed is:

1. A bispecific antibody, comprising a first antigen binding site specific for extracellular domain II of HER2 and a second antigen binding site specific for extracellular domain IV of HER2, wherein the antibody comprises:
   (a) a first heavy chain comprising a heavy chain CDR1 of SEQ ID NO: 58, a heavy chain CDR2 of SEQ ID NO: 15, and a heavy chain CDR3 of SEQ ID NO: 59, and
   (b) a second heavy chain comprising a heavy chain CDR1 of SEQ ID NO: 20, a heavy chain CDR2 of SEQ ID NO: 29 and a heavy chain CDR3 of SEQ ID NO: 30
   (c) a first light chain, comprising a light chain CDR1 of SEQ ID NO: 89, a light chain CDR2 of SEQ ID NO: 90, and a light chain CDR3 SEQ ID NO: 19, and
   (d) a second light chain, comprising a light chain CDR1 of SEQ ID NO: 89, a light chain CDR2 of SEQ ID NO: 90, and a light chain CDR3 SEQ ID NO: 19.

2. The bispecific antibody of claim 1, comprising a first light chain comprising a variable light chain comprising an amino acid sequence of SEQ ID NO: 54, a second light chain comprising variable light chain comprising an amino acid sequence of SEQ ID NO: 54, a first heavy chain comprising a variable heavy chain comprising an amino acid sequence of SEQ ID NO: 68, and a second heavy chain comprising a variable heavy chain comprising an amino acid sequence of SEQ ID NO: 92.

3. A nucleic acid comprising a nucleic acid sequence encoding the heavy chain of a bispecific antibody of claim 1.

4. A nucleic acid comprising a nucleic acid sequence encoding the light chain of a bispecific antibody of claim 1.

5. The bispecific antibody of claim 1, wherein the bispecific antibody is monovalent for both the extracellular domain II and IV of HER2.

6. The bispecific antibody of claim 1, comprising a first Fab molecule capable of specific binding to extracellular domain II of HER2 and a second Fab molecule capable of specific binding to extracellular domain IV of HER2, wherein the sequence of the variable light chain of the first Fab molecule is identical to the sequence of the variable light chain of the second Fab molecule.

7. The bispecific antibody of claim 1, comprising a first Fab molecule capable of specific binding to extracellular domain II of HER2 and a second Fab molecule capable of specific binding to extracellular domain IV of HER2, wherein either the variable regions or the constant regions of the heavy and light chain of at least one Fab fragment are exchanged.

8. An expression vector comprising a nucleic acid sequence encoding the light chain of the bispecific antibody of claim 1.

9. A prokaryotic or eukaryotic host cell comprising a vector according to claim 8.

10. A method of producing an antibody comprising culturing the host cell of claim 9 so that the antibody is produced.

11. An expression vector comprising a nucleic acid sequence encoding the heavy chain of the bispecific antibody of claim 1.

12. A prokaryotic or eukaryotic host cell comprising a vector according to claim 11.

13. The bispecific antibody of claim 1, wherein the antibody induces complement-dependent cytotoxicity to a higher degree than the combination of Pertuzumab or Trastuzumab.

14. The bispecific antibody of claim 13, wherein the complement dependent cytotoxicity of the bispecific antibody is determined by a LDH assay or a complement assay and compared to the complement dependent cytotoxicity of the combination of Pertuzumab and Trastuzumab as determined by the same assay.

15. The bispecific antibody of claim 14, wherein the complement dependent cytotoxicity is determined in vitro on cancer cells.

16. The bispecific antibody of claim 14, wherein the first Fab molecule comprises a heavy chain CDR1 of SEQ ID NO: 58, a heavy chain CDR2 of SEQ ID NO: 15, and a heavy chain CDR3 of SEQ ID NO: 59; and a light chain CDR1 of SEQ ID NO: 89, a light chain CDR2 of SEQ ID NO: 90, and a light chain CDR3 SEQ ID NO: 19, and the second Fab molecule comprises a heavy chain CDR1 of SEQ ID NO: 20, a heavy chain CDR2 of SEQ ID NO: 29, and a heavy chain CDR3 of SEQ ID NO: 30; and a light chain CDR1 of SEQ ID NO: 89, a light chain CDR2 of SEQ ID NO: 90, and a light chain CDR3 SEQ ID NO: 19.

17. The bispecific antibody of claim 14, wherein the first Fab molecule comprises
- a variable heavy chain comprising an amino acid sequence of SEQ ID NO: 68 and a variable light chain comprising an amino acid sequence of SEQ ID NO: 54 and wherein the second Fab molecule comprises an amino acid sequence of SEQ ID NO: 92 and a light chain variable region comprising an amino acid sequence of SEQ ID NO: 54.

* * * * *

UNITED STATES PATENT AND TRADEMARK OFFICE
CERTIFICATE OF CORRECTION

| | |
|---|---|
| PATENT NO. | : 11,787,873 B2 |
| APPLICATION NO. | : 16/744697 |
| DATED | : October 17, 2023 |
| INVENTOR(S) | : Rebecca Croasdale-Wood et al. |

It is certified that error appears in the above-identified patent and that said Letters Patent is hereby corrected as shown below:

On the Title Page

In Column 1, insert -- (30) Foreign Application Priority Data Dec. 20, 2013 (EP)............. 13198819 --

Signed and Sealed this
Eighth Day of October, 2024

Katherine Kelly Vidal
*Director of the United States Patent and Trademark Office*

SEQUENCE LISTING

<160> NUMBER OF SEQ ID NOS: 164

<210> SEQ ID NO 1
<211> LENGTH: 1995
<212> TYPE: DNA
<213> ORGANISM: Artificial sequence
<220> FEATURE:
<223> OTHER INFORMATION: HER2 ECD DNA

<400> SEQUENCE: 1

```
acccaagtgt gcaccggcac agacatgaag ctgcggctcc ctgccagtcc cgagacccac      60
ctggacatgc tccgccacct ctaccagggc tgccaggtgg tgcagggaaa cctggaactc     120
acctacctgc ccaccaatgc cagcctgtcc ttcctgcagg atatccagga ggtgcagggc     180
tacgtgctca tcgctcacaa ccaagtgagg caggtccacc tgcagaggct gcggattgtg     240
cgaggcaccc agctctttga ggacaactat gccctggccg tgctagacaa tggagacccg     300
ctgaacaata ccacccctgt cacaggggcc tccccaggag gcctgcggga gctgcagctt     360
cgaagcctca cagagatctt gaaggagggg gtcttgatcc agcggaaccc ccagctctgc     420
taccaggaca cgattttgtg gaaggacatc ttccacaaga caaccagct ggctctcaca      480 ctgatagaca ccaaccgctc tcgggcctgc caccccctgtt ctccgatgtg taagggctcc     540
cgctgctggg gagagagttc tgaggattgt cagagcctga cgcgcactgt ctgtgccggt     600
ggctgtgccc gctgcaaggg gccactgccc actgactgct gccatgagca gtgtgctgcc     660
ggctgcacgg gccccaagca ctctgactgc ctggcctgcc tccacttcaa ccacagtggc     720
atctgtgagc tgcactgccc agccctggtc acctacaaca gagacacgtt tgagtccatg     780
cccaatcccg agggccggta cacattcggc gccagctgtg tgactgcctg tccctacaac     840 taccttttcta cggacgtggg atcctgcacc ctcgtctgcc cctgcacaa ccaagaggtg      900 acagcagagg atggaacaca gcggtgtgag aagtgcagca gccctgtgc ccgagtgtgc       960 tatggtctgg gcatggagca cttgcgagag gtgagggcag ttaccagtgc caatatccag    1020
gagtttgctg gctgcaagaa gatctttggg agcctggcat ttctgccgga gagctttgat    1080
ggggacccag cctccaacac tgccccgctc cagccagagc agctccaagt gtttgagact    1140
ctggaagaga tcacaggtta cctatacatc tcagcatggc cggacagcct gcctgacctc    1200
agcgtcttcc agaacctgca agtaatccgg ggacgaattc tgcacaatgg cgcctactcg    1260
ctgacccgtc aagggctggg catcagctgg ctggggctgc gctcactgag ggaactgggc    1320
agtggactgg ccctcatcca ccataacacc cacctctgct tcgtgcacac ggtgccctgg    1380
gaccagctct ttcggaaccc gcaccaagct ctgctccaca ctgccaaccg gccagaggac    1440
gagtgtgtgg gcgagggcct ggcctgccac cagctgtgcg cccgagggca ctgctggggt    1500 ccaggggccca cccagtgtgt caactgcagc cagttccttc ggggccagga gtgcgtggag    1560
```

-continued

```
gaatgccgag tactgcaggg gctccccagg gagtatgtga atgccaggca ctgtttgccg      1620
tgccaccctg agtgtcagcc ccagaatggc tcagtgacct gttttggact ggaggctgac      1680
cagtgtgtgg cctgtgccca ctataaggac cctcccttct gcgtggcccg ctgccccagc      1740
ggtgtgaaac ctgacctctc ctacatgccc atctggaagt ttccagatga ggagggcgca      1800
tgccagcctt gccccatcaa ctgcacccac tcctgtgtgg acctggatga caagggctgc      1860
cccgccgagc agagagccag ccctctgacg gtcgacgaac agttatattt tcagggcggc      1920
tcaggcctga acgacatctt cgaggcccag aagatcgagt ggcacgaggc tcgagctcac      1980
caccatcacc atcac                                                       1995
```

<210> SEQ ID NO 2
<211> LENGTH: 684
<212> TYPE: PRT
<213> ORGANISM: Artificial sequence
<220> FEATURE:
<223> OTHER INFORMATION: HER2 ECD

<400> SEQUENCE: 2

```
Met Gly Trp Ser Cys Ile Ile Leu Phe Leu Val Ala Thr Ala Thr Gly
1               5                   10                  15

Val His Ser Thr Gln Val Cys Thr Gly Thr Asp Met Lys Leu Arg Leu
                20                  25                  30

Pro Ala Ser Pro Glu Thr His Leu Asp Met Leu Arg His Leu Tyr Gln
            35                  40                  45

Gly Cys Gln Val Val Gln Gly Asn Leu Glu Leu Thr Tyr Leu Pro Thr
        50                  55                  60

Asn Ala Ser Leu Ser Phe Leu Gln Asp Ile Gln Glu Val Gln Gly Tyr
65                  70                  75                  80

Val Leu Ile Ala His Asn Gln Val Arg Gln Val Pro Leu Gln Arg Leu
                85                  90                  95

Arg Ile Val Arg Gly Thr Gln Leu Phe Glu Asp Asn Tyr Ala Leu Ala
            100                 105                 110

Val Leu Asp Asn Gly Asp Pro Leu Asn Asn Thr Thr Pro Val Thr Gly
        115                 120                 125

Ala Ser Pro Gly Gly Leu Arg Glu Leu Gln Leu Arg Ser Leu Thr Glu
    130                 135                 140

Ile Leu Lys Gly Gly Val Leu Ile Gln Arg Asn Pro Gln Leu Cys Tyr
145                 150                 155                 160

Gln Asp Thr Ile Leu Trp Lys Asp Ile Phe His Lys Asn Asn Gln Leu
                165                 170                 175

Ala Leu Thr Leu Ile Asp Thr Asn Arg Ser Arg Ala Cys His Pro Cys
            180                 185                 190

Ser Pro Met Cys Lys Gly Ser Arg Cys Trp Gly Glu Ser Ser Glu Asp
        195                 200                 205

Cys Gln Ser Leu Thr Arg Thr Val Cys Ala Gly Cys Ala Arg Cys
    210                 215                 220

Lys Gly Pro Leu Pro Thr Asp Cys Cys His Glu Gln Cys Ala Ala Gly
225                 230                 235                 240

Cys Thr Gly Pro Lys His Ser Asp Cys Leu Ala Cys Leu His Phe Asn
                245                 250                 255

His Ser Gly Ile Cys Glu Leu His Cys Pro Ala Leu Val Thr Tyr Asn
            260                 265                 270

Thr Asp Thr Phe Glu Ser Met Pro Asn Pro Glu Gly Arg Tyr Thr Phe
        275                 280                 285
```

Gly Ala Ser Cys Val Thr Ala Cys Pro Tyr Asn Tyr Leu Ser Thr Asp
            290                 295                 300

Val Gly Ser Cys Thr Leu Val Cys Pro Leu His Asn Gln Glu Val Thr
305                 310                 315                 320

Ala Glu Asp Gly Thr Gln Arg Cys Glu Lys Cys Ser Lys Pro Cys Ala
                325                 330                 335

Arg Val Cys Tyr Gly Leu Gly Met Glu His Leu Arg Glu Val Arg Ala
                340                 345                 350

Val Thr Ser Ala Asn Ile Gln Glu Phe Ala Gly Cys Lys Lys Ile Phe
            355                 360                 365

Gly Ser Leu Ala Phe Leu Pro Glu Ser Phe Asp Gly Asp Pro Ala Ser
        370                 375                 380

Asn Thr Ala Pro Leu Gln Pro Glu Gln Leu Gln Val Phe Glu Thr Leu
385                 390                 395                 400

Glu Glu Ile Thr Gly Tyr Leu Tyr Ile Ser Ala Trp Pro Asp Ser Leu
                405                 410                 415

Pro Asp Leu Ser Val Phe Gln Asn Leu Gln Val Ile Arg Gly Arg Ile
                420                 425                 430

Leu His Asn Gly Ala Tyr Ser Leu Thr Leu Gln Gly Leu Gly Ile Ser
            435                 440                 445

Trp Leu Gly Leu Arg Ser Leu Arg Glu Leu Gly Ser Gly Leu Ala Leu
450                 455                 460

Ile His His Asn Thr His Leu Cys Phe Val His Thr Val Pro Trp Asp
465                 470                 475                 480

Gln Leu Phe Arg Asn Pro His Gln Ala Leu Leu His Thr Ala Asn Arg
                485                 490                 495

Pro Glu Asp Glu Cys Val Gly Glu Gly Leu Ala Cys His Gln Leu Cys
            500                 505                 510

Ala Arg Gly His Cys Trp Gly Pro Gly Pro Thr Gln Cys Val Asn Cys
        515                 520                 525

Ser Gln Phe Leu Arg Gly Gln Glu Cys Val Glu Glu Cys Arg Val Leu
530                 535                 540

Gln Gly Leu Pro Arg Glu Tyr Val Asn Ala Arg His Cys Leu Pro Cys
545                 550                 555                 560

His Pro Glu Cys Gln Pro Gln Asn Gly Ser Val Thr Cys Phe Gly Leu
                565                 570                 575

Glu Ala Asp Gln Cys Val Ala Cys Ala His Tyr Lys Asp Pro Pro Phe
            580                 585                 590

Cys Val Ala Arg Cys Pro Ser Gly Val Lys Pro Asp Leu Ser Tyr Met
        595                 600                 605

Pro Ile Trp Lys Phe Pro Asp Glu Glu Gly Ala Cys Gln Pro Cys Pro
610                 615                 620

Ile Asn Cys Thr His Ser Cys Val Asp Leu Asp Asp Lys Gly Cys Pro
625                 630                 635                 640

Ala Glu Gln Arg Ala Ser Pro Leu Thr Val Asp Glu Gln Leu Tyr Phe
                645                 650                 655

Gln Gly Gly Ser Gly Leu Asn Asp Ile Phe Glu Ala Gln Lys Ile Glu
                660                 665                 670

Trp His Glu Ala Arg Ala His His His His His
            675                 680

<210> SEQ ID NO 3
<211> LENGTH: 681

-continued

<210> SEQ ID NO 3
<211> LENGTH: 681
<212> TYPE: DNA
<213> ORGANISM: Artificial sequence
<220> FEATURE:
<223> OTHER INFORMATION: Fc(hole)DNA

<400> SEQUENCE: 3

```
gacaaaactc acacatgccc accgtgccca gcacctgaac tcctgggggg accgtcagtc      60
ttcctcttcc ccccaaaacc caaggacacc ctcatgatct cccggacccc tgaggtcaca     120
tgcgtggtgg tggacgtgag ccacgaagac cctgaggtca agttcaactg gtacgtggac     180
ggcgtggagg tgcataatgc caagacaaag ccgcgggagg agcagtacaa cagcacgtac     240
cgtgtggtca gcgtcctcac cgtcctgcac caggactggc tgaatggcaa ggagtacaag     300
tgcaaggtct ccaacaaagc cctcccagcc cccatcgaga aaaccatctc caaagccaaa     360
gggcagcccc gagaaccaca ggtgtgcacc ctgcccccat cccgggatga gctgaccaag     420
aaccaggtca gcctctcgtg cgcagtcaaa ggcttctatc cagcgacat cgccgtggag      480
tgggagagca atgggcagcc ggagaacaac tacaagacca cgcctcccgt gctggactcc     540
gacggctcct tcttcctcgt gagcaagctc accgtggaca agagcaggtg gcagcagggg     600
aacgtcttct catgctccgt gatgcatgag gctctgcaca accgcttcac gcagaagagc     660
ctctcctgt ctccgggtaa a                                                681
```

<210> SEQ ID NO 4
<211> LENGTH: 227
<212> TYPE: PRT
<213> ORGANISM: Artificial sequence
<220> FEATURE:
<223> OTHER INFORMATION: Fc(hole)

<400> SEQUENCE: 4

```
Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Cys Thr Leu Pro Pro Ser Arg Asp Glu Leu Thr Lys Asn Gln Val Ser
    130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Val Ser Lys Leu Thr Val
            180                 185                 190
Asp Lys Ser Arg Trp Gln Gln Gly Asn Val Phe Ser Cys Ser Val Met
        195                 200                 205
```

His Glu Ala Leu His Asn Arg Phe Thr Gln Lys Ser Leu Ser Leu Ser
    210                 215                 220

Pro Gly Lys
225

<210> SEQ ID NO 5
<211> LENGTH: 2670
<212> TYPE: DNA
<213> ORGANISM: Artificial sequence
<220> FEATURE:
<223> OTHER INFORMATION: Her2 ECD-Fc(knob)DNA

<400> SEQUENCE: 5

| | | | | |
|---|---|---|---|---|
| acccaagtgt | gcaccggcac | agacatgaag | ctgcggctcc | ctgccagtcc | cgagacccac | 60 |
| ctggacatgc | tccgccacct | ctaccagggc | tgccaggtgg | tgcagggaaa | cctggaactc | 120 |
| acctacctgc | ccaccaatgc | cagcctgtcc | ttcctgcagg | atatccagga | ggtgcagggc | 180 |
| tacgtgctca | tcgctcacaa | ccaagtgagg | caggtccac | tgcagaggct | gcggattgtg | 240 |
| cgaggcaccc | agctctttga | ggacaactat | gccctggccg | tgctagacaa | tggagacccg | 300 |
| ctgaacaata | ccacccctgt | cacagggggcc | tccccaggag | cctgcggga | gctgcagctt | 360 |
| cgaagcctca | cagagatctt | gaaggaggg | gtcttgatcc | agcggaaccc | ccagctctgc | 420 |
| taccaggaca | cgattttgtg | gaaggacatc | ttccacaaga | caaccagct | ggctctcaca | 480 |
| ctgatagaca | ccaaccgctc | tcgggcctgc | caccccctgtt | ctccgatgtg | taagggctcc | 540 |
| cgctgctggg | gagagagttc | tgaggattgt | cagagcctga | cgcgcactgt | ctgtgccggt | 600 |
| ggctgtgccc | gctgcaaggg | gccactgccc | actgactgct | gccatgagca | gtgtgctgcc | 660 |
| ggctgcacgg | gccccaagca | ctctgactgc | ctggcctgcc | tccacttcaa | ccacagtggc | 720 |
| atctgtgagc | tgcactgccc | agccctggtc | acctacaaca | cagacacgtt | tgagtccatg | 780 |
| cccaatcccg | agggcggta | cacattcggc | gccagctgtg | tgactgcctg | tccctacaac | 840 |
| tacctttcta | cggacgtggg | atcctgcacc | ctcgtctgcc | ccctgcacaa | ccaagaggtg | 900 |
| acagcagagg | atggaacaca | gcggtgtgag | aagtgcagca | agccctgtgc | ccgagtgtgc | 960 |
| tatggtctgg | gcatggagca | cttgcgagag | gtgagggcag | ttaccagtgc | caatatccag | 1020 |
| gagtttgctg | gctgcaagaa | gatctttggg | agcctggcat | ttctgccgga | gagctttgat | 1080 |
| ggggacccag | cctccaacac | tgccccgctc | agccagagc | agctccaagt | gtttgagact | 1140 |
| ctggaagaga | tcacaggtta | cctatacatc | tcagcatggc | cggacagcct | gcctgacctc | 1200 |
| agcgtcttcc | agaacctgca | agtaatccgg | ggacgaattc | tgcacaatgg | cgcctactcg | 1260 |
| ctgaccctgc | aagggctggg | catcagctgg | ctggggctgc | gctcactgag | ggaactgggc | 1320 |
| agtggactgg | ccctcatcca | ccataacacc | cacctctgct | tcgtgcacac | ggtgccctgg | 1380 |
| gaccagctct | ttcggaaccc | gcaccaagct | ctgctccaca | ctgccaaccg | gccagaggac | 1440 |
| gagtgtgtgg | gcgagggcct | ggcctgccac | cagctgtgcg | cccagggca | ctgctggggt | 1500 |
| ccagggccca | cccagtgtgt | caactgcagc | cagttccttc | ggggccagga | gtgcgtggag | 1560 |
| gaatgccgag | tactgcaggg | gctccccagg | gagtatgtga | atgccaggca | ctgttttgccg | 1620 |
| tgccaccctg | agtgtcagcc | ccagaatggc | tcagtgacct | gttttggact | ggaggctgac | 1680 |
| cagtgtgtgg | cctgtgccca | ctataaggac | cctcccttct | gcgtggcccg | ctgccccagc | 1740 |
| ggtgtgaaac | ctgacctctc | ctacatgccc | atctggaagt | ttccagatga | ggagggcgca | 1800 |
| tgccagcctt | gccccatcaa | ctgcacccac | tcctgtgtgg | acctggatga | caagggctgc | 1860 |

```
cccgccgagc agagagccag ccctctgacg gtcgacggtg gtagtccgac acctccgaca   1920
cccgggggtg gttctgcaga caaaactcac acatgcccac cgtgcccagc acctgaactc   1980
ctggggggac cgtcagtctt cctcttcccc ccaaaaccca aggacaccct catgatctcc   2040 cggaccctg aggtcacatg cgtggtggtg gacgtgagcc acgaagaccc tgaggtcaag   2100
ttcaactggt acgtggacgg cgtggaggtg cataatgcca agacaaagcc gcgggaggag   2160
cagtacaaca gcacgtaccg tgtggtcagc gtcctcaccg tcctgcacca ggactggctg   2220
aatggcaagg agtacaagtg caaggtctcc aacaaagccc tcccagcccc catcgagaaa   2280
accatctcca aagccaaagg gcagcccga gaaccacagg tgtacaccct gcccccatgc   2340
cgggatgagc tgaccaagaa ccaggtcagc ctgtggtgcc tggtcaaagg cttctatccc   2400
agcgacatcg ccgtggagtg ggagagcaat gggcagccgg agaacaacta caagaccacg   2460
cctcccgtgc tggactccga cggctccttc ttcctctaca gcaagctcac cgtggacaag   2520
agcaggtggc agcaggggaa cgtcttctca tgctccgtga tgcatgaggc tctgcacaac   2580
cactacacgc agaagagcct ctccctgtct ccgggtaaat ccggaggcct gaacgacatc   2640
ttcgaggccc agaagattga atggcacgag                                    2670
```

<210> SEQ ID NO 6
<211> LENGTH: 890
<212> TYPE: PRT
<213> ORGANISM: Artificial sequence
<220> FEATURE:
<223> OTHER INFORMATION: Her2 ECD-Fc(knob)

<400> SEQUENCE: 6

```
Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220
```

```
Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
            245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
        290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
        370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
        530                 535                 540

Cys Gln Pro Gln Asn Gly Ser Val Thr Cys Phe Gly Leu Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
        595                 600                 605

Thr His Ser Cys Val Asp Leu Asp Asp Lys Gly Cys Pro Ala Glu Gln
        610                 615                 620

Arg Ala Ser Pro Leu Thr Val Asp Gly Gly Ser Pro Thr Pro Pro Thr
625                 630                 635                 640
```

Pro Gly Gly Gly Ser Ala Asp Lys Thr His Thr Cys Pro Pro Cys Pro
                645                 650                 655

Ala Pro Glu Leu Leu Gly Gly Pro Ser Val Phe Leu Phe Pro Pro Lys
        660                 665                 670

Pro Lys Asp Thr Leu Met Ile Ser Arg Thr Pro Glu Val Thr Cys Val
    675                 680                 685

Val Val Asp Val Ser His Glu Asp Pro Glu Val Lys Phe Asn Trp Tyr
690                 695                 700

Val Asp Gly Val Glu Val His Asn Ala Lys Thr Lys Pro Arg Glu Glu
705                 710                 715                 720

Gln Tyr Asn Ser Thr Tyr Arg Val Val Ser Val Leu Thr Val Leu His
                725                 730                 735

Gln Asp Trp Leu Asn Gly Lys Glu Tyr Lys Cys Lys Val Ser Asn Lys
            740                 745                 750

Ala Leu Pro Ala Pro Ile Glu Lys Thr Ile Ser Lys Ala Lys Gly Gln
        755                 760                 765

Pro Arg Glu Pro Gln Val Tyr Thr Leu Pro Pro Cys Arg Asp Glu Leu
    770                 775                 780

Thr Lys Asn Gln Val Ser Leu Trp Cys Leu Val Lys Gly Phe Tyr Pro
785                 790                 795                 800

Ser Asp Ile Ala Val Glu Trp Glu Ser Asn Gly Gln Pro Glu Asn Asn
                805                 810                 815

Tyr Lys Thr Thr Pro Pro Val Leu Asp Ser Asp Gly Ser Phe Phe Leu
            820                 825                 830

Tyr Ser Lys Leu Thr Val Asp Lys Ser Arg Trp Gln Gln Gly Asn Val
        835                 840                 845

Phe Ser Cys Ser Val Met His Glu Ala Leu His Asn His Tyr Thr Gln
    850                 855                 860

Lys Ser Leu Ser Leu Ser Pro Gly Lys Ser Gly Gly Leu Asn Asp Ile
865                 870                 875                 880

Phe Glu Ala Gln Lys Ile Glu Trp His Glu
                885                 890

<210> SEQ ID NO 7
<211> LENGTH: 2670
<212> TYPE: DNA
<213> ORGANISM: Artificial sequence
<220> FEATURE:
<223> OTHER INFORMATION: Her2 ECD(pertuzumab KO)-Fc(knob)DNA

<400> SEQUENCE: 7
acccaagtgt gcaccggcac agacatgaag ctgcggctcc ctgccagtcc cgagacccac      60
ctggacatgc tccgccacct ctaccagggc tgccaggtgg tgcagggaaa cctggaactc     120
acctacctgc ccaccaatgc cagcctgtcc ttcctgcagg atatccagga ggtgcagggc     180
tacgtgctca tcgctcacaa ccaagtgagg caggtcccac tgcagaggct gcggattgtg     240
cgaggcaccc agctctttga ggacaactat gccctgccg tgctagacaa tggagacccg     300
ctgaacaata ccaccccgt cacaggggcc tccccaggag gcctgcggga gctgcagctt     360
cgaagcctca cagagatctt gaaggagggg gtcttgatcc agcggaaccc ccagctctgc     420
taccaggaca cgattttgtg gaaggacatc ttccacaaga caaccagct ggctctcaca     480 ctgatagaca ccaaccgctc tcgggcctgc caccctgtt ctccgatgtg taagggctcc     540
cgctgctggg gagagagttc tgaggattgt cagagcctga cgcgcactgt ctgtgccggt     600
ggctgtgccc gctgcaaggg gccactgccc actgactgct gccatgagca gtgtgctgcc     660

```
ggctgcacgg gccccaagca ctctgactgc ctggcctgcc tccacttcaa ccacagtggc    720
atctgtgagc tgcactgccc agccctggtc acctacaaca cagacacgcg ggagtccatg    780
cccaatcccg agggccggta tagattcggc gccagctgtg tgactgcctg tccctacaac    840
tacctttcta cggaccgggg atcctgcacc ctcgtctgcc ccctggccaa ccaagaggtg    900
acagcagagg atggaacaca gcggtgtgag aagtgcagca agccctgtgc ccgagtgtgc    960
tatggtctgg gcatggagca cttgcgagag gtgagggcag ttaccagtgc aatatccag   1020 gagtttgctg gctgcaagaa gatctttggg agcctggcat ttctgccgga gagctttgat   1080
ggggacccag cctccaacac tgccccgctc cagccagagc agctccaagt gtttgagact   1140
ctggaagaga tcacaggtta cctatacatc tcagcatggc cggacagcct gcctgacctc   1200
agcgtcttcc agaacctgca gtaatccgg gacgaattc tgcacaatgg cgcctactcg   1260
ctgacccctg aagggctggg catcagctgg ctggggctgc gctcactgag ggaactgggc   1320
agtggactgg ccctcatcca ccataacacc cacctctgct tcgtgcacac ggtgccctgg   1380
gaccagctct ttcggaaccc gcaccaagct ctgctccaca ctgccaaccg gccagaggac   1440
gagtgtgtgg gcgagggcct ggcctgccac cagctgtgcg cccgagggca ctgctggggt   1500
ccagggccca cccagtgtgt caactgcagc cagttccttc ggggccagga gtgcgtggag   1560
gaatgccgag tactgcaggg gctccccagg gagtatgtga atgccaggca ctgtttgccg   1620
tgccaccctg agtgtcagcc ccagaatggc tcagtgacct gttttggact ggaggctgac   1680
cagtgtgtgg cctgtgccca ctataaggac cctccttct gcgtggcccg ctgccccagc   1740
ggtgtgaaac ctgacctctc ctacatgccc atctggaagt ttccagatga ggagggcgca   1800
tgccagcctt gccccatcaa ctgcacccac tcctgtgtgg acctggatga caagggctgc   1860
cccgccgagc agagagccag ccctctgacg gtcgacggtg gtagtccgac acctccgaca   1920
cccgggggtg gttctgcaga caaaactcac acatgcccac cgtgcccagc acctgaactc   1980
ctggggggac cgtcagtctt cctcttcccc ccaaaaccca aggacaccct catgatctcc   2040
cggacccctg aggtcacatg cgtggtggtg gacgtgagcc acgaagaccc tgaggtcaag   2100
ttcaactggt acgtggacgg cgtggaggtg cataatgcca agacaaagcc gcgggaggag   2160
cagtacaaca gcacgtaccg tgtggtcagc gtcctcaccg tcctgcacca ggactggctg   2220
aatggcaagg agtacaagtg caaggtctcc aacaaagccc tccagccccc atcgagaaa   2280 accatctcca aagccaaagg gcagccccga gaaccacagg tgtacaccct gcccccatgc   2340
cgggatgagc tgaccaagaa ccaggtcagc ctgtggtgcc tggtcaaagg cttctatccc   2400
agcgacatcg ccgtggagtg ggagagcaat gggcagccgg agaacaacta caagaccacg   2460
cctcccgtgc tggactccga cggctccttc ttcctctaca gcaagctcac cgtggacaag   2520
agcaggtggc agcaggggaa cgtcttctca tgctccgtga tgcatgaggc tctgcacaac   2580
cactacacgc agaagagcct ctccctgtct ccgggtaaat ccggaggcct gaacgacatc   2640
ttcgaggccc agaagattga atggcacgag                                    2670
```

<210> SEQ ID NO 8
<211> LENGTH: 890
<212> TYPE: PRT
<213> ORGANISM: Artificial sequence
<220> FEATURE:
<223> OTHER INFORMATION: Her2 ECD(pertuzumab KO)-Fc(knob)

<400> SEQUENCE: 8

```
Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
                20                  25                  30

Val Val Gln Gly Asn Leu Glu Leu Thr Tyr Leu Pro Thr Asn Ala Ser
            35                  40                  45

Leu Ser Phe Leu Gln Asp Ile Gln Glu Val Gln Gly Tyr Val Leu Ile
        50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
                100                 105                 110

Gly Gly Leu Arg Glu Leu Gln Leu Arg Ser Leu Thr Glu Ile Leu Lys
            115                 120                 125

Gly Gly Val Leu Ile Gln Arg Asn Pro Gln Leu Cys Tyr Gln Asp Thr
        130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Arg Glu Ser Met Pro Asn Pro Glu Gly Arg Tyr Arg Phe Gly Ala Ser
            260                 265                 270

Cys Val Thr Ala Cys Pro Tyr Asn Tyr Leu Ser Thr Asp Arg Gly Ser
        275                 280                 285

Cys Thr Leu Val Cys Pro Leu Ala Asn Gln Glu Val Thr Ala Glu Asp
290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
```

-continued

```
                420             425             430
Leu Arg Ser Leu Arg Glu Leu Gly Ser Gly Leu Ala Leu Ile His His
            435             440             445

Asn Thr His Leu Cys Phe Val His Thr Val Pro Trp Asp Gln Leu Phe
450             455             460

Arg Asn Pro His Gln Ala Leu Leu His Thr Ala Asn Arg Pro Glu Asp
465             470             475             480

Glu Cys Val Gly Glu Gly Leu Ala Cys His Gln Leu Cys Ala Arg Gly
                485             490             495

His Cys Trp Gly Pro Gly Pro Thr Gln Cys Val Asn Cys Ser Gln Phe
            500             505             510

Leu Arg Gly Gln Glu Cys Val Glu Glu Cys Arg Val Leu Gln Gly Leu
            515             520             525

Pro Arg Glu Tyr Val Asn Ala Arg His Cys Leu Pro Cys His Pro Glu
            530             535             540

Cys Gln Pro Gln Asn Gly Ser Val Thr Cys Phe Gly Leu Glu Ala Asp
545             550             555             560

Gln Cys Val Ala Cys Ala His Tyr Lys Asp Pro Pro Phe Cys Val Ala
                565             570             575

Arg Cys Pro Ser Gly Val Lys Pro Asp Leu Ser Tyr Met Pro Ile Trp
            580             585             590

Lys Phe Pro Asp Glu Glu Gly Ala Cys Gln Pro Cys Pro Ile Asn Cys
            595             600             605

Thr His Ser Cys Val Asp Leu Asp Asp Lys Gly Cys Pro Ala Glu Gln
            610             615             620

Arg Ala Ser Pro Leu Thr Val Asp Gly Gly Ser Pro Thr Pro Pro Thr
625             630             635             640

Pro Gly Gly Gly Ser Ala Asp Lys Thr His Thr Cys Pro Pro Cys Pro
            645             650             655

Ala Pro Glu Leu Leu Gly Gly Pro Ser Val Phe Leu Phe Pro Pro Lys
            660             665             670

Pro Lys Asp Thr Leu Met Ile Ser Arg Thr Pro Glu Val Thr Cys Val
            675             680             685

Val Val Asp Val Ser His Glu Asp Pro Glu Val Lys Phe Asn Trp Tyr
            690             695             700

Val Asp Gly Val Glu Val His Asn Ala Lys Thr Lys Pro Arg Glu Glu
705             710             715             720

Gln Tyr Asn Ser Thr Tyr Arg Val Val Ser Val Leu Thr Val Leu His
                725             730             735

Gln Asp Trp Leu Asn Gly Lys Glu Tyr Lys Cys Lys Val Ser Asn Lys
            740             745             750

Ala Leu Pro Ala Pro Ile Glu Lys Thr Ile Ser Lys Ala Lys Gly Gln
            755             760             765

Pro Arg Glu Pro Gln Val Tyr Thr Leu Pro Pro Cys Arg Asp Glu Leu
            770             775             780

Thr Lys Asn Gln Val Ser Leu Trp Cys Leu Val Lys Gly Phe Tyr Pro
785             790             795             800

Ser Asp Ile Ala Val Glu Trp Glu Ser Asn Gly Gln Pro Glu Asn Asn
                805             810             815

Tyr Lys Thr Thr Pro Pro Val Leu Asp Ser Asp Gly Ser Phe Phe Leu
            820             825             830

Tyr Ser Lys Leu Thr Val Asp Lys Ser Arg Trp Gln Gln Gly Asn Val
            835             840             845
```

Phe Ser Cys Ser Val Met His Glu Ala Leu His Asn His Tyr Thr Gln
850                 855                 860

Lys Ser Leu Ser Leu Ser Pro Gly Lys Ser Gly Gly Leu Asn Asp Ile
865                 870                 875                 880

Phe Glu Ala Gln Lys Ile Glu Trp His Glu
                885                 890

<210> SEQ ID NO 9
<211> LENGTH: 2667
<212> TYPE: DNA
<213> ORGANISM: Artificial sequence
<220> FEATURE:
<223> OTHER INFORMATION: Her2 ECD(trastuzumab KO)-Fc(knob)DNA

<400> SEQUENCE: 9

| | | | | | |
|---|---|---|---|---|---|
| acccaagtgt | gcaccggcac | agacatgaag | ctgcggctcc | ctgccagtcc | cgagacccac | 60 |
| ctggacatgc | tccgccacct | ctaccagggc | tgccaggtgg | tgcagggaaa | cctggaactc | 120 |
| acctacctgc | ccaccaatgc | cagcctgtcc | ttcctgcagg | atatccagga | ggtgcagggc | 180 |
| tacgtgctca | tcgctcacaa | ccaagtgagg | caggtcccac | tgcagaggct | gcggattgtg | 240 |
| cgaggcaccc | agctctttga | ggacaactat | gccctggccg | tgctagacaa | tggagacccg | 300 |
| ctgaacaata | ccaccccctgt | cacaggggcc | tccccaggag | cctgcggga | gctgcagctt | 360 |
| cgaagcctca | cagagatctt | gaaggaggg | gtcttgatcc | agcggaaccc | ccagctctgc | 420 |
| taccaggaca | cgattttgtg | gaaggacatc | ttccacaaga | caaccagct | ggctctcaca | 480 |
| ctgatagaca | ccaaccgctc | tcgggcctgc | caccccctgtt | ctccgatgtg | taagggctcc | 540 |
| cgctgctggg | gagagagttc | tgaggattgt | cagagcctga | cgcgcactgt | ctgtgccggt | 600 |
| ggctgtgccc | gctgcaaggg | gccactgccc | actgactgct | gccatgagca | gtgtgctgcc | 660 |
| ggctgcacgg | gccccaagca | ctctgactgc | ctggcctgcc | tccacttcaa | ccacagtggc | 720 |
| atctgtgagc | tgcactgccc | agccctggtc | acctacaaca | cagacacgtt | tgagtccatg | 780 |
| cccaatcccg | agggccggta | cacattcggc | gccagctgtg | tgactgcctg | tccctacaac | 840 |
| tacctttcta | cggacgtggg | atcctgcacc | ctcgtctgcc | cctgcacaa | ccaagaggtg | 900 |
| acagcagagg | atggaacaca | gcggtgtgag | aagtgcagca | agccctgtgc | ccgagtgtgc | 960 |
| tatggtctgg | gcatggagca | cttgcgagag | gtgagggcag | ttaccagtgc | caatatccag | 1020 |
| gagtttgctg | gctgcaagaa | gatctttggg | agcctggcat | ttctgccgga | gagctttgat | 1080 |
| ggggacccag | cctccaacac | tgccccgctc | cagccagagc | agctccaagt | gtttgagact | 1140 |
| ctggaagaga | tcacaggtta | cctatacatc | tcagcatggc | cggacagcct | gcctgacctc | 1200 |
| agcgtcttcc | agaacctgca | agtaatccgg | ggacgaattc | tgcacaatgg | cgcctactcg | 1260 |
| ctgaccctgc | aagggctggg | catcagctgg | ctggggctgc | gctcactgag | ggaactgggc | 1320 |
| agtggactgg | ccctcatcca | ccataacacc | cacctctgct | tcgtgcacac | ggtgccctgg | 1380 |
| gaccagctct | ttcggaaccc | gcaccaagct | ctgctccaca | ctgccaaccg | gccagaggac | 1440 |
| gagtgtgtgg | gcgagggcct | ggcctgccac | cagctgtgcg | cccgagggca | ctgctgggt | 1500 |
| ccagggccca | cccagtgtgt | caactgcagc | cagttccttc | ggggccagga | gtgcgtggag | 1560 |
| gaatgccgag | tactgcaggg | gctccccagg | gagtatgtga | atgccaggca | ctgtttgccg | 1620 |
| tgccacccctg | agtgtcagcc | ccagaatggc | tcagtgacct | gttttggact | ggaggctcgg | 1680 |
| cagtgtgtgg | cctgtgccca | ctataaggac | agacggtgcg | tggcccgctg | ccccagcggt | 1740 |
| gtgaaacctg | acctctcccta | catgcccatc | tggaagtttc | cagatgagga | gggcgcatgc | 1800 |

-continued

```
cagccttgcc ccatcaactg cacccactcc tgtgtggacc tggatgacaa gggctgcccc    1860
gccgagcaga gagccagccc tctgacggtc gacggtggta gtccgacacc tccgacaccc    1920
gggggtggtt ctgcagacaa aactcacaca tgcccaccgt gcccagcacc tgaactcctg    1980 ggggaccgt cagtcttcct cttccccca aaacccaagg acaccctcat gatctcccgg      2040 accccctgagg tcacatgcgt ggtggtggac gtgagccacg aagaccctga ggtcaagttc    2100
aactggtacg tggacggcgt ggaggtgcat aatgccaaga caaagccgcg ggaggagcag    2160
tacaacagca cgtaccgtgt ggtcagcgtc ctcaccgtcc tgcaccagga ctggctgaat    2220
ggcaaggagt acaagtgcaa ggtctccaac aaagcccctcc cagcccccat cgagaaaacc   2280
atctccaaag ccaaagggca gccccgagaa ccacaggtgt acaccctgcc cccatgccgg    2340
gatgagctga ccaagaacca ggtcagcctg tggtgcctgg tcaaaggctt ctatcccagc    2400
gacatcgccg tggagtggga gagcaatggg cagccggaga caactacaa gaccacgcct     2460 cccgtgctgg actccgacgg ctccttcttc ctctacagca agctcaccgt ggacaagagc    2520
aggtggcagc aggggaacgt cttctcatgc tccgtgatgc atgaggctct gcacaaccac    2580
tacacgcaga agagcctctc cctgtctccg ggtaaatccg gaggcctgaa cgacatcttc    2640
gaggcccaga agattgaatg gcacgag                                         2667
```

```
<210> SEQ ID NO 10
<211> LENGTH: 889
<212> TYPE: PRT
<213> ORGANISM: Artificial sequence
<220> FEATURE:
<223> OTHER INFORMATION: Her2 ECD(trastuzumab KO)-Fc(knob)

<400> SEQUENCE: 10
```

```
Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205
```

```
Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
    370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
    450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Cys Arg Val Leu Gln Gly Leu
        515                 520                 525

Pro Arg Glu Tyr Val Asn Ala Arg His Cys Leu Pro Cys His Pro Glu
    530                 535                 540

Cys Gln Pro Gln Asn Gly Ser Val Thr Cys Phe Gly Leu Glu Ala Arg
545                 550                 555                 560

Gln Cys Val Ala Cys Ala His Tyr Lys Asp Arg Arg Cys Val Ala Arg
                565                 570                 575

Cys Pro Ser Gly Val Lys Pro Asp Leu Ser Tyr Met Pro Ile Trp Lys
            580                 585                 590

Phe Pro Asp Glu Glu Gly Ala Cys Gln Pro Cys Pro Ile Asn Cys Thr
        595                 600                 605

His Ser Cys Val Asp Leu Asp Asp Lys Gly Cys Pro Ala Glu Gln Arg
    610                 615                 620
```

```
Ala Ser Pro Leu Thr Val Asp Gly Gly Ser Pro Thr Pro Thr Pro
625                 630                 635                 640

Gly Gly Gly Ser Ala Asp Lys Thr His Thr Cys Pro Pro Cys Pro Ala
            645                 650                 655

Pro Glu Leu Leu Gly Gly Pro Ser Val Phe Leu Phe Pro Pro Lys Pro
        660                 665                 670

Lys Asp Thr Leu Met Ile Ser Arg Thr Pro Glu Val Thr Cys Val Val
    675                 680                 685

Val Asp Val Ser His Glu Asp Pro Glu Val Lys Phe Asn Trp Tyr Val
690                 695                 700

Asp Gly Val Glu Val His Asn Ala Lys Thr Lys Pro Arg Glu Glu Gln
705                 710                 715                 720

Tyr Asn Ser Thr Tyr Arg Val Val Ser Val Leu Thr Val Leu His Gln
            725                 730                 735

Asp Trp Leu Asn Gly Lys Glu Tyr Lys Cys Lys Val Ser Asn Lys Ala
        740                 745                 750

Leu Pro Ala Pro Ile Glu Lys Thr Ile Ser Lys Ala Lys Gly Gln Pro
    755                 760                 765

Arg Glu Pro Gln Val Tyr Thr Leu Pro Pro Cys Arg Asp Glu Leu Thr
770                 775                 780

Lys Asn Gln Val Ser Leu Trp Cys Leu Val Lys Gly Phe Tyr Pro Ser
785                 790                 795                 800

Asp Ile Ala Val Glu Trp Glu Ser Asn Gly Gln Pro Glu Asn Asn Tyr
            805                 810                 815

Lys Thr Thr Pro Pro Val Leu Asp Ser Asp Gly Ser Phe Phe Leu Tyr
        820                 825                 830

Ser Lys Leu Thr Val Asp Lys Ser Arg Trp Gln Gln Gly Asn Val Phe
    835                 840                 845

Ser Cys Ser Val Met His Glu Ala Leu His Asn His Tyr Thr Gln Lys
850                 855                 860

Ser Leu Ser Leu Ser Pro Gly Lys Ser Gly Gly Leu Asn Asp Ile Phe
865                 870                 875                 880

Glu Ala Gln Lys Ile Glu Trp His Glu
            885

<210> SEQ ID NO 11
<211> LENGTH: 11
<212> TYPE: PRT
<213> ORGANISM: Artificial sequence
<220> FEATURE:
<223> OTHER INFORMATION: Pertuzumab wt VL CDR1

<400> SEQUENCE: 11

Lys Ala Ser Gln Asp Val Ser Ile Gly Val Ala
1               5                   10

<210> SEQ ID NO 12
<211> LENGTH: 7
<212> TYPE: PRT
<213> ORGANISM: Artificial sequence
<220> FEATURE:
<223> OTHER INFORMATION: Pertuzumab wt VL CDR2

<400> SEQUENCE: 12

Ser Ala Ser Tyr Arg Tyr Thr
1               5

<210> SEQ ID NO 13
```

```
<211> LENGTH: 9
<212> TYPE: PRT
<213> ORGANISM: Artificial sequence
<220> FEATURE:
<223> OTHER INFORMATION: Pertuzumab wt VL CDR3

<400> SEQUENCE: 13

Gln Gln Tyr Tyr Ile Tyr Pro Tyr Thr
1               5

<210> SEQ ID NO 14
<211> LENGTH: 10
<212> TYPE: PRT
<213> ORGANISM: Artificial sequence
<220> FEATURE:
<223> OTHER INFORMATION: Pertuzumab wt VH CDR1

<400> SEQUENCE: 14

Gly Phe Thr Phe Thr Asp Tyr Thr Met Asp
1               5                   10

<210> SEQ ID NO 15
<211> LENGTH: 17
<212> TYPE: PRT
<213> ORGANISM: Artificial sequence
<220> FEATURE:
<223> OTHER INFORMATION: Pertuzumab wt VH CDR2

<400> SEQUENCE: 15

Asp Val Asn Pro Asn Ser Gly Gly Ser Ile Tyr Asn Gln Arg Phe Lys
1               5                   10                  15

Gly

<210> SEQ ID NO 16
<211> LENGTH: 10
<212> TYPE: PRT
<213> ORGANISM: Artificial sequence
<220> FEATURE:
<223> OTHER INFORMATION: Pertuzumab wt VH CDR3

<400> SEQUENCE: 16

Asn Leu Gly Pro Ser Phe Tyr Phe Asp Tyr
1               5                   10

<210> SEQ ID NO 17
<211> LENGTH: 11
<212> TYPE: PRT
<213> ORGANISM: Artificial sequence
<220> FEATURE:
<223> OTHER INFORMATION: Trastuzumab wt VL CDR1

<400> SEQUENCE: 17

Arg Ala Ser Gln Asp Val Asn Thr Ala Val Ala
1               5                   10

<210> SEQ ID NO 18
<211> LENGTH: 7
<212> TYPE: PRT
<213> ORGANISM: Artificial sequence
<220> FEATURE:
<223> OTHER INFORMATION: Trastuzumab wt VL CDR2

<400> SEQUENCE: 18

Ser Ala Ser Phe Leu Tyr Ser
1               5
```

```
<210> SEQ ID NO 19
<211> LENGTH: 9
<212> TYPE: PRT
<213> ORGANISM: Artificial sequence
<220> FEATURE:
<223> OTHER INFORMATION: Trastuzumab wt VL CDR3

<400> SEQUENCE: 19

Gln Gln His Tyr Thr Thr Pro Pro Thr
1               5

<210> SEQ ID NO 20
<211> LENGTH: 10
<212> TYPE: PRT
<213> ORGANISM: Artificial sequence
<220> FEATURE:
<223> OTHER INFORMATION: Trastuzumab wt VH CDR1

<400> SEQUENCE: 20

Gly Phe Asn Ile Lys Asp Thr Tyr Ile His
1               5                   10

<210> SEQ ID NO 21
<211> LENGTH: 558
<212> TYPE: DNA
<213> ORGANISM: Artificial sequence
<220> FEATURE:
<223> OTHER INFORMATION: Pertuzumab wt VH (10289)DNA

<400> SEQUENCE: 21
gaggtgcagc tggtcgagtc tggcggcgga ctggtgcagc ctggcggcag cctgagactg      60
agctgcgccg ccagcggctt caccttcacc gactacacca tggactgggt gcggcaggcc     120
cctggcaagg gcctggaatg gtggccgac gtgaacccca cagcggcgg cagcatctac      180 aaccagcggt tcaagggccg gttcaccctg agcgtggaca agagcaagaa caccctgtac     240
ctccagatga acagcctgcg ggccgaggac accgccgtgt actactgcgc ccggaacctg     300
ggccccagct tctacttcga ctactgggc cagggcaccc tggtgaccgt gagcagcgct      360
agcaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagc                                                  558

<210> SEQ ID NO 22
<211> LENGTH: 119
<212> TYPE: PRT
<213> ORGANISM: Artificial sequence
<220> FEATURE:
<223> OTHER INFORMATION: Pertuzumab wt VH (10289)

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 23
<211> LENGTH: 321
<212> TYPE: DNA
<213> ORGANISM: Artificial sequence
<220> FEATURE:
<223> OTHER INFORMATION: Pertuzumab wt VL(10290)DNA

<400> SEQUENCE: 23
gacatccaga tgacccagag ccccagcagc ctgagcgcca gcgtgggcga cagagtgacc      60
atcacctgca aggccagcca ggacgtgtcc atcggcgtgg cctggtatca gcagaagccc     120
ggcaaggccc ccaagctgct gatctacagc gccagctacc ggtacacagg cgtgcccagc     180
cggttcagcg gcagcggctc cggcaccgac ttcaccctga ccatcagcag cctgcagccc     240
gaggacttcg ccacctacta ctgccagcag tactacatct accctacac cttcggccag      300 ggcaccaagg tggagatcaa g                                                321

<210> SEQ ID NO 24
<211> LENGTH: 107
<212> TYPE: PRT
<213> ORGANISM: Artificial sequence
<220> FEATURE:
<223> OTHER INFORMATION: Pertuzumab wt VL(10290)

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 25
<211> LENGTH: 321
<212> TYPE: DNA
<213> ORGANISM: Artificial sequence
<220> FEATURE:
<223> OTHER INFORMATION: Pertuzumab VL (Trast. L3)(10403)DNA

<400> SEQUENCE: 25
gacatccaga tgacccagag ccccagcagc ctgagcgcca gcgtgggcga cagagtgacc      60
atcacatgca aggccagcca ggacgtgtcc atcggcgtgg cctggtatca gcagaagccc     120
ggcaaggccc ccaagctgct gatctacagc gccagctacc ggtacaccgg cgtgcccagc     180

```
agattcagcg gcagcggctc cggcaccgac ttcaccctga ccatcagcag cctgcagccc    240
gaggacttcg ccacctacta ctgccagcag cactacacca ccccccccac cttcggccag    300
ggcaccaagg tggaaatcaa g                                              321
```

<210> SEQ ID NO 26
<211> LENGTH: 107
<212> TYPE: PRT
<213> ORGANISM: Artificial sequence
<220> FEATURE:
<223> OTHER INFORMATION: Pertuzumab VL (Trast. L3)(10403)

<400> SEQUENCE: 26

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 27
<211> LENGTH: 321
<212> TYPE: DNA
<213> ORGANISM: Artificial sequence
<220> FEATURE:
<223> OTHER INFORMATION: Pertuzumab VL (Trast. H91)(10404)DNA

<400> SEQUENCE: 27

```
gacatccaga tgacccagag ccccagcagc ctgagcgcca gcgtgggcga cagagtgacc     60
atcacctgca aggccagcca ggacgtgtcc atcggcgtgg cctggtatca gcagaagccc    120
ggcaaggccc ccaagctgct gatctacagc gccagctacc ggtacacagg cgtgcccagc    180
cggttcagcg gcagcggctc cggcaccgac ttcaccctga ccatcagcag cctgcagccc    240
gaggacttcg ccacctacta ctgccagcag cactacatct accctacac cttcggccag     300 ggcaccaagg tggagatcaa g                                              321
```

<210> SEQ ID NO 28
<211> LENGTH: 107
<212> TYPE: PRT
<213> ORGANISM: Artificial sequence
<220> FEATURE:
<223> OTHER INFORMATION: Pertuzumab VL (Trast. H91)(10404)

<400> SEQUENCE: 28

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
```

```
                50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Ile Tyr Pro Tyr
                 85                  90                  95

Thr Phe Gly Gln Gly Thr Lys Val Glu Ile Lys
            100                 105

<210> SEQ ID NO 29
<211> LENGTH: 17
<212> TYPE: PRT
<213> ORGANISM: Artificial sequence
<220> FEATURE:
<223> OTHER INFORMATION: Trastuzumab wt VH CDR2

<400> SEQUENCE: 29

Arg Ile Tyr Pro Thr Asn Gly Tyr Thr Arg Tyr Ala Asp Ser Val Lys
 1               5                   10                  15

Gly

<210> SEQ ID NO 30
<211> LENGTH: 11
<212> TYPE: PRT
<213> ORGANISM: Artificial sequence
<220> FEATURE:
<223> OTHER INFORMATION: Trastuzumab wt VH CDR3

<400> SEQUENCE: 30

Trp Gly Gly Asp Gly Phe Tyr Ala Met Asp Tyr
 1               5                   10

<210> SEQ ID NO 31
<211> LENGTH: 321
<212> TYPE: DNA
<213> ORGANISM: Artificial sequence
<220> FEATURE:
<223> OTHER INFORMATION: Pertuzumab VL (Tras.L3) K24R(10949)DNA

<400> SEQUENCE: 31
gacatccaga tgacccagag ccccagcagc ctgagcgcca gcgtgggcga cagagtgacc      60
atcacatgcc gggccagcca ggacgtgtcc atcggcgtgg cctggtatca gcagaagccc     120
ggcaaggccc ccaagctgct gatctacagc gccagctacc ggtacaccgg cgtgcccagc     180
agattcagcg gcagcggctc cggcaccgac ttcaccctga ccatcagcag cctgcagccc     240
gaggacttcg ccacctacta ctgccagcag cactacacca cccccccac cttcggccag     300 ggcaccaagg tggaaatcaa g                                                321

<210> SEQ ID NO 32
<211> LENGTH: 107
<212> TYPE: PRT
<213> ORGANISM: Artificial sequence
<220> FEATURE:
<223> OTHER INFORMATION: Pertuzumab VL (Tras.L3) K24R(10949)

<400> SEQUENCE: 32

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Asp Val Ser Ile Gly
                20                  25                  30

Val Ala Trp Tyr Gln Gln Lys Pro Gly Lys Ala Pro Lys Leu Leu Ile
            35                  40                  45
```

Tyr Ser Ala Ser Tyr Arg Tyr Thr Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
                100                 105

<210> SEQ ID NO 33
<211> LENGTH: 321
<212> TYPE: DNA
<213> ORGANISM: Artificial sequence
<220> FEATURE:
<223> OTHER INFORMATION: Pertuzumab VL(Tras.L3) S30N (10950)DNA

<400> SEQUENCE: 33
gacatccaga tgacccagag ccccagcagc ctgagcgcca gcgtgggcga cagagtgacc      60
atcacatgca aggccagcca ggacgtgaac atcggcgtgg cctggtatca gcagaagccc     120
ggcaaggccc ccaagctgct gatctacagc gccagctacc ggtacaccgg cgtgcccagc     180
agattcagcg gcagcggctc cggcaccgac ttcaccctga ccatcagcag cctgcagccc     240
gaggacttcg ccacctacta ctgccagcag cactacacca ccccccccac cttcggccag     300
ggcaccaagg tggaaatcaa g                                               321

<210> SEQ ID NO 34
<211> LENGTH: 107
<212> TYPE: PRT
<213> ORGANISM: Artificial sequence
<220> FEATURE:
<223> OTHER INFORMATION: Pertuzumab VL(Tras.L3) S30N (10950)

<400> SEQUENCE: 34

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Asn Ile Gly
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
                100                 105

<210> SEQ ID NO 35
<211> LENGTH: 321
<212> TYPE: DNA
<213> ORGANISM: Artificial sequence
<220> FEATURE:
<223> OTHER INFORMATION: Pertuzumab VL (Tras.L3) I31T (10951)DNA

<400> SEQUENCE: 35
gacatccaga tgacccagag ccccagcagc ctgagcgcca gcgtgggcga cagagtgacc      60
atcacatgca aggccagcca ggacgtgtcc accggcgtgg cctggtatca gcagaagccc     120

```
ggcaaggccc ccaagctgct gatctacagc gccagctacc ggtacaccgg cgtgcccagc    180
agattcagcg gcagcggctc cggcaccgac ttcaccctga ccatcagcag cctgcagccc    240
gaggacttcg ccacctacta ctgccagcag cactacacca ccccccccac cttcggccag    300
ggcaccaagg tggaaatcaa g                                              321
```

<210> SEQ ID NO 36
<211> LENGTH: 107
<212> TYPE: PRT
<213> ORGANISM: Artificial sequence
<220> FEATURE:
<223> OTHER INFORMATION: Pertuzumab VL (Tras.L3) I31T (10951)

<400> SEQUENCE: 36

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 37
<211> LENGTH: 321
<212> TYPE: DNA
<213> ORGANISM: Artificial sequence
<220> FEATURE:
<223> OTHER INFORMATION: Pertuzumab VL (Tras.L3) I31V (10952)DNA

<400> SEQUENCE: 37

```
gacatccaga tgacccagag ccccagcagc ctgagcgcca gcgtgggcga cagagtgacc     60
atcacatgca aggccagcca ggacgtgtcc gtcggcgtgg cctggtatca gcagaagccc    120
ggcaaggccc ccaagctgct gatctacagc gccagctacc ggtacaccgg cgtgcccagc    180
agattcagcg gcagcggctc cggcaccgac ttcaccctga ccatcagcag cctgcagccc    240
gaggacttcg ccacctacta ctgccagcag cactacacca ccccccccac cttcggccag    300
ggcaccaagg tggaaatcaa g                                              321
```

<210> SEQ ID NO 38
<211> LENGTH: 107
<212> TYPE: PRT
<213> ORGANISM: Artificial sequence
<220> FEATURE:
<223> OTHER INFORMATION: Pertuzumab VL (Tras.L3) I31V

<400> SEQUENCE: 38

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Val Gly
            20                  25                  30

Val Ala Trp Tyr Gln Gln Lys Pro Gly Lys Ala Pro Lys Leu Leu Ile
```

35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 39
<211> LENGTH: 321
<212> TYPE: DNA
<213> ORGANISM: Artificial sequence
<220> FEATURE:
<223> OTHER INFORMATION: Pertuzumab VL (Tras.L3) G32A(10953)DNA

<400> SEQUENCE: 39
gacatccaga tgacccagag ccccagcagc ctgagcgcca gcgtgggcga cagagtgacc      60
atcacatgca aggccagcca ggacgtgtcc atcgccgtgg cctggtatca gcagaagccc     120
ggcaaggccc ccaagctgct gatctacagc gccagctacc ggtacaccgg cgtgcccagc     180
agattcagcg gcagcggctc cggcaccgac ttcaccctga ccatcagcag cctgcagccc     240
gaggacttcg ccacctacta ctgccagcag cactacacca cccccccccac cttcggccag    300 ggcaccaagg tggaaatcaa g                                               321

<210> SEQ ID NO 40
<211> LENGTH: 107
<212> TYPE: PRT
<213> ORGANISM: Artificial sequence
<220> FEATURE:
<223> OTHER INFORMATION: Pertuzumab VL (Tras.L3) G32A(10953)

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 41
<211> LENGTH: 321
<212> TYPE: DNA
<213> ORGANISM: Artificial sequence
<220> FEATURE:
<223> OTHER INFORMATION: Pertuzumab VL(Tras.L3) Y53F(10954)DNA

<400> SEQUENCE: 41
gacatccaga tgacccagag ccccagcagc ctgagcgcca gcgtgggcga cagagtgacc      60

```
atcacatgca aggccagcca ggacgtgtcc atcggcgtgg cctggtatca gcagaagccc    120
ggcaaggccc ccaagctgct gatctacagc gccagcttcc ggtacaccgg cgtgcccagc    180
agattcagcg gcagcggctc cggcaccgac ttcaccctga ccatcagcag cctgcagccc    240
gaggacttcg ccacctacta ctgccagcag cactacacca cccccccac cttcggccag    300 ggcaccaagg tggaaatcaa g                                              321
```

```
<210> SEQ ID NO 42
<211> LENGTH: 107
<212> TYPE: PRT
<213> ORGANISM: Artificial sequence
<220> FEATURE:
<223> OTHER INFORMATION: Pertuzumab VL(Tras.L3) Y53F(10954)

<400> SEQUENCE: 42
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Phe Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

```
<210> SEQ ID NO 43
<211> LENGTH: 321
<212> TYPE: DNA
<213> ORGANISM: Artificial sequence
<220> FEATURE:
<223> OTHER INFORMATION: Pertuzumab (Tras.L3) R54L(10955)DNA

<400> SEQUENCE: 43
gacatccaga tgacccagag ccccagcagc ctgagcgcca gcgtgggcga cagagtgacc    60
atcacatgca aggccagcca ggacgtgtcc atcggcgtgg cctggtatca gcagaagccc    120
ggcaaggccc ccaagctgct gatctacagc gccagctacc tgtacaccgg cgtgcccagc    180
agattcagcg gcagcggctc cggcaccgac ttcaccctga ccatcagcag cctgcagccc    240
gaggacttcg ccacctacta ctgccagcag cactacacca cccccccac cttcggccag    300 ggcaccaagg tggaaatcaa g                                              321
```

```
<210> SEQ ID NO 44
<211> LENGTH: 107
<212> TYPE: PRT
<213> ORGANISM: Artificial sequence
<220> FEATURE:
<223> OTHER INFORMATION: Pertuzumab (Tras.L3) R54L(10955)

<400> SEQUENCE: 44
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
            35                  40                  45

Tyr Ser Ala Ser Tyr Leu Tyr Thr Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 45
<211> LENGTH: 321
<212> TYPE: DNA
<213> ORGANISM: Artificial sequence
<220> FEATURE:
<223> OTHER INFORMATION: Pertuzumab (Tras.L3) T56S(10956)DNA

<400> SEQUENCE: 45
gacatccaga tgacccagag ccccagcagc ctgagcgcca gcgtgggcga cagagtgacc      60
atcacatgca aggccagcca ggacgtgtcc atcggcgtgg cctggtatca gcagaagccc     120
ggcaaggccc ccaagctgct gatctacagc gccagctacc ggtacagcgg cgtgcccagc     180
agattcagcg gcagcggctc cggcaccgac ttcaccctga ccatcagcag cctgcagccc     240
gaggacttcg ccacctacta ctgccagcag cactacacca cccccccac cttcggccag      300 ggcaccaagg tggaaatcaa g                                                321

<210> SEQ ID NO 46
<211> LENGTH: 107
<212> TYPE: PRT
<213> ORGANISM: Artificial sequence
<220> FEATURE:
<223> OTHER INFORMATION: Pertuzumab (Tras.L3) T56S(10956)

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 47
<211> LENGTH: 321
<212> TYPE: DNA
<213> ORGANISM: Artificial sequence
<220> FEATURE:
<223> OTHER INFORMATION: Pertuzumab (Tras.L3) G66R(10957)DNA

<400> SEQUENCE: 47
gacatccaga tgacccagag ccccagcagc ctgagcgcca gcgtgggcga cagagtgacc      60

```
atcacatgca aggccagcca ggacgtgtcc atcggcgtgg cctggtatca gcagaagccc    120
ggcaaggccc ccaagctgct gatctacagc gccagctacc ggtacaccgg cgtgcccagc    180
agattcagcg gcagccgctc cggcaccgac ttcaccctga ccatcagcag cctgcagccc    240
gaggacttcg ccacctacta ctgccagcag cactacacca cccccccac cttcggccag     300 ggcaccaagg tggaaatcaa g                                              321
```

<210> SEQ ID NO 48
<211> LENGTH: 107
<212> TYPE: PRT
<213> ORGANISM: Artificial sequence
<220> FEATURE:
<223> OTHER INFORMATION: Pertuzumab (Tras.L3) G66R(10957)

<400> SEQUENCE: 48

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 49
<211> LENGTH: 320
<212> TYPE: DNA
<213> ORGANISM: Artificial sequence
<220> FEATURE:
<223> OTHER INFORMATION: Pertuzumab (Tras.L3) T94Y(10958)DNA

<400> SEQUENCE: 49

```
acatccagat gacccagagc cccagcagcc tgagcgccag cgtgggcgac agagtgacca    60
tcacatgcaa ggccagccag gacgtgtcca tcggcgtggc ctggtatcag cagaagcccg   120
gcaaggcccc caagctgctg atctacagcg ccagctaccg gtacaccggc gtgcccagca   180
gattcagcgg cagcggctcc ggcaccgact tcaccctgac catcagcagc ctgcagcccg   240
aggacttcgc cacctactac tgccagcagc actaccccta cccccccacc ttcggccagg   300
gcaccaaggt ggaaatcaag                                               320
```

<210> SEQ ID NO 50
<211> LENGTH: 107
<212> TYPE: PRT
<213> ORGANISM: Artificial sequence
<220> FEATURE:
<223> OTHER INFORMATION: Pertuzumab (Tras.L3) T94Y(10958)

<400> SEQUENCE: 50

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30
```

```
Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Tyr Pro Pro
                85                  90                  95

Thr Phe Gly Gln Gly Thr Lys Val Glu Ile Lys
            100                 105
```

<210> SEQ ID NO 51
<211> LENGTH: 321
<212> TYPE: DNA
<213> ORGANISM: Artificial sequence
<220> FEATURE:
<223> OTHER INFORMATION: Pertuzumab (Tras.L3) P96Y(10959)DNA

<400> SEQUENCE: 51

```
gacatccaga tgacccagag ccccagcagc ctgagcgcca gcgtgggcga cagagtgacc    60
atcacatgca aggccagcca ggacgtgtcc atcggcgtgg cctggtatca gcagaagccc   120
ggcaaggccc ccaagctgct gatctacagc gccagctacc ggtacaccgg cgtgcccagc   180
agattcagcg gcagcggctc cggcaccgac ttcaccctga ccatcagcag cctgcagccc   240
gaggacttcg ccacctacta ctgccagcag cactacacca ccccctacac cttcggccag   300
ggcaccaagg tggaaatcaa g                                             321
```

<210> SEQ ID NO 52
<211> LENGTH: 107
<212> TYPE: PRT
<213> ORGANISM: Artificial sequence
<220> FEATURE:
<223> OTHER INFORMATION: Pertuzumab (Tras.L3) P96Y(10959)

<400> SEQUENCE: 52

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Tyr
                85                  90                  95

Thr Phe Gly Gln Gly Thr Lys Val Glu Ile Lys
            100                 105
```

<210> SEQ ID NO 53
<211> LENGTH: 321
<212> TYPE: DNA
<213> ORGANISM: Artificial sequence
<220> FEATURE:
<223> OTHER INFORMATION: Pertuzumab (Tras.L3) (QM) (11055)DNA

<400> SEQUENCE: 53

```
gacatccaga tgacccagag ccccagcagc ctgtctgcca gcgtgggcga cagagtgacc    60
atcacatgca aggccagcca ggacgtgtcc acagccgtgg cctggtatca gcagaagcct   120
ggcaaggccc ccaagctgct gatctacagc gccagcttcc ggtacaccgg cgtgcccagc   180
agattcagcg gcagcagatc cggcaccgac ttcaccctga ccatcagctc cctgcagccc   240
gaggacttcg ccacctacta ctgccagcag cactacacca cccccccac atttggccag    300 ggcaccaagg tggaaatcaa g                                             321
```

<210> SEQ ID NO 54
<211> LENGTH: 107
<212> TYPE: PRT
<213> ORGANISM: Artificial sequence
<220> FEATURE:
<223> OTHER INFORMATION: Pertuzumab (Tras.L3) (QM) (11055)

<400> SEQUENCE: 54

```
Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asp Val Ser Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Arg Tyr Thr Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys
            100                 105
```

<210> SEQ ID NO 55
<211> LENGTH: 10
<212> TYPE: PRT
<213> ORGANISM: Artificial sequence
<220> FEATURE:
<223> OTHER INFORMATION: Pertuzumab aff.mat. clone D1-derived VH CDR1

<400> SEQUENCE: 55

```
Gly Phe Thr Phe Asn Asp Tyr Thr Met Asp
1               5                   10
```

<210> SEQ ID NO 56
<211> LENGTH: 10
<212> TYPE: PRT
<213> ORGANISM: Artificial sequence
<220> FEATURE:
<223> OTHER INFORMATION: Pertuzumab aff.mat. clone D1- derived VH CDR3

<400> SEQUENCE: 56

```
Asn Leu Gly Pro Phe Phe Tyr Phe Asp Tyr
1               5                   10
```

<210> SEQ ID NO 57
<211> LENGTH: 10
<212> TYPE: PRT
<213> ORGANISM: Artificial sequence
<220> FEATURE:
<223> OTHER INFORMATION: Pertuzumab aff.mat. clone B2- VH CDR3

<400> SEQUENCE: 57

Asn Leu Gly Pro Asn Phe Tyr Phe Asp Tyr
1               5                   10

<210> SEQ ID NO 58
<211> LENGTH: 10
<212> TYPE: PRT
<213> ORGANISM: Artificial sequence
<220> FEATURE:
<223> OTHER INFORMATION: Pertuzumab aff.mat. clone E1- VH CDR1

<400> SEQUENCE: 58

Gly Phe Thr Phe Ala Asp Tyr Thr Met Asp
1               5                   10

<210> SEQ ID NO 59
<211> LENGTH: 10
<212> TYPE: PRT
<213> ORGANISM: Artificial sequence
<220> FEATURE:
<223> OTHER INFORMATION: Pertuzumab aff.mat. clone E1- VH CDR3

<400> SEQUENCE: 59

Asn Leu Gly Pro Trp Phe Tyr Phe Asp Tyr
1               5                   10

<210> SEQ ID NO 60
<211> LENGTH: 17
<212> TYPE: PRT
<213> ORGANISM: Artificial sequence
<220> FEATURE:
<223> OTHER INFORMATION: Pertuzumab aff.mat. clone G2- VH CDR2

<400> SEQUENCE: 60

Asp Val Asn Pro Asn Ser Gly Gly Tyr Ile Val Asn Arg Arg Phe Lys
1               5                   10                  15

Gly

<210> SEQ ID NO 61
<211> LENGTH: 357
<212> TYPE: DNA
<213> ORGANISM: Artificial sequence
<220> FEATURE:
<223> OTHER INFORMATION: Pertuzumab aff.mat. clone D1 DNA

<400> SEQUENCE: 61
gaggtgcaat tggttgaaag cggtggtggt ctggttcagc ctggtggtag cctgcgtctg      60
agctgtgcag caagcggttt tacctttaac gattatacca tggattgggt tcgtcaggca     120
ccgggtaaag gtctggaatg ggttgcagat gttaatccga atagcggtgg tagcatttat     180
aaccagcgtt ttaaaggtcg ttttacccct agcgttgatc gtagcaaaaa tacccctgtat    240 ctgcaaatga atagtctgcg tgcagaggat accgcagtgt attattgtgc acgtaacctg     300
ggtccgttct tctactttga ttattggggt cagggcaccc tggttaccgt tagcagc        357

<210> SEQ ID NO 62
<211> LENGTH: 119
<212> TYPE: PRT
<213> ORGANISM: Artificial sequence
<220> FEATURE:
<223> OTHER INFORMATION: Pertuzumab aff.mat. clone D1

<400> SEQUENCE: 62

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Asn Asp Tyr
            20                  25                  30

Thr Met Asp Trp Val Arg Gln Ala Pro Gly Lys Gly Leu Glu Trp Val
            35                  40                  45

Ala Asp Val Asn Pro Asn Ser Gly Gly Ser Ile Tyr Asn Gln Arg Phe
        50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asn Leu Gly Pro Phe Phe Tyr Phe Asp Tyr Trp Gly Gln Gly
            100                 105                 110

Thr Leu Val Thr Val Ser Ser
            115

<210> SEQ ID NO 63
<211> LENGTH: 357
<212> TYPE: DNA
<213> ORGANISM: Artificial sequence
<220> FEATURE:
<223> OTHER INFORMATION: Pertuzumab aff.mat. clone D1-derived DNA

<400> SEQUENCE: 63
gaggtgcaat tggttgaaag cggtggtggt ctggttcagc ctggtggtag cctgcgtctg      60
agctgtgcag caagcggttt tacctttaac gattatacca tggattgggt tcgtcaggca     120
ccgggtaaag gtctggaatg ggttgcagat gttaatccga atagcggtgg tagcattgtt     180
aaccgtcgtt ttaaaggtcg ttttaccctg agcgttgatc gtagcaaaaa taccctgtat     240
ctgcaaatga atagtctgcg tgcagaggat accgcagtgt attattgtgc acgtaacctg     300
ggtccgttct tctactttga ttattggggt cagggcaccc tggttaccgt tagcagc       357

<210> SEQ ID NO 64
<211> LENGTH: 119
<212> TYPE: PRT
<213> ORGANISM: Artificial sequence
<220> FEATURE:
<223> OTHER INFORMATION: Pertuzumab aff.mat. clone D1-derived

<400> SEQUENCE: 64

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Asp Tyr
            20                  25                  30

Thr Met Asp Trp Val Arg Gln Ala Pro Gly Lys Gly Leu Glu Trp Val
            35                  40                  45

Ala Asp Val Asn Pro Asn Ser Gly Gly Ser Ile Val Asn Arg Arg Phe
        50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asn Leu Gly Pro Phe Phe Tyr Phe Asp Tyr Trp Gly Gln Gly
            100                 105                 110

Thr Leu Val Thr Val Ser Ser
            115

<210> SEQ ID NO 65
```

<211> LENGTH: 357
<212> TYPE: DNA
<213> ORGANISM: Artificial sequence
<220> FEATURE:
<223> OTHER INFORMATION: Pertuzumab aff.mat. clone B2 DNA

<400> SEQUENCE: 65

```
gaggtgcaat tggttgaaag cggtggtggt ctggttcagc ctggtggtag cctgcgtctg     60
agctgtgcag caagcggttt tacctttaac gattatacca tggattggtt tcgtcaggca    120
ccgggtaaag gtctggaatg ggttgcagat gttaatccga atagcggtgg tagcatttat    180
aaccagcgtt ttaaaggtcg ttttaccctg agcgttgatc gtagcaaaaa taccctgtat    240
ctgcaaatga atagtctgcg tgcagaggat accgcagtgt attattgtgc acgtaatctg    300
ggtccgaact tctactttga ttattggggt cagggcaccc tggttaccgt tagcagc       357
```

<210> SEQ ID NO 66
<211> LENGTH: 119
<212> TYPE: PRT
<213> ORGANISM: Artificial sequence
<220> FEATURE:
<223> OTHER INFORMATION: Pertuzumab aff.mat. clone B2

<400> SEQUENCE: 66

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asp Tyr
            20                  25                  30

Thr Met Asp Trp Phe Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Asn Phe Tyr Phe Asp Tyr Trp Gly Gln Gly
            100                 105                 110

Thr Leu Val Thr Val Ser Ser
        115
```

<210> SEQ ID NO 67
<211> LENGTH: 357
<212> TYPE: DNA
<213> ORGANISM: Artificial sequence
<220> FEATURE:
<223> OTHER INFORMATION: Pertuzumab aff.mat. clone E1 DNA

<400> SEQUENCE: 67

```
gaggtgcaat tggttgaaag cggtggtggt ctggttcagc ctggtggtag cctgcgtctg     60
agctgtgcag caagcggttt tacctttgca gattatacca tggattgggt tcgtcaggca    120
ccgggtaaag gtctggaatg ggttgcagat gttaatccga atagcggtgg tagcatttat    180
aaccagcgtt ttaaaggtcg ttttaccctg agcgttgatc gtagcaaaaa taccctgtat    240
ctgcaaatga atagtctgcg tgcagaggat accgcagtgt attattgtgc acgtaatctg    300
ggtccgtggt tctactttga ttattggggt cagggcaccc tggttaccgt tagcagc       357
```

<210> SEQ ID NO 68
<211> LENGTH: 119

```
<212> TYPE: PRT
<213> ORGANISM: Artificial sequence
<220> FEATURE:
<223> OTHER INFORMATION: Pertuzumab aff.mat. clone E1

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ala Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Trp Phe Tyr Phe Asp Tyr Trp Gly Gln Gly
            100                 105                 110

Thr Leu Val Thr Val Ser Ser
        115

<210> SEQ ID NO 69
<211> LENGTH: 357
<212> TYPE: DNA
<213> ORGANISM: Artificial sequence
<220> FEATURE:
<223> OTHER INFORMATION: Pertuzumab aff.mat. clone G2 DNA

<400> SEQUENCE: 69
gaggtgcaat tggttgaaag cggtggtggt ctggttcagc ctggtggtag cctgcgtctg      60
agctgtgcag caagcggttt tacctttacc gattacacaa tggattgggt tcgtcaggca     120
ccgggtaaag gtctggaatg ggttgcagat gttaatccga actctggtgg ttacattgtt     180
aaccgtcgtt ttaaaggtcg ttttacccctg agcgttgatc gtagcaaaaa tacccctgtat    240 ctgcaaatga atagtctgcg tgcagaggat accgcagtgt attattgtgc acgtaatctg     300
ggtccgagct tctattttga ttattggggt caggcaccc tggttaccgt tagcagc         357

<210> SEQ ID NO 70
<211> LENGTH: 119
<212> TYPE: PRT
<213> ORGANISM: Artificial sequence
<220> FEATURE:
<223> OTHER INFORMATION: Pertuzumab aff.mat. clone G2

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Tyr Ile Val Asn Arg Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
```

85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 71
<211> LENGTH: 357
<212> TYPE: DNA
<213> ORGANISM: Artificial sequence
<220> FEATURE:
<223> OTHER INFORMATION: Pertuzumab aff.mat. clone C8 DNA

<400> SEQUENCE: 71
gaggtgcaat tggttgaaag cggtggtggt ctggttcagc ctggtggtag cctgcgtctg     60
agctgtgcag caagcggttt tacctttacc gattacacaa tggattgggt tcgtcaggca    120
ccgggtaaag gtctggaatg ggttgcagat gttaatccga actctggtgg ttctattatg    180
aaccgtcgtt ttaaaggtcg ttttaccctg agcgttgatc gtagcaaaaa taccctgtat    240
ctgcaaatga atagtctgcg tgcagaggat accgcagtgt attattgtgc acgtaatctg    300
ggtccgagct ctatttttga ttattggggt cagggcaccc tggttaccgt tagcagc      357

<210> SEQ ID NO 72
<211> LENGTH: 119
<212> TYPE: PRT
<213> ORGANISM: Artificial sequence
<220> FEATURE:
<223> OTHER INFORMATION: Pertuzumab aff.mat. clone C8

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Met Asn Arg Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 73
<211> LENGTH: 357
<212> TYPE: DNA
<213> ORGANISM: Artificial sequence
<220> FEATURE:
<223> OTHER INFORMATION: Pertuzumab aff.mat. clone A1 DNA

<400> SEQUENCE: 73
gaggtgcaat tggttgaaag cggtggtggt ctggttcagc ctggtggtag cctgcgtctg     60
agctgtgcag caagcggttt tacctttacc gattacacaa tggattgggt tcgtcaggca    120
ccgggtaaag gtctggaatg ggttgcagat gttaatccga actctggtgg ttctattgtt    180

```
aaccagcgtt ttaaaggtcg ttttaccctg agcgttgatc gtagcaaaaa taccctgtat    240
ctgcaaatga atagtctgcg tgcagaggat accgcagtgt attattgtgc acgtaatctg    300
ggtccgtggt tctactttga ttattggggt cagggcaccc tggttaccgt tagcagc       357
```

```
<210> SEQ ID NO 74
<211> LENGTH: 119
<212> TYPE: PRT
<213> ORGANISM: Artificial sequence
<220> FEATURE:
<223> OTHER INFORMATION: Pertuzumab aff.mat. clone A1

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Val Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Trp Phe Tyr Phe Asp Tyr Trp Gly Gln Gly
            100                 105                 110

Thr Leu Val Thr Val Ser Ser
        115
```

```
<210> SEQ ID NO 75
<211> LENGTH: 17
<212> TYPE: PRT
<213> ORGANISM: Artificial sequence
<220> FEATURE:
<223> OTHER INFORMATION: Pertuzumab aff.mat. clone C8- VH CDR2

<400> SEQUENCE: 75

Asp Val Asn Pro Asn Ser Gly Gly Ser Ile Met Asn Arg Arg Phe Lys
1               5                   10                  15

Gly
```

```
<210> SEQ ID NO 76
<211> LENGTH: 17
<212> TYPE: PRT
<213> ORGANISM: Artificial sequence
<220> FEATURE:
<223> OTHER INFORMATION: Pertuzumab aff.mat. clone A1- VH CDR2

<400> SEQUENCE: 76

Asp Val Asn Pro Asn Ser Gly Gly Ser Ile Val Asn Gln Arg Phe Lys
1               5                   10                  15

Gly
```

```
<210> SEQ ID NO 77
<211> LENGTH: 17
<212> TYPE: PRT
<213> ORGANISM: Artificial sequence
<220> FEATURE:
<223> OTHER INFORMATION: Pertuzumab aff.mat. clone D1-derived VH CDR2
```

<400> SEQUENCE: 77

Asp Val Asn Pro Asn Ser Gly Gly Ser Ile Val Asn Arg Arg Phe Lys
1               5                   10                  15

Gly

<210> SEQ ID NO 78
<211> LENGTH: 11
<212> TYPE: PRT
<213> ORGANISM: Artificial sequence
<220> FEATURE:
<223> OTHER INFORMATION: Trastuzumab VH (D98N)(6636)CDR3

<400> SEQUENCE: 78

Trp Gly Gly Asn Gly Phe Tyr Ala Met Asp Tyr
1               5                   10

<210> SEQ ID NO 79
<211> LENGTH: 11
<212> TYPE: PRT
<213> ORGANISM: Artificial sequence
<220> FEATURE:
<223> OTHER INFORMATION: Trastuzumab VH (D98E)(6637)CDR3

<400> SEQUENCE: 79

Trp Gly Gly Glu Gly Phe Tyr Ala Met Asp Tyr
1               5                   10

<210> SEQ ID NO 80
<211> LENGTH: 11
<212> TYPE: PRT
<213> ORGANISM: Artificial sequence
<220> FEATURE:
<223> OTHER INFORMATION: Trastuzumab VH (D98T)(6638)CDR3

<400> SEQUENCE: 80

Trp Gly Gly Thr Gly Phe Tyr Ala Met Asp Tyr
1               5                   10

<210> SEQ ID NO 81
<211> LENGTH: 321
<212> TYPE: DNA
<213> ORGANISM: Artificial sequence
<220> FEATURE:
<223> OTHER INFORMATION: Trastuzumab VL(4245)DNA

<400> SEQUENCE: 81
gacatccaga tgacccagag cccaagctct ctgtctgcct ctgtgggcga cagagtgacc      60
atcacctgca gagccagcca ggacgtgaac acagccgtgg cctggtatca gcagaagcca     120
ggcaaggccc caaagctgct gatctacagc gccagcttcc tgtacagcgg cgtgccaagc     180
agattcagcg gcagcagaag cggcacagac ttcaccctga ccatcagcag cctgcagcca     240
gaggacttcg ccacctacta ctgccagcag cactacacca ccccaccaac cttcggacag     300
ggcaccaagg tggagatcaa g                                               321

<210> SEQ ID NO 82
<211> LENGTH: 107
<212> TYPE: PRT
<213> ORGANISM: Artificial sequence
<220> FEATURE:
<223> OTHER INFORMATION: Trastuzumab VL(4245)

<400> SEQUENCE: 82

Asp Ile Gln Met Thr Gln Ser Pro Ser Ser Leu Ser Ala Ser Val Gly

```
  1               5                  10                 15
Asp Arg Val Thr Ile Thr Cys Arg Ala Ser Gln Asp Val Asn Thr Ala
                 20                 25                 30

Val Ala Trp Tyr Gln Gln Lys Pro Gly Lys Ala Pro Lys Leu Leu Ile
         35                 40                 45

Tyr Ser Ala Ser Phe Leu Tyr Ser Gly Val Pro Ser Arg Phe Ser Gly
         50                 55                 60

Ser Arg Ser Gly Thr Asp Phe Thr Leu Thr Ile Ser Ser Leu Gln Pro
65                  70                 75                 80

Glu Asp Phe Ala Thr Tyr Tyr Cys Gln Gln His Tyr Thr Thr Pro Pro
                 85                 90                 95

Thr Phe Gly Gln Gly Thr Lys Val Glu Ile Lys
            100                105

<210> SEQ ID NO 83
<211> LENGTH: 321
<212> TYPE: DNA
<213> ORGANISM: Artificial sequence
<220> FEATURE:
<223> OTHER INFORMATION: Trastuzumab VL T31A (6641)DNA

<400> SEQUENCE: 83
gatatccaga tgacccagtc tccatcctcc ctgtctgcat ctgtaggaga cagagtcacc     60
atcacttgcc gggcaagtca ggacgtgaac gccgctgtag cgtggtacca gcagaaacca    120
ggtaaggcac cgaagctatt aatttatagt gcgagcttcc tgtacagtgg ggtcccgtcg    180
cgttttagcg gctctcgatc cggcacggat tttaccctga ccattagcag cctgcagcct    240
gaagactttg cgacatatta ttgccaacag cactacacaa ctcctcccac ctttggccag    300
ggtacgaaag ttgaaattaa a                                              321

<210> SEQ ID NO 84
<211> LENGTH: 107
<212> TYPE: PRT
<213> ORGANISM: Artificial sequence
<220> FEATURE:
<223> OTHER INFORMATION: Trastuzumab VL T31A (6641)

<400> SEQUENCE: 84

Asp Ile Gln Met Thr Gln Ser Pro Ser Ser Leu Ser Ala Ser Val Gly
1               5                  10                 15

Asp Arg Val Thr Ile Thr Cys Arg Ala Ser Gln Asp Val Asn Ala Ala
                 20                 25                 30

Val Ala Trp Tyr Gln Gln Lys Pro Gly Lys Ala Pro Lys Leu Leu Ile
         35                 40                 45

Tyr Ser Ala Ser Phe Leu Tyr Ser Gly Val Pro Ser Arg Phe Ser Gly
         50                 55                 60

Ser Arg Ser Gly Thr Asp Phe Thr Leu Thr Ile Ser Ser Leu Gln Pro
65                  70                 75                 80

Glu Asp Phe Ala Thr Tyr Tyr Cys Gln Gln His Tyr Thr Thr Pro Pro
                 85                 90                 95

Thr Phe Gly Gln Gly Thr Lys Val Glu Ile Lys
            100                105

<210> SEQ ID NO 85
<211> LENGTH: 322
<212> TYPE: DNA
<213> ORGANISM: Artificial sequence
<220> FEATURE:
```

<223> OTHER INFORMATION: Trastuzumab VL T31V (6642)DNA

<400> SEQUENCE: 85

```
gatatccaga tgacccagtc tccatcctcc ctgtctgcat ctgtaggaga cagagtcacc      60
atcacttgcc gggcaagtca ggacgtgaac gtggctgtag cgtggtacca gcagaaacca    120
ggtaaggcac cgaagctatt aatttatagt gcgagcttcc tgtacagtgg ggtcccgtcg    180
cgttttagcg gctctcgatc cggcacggat tttacccctga ccattagcag cctgcagcct   240
gaagactttg cgacatatta ttgccaacag cactacacaa ctcctcccac ctttggccag    300
ggtacgaaag ttgaaattaa ag                                             322
```

<210> SEQ ID NO 86
<211> LENGTH: 107
<212> TYPE: PRT
<213> ORGANISM: Artificial sequence
<220> FEATURE:
<223> OTHER INFORMATION: Trastuzumab VL T31V (6642)

<400> SEQUENCE: 86

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Val Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 87
<211> LENGTH: 11
<212> TYPE: PRT
<213> ORGANISM: Artificial sequence
<220> FEATURE:
<223> OTHER INFORMATION: Trastuzumab VH (G99A)(6639)CDR3

<400> SEQUENCE: 87

```
Trp Gly Gly Asp Ala Phe Tyr Ala Met Asp Tyr
1               5                   10
```

<210> SEQ ID NO 88
<211> LENGTH: 11
<212> TYPE: PRT
<213> ORGANISM: Artificial sequence
<220> FEATURE:
<223> OTHER INFORMATION: Trastuzumab VH (G99S)(6640)CDR3

<400> SEQUENCE: 88

```
Trp Gly Gly Asp Ser Phe Tyr Ala Met Asp Tyr
1               5                   10
```

<210> SEQ ID NO 89
<211> LENGTH: 11
<212> TYPE: PRT
<213> ORGANISM: Artificial sequence
<220> FEATURE:

<223> OTHER INFORMATION: Pertuzumab (Tras.L3) (QM)-CDR1

<400> SEQUENCE: 89

Lys Ala Ser Gln Asp Val Ser Thr Ala Val Ala
1               5                   10

<210> SEQ ID NO 90
<211> LENGTH: 7
<212> TYPE: PRT
<213> ORGANISM: Artificial sequence
<220> FEATURE:
<223> OTHER INFORMATION: Pertuzumab (Tras.L3) (QM)-CDR2

<400> SEQUENCE: 90

Ser Ala Ser Phe Arg Tyr Thr
1               5

<210> SEQ ID NO 91
<211> LENGTH: 360
<212> TYPE: DNA
<213> ORGANISM: Artificial sequence
<220> FEATURE:
<223> OTHER INFORMATION: Trastuzumab VH (11345)DNA

<400> SEQUENCE: 91

```
gaagtgcaat tggtggaaag cggcggcggc ctggtgcaac cgggcggcag cctgcgtctg        60
agctgcgcgg cctccggatt aacataaag gacacataca tccactgggt gcgccaagca       120
cctgggaagg gtctcgagtg ggtggctcgg atttacccaa caaatggcta caccaggtat       180
gcggatagcg tgaaaggccg ttttaccatt tcagctgata cttcgaagaa caccgcctat       240
ctgcaaatga acagcctgcg tgcggaagat acggccgtgt attattgctc gcgttgggga       300
ggagacgggt tctatgctat ggattactgg ggccaaggca ccctggtgac ggttagctca       360
```

<210> SEQ ID NO 92
<211> LENGTH: 120
<212> TYPE: PRT
<213> ORGANISM: Artificial sequence
<220> FEATURE:
<223> OTHER INFORMATION: Trastuzumab VH (11345)

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 93
<211> LENGTH: 360

<212> TYPE: DNA
<213> ORGANISM: Artificial sequence
<220> FEATURE:
<223> OTHER INFORMATION: Trastuzumab VH (D98N)(6636)DNA

<400> SEQUENCE: 93

```
gaagtgcaat tggtggaaag cggcggcggc ctggtgcaac cgggcggcag cctgcgtctg    60
agctgcgcgg cctccggatt taacataaag gacacataca tccactgggt gcgccaagca   120
cctgggaagg gtctcgagtg ggtggctcgg atttacccaa caaatggcta caccaggtat   180
gcggatagcg tgaaaggccg ttttaccatt tcagctgata cttcgaagaa caccgcctat   240
ctgcaaatga acagcctgcg tgcggaagat acggccgtgt attattgctc gcgttgggga   300
ggaaacgggt tctatgctat ggattactgg ggccaaggca ccctggtgac ggttagctca   360
```

<210> SEQ ID NO 94
<211> LENGTH: 120
<212> TYPE: PRT
<213> ORGANISM: Artificial sequence
<220> FEATURE:
<223> OTHER INFORMATION: Trastuzumab VH (D98N)(6636)

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asn Gly Phe Tyr Ala Met Asp Tyr Trp Gly Gln
            100                 105                 110

Gly Thr Leu Val Thr Val Ser Ser
        115                 120

<210> SEQ ID NO 95
<211> LENGTH: 360
<212> TYPE: DNA
<213> ORGANISM: Artificial sequence
<220> FEATURE:
<223> OTHER INFORMATION: Trastuzumab VH (D98E)(6637)DNA

<400> SEQUENCE: 95

```
gaagtgcaat tggtggaaag cggcggcggc ctggtgcaac cgggcggcag cctgcgtctg    60
agctgcgcgg cctccggatt taacataaag gacacataca tccactgggt gcgccaagca   120
cctgggaagg gtctcgagtg ggtggctcgg atttacccaa caaatggcta caccaggtat   180
gcggatagcg tgaaaggccg ttttaccatt tcagctgata cttcgaagaa caccgcctat   240
ctgcaaatga acagcctgcg tgcggaagat acggccgtgt attattgctc gcgttgggga   300
ggagagggt tctatgctat ggattactgg ggccaaggca ccctggtgac ggttagctca   360
```

<210> SEQ ID NO 96
<211> LENGTH: 120
<212> TYPE: PRT

<213> ORGANISM: Artificial sequence
<220> FEATURE:
<223> OTHER INFORMATION: Trastuzumab VH (D98E)(6637)

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Glu Gly Phe Tyr Ala Met Asp Tyr Trp Gly Gln
            100                 105                 110

Gly Thr Leu Val Thr Val Ser Ser
        115                 120

<210> SEQ ID NO 97
<211> LENGTH: 360
<212> TYPE: DNA
<213> ORGANISM: Artificial sequence
<220> FEATURE:
<223> OTHER INFORMATION: Trastuzumab VH (D98T)(6638)DNA

<400> SEQUENCE: 97
gaagtgcaat tggtggaaag cggcggcggc ctggtgcaac cgggcggcag cctgcgtctg      60
agctgcgcgg cctccggatt taacataaag gacacataca tccactgggt gcgccaagca     120
cctgggaagg gtctcgagtg ggtggctcgg atttacccaa caaatggcta caccaggtat     180
gcggatagcg tgaaaggccg ttttaccatt tcagctgata cttcgaagaa caccgcctat     240
ctgcaaatga acagcctgcg tgcggaagat acggccgtgt attattgctc gcgttgggga     300
ggaaccgggt tctatgctat ggattactgg ggccaaggca ccctggtgac ggttagctca     360

<210> SEQ ID NO 98
<211> LENGTH: 120
<212> TYPE: PRT
<213> ORGANISM: Artificial sequence
<220> FEATURE:
<223> OTHER INFORMATION: Trastuzumab VH (D98T)(6638)

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

```
Ser Arg Trp Gly Gly Thr Gly Phe Tyr Ala Met Asp Tyr Trp Gly Gln
            100                 105                 110

Gly Thr Leu Val Thr Val Ser Ser
        115                 120

<210> SEQ ID NO 99
<211> LENGTH: 360
<212> TYPE: DNA
<213> ORGANISM: Artificial sequence
<220> FEATURE:
<223> OTHER INFORMATION: Trastuzumab VH (G99A)(6639)DNA

<400> SEQUENCE: 99
gaagtgcaat tggtggaaag cggcggcggc ctggtgcaac cgggcggcag cctgcgtctg      60
agctgcgcgg cctccggatt taacataaag gacacataca tccactgggt gcgccaagca     120
cctgggaagg gtctcgagtg ggtggctcgg atttacccaa caaatggcta caccaggtat     180
gcggatagcg tgaaaggccg ttttaccatt cagctgata cttcgaagaa caccgcctat      240
ctgcaaatga acagcctgcg tgcggaagat acggccgtgt attattgctc gcgttgggga     300
ggagacgcct ctatgctat ggattactgg ggccaaggca ccctggtgac ggttagctca     360

<210> SEQ ID NO 100
<211> LENGTH: 120
<212> TYPE: PRT
<213> ORGANISM: Artificial sequence
<220> FEATURE:
<223> OTHER INFORMATION: Trastuzumab VH (G99A)(6639)

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Ala Ser Tyr Ala Met Asp Tyr Trp Gly Gln
            100                 105                 110

Gly Thr Leu Val Thr Val Ser Ser
        115                 120

<210> SEQ ID NO 101
<211> LENGTH: 360
<212> TYPE: DNA
<213> ORGANISM: Artificial sequence
<220> FEATURE:
<223> OTHER INFORMATION: Trastuzumab VH (G99S)(6640)DNA

<400> SEQUENCE: 101
gaagtgcaat tggtggaaag cggcggcggc ctggtgcaac cgggcggcag cctgcgtctg      60
agctgcgcgg cctccggatt taacataaag gacacataca tccactgggt gcgccaagca     120
cctgggaagg gtctcgagtg ggtggctcgg atttacccaa caaatggcta caccaggtat     180
```

-continued

```
gcggatagcg tgaaaggccg ttttaccatt tcagctgata cttcgaagaa caccgcctat    240
ctgcaaatga acagcctgcg tgcggaagat acggccgtgt attattgctc gcgttgggga    300
ggagacagct tctatgctat ggattactgg ggccaaggca ccctggtgac ggttagctca    360
```

<210> SEQ ID NO 102
<211> LENGTH: 120
<212> TYPE: PRT
<213> ORGANISM: Artificial sequence
<220> FEATURE:
<223> OTHER INFORMATION: Trastuzumab VH (G99S)(6640)

<400> SEQUENCE: 102

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Ser Phe Tyr Ala Met Asp Tyr Trp Gly Gln
            100                 105                 110

Gly Thr Leu Val Thr Val Ser Ser
        115                 120
```

<210> SEQ ID NO 103
<211> LENGTH: 11
<212> TYPE: PRT
<213> ORGANISM: Artificial sequence
<220> FEATURE:
<223> OTHER INFORMATION: Trastuzumab VL T31A (6641)CDR1

<400> SEQUENCE: 103

```
Arg Ala Ser Gln Asp Val Asn Ala Ala Val Ala
1               5                   10
```

<210> SEQ ID NO 104
<211> LENGTH: 11
<212> TYPE: PRT
<213> ORGANISM: Artificial sequence
<220> FEATURE:
<223> OTHER INFORMATION: Trastuzumab VL T31V (6642)CDR1

<400> SEQUENCE: 104

```
Arg Ala Ser Gln Asp Val Asn Val Ala Val Ala
1               5                   10
```

<210> SEQ ID NO 105
<211> LENGTH: 120
<212> TYPE: PRT
<213> ORGANISM: Artificial sequence
<220> FEATURE:
<223> OTHER INFORMATION: Trastuzumab CDRG VH (D98ECDRG)

<400> SEQUENCE: 105

```
Glu Val Gln Leu Val Gln Ser Gly Ala Glu Val Lys Lys Pro Gly Ala
1               5                   10                  15
```

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Arg Ile Tyr Pro Thr Asn Gly Tyr Thr Arg Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ser Arg Trp Gly Gly Glu Gly Phe Tyr Ala Met Asp Tyr Trp Gly Gln
            100                 105                 110

Gly Thr Met Val Thr Val Ser Ser
        115                 120

<210> SEQ ID NO 106
<211> LENGTH: 107
<212> TYPE: PRT
<213> ORGANISM: Artificial sequence
<220> FEATURE:
<223> OTHER INFORMATION: Trastuzumab CDRG VL (N30TCDRG)

<400> SEQUENCE: 106

Asp Ile Gln Leu Thr Gln Pro Pro Ser Val Ser Val Ala Pro Gly Gln
1               5                   10                  15

Thr Ala Arg Ile Thr Cys Gly Ala Ser Gln Asp Val Ser Thr Ala Val
            20                  25                  30

Ala Trp Tyr Gln Gln Lys Pro Gly Gln Ala Pro Val Leu Val Val Tyr
        35                  40                  45

Ser Ala Ser Phe Leu Tyr Ser Gly Ile Pro Ser Arg Phe Ser Gly Ser
    50                  55                  60

Arg Ser Gly Thr Asp Phe Thr Leu Thr Ile Ser Arg Val Glu Ala Gly
65                  70                  75                  80

Asp Glu Ala Asp Tyr Tyr Cys Gln Gln His Tyr Thr Thr Pro Pro Thr
                85                  90                  95

Phe Gly Thr Gly Thr Lys Val Thr Val Leu Arg
            100                 105

<210> SEQ ID NO 107
<211> LENGTH: 11
<212> TYPE: PRT
<213> ORGANISM: Artificial sequence
<220> FEATURE:
<223> OTHER INFORMATION: Trastuzumab CDRG VL CDR1

<400> SEQUENCE: 107

Gly Ala Ser Gln Asp Val Ser Thr Ala Val Ala
1               5                   10

<210> SEQ ID NO 108
<211> LENGTH: 17
<212> TYPE: PRT
<213> ORGANISM: Artificial sequence
<220> FEATURE:
<223> OTHER INFORMATION: Trastuzumab CDRG VH CDR2

<400> SEQUENCE: 108

Arg Ile Tyr Pro Thr Asn Gly Tyr Thr Arg Tyr Ala Gln Lys Phe Gln
1               5                   10                  15

Gly

<210> SEQ ID NO 109
<211> LENGTH: 453
<212> TYPE: PRT
<213> ORGANISM: Artificial sequence
<220> FEATURE:
<223> OTHER INFORMATION: XPertuzumab heavy chain (VHCL)

<400> SEQUENCE: 109

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Val Ala Ala Pro Ser Val Phe
        115                 120                 125

Ile Phe Pro Pro Ser Asp Glu Gln Leu Lys Ser Gly Thr Ala Ser Val
    130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
        195                 200                 205

Thr His Gln Gly Leu Ser Ser Pro Val Thr Lys Ser Phe Asn Arg Gly
    210                 215                 220

Glu Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
        355                 360                 365
```

```
Val Ser Leu Trp Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
        450

<210> SEQ ID NO 110
<211> LENGTH: 212
<212> TYPE: PRT
<213> ORGANISM: Artificial sequence
<220> FEATURE:
<223> OTHER INFORMATION: Pertuzumab light chain (VLCH1)

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys
    210

<210> SEQ ID NO 111
<211> LENGTH: 450
<212> TYPE: PRT
<213> ORGANISM: Artificial sequence
<220> FEATURE:
<223> OTHER INFORMATION: Trastuzumab CDRG heavy chain (VHCH1)
```

<400> SEQUENCE: 111

```
Gln Val Gln Leu Val Gln Ser Gly Ala Glu Val Lys Lys Pro Gly Ala
1               5                   10                  15
Ser Val Lys Val Ser Cys Lys Ala Ser Gly Phe Asn Ile Lys Asp Thr
            20                  25                  30
Tyr Ile His Trp Val Arg Gln Ala Pro Gly Gln Gly Leu Glu Trp Met
        35                  40                  45
Gly Arg Ile Tyr Pro Thr Asn Gly Tyr Thr Arg Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ser Arg Trp Gly Gly Glu Gly Phe Tyr Ala Met Asp Tyr Trp Gly Gln
            100                 105                 110
Gly Thr Met Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Cys
            340                 345                 350
Thr Leu Pro Pro Ser Arg Asp Glu Leu Thr Lys Asn Gln Val Ser Leu
        355                 360                 365
Ser Cys Ala Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Val Ser Lys Leu Thr Val Asp
                405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 112
<211> LENGTH: 213
<212> TYPE: PRT
<213> ORGANISM: Artificial sequence
<220> FEATURE:
<223> OTHER INFORMATION: Trastuzumab CDRG light chain (VLCL)

<400> SEQUENCE: 112

Asp Ile Gln Leu Thr Gln Pro Pro Ser Val Ser Val Ala Pro Gly Gln
1               5                   10                  15

Thr Ala Arg Ile Thr Cys Gly Ala Ser Gln Asp Val Ser Thr Ala Val
            20                  25                  30

Ala Trp Tyr Gln Gln Lys Pro Gly Gln Ala Pro Val Leu Val Val Tyr
        35                  40                  45

Ser Ala Ser Phe Leu Tyr Ser Gly Ile Pro Ser Arg Phe Ser Gly Ser
    50                  55                  60

Arg Ser Gly Thr Asp Phe Thr Leu Thr Ile Ser Arg Val Glu Ala Gly
65                  70                  75                  80

Asp Glu Ala Asp Tyr Tyr Cys Gln Gln His Tyr Thr Thr Pro Pro Thr
                85                  90                  95

Phe Gly Thr Gly Thr Lys Val Thr Val Leu Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 113
<211> LENGTH: 107
<212> TYPE: PRT
<213> ORGANISM: Artificial sequence
<220> FEATURE:
<223> OTHER INFORMATION: Pertuzumab wt CL

<400> SEQUENCE: 113

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
```

```
                35                  40                  45
Ser Gly Asn Ser Gln Glu Ser Val Thr Glu Gln Asp Ser Lys Asp Ser
 50                  55                  60
Thr Tyr Ser Leu Ser Ser Thr Leu Thr Leu Ser Lys Ala Asp Tyr Glu
 65                  70                  75                  80
Lys His Lys Val Tyr Ala Cys Glu Val Thr His Gln Gly Leu Ser Ser
                 85                  90                  95
Pro Val Thr Lys Ser Phe Asn Arg Gly Glu Cys
            100                 105
```

<210> SEQ ID NO 114
<211> LENGTH: 98
<212> TYPE: PRT
<213> ORGANISM: Artificial sequence
<220> FEATURE:
<223> OTHER INFORMATION: Pertuzumab wt CH1

<400> SEQUENCE: 114

```
Ala Ser Thr Lys Gly Pro Ser Val Phe Pro Leu Ala Pro Ser Ser Lys
 1               5                  10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
 50                  55                  60
Leu Ser Ser Val Val Thr Val Pro Ser Ser Ser Leu Gly Thr Gln Thr
 65                  70                  75                  80
Tyr Ile Cys Asn Val Asn His Lys Pro Ser Asn Thr Lys Val Asp Lys
                 85                  90                  95
Lys Val
```

<210> SEQ ID NO 115
<211> LENGTH: 107
<212> TYPE: PRT
<213> ORGANISM: Artificial sequence
<220> FEATURE:
<223> OTHER INFORMATION: Trastuzumab CH1

<400> SEQUENCE: 115

```
Ala Ser Thr Lys Gly Pro Ser Val Phe Pro Leu Ala Pro Ser Ser Lys
 1               5                  10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
 50                  55                  60
Leu Ser Ser Val Val Thr Val Pro Ser Ser Ser Leu Gly Thr Gln Thr
 65                  70                  75                  80
Tyr Ile Cys Asn Val Asn His Lys Pro Ser Asn Thr Lys Val Asp Lys
                 85                  90                  95
Lys Val Glu Pro Lys Ser Cys Asp Lys Thr His
            100                 105
```

<210> SEQ ID NO 116
<211> LENGTH: 106
<212> TYPE: PRT

<213> ORGANISM: Artificial sequence
<220> FEATURE:
<223> OTHER INFORMATION: Trastuzumab CL

<400> SEQUENCE: 116

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 117
<211> LENGTH: 120
<212> TYPE: PRT
<213> ORGANISM: Artificial sequence
<220> FEATURE:
<223> OTHER INFORMATION: Trastuzumab VH (D98E)

<400> SEQUENCE: 117

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Glu Gly Phe Tyr Ala Met Asp Tyr Trp Gly Gln
            100                 105                 110

Gly Thr Leu Val Thr Val Ser Ser
        115                 120
```

<210> SEQ ID NO 118
<211> LENGTH: 108
<212> TYPE: PRT
<213> ORGANISM: Artificial sequence
<220> FEATURE:
<223> OTHER INFORMATION: Trastuzumab VL (T31V)

<400> SEQUENCE: 118

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Val Ala
            20                  25                  30

Val Ala Trp Tyr Gln Gln Lys Pro Gly Lys Ala Pro Lys Leu Leu Ile
        35                  40                  45
```

```
Tyr Ser Ala Ser Phe Leu Tyr Ser Gly Val Pro Ser Arg Phe Ser Gly
         50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                     85                  90                  95

Thr Phe Gly Gln Gly Thr Lys Val Glu Ile Lys Arg
                    100                 105
```

<210> SEQ ID NO 119
<211> LENGTH: 453
<212> TYPE: PRT
<213> ORGANISM: Artificial sequence
<220> FEATURE:
<223> OTHER INFORMATION: Pertuzumab heavy chain

<400> SEQUENCE: 119

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
             20                  25                  30

Thr Met Asp Trp Val Arg Gln Ala Pro Gly Lys Gly Leu Glu Trp Val
         35                  40                  45

Ala Asp Val Asn Pro Asn Ser Gly Gly Ser Ile Tyr Asn Gln Arg Phe
 50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Asn Leu Gly Pro Ser Phe Tyr Phe Asp Tyr Trp Gly Gln Gly
                    100                 105                 110

Thr Leu Val Thr Val Ser Ser Ala Ser Val Ala Ala Pro Ser Val Phe
            115                 120                 125

Ile Phe Pro Pro Ser Asp Glu Gln Leu Lys Ser Gly Thr Ala Ser Val
        130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                    165                 170                 175

Glu Gln Asp Ser Lys Asp Ser Thr Tyr Ser Leu Ser Ser Thr Leu Thr
                180                 185                 190

Leu Ser Lys Ala Asp Tyr Glu Lys His Lys Val Tyr Ala Cys Glu Val
            195                 200                 205

Thr His Gln Gly Leu Ser Ser Pro Val Thr Lys Ser Phe Asn Arg Gly
        210                 215                 220

Glu Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                    245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300
```

```
Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Cys Thr Leu Pro Pro Ser Arg Asp Glu Leu Thr Lys Asn Gln
        355                 360                 365

Val Ser Leu Ser Cys Ala Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 120
<211> LENGTH: 214
<212> TYPE: PRT
<213> ORGANISM: Artificial sequence
<220> FEATURE:
<223> OTHER INFORMATION: Pertuzumab light chain

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210

<210> SEQ ID NO 121
<211> LENGTH: 450
<212> TYPE: PRT
<213> ORGANISM: Artificial sequence
<220> FEATURE:
<223> OTHER INFORMATION: XTrastuzumab heavy chain

<400> SEQUENCE: 121

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Glu Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

```
Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 122
<211> LENGTH: 212
<212> TYPE: PRT
<213> ORGANISM: Artificial sequence
<220> FEATURE:
<223> OTHER INFORMATION: XTrastuzumab light chain

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Val Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys
    210

<210> SEQ ID NO 123
<211> LENGTH: 214
<212> TYPE: PRT
<213> ORGANISM: Artificial sequence
```

```
<220> FEATURE:
<223> OTHER INFORMATION: Light chain (kappa) [Trastuzumab 1016]

<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 124
<211> LENGTH: 711
<212> TYPE: PRT
<213> ORGANISM: Artificial sequence
<220> FEATURE:
<223> OTHER INFORMATION: Heavy chain [Trastuzumab + scFv Omnitarg RB40]

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
```

```
            115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys Gly Gly Gly Gly Ser Gly Gly Gly Gly Ser Gly Gly Gly Gly
450                 455                 460
Ser Glu Val Gln Leu Val Glu Ser Gly Gly Leu Val Gln Pro Gly Gly
465                 470                 475                 480
Gly Ser Leu Arg Leu Ser Cys Ala Ala Ser Gly Phe Thr Phe Thr Asp
                485                 490                 495
Tyr Thr Met Asp Trp Val Arg Gln Ala Pro Gly Lys Cys Leu Glu Trp
            500                 505                 510
Val Ala Asp Val Asn Pro Asn Ser Gly Gly Ser Ile Tyr Asn Gln Arg
        515                 520                 525
Phe Lys Gly Arg Phe Thr Leu Ser Val Asp Arg Ser Lys Asn Thr Leu
530                 535                 540
```

```
Tyr Leu Gln Met Asn Ser Leu Arg Ala Glu Asp Thr Ala Val Tyr Tyr
545                 550                 555                 560

Cys Ala Arg Asn Leu Gly Pro Ser Phe Tyr Phe Asp Tyr Trp Gly Gln
            565                 570                 575

Gly Thr Leu Val Thr Val Ser Ser Gly Gly Gly Gly Ser Gly Gly Gly
        580                 585                 590

Gly Ser Gly Gly Gly Ser Gly Gly Gly Ser Asp Ile Gln Met
    595                 600                 605

Thr Gln Ser Pro Ser Ser Leu Ser Ala Ser Val Gly Asp Arg Val Thr
        610                 615                 620

Ile Thr Cys Lys Ala Ser Gln Asp Val Ser Ile Gly Val Ala Trp Tyr
625                 630                 635                 640

Gln Gln Lys Pro Gly Lys Ala Pro Lys Leu Leu Ile Tyr Ser Ala Ser
            645                 650                 655

Tyr Arg Tyr Thr Gly Val Pro Ser Arg Phe Ser Gly Ser Gly Ser Gly
            660                 665                 670

Thr Asp Phe Thr Leu Thr Ile Ser Ser Leu Gln Pro Glu Asp Phe Ala
            675                 680                 685

Thr Tyr Tyr Cys Gln Gln Tyr Tyr Ile Tyr Pro Tyr Thr Phe Gly Cys
            690                 695                 700

Gly Thr Lys Val Glu Ile Lys
705                 710

<210> SEQ ID NO 125
<211> LENGTH: 471
<212> TYPE: PRT
<213> ORGANISM: Artificial sequence
<220> FEATURE:
<223> OTHER INFORMATION: Light chain [scFv Trastuzumab + Omnitarg RB34]

<400> SEQUENCE: 125

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Arg Ile Tyr Pro Thr
                165                 170                 175

Asn Gly Tyr Thr Arg Tyr Ala Asp Ser Val Lys Gly Arg Phe Thr Ile
            180                 185                 190
```

```
Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser Gly Gly Gly Gly Ser Gly Gly Gly Gly Ser Gly Gly Gly Gly
                245                 250                 255

Ser Asp Ile Gln Met Thr Gln Ser Pro Ser Ser Leu Ser Ala Ser Val
            260                 265                 270

Gly Asp Arg Val Thr Ile Thr Cys Lys Ala Ser Gln Asp Val Ser Ile
        275                 280                 285

Gly Val Ala Trp Tyr Gln Gln Lys Pro Gly Lys Ala Pro Lys Leu Leu
    290                 295                 300

Ile Tyr Ser Ala Ser Tyr Arg Tyr Thr Gly Val Pro Ser Arg Phe Ser
305                 310                 315                 320

Gly Ser Gly Ser Gly Thr Asp Phe Thr Leu Thr Ile Ser Ser Leu Gln
                325                 330                 335

Pro Glu Asp Phe Ala Thr Tyr Tyr Cys Gln Gln Tyr Tyr Ile Tyr Pro
            340                 345                 350

Tyr Thr Phe Gly Gln Gly Thr Lys Val Glu Ile Lys Arg Thr Val Ala
        355                 360                 365

Ala Pro Ser Val Phe Ile Phe Pro Pro Ser Asp Glu Gln Leu Lys Ser
    370                 375                 380

Gly Thr Ala Ser Val Val Cys Leu Leu Asn Asn Phe Tyr Pro Arg Glu
385                 390                 395                 400

Ala Lys Val Gln Trp Lys Val Asp Asn Ala Leu Gln Ser Gly Asn Ser
                405                 410                 415

Gln Glu Ser Val Thr Glu Gln Asp Ser Lys Asp Ser Thr Tyr Ser Leu
            420                 425                 430

Ser Ser Thr Leu Thr Leu Ser Lys Ala Asp Tyr Glu Lys His Lys Val
        435                 440                 445

Tyr Ala Cys Glu Val Thr His Gln Gly Leu Ser Ser Pro Val Thr Lys
    450                 455                 460

Ser Phe Asn Arg Gly Glu Cys
465                 470

<210> SEQ ID NO 126
<211> LENGTH: 449
<212> TYPE: PRT
<213> ORGANISM: Artificial sequence
<220> FEATURE:
<223> OTHER INFORMATION: Heavy chain (Omnitarg RB33)

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 127
<211> LENGTH: 470
<212> TYPE: PRT
<213> ORGANISM: Artificial sequence
<220> FEATURE:
<223> OTHER INFORMATION: Light chain [Trastuzumab + scFvOmnitarg RB35]

<400> SEQUENCE: 127

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Gly Gly Gly Gly Ser Asp Ile Gln Met Thr Gln Ser Pro Ser Ser Leu
225                 230                 235                 240

Ser Ala Ser Val Gly Asp Arg Val Thr Ile Thr Cys Lys Ala Ser Gln
                245                 250                 255

Asp Val Ser Ile Gly Val Ala Trp Tyr Gln Gln Lys Pro Gly Lys Ala
            260                 265                 270

Pro Lys Leu Leu Ile Tyr Ser Ala Ser Tyr Arg Tyr Thr Gly Val Pro
        275                 280                 285

Ser Arg Phe Ser Gly Ser Gly Ser Gly Thr Asp Phe Thr Leu Thr Ile
    290                 295                 300

Ser Ser Leu Gln Pro Glu Asp Phe Ala Thr Tyr Tyr Cys Gln Gln Tyr
305                 310                 315                 320

Tyr Ile Tyr Pro Tyr Thr Phe Gly Gln Gly Thr Lys Val Glu Ile Lys
                325                 330                 335

Gly Gly Gly Gly Ser Gly Gly Gly Gly Ser Gly Gly Gly Gly Ser Glu
            340                 345                 350

Val Gln Leu Val Glu Ser Gly Gly Gly Leu Val Gln Pro Gly Gly Ser
        355                 360                 365

Leu Arg Leu Ser Cys Ala Ala Ser Gly Phe Thr Phe Thr Asp Tyr Thr
    370                 375                 380

Met Asp Trp Val Arg Gln Ala Pro Gly Lys Gly Leu Glu Trp Val Ala
385                 390                 395                 400

Asp Val Asn Pro Asn Ser Gly Gly Ser Ile Tyr Asn Gln Arg Phe Lys
```

```
                            405                 410                 415

Gly Arg Phe Thr Leu Ser Val Asp Arg Ser Lys Asn Thr Leu Tyr Leu
            420                 425                 430

Gln Met Asn Ser Leu Arg Ala Glu Asp Thr Ala Val Tyr Tyr Cys Ala
            435                 440                 445

Arg Asn Leu Gly Pro Ser Phe Tyr Phe Asp Tyr Trp Gly Gln Gly Thr
450                 455                 460

Leu Val Thr Val Ser Ser
465                 470

<210> SEQ ID NO 128
<211> LENGTH: 450
<212> TYPE: PRT
<213> ORGANISM: Artificial sequence
<220> FEATURE:
<223> OTHER INFORMATION: Heavy chain [Trastuzumab 1036]

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
```

```
                290                 295                 300
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 129
<211> LENGTH: 214
<212> TYPE: PRT
<213> ORGANISM: Artificial sequence
<220> FEATURE:
<223> OTHER INFORMATION: Light chain (kappa) [Trastuzumab 1016]

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
```

Phe Asn Arg Gly Glu Cys
210

<210> SEQ ID NO 130
<211> LENGTH: 711
<212> TYPE: PRT
<213> ORGANISM: Artificial sequence
<220> FEATURE:
<223> OTHER INFORMATION: Heavy chain [Trastuzumab + scFvOmnitarg RB43]

<400> SEQUENCE: 130

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr

```
                   340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys Gly Gly Gly Gly Ser Gly Gly Gly Gly Ser Gly Gly Gly Gly
    450                 455                 460
Ser Asp Ile Gln Met Thr Gln Ser Pro Ser Ser Leu Ser Ala Ser Val
465                 470                 475                 480
Gly Asp Arg Val Thr Ile Thr Cys Lys Ala Ser Gln Asp Val Ser Ile
                485                 490                 495
Gly Val Ala Trp Tyr Gln Gln Lys Pro Gly Lys Ala Pro Lys Leu Leu
            500                 505                 510
Ile Tyr Ser Ala Ser Tyr Arg Tyr Thr Gly Val Pro Ser Arg Phe Ser
        515                 520                 525
Gly Ser Gly Ser Gly Thr Asp Phe Thr Leu Thr Ile Ser Ser Leu Gln
    530                 535                 540
Pro Glu Asp Phe Ala Thr Tyr Tyr Cys Gln Gln Tyr Tyr Ile Tyr Pro
545                 550                 555                 560
Tyr Thr Phe Gly Cys Gly Thr Lys Val Glu Ile Lys Gly Gly Gly Gly
                565                 570                 575
Ser Gly Gly Gly Gly Ser Gly Gly Gly Gly Ser Gly Gly Gly Gly Ser
            580                 585                 590
Glu Val Gln Leu Val Glu Ser Gly Gly Gly Leu Val Gln Pro Gly Gly
        595                 600                 605
Ser Leu Arg Leu Ser Cys Ala Ala Ser Gly Phe Thr Phe Thr Asp Tyr
    610                 615                 620
Thr Met Asp Trp Val Arg Gln Ala Pro Gly Lys Cys Leu Glu Trp Val
625                 630                 635                 640
Ala Asp Val Asn Pro Asn Ser Gly Gly Ser Ile Tyr Asn Gln Arg Phe
                645                 650                 655
Lys Gly Arg Phe Thr Leu Ser Val Asp Arg Ser Lys Asn Thr Leu Tyr
            660                 665                 670
Leu Gln Met Asn Ser Leu Arg Ala Glu Asp Thr Ala Val Tyr Tyr Cys
        675                 680                 685
Ala Arg Asn Leu Gly Pro Ser Phe Tyr Phe Asp Tyr Trp Gly Gln Gly
    690                 695                 700
Thr Leu Val Thr Val Ser Ser
705                 710

<210> SEQ ID NO 131
<211> LENGTH: 480
<212> TYPE: PRT
<213> ORGANISM: Artificial sequence
<220> FEATURE:
<223> OTHER INFORMATION: Light chain [Trastuzumab + scFv Omnitarg RB61]
```

<400> SEQUENCE: 131

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Gly Gly Gly Gly Ser Gly Gly Gly Ser Asp Ile Gln Met Thr Gln
225                 230                 235                 240

Ser Pro Ser Ser Leu Ser Ala Ser Val Gly Asp Arg Val Thr Ile Thr
                245                 250                 255

Cys Lys Ala Ser Gln Asp Val Ser Ile Gly Val Ala Trp Tyr Gln Gln
            260                 265                 270

Lys Pro Gly Lys Ala Pro Lys Leu Leu Ile Tyr Ser Ala Ser Tyr Arg
        275                 280                 285

Tyr Thr Gly Val Pro Ser Arg Phe Ser Gly Ser Gly Ser Gly Thr Asp
    290                 295                 300

Phe Thr Leu Thr Ile Ser Ser Leu Gln Pro Glu Asp Phe Ala Thr Tyr
305                 310                 315                 320

Tyr Cys Gln Gln Tyr Tyr Ile Tyr Pro Tyr Thr Phe Gly Cys Gly Thr
                325                 330                 335

Lys Val Glu Ile Lys Gly Gly Gly Ser Gly Gly Gly Gly Ser Gly
            340                 345                 350

Gly Gly Gly Ser Gly Gly Gly Ser Glu Val Gln Leu Val Glu Ser
        355                 360                 365

Gly Gly Gly Leu Val Gln Pro Gly Gly Ser Leu Arg Leu Ser Cys Ala
    370                 375                 380

Ala Ser Gly Phe Thr Phe Thr Asp Tyr Thr Met Asp Trp Val Arg Gln
385                 390                 395                 400

Ala Pro Gly Lys Cys Leu Glu Trp Val Ala Asp Val Asn Pro Asn Ser
                405                 410                 415
```

```
Gly Gly Ser Ile Tyr Asn Gln Arg Phe Lys Gly Arg Phe Thr Leu Ser
            420                 425                 430

Val Asp Arg Ser Lys Asn Thr Leu Tyr Leu Gln Met Asn Ser Leu Arg
            435                 440                 445

Ala Glu Asp Thr Ala Val Tyr Tyr Cys Ala Arg Asn Leu Gly Pro Ser
            450                 455                 460

Phe Tyr Phe Asp Tyr Trp Gly Gln Gly Thr Leu Val Thr Val Ser Ser
465             470                 475                 480

<210> SEQ ID NO 132
<211> LENGTH: 450
<212> TYPE: PRT
<213> ORGANISM: Artificial sequence
<220> FEATURE:
<223> OTHER INFORMATION: Heavy chain [Trastuzumab 1036]

<400> SEQUENCE: 132

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
65              70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 133
<211> LENGTH: 696
<212> TYPE: PRT
<213> ORGANISM: Artificial sequence
<220> FEATURE:
<223> OTHER INFORMATION: scFab Trastuzumab heavy chain 1

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Val Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys Gly Gly Gly Ser Gly Gly Gly Ser
    210             215             220
Gly Gly Gly Gly Ser Gly Gly Gly Ser Gly Gly Gly Ser Gly
225             230             235             240
Gly Gly Gly Ser Gly Gly Glu Val Gln Leu Val Glu Ser Gly Gly Gly
            245             250             255
Leu Val Gln Pro Gly Gly Ser Leu Arg Leu Ser Cys Ala Ala Ser Gly
        260             265             270
Phe Asn Ile Lys Asp Thr Tyr Ile His Trp Val Arg Gln Ala Pro Gly
    275             280             285
Lys Gly Leu Glu Trp Val Ala Arg Ile Tyr Pro Thr Asn Gly Tyr Thr
290             295             300
Arg Tyr Ala Asp Ser Val Lys Gly Arg Phe Thr Ile Ser Ala Asp Thr
305             310             315             320
Ser Lys Asn Thr Ala Tyr Leu Gln Met Asn Ser Leu Arg Ala Glu Asp
            325             330             335
Thr Ala Val Tyr Tyr Cys Ser Arg Trp Gly Gly Gly Phe Tyr Ala
        340             345             350
Met Asp Tyr Trp Gly Gln Gly Thr Leu Val Thr Val Ser Ser Ala Ser
    355             360             365
Thr Lys Gly Pro Ser Val Phe Pro Leu Ala Pro Ser Ser Lys Ser Thr
370             375             380
Ser Gly Gly Thr Ala Ala Leu Gly Cys Leu Val Lys Asp Tyr Phe Pro
385             390             395             400
Glu Pro Val Thr Val Ser Trp Asn Ser Gly Ala Leu Thr Ser Gly Val
            405             410             415
His Thr Phe Pro Ala Val Leu Gln Ser Ser Gly Leu Tyr Ser Leu Ser
        420             425             430
Ser Val Val Thr Val Pro Ser Ser Ser Leu Gly Thr Gln Thr Tyr Ile
    435             440             445
Cys Asn Val Asn His Lys Pro Ser Asn Thr Lys Val Asp Lys Lys Val
450             455             460
Glu Pro Lys Ser Cys Asp Lys Thr His Thr Cys Pro Pro Cys Pro Ala
465             470             475             480
Pro Glu Leu Leu Gly Gly Pro Ser Val Phe Leu Phe Pro Pro Lys Pro
            485             490             495
Lys Asp Thr Leu Met Ile Ser Arg Thr Pro Glu Val Thr Cys Val Val
        500             505             510
Val Asp Val Ser His Glu Asp Pro Glu Val Lys Phe Asn Trp Tyr Val
    515             520             525
Asp Gly Val Glu Val His Asn Ala Lys Thr Lys Pro Arg Glu Glu Gln
530             535             540
Tyr Asn Ser Thr Tyr Arg Val Val Ser Val Leu Thr Val Leu His Gln
545             550             555             560
Asp Trp Leu Asn Gly Lys Glu Tyr Lys Cys Lys Val Ser Asn Lys Ala
            565             570             575
Leu Pro Ala Pro Ile Glu Lys Thr Ile Ser Lys Ala Lys Gly Gln Pro
        580             585             590
Arg Glu Pro Gln Val Tyr Thr Leu Pro Pro Cys Arg Asp Glu Leu Thr
    595             600             605
Lys Asn Gln Val Ser Leu Trp Cys Leu Val Lys Gly Phe Tyr Pro Ser
610             615             620
```

Asp Ile Ala Val Glu Trp Glu Ser Asn Gly Gln Pro Glu Asn Asn Tyr
625                 630                 635                 640

Lys Thr Thr Pro Pro Val Leu Asp Ser Asp Gly Ser Phe Phe Leu Tyr
            645                 650                 655

Ser Lys Leu Thr Val Asp Lys Ser Arg Trp Gln Gln Gly Asn Val Phe
        660                 665                 670

Ser Cys Ser Val Met His Glu Ala Leu His Asn His Tyr Thr Gln Lys
    675                 680                 685

Ser Leu Ser Leu Ser Pro Gly Lys
    690                 695

<210> SEQ ID NO 134
<211> LENGTH: 449
<212> TYPE: PRT
<213> ORGANISM: Artificial sequence
<220> FEATURE:
<223> OTHER INFORMATION: Pertuzumab heavy chain 2

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

```
Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 135
<211> LENGTH: 214
<212> TYPE: PRT
<213> ORGANISM: Artificial sequence
<220> FEATURE:
<223> OTHER INFORMATION: Pertuzumab light chain 1

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

-continued

```
                195                 200                 205
Phe Asn Arg Gly Glu Cys
    210

<210> SEQ ID NO 136
<211> LENGTH: 449
<212> TYPE: PRT
<213> ORGANISM: Artificial sequence
<220> FEATURE:
<223> OTHER INFORMATION: Pertuzumab heavy chain 1

<400> SEQUENCE: 136

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
```

```
                    340                 345                 350
Leu Pro Pro Ser Arg Asp Glu Leu Thr Lys Asn Gln Val Ser Leu Ser
                355                 360                 365

Cys Ala Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 137
<211> LENGTH: 214
<212> TYPE: PRT
<213> ORGANISM: Artificial sequence
<220> FEATURE:
<223> OTHER INFORMATION: Pertuzumab light chain 1

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 138
<211> LENGTH: 696
<212> TYPE: PRT
<213> ORGANISM: Artificial sequence
```

```
<220> FEATURE:
<223> OTHER INFORMATION: scFab Trastuzumab heavy chain 2

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Glu Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys Gly Gly Gly Gly Ser Gly Gly Gly Gly Ser Gly Gly Gly Gly
            450                 455                 460

Ser Gly Gly Gly Gly Ser Gly Gly Gly Ser Gly Gly Gly Gly Ser
465                 470                 475                 480

Gly Gly Asp Ile Gln Met Thr Gln Ser Pro Ser Ser Leu Ser Ala Ser
                485                 490                 495

Val Gly Asp Arg Val Thr Ile Thr Cys Arg Ala Ser Gln Asp Val Asn
            500                 505                 510

Val Ala Val Ala Trp Tyr Gln Gln Lys Pro Gly Lys Ala Pro Lys Leu
            515                 520                 525

Leu Ile Tyr Ser Ala Ser Phe Leu Tyr Ser Gly Val Pro Ser Arg Phe
            530                 535                 540

Ser Gly Ser Arg Ser Gly Thr Asp Phe Thr Leu Thr Ile Ser Ser Leu
545                 550                 555                 560

Gln Pro Glu Asp Phe Ala Thr Tyr Tyr Cys Gln Gln His Tyr Thr Thr
            565                 570                 575

Pro Pro Thr Phe Gly Gln Gly Thr Lys Val Glu Ile Lys Arg Thr Val
            580                 585                 590

Ala Ala Pro Ser Val Phe Ile Phe Pro Pro Ser Asp Glu Gln Leu Lys
            595                 600                 605

Ser Gly Thr Ala Ser Val Val Cys Leu Leu Asn Asn Phe Tyr Pro Arg
            610                 615                 620

Glu Ala Lys Val Gln Trp Lys Val Asp Asn Ala Leu Gln Ser Gly Asn
625                 630                 635                 640

Ser Gln Glu Ser Val Thr Glu Gln Asp Ser Lys Asp Ser Thr Tyr Ser
            645                 650                 655

Leu Ser Ser Thr Leu Thr Leu Ser Lys Ala Asp Tyr Glu Lys His Lys
            660                 665                 670

Val Tyr Ala Cys Glu Val Thr His Gln Gly Leu Ser Ser Pro Val Thr
            675                 680                 685

Lys Ser Phe Asn Arg Gly Glu Cys
            690                 695

<210> SEQ ID NO 139
<211> LENGTH: 695
<212> TYPE: PRT
<213> ORGANISM: Artificial sequence
<220> FEATURE:
<223> OTHER INFORMATION: scFab Pertuzumab heavy chain 1

<400> SEQUENCE: 139

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
            35                  40                  45

Ala Asp Val Asn Pro Asn Ser Gly Gly Ser Ile Tyr Asn Gln Arg Phe
        50                  55                  60
```

```
Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
            355                 360                 365

Cys Ala Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys Gly Gly Gly Gly Ser Gly Gly Gly Gly Ser Gly Gly Gly Gly Ser
            450                 455                 460

Gly Gly Gly Gly Ser Gly Gly Gly Gly Ser Gly Gly Gly Gly Ser Gly
465                 470                 475                 480
```

```
Gly Asp Ile Gln Met Thr Gln Ser Pro Ser Ser Leu Ser Ala Ser Val
            485                 490                 495

Gly Asp Arg Val Thr Ile Thr Cys Lys Ala Ser Gln Asp Val Ser Ile
        500                 505                 510

Gly Val Ala Trp Tyr Gln Gln Lys Pro Gly Lys Ala Pro Lys Leu Leu
            515                 520                 525

Ile Tyr Ser Ala Ser Tyr Arg Tyr Thr Gly Val Pro Ser Arg Phe Ser
    530                 535                 540

Gly Ser Gly Ser Gly Thr Asp Phe Thr Leu Thr Ile Ser Ser Leu Gln
545                 550                 555                 560

Pro Glu Asp Phe Ala Thr Tyr Tyr Cys Gln Gln Tyr Tyr Ile Tyr Pro
                565                 570                 575

Tyr Thr Phe Gly Gln Gly Thr Lys Val Glu Ile Lys Arg Thr Val Ala
            580                 585                 590

Ala Pro Ser Val Phe Ile Phe Pro Pro Ser Asp Glu Gln Leu Lys Ser
        595                 600                 605

Gly Thr Ala Ser Val Val Cys Leu Leu Asn Asn Phe Tyr Pro Arg Glu
    610                 615                 620

Ala Lys Val Gln Trp Lys Val Asp Asn Ala Leu Gln Ser Gly Asn Ser
625                 630                 635                 640

Gln Glu Ser Val Thr Glu Gln Asp Ser Lys Asp Ser Thr Tyr Ser Leu
                645                 650                 655

Ser Ser Thr Leu Thr Leu Ser Lys Ala Asp Tyr Glu Lys His Lys Val
            660                 665                 670

Tyr Ala Cys Glu Val Thr His Gln Gly Leu Ser Ser Pro Val Thr Lys
        675                 680                 685

Ser Phe Asn Arg Gly Glu Cys
    690                 695

<210> SEQ ID NO 140
<211> LENGTH: 450
<212> TYPE: PRT
<213> ORGANISM: Artificial sequence
<220> FEATURE:
<223> OTHER INFORMATION: Trastuzumab heavy chain 2

<400> SEQUENCE: 140

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Glu Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Cys Arg Asp Glu Leu Thr Lys Asn Gln Val Ser Leu
    355                 360                 365

Trp Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 141
<211> LENGTH: 213
<212> TYPE: PRT
<213> ORGANISM: Artificial sequence
<220> FEATURE:
<223> OTHER INFORMATION: Trastuzumab light chain 2

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Val Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
            50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                    85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu
            210

<210> SEQ ID NO 142
<211> LENGTH: 450
<212> TYPE: PRT
<213> ORGANISM: Artificial sequence
<220> FEATURE:
<223> OTHER INFORMATION: Trastuzumab heavy chain 1

<400> SEQUENCE: 142

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                    85                  90                  95

Ser Arg Trp Gly Gly Glu Gly Phe Tyr Ala Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                    165                 170                 175

Leu Gln Ser Ser Gly Leu Tyr Ser Leu Ser Ser Val Val Thr Val Pro
                180                 185                 190

```
Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 143
<211> LENGTH: 214
<212> TYPE: PRT
<213> ORGANISM: Artificial sequence
<220> FEATURE:
<223> OTHER INFORMATION: Trastuzumab light chain 1

<400> SEQUENCE: 143

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Val Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95
```

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
            210

<210> SEQ ID NO 144
<211> LENGTH: 695
<212> TYPE: PRT
<213> ORGANISM: Artificial sequence
<220> FEATURE:
<223> OTHER INFORMATION: scFab Pertuzumab heavy chain 2

<400> SEQUENCE: 144

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Gly Ser Gly Gly Gly Gly Ser Gly Gly Gly Gly Ser
    450                 455                 460

Gly Gly Gly Gly Ser Gly Gly Gly Ser Gly Gly Gly Gly Ser Gly
465                 470                 475                 480

Gly Asp Ile Gln Met Thr Gln Ser Pro Ser Ser Leu Ser Ala Ser Val
                485                 490                 495

Gly Asp Arg Val Thr Ile Thr Cys Lys Ala Ser Gln Asp Val Ser Ile
            500                 505                 510

Gly Val Ala Trp Tyr Gln Gln Lys Pro Gly Lys Ala Pro Lys Leu Leu
        515                 520                 525

Ile Tyr Ser Ala Ser Tyr Arg Tyr Thr Gly Val Pro Ser Arg Phe Ser
    530                 535                 540

Gly Ser Gly Ser Gly Thr Asp Phe Thr Leu Thr Ile Ser Ser Leu Gln
545                 550                 555                 560

Pro Glu Asp Phe Ala Thr Tyr Tyr Cys Gln Gln Tyr Tyr Ile Tyr Pro
                565                 570                 575

Tyr Thr Phe Gly Gln Gly Thr Lys Val Glu Ile Lys Arg Thr Val Ala
            580                 585                 590

Ala Pro Ser Val Phe Ile Phe Pro Pro Ser Asp Glu Gln Leu Lys Ser
        595                 600                 605

Gly Thr Ala Ser Val Val Cys Leu Leu Asn Asn Phe Tyr Pro Arg Glu
    610                 615                 620

Ala Lys Val Gln Trp Lys Val Asp Asn Ala Leu Gln Ser Gly Asn Ser
625                 630                 635                 640

Gln Glu Ser Val Thr Glu Gln Asp Ser Lys Asp Ser Thr Tyr Ser Leu
                645                 650                 655

Ser Ser Thr Leu Thr Leu Ser Lys Ala Asp Tyr Glu Lys His Lys Val
```

```
              660             665             670
Tyr Ala Cys Glu Val Thr His Gln Gly Leu Ser Ser Pro Val Thr Lys
            675             680             685

Ser Phe Asn Arg Gly Glu Cys
        690             695

<210> SEQ ID NO 145
<211> LENGTH: 701
<212> TYPE: PRT
<213> ORGANISM: Artificial sequence
<220> FEATURE:
<223> OTHER INFORMATION: Heavy chain with scFv Trastuzumab stabilized
      with disulphide bonding

<400> SEQUENCE: 145

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Gly Ser Gly Gly Gly Gly Ser Glu Val Gln Leu Val
450                 455                 460

Glu Ser Gly Gly Gly Leu Val Gln Pro Gly Gly Ser Leu Arg Leu Ser
465                 470                 475                 480

Cys Ala Ala Ser Gly Phe Asn Ile Lys Asp Thr Tyr Ile His Trp Val
                    485                 490                 495

Arg Gln Ala Pro Gly Lys Gly Leu Glu Trp Val Ala Arg Ile Tyr Pro
            500                 505                 510

Thr Asn Gly Tyr Thr Arg Tyr Ala Asp Ser Val Lys Gly Arg Phe Thr
        515                 520                 525

Ile Ser Ala Asp Thr Ser Lys Asn Thr Ala Tyr Leu Gln Met Asn Ser
530                 535                 540

Leu Arg Ala Glu Asp Thr Ala Val Tyr Tyr Cys Ser Arg Trp Gly Gly
545                 550                 555                 560

Glu Gly Phe Tyr Ala Met Asp Tyr Trp Gly Cys Gly Thr Leu Val Thr
                    565                 570                 575

Val Ser Ser Gly Gly Gly Gly Ser Gly Gly Gly Gly Ser Gly Gly Gly
            580                 585                 590

Gly Ser Asp Ile Gln Met Thr Gln Ser Pro Ser Ser Leu Ser Ala Ser
        595                 600                 605

Val Gly Asp Arg Val Thr Ile Thr Cys Arg Ala Ser Gln Asp Val Asn
610                 615                 620

Val Ala Val Ala Trp Tyr Gln Gln Lys Pro Gly Lys Cys Pro Lys Leu
625                 630                 635                 640

Leu Ile Tyr Ser Ala Ser Phe Leu Tyr Ser Gly Val Pro Ser Arg Phe
                    645                 650                 655

Ser Gly Ser Arg Ser Gly Thr Asp Phe Thr Leu Thr Ile Ser Ser Leu
            660                 665                 670

Gln Pro Glu Asp Phe Ala Thr Tyr Tyr Cys Gln Gln His Tyr Thr Thr
        675                 680                 685

Pro Pro Thr Phe Gly Gln Gly Thr Lys Val Glu Ile Lys
690                 695                 700

<210> SEQ ID NO 146
<211> LENGTH: 214
<212> TYPE: PRT
<213> ORGANISM: Artificial sequence
<220> FEATURE:
<223> OTHER INFORMATION: Pertuzumab light chain
```

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 147
<211> LENGTH: 26
<212> TYPE: DNA
<213> ORGANISM: Artificial sequence
<220> FEATURE:
<223> OTHER INFORMATION: LMB3

<400> SEQUENCE: 147
caggaaacag ctatgaccat gattac                                    26

<210> SEQ ID NO 148
<211> LENGTH: 53
<212> TYPE: DNA
<213> ORGANISM: Artificial sequence
<220> FEATURE:
<223> OTHER INFORMATION: AM_omni_H1_TN-ba

<400> SEQUENCE: 148
ccggtgcctg acgaacccaa tccataaagg taaaaccgct tgctgcacag ctc      53

<210> SEQ ID NO 149
<211> LENGTH: 32
<212> TYPE: DNA
<213> ORGANISM: Artificial sequence
<220> FEATURE:
<223> OTHER INFORMATION: RJH108 (omni_3H1_fo)

<400> SEQUENCE: 149

```
atggattggg ttcgtcaggc accgggtaaa gg                             32
```

<210> SEQ ID NO 150
<211> LENGTH: 33
<212> TYPE: DNA
<213> ORGANISM: Artificial sequence
<220> FEATURE:
<223> OTHER INFORMATION: RJH109 (omni_5H3_re)

<400> SEQUENCE: 150

```
attacgtgca caataataca ctgcggtatc ctc                            33
```

<210> SEQ ID NO 151
<211> LENGTH: 60
<212> TYPE: DNA
<213> ORGANISM: Artificial sequence
<220> FEATURE:
<223> OTHER INFORMATION: AM_omni_H3_TN_fo

<400> SEQUENCE: 151

```
taccgcagtg tattattgtg cacgtttctt tgattattgg ggtcagggca ccctggttac   60
```

<210> SEQ ID NO 152
<211> LENGTH: 28
<212> TYPE: DNA
<213> ORGANISM: Artificial sequence
<220> FEATURE:
<223> OTHER INFORMATION: RJH99

<400> SEQUENCE: 152

```
ggctgagact cctcaagaga aggattag                                  28
```

<210> SEQ ID NO 153
<211> LENGTH: 32
<212> TYPE: DNA
<213> ORGANISM: Artificial sequence
<220> FEATURE:
<223> OTHER INFORMATION: RJH110(omni_5H2_ba)

<400> SEQUENCE: 153

```
attaacatct gcaacccatt ccagacctttt ac                            32
```

<210> SEQ ID NO 154
<211> LENGTH: 62
<212> TYPE: DNA
<213> ORGANISM: Artificial sequence
<220> FEATURE:
<223> OTHER INFORMATION: AM_omni_h2_TN_fo

<400> SEQUENCE: 154

```
ggtctggaat gggttgcaga tgttaatggt attaaccgtt ttaaaggtcg ttttaccctg   60
ag                                                                  62
```

<210> SEQ ID NO 155
<211> LENGTH: 19
<212> TYPE: PRT
<213> ORGANISM: Artificial sequence
<220> FEATURE:
<223> OTHER INFORMATION: Leader peptide

<400> SEQUENCE: 155

```
Met Asp Trp Thr Trp Arg Ile Leu Phe Leu Val Ala Ala Ala Thr Gly
1               5                   10                  15

Ala His Ser
```

<210> SEQ ID NO 156
<211> LENGTH: 22
<212> TYPE: PRT
<213> ORGANISM: Artificial sequence
<220> FEATURE:
<223> OTHER INFORMATION: Leader peptide

<400> SEQUENCE: 156

Met Asp Met Arg Val Pro Ala Gln Leu Leu Gly Leu Leu Leu Leu Trp
1               5                   10                  15

Phe Pro Gly Ala Arg Cys
            20

<210> SEQ ID NO 157
<211> LENGTH: 19
<212> TYPE: PRT
<213> ORGANISM: Artificial sequence
<220> FEATURE:
<223> OTHER INFORMATION: Leader peptide

<400> SEQUENCE: 157

Met Gly Trp Ser Cys Ile Ile Leu Phe Leu Val Ala Thr Ala Thr Gly
1               5                   10                  15

Val His Ser

<210> SEQ ID NO 158
<211> LENGTH: 11
<212> TYPE: PRT
<213> ORGANISM: Artificial Sequence
<220> FEATURE:
<223> OTHER INFORMATION: Trastuzumab VL N30S CDR1

<400> SEQUENCE: 158

Arg Ala Ser Gln Asp Val Ser Thr Ala Val Ala
1               5                   10

<210> SEQ ID NO 159
<211> LENGTH: 450
<212> TYPE: PRT
<213> ORGANISM: Artificial Sequence
<220> FEATURE:
<223> OTHER INFORMATION: Trastuzumab VHCH1- Fc KNOB

<400> SEQUENCE: 159

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala

```
                130                 135                 140
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Cys Arg Asp Glu Leu Thr Lys Asn Gln Val Ser Leu
            355                 360                 365

Trp Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 160
<211> LENGTH: 1350
<212> TYPE: DNA
<213> ORGANISM: Artificial Sequence
<220> FEATURE:
<223> OTHER INFORMATION: Trastuzumab VHCH1- Fc KNOB DNA

<400> SEQUENCE: 160
gaagtgcaat tggtggaaag cggcggcggc ctggtgcaac cgggcggcag cctgcgtctg      60
agctgcgcgg cctccggatt taacataaag gacacataca tccactgggt gcgccaagca     120
cctgggaagg gtctcgagtg ggtggctcgg atttacccaa caaatggcta caccaggtat    180
gcggatagcg tgaaaggccg ttttaccatt tcagctgata cttcgaagaa caccgcctat     240
```

```
ctgcaaatga acagcctgcg tgcggaagat acggccgtgt attattgctc gcgttgggga    300
ggagacgggt tctatgctat ggattactgg ggccaaggca ccctggtgac ggttagctca    360
gctagcacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag gcagccccg agaaccacag gtgtacaccc tgcccccatg ccgggatgag   1080
ctgaccaaga accaggtcag cctgtggtgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctac agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa                                    1350
```

<210> SEQ ID NO 161
<211> LENGTH: 214
<212> TYPE: PRT
<213> ORGANISM: Artificial Sequence
<220> FEATURE:
<223> OTHER INFORMATION: Common light chain VLCL

<400> SEQUENCE: 161

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Arg Tyr Thr Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 162
<211> LENGTH: 642
<212> TYPE: DNA
<213> ORGANISM: Artificial Sequence
<220> FEATURE:
<223> OTHER INFORMATION: Common light chain VLCL - DNA

<400> SEQUENCE: 162
gacatccaga tgacccagag ccccagcagc ctgtctgcca gcgtgggcga cagagtgacc      60
atcacatgca aggccagcca ggacgtgtcc acagccgtgg cctggtatca gcagaagcct    120
ggcaaggccc ccaagctgct gatctacagc gccagcttcc ggtacaccgg cgtgcccagc    180
agattcagcg gcagcagatc cggcaccgac ttcaccctga ccatcagctc cctgcagccc    240
gaggacttcg ccacctacta ctgccagcag cactacacca ccccccccac atttggccag    300
ggcaccaagg tggaaatcaa gcgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642

<210> SEQ ID NO 163
<211> LENGTH: 449
<212> TYPE: PRT
<213> ORGANISM: Artificial Sequence
<220> FEATURE:
<223> OTHER INFORMATION: Pertuzumab VHCH1 Fc hole

<400> SEQUENCE: 163

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Val Asn Arg Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Phe Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
```

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
                340                 345                 350

Leu Pro Pro Ser Arg Asp Glu Leu Thr Lys Asn Gln Val Ser Leu Ser
            355                 360                 365

Cys Ala Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 164
<211> LENGTH: 1347
<212> TYPE: DNA
<213> ORGANISM: Artificial Sequence
<220> FEATURE:
<223> OTHER INFORMATION: Pertuzumab VHCH1 Fc hole DNA

<400> SEQUENCE: 164
gaagttcagc tggttgaaag cggtggtggt ctggttcagc ctggtggtag cctgcgtctg     60
agctgtgcag caagcggttt tacctttaac gattatacca tggattgggt tcgtcaggca    120
ccgggtaaag gtctggaatg ggttgcagat gttaatccga atagcggtgg tagcattgtt    180
aaccgtcgtt ttaaaggtcg ttttacccct gagcgttgat cgtagcaaaa taccctgtat    240

```
ctgcaaatga atagtctgcg tgcagaggat accgcagtgt attattgtgc acgtaacctg    300
ggtccgttct tctactttga ttattggggt cagggcaccc tggttaccgt tagcagcgct    360
agcaccaagg gcccaagcgt gttccctctg gcccccagca gcaagagcac aagcggcgga    420
acagccgccc tgggctgcct ggtcaaggac tacttcsccg agcccgtgac agtgtcctgg    480
aacagcggag ccctgaccag cggcgtgcac acctttccag ccgtgctgca gagcagcggc    540
ctgtacagcc tgagcagcgt ggtcacagtg cctagcagca gcctgggcac ccagacctac    600
atctgcaacg tgaaccacaa gcccagcaac accaaggtgg acaagaaggt ggagcccaag    660
agctgcgaca agacccacac ctgtccccct tgtcctgccc ctgagctgct gggcggaccc    720
agcgtgttcc tgttccccc  aaagcccaag gacaccctga tgatcagccg gacccccgaa    780
gtgacctgcg tggtggtgga cgtgtcccac gaggaccctg aagtgaagtt caattggtac    840
gtggacggcg tggaggtgca caatgccaag accaagcccc gggaggaaca gtacaacagc    900
acctaccggg tggtgtccgt gctgaccgtg ctgcaccagg actggctgaa cggcaaagag    960
tacaagtgca aggtctccaa caaggccctg cctgccccca tcgagaaaac catcagcaag   1020
gccaagggcc agcccagaga accccaggtg tgcaccctgc ccccagcag agatgagctg    1080 accaagaacc aggtgtccct gagctgtgcc gtcaagggct tctacccag  cgatatcgcc   1140 gtggagtggg agagcaacgg ccagcctgag aacaactaca agaccacccc ccctgtgctg   1200
gacagcgacg gcagcttctt cctggtgtcc aaactgaccg tggacaagag ccggtggcag   1260
cagggcaacg tgttcagctg cagcgtgatg cacgaggccc tgcacaacca ctacacccag   1320
aagtccctga gcctgagccc cggcaag                                       1347
```